(12) United States Patent
Yang et al.

(10) Patent No.: US 10,266,537 B2
(45) Date of Patent: Apr. 23, 2019

(54) 3-ACETYLENYL-PYRAZOLE-PYRIMIDINE DERIVATIVE, AND PREPARATION METHOD THEREFOR AND USES THEREOF

(71) Applicant: Si Chuan University, Sichuan (CN)

(72) Inventors: Shengyong Yang, Sichuan (CN); Yuquan Wei, Sichuan (CN)

(73) Assignee: St. Chuan University, Sichuan (CN)

( * ) Notice: Subject to any disclaimer, the term of this patent is extended or adjusted under 35 U.S.C. 154(b) by 0 days.

(21) Appl. No.: 15/648,223

(22) Filed: Jul. 12, 2017

(65) Prior Publication Data

US 2017/0305920 A1   Oct. 26, 2017

Related U.S. Application Data

(63) Continuation-in-part of application No. PCT/CN2016/070725, filed on Jan. 12, 2016.

(30) Foreign Application Priority Data

Jan. 13, 2015   (CN) .......................... 2015 1 0016197

(51) Int. Cl.
*C07D 487/04* (2006.01)
*A61K 31/4188* (2006.01)
*A61K 31/519* (2006.01)
*A61K 31/5377* (2006.01)

(52) U.S. Cl.
CPC .......... *C07D 487/04* (2013.01); *A61K 31/519* (2013.01); *A61K 31/5377* (2013.01)

(58) Field of Classification Search
CPC .......................... C07D 487/04; A61K 31/4188
See application file for complete search history.

(56) References Cited

U.S. PATENT DOCUMENTS

| 9,108,973 | B2 | 8/2015 | Sagara et al. |
| 2014/0343035 | A1 | 11/2014 | Sagara et al. |

FOREIGN PATENT DOCUMENTS

| CN | 103958512 A | | 7/2014 |
| EP | 2657233 A1 | | 10/2013 |
| WO | 2013108809 A1 | | 7/2013 |
| WO | WO2013/108809 | * | 7/2013 |
| WO | 2015008839 A1 | | 1/2015 |
| WO | 2015008844 A1 | | 1/2015 |
| WO | 2016112846 A1 | | 7/2016 |

OTHER PUBLICATIONS

Berge, Pharmaceutical Salts, Jan. 1977, Journal of Pharmaceutical Sciences, vol. 66, No. 1, p. 1-19. (Year: 1977).*
Zhang et al, From Lead to Drug Candidate: Optimization of 3-(Phenylethynyl)-1H-pyrazolo[3,4-d]pyrimidin-4-amine derivatives as agents for the treatment of triple negative breast cancer, Oct. 2016, J. Med. Chem. vol. 59, p. 9788-9805 (Year: 2016).*
Written Opinion of the International Searching Authority for International Application No. PCT/CN2016/070725, dated Apr. 22, 2016, 20 pages.
International Search Report for International Application PCT/CN2016/070725, dated Jan. 1, 2016, 7 pages.
Diner, P. et al., Preparation of 3-Substituted-1-Isopropyl-1H-Pyrazolo[3,4-d]Pyrimidin-4-Amines as RET Kinase Inhibitors, Journal of Medicinal Chemistry, vol. 55, No. 10, S1-S37.
Klein, M. et al, Design, Synthesis and Characterization of a Highly Effective Inhibitor for Analog-Sensitive (as) Kinases, PLoS ONE, Jun. 2011, vol. 6, No. 6, pp. 1-10.
First Office Action of Chinese Application No. 201510016197.2, dated Aug. 3, 2017, 8 pages.
Liu, Xu et al., "Development of Alkyne-Containing Pyrazolopyrimidines to Overcome Drug Resistance of Bcr-Abl Kinase", Journal of Medicinal Chemistry, vol. 58, No. 23, Nov. 12, 2015 (Nov. 12, 2015), pp. 9228-9237.
Zhang, C.H. et al., "Design, Synthesis, and Structure-Activity Relationship Studies of 3-(Phenylethynyl)-1H-pyrazolo [3, 4-d] pyrimidin-4-amine Derivatives as a New Class of Src Inhibitors with Potent Activities in Models of Triple Negative Breast Cancer", Journal of Medicinal Chemistry, vol. 58, No. 9, Apr. 2, 2015 (Apr. 2, 2015), pp. 3957-3974.
Diner, P. et al., "Preparation of 3-Substituted-I-Isoprpyl-1H-pyrazolo[3, 4-d]pyrimidin-4-amines as RET Kinase Inhibitors", Journal of Medicinal Chemistry, vol. 55, No. 10, May 7, 2012, pp. 4872-4876.
Klein, M. et al., "Design, Synthesis and Characterization of a Highly Effective Inhibitor for Analog-Sensitive (as) Kineses", PLOS ONE, vol. 6, No. 6, Jun. 17, 2011 (Jun. 17, 2011), p. e20789.

(Continued)

*Primary Examiner* — Karen Cheng
(74) *Attorney, Agent, or Firm* — Armstrong Teasdale LLP

(57) ABSTRACT

The present invention relates to the field of chemical and medicine, more particularly, 3-ethynylpyrazolopyrimidine derivatives and their preparation methods and uses. The invention provides a 3-ethynylpyrazolopyrimidine derivative, and the structure is shown in formula I. The present invention also provides preparation methods and use of 3-ethynylpyrazolopyrimidine derivatives, comprising the compounds and derivatives, and their pharmaceutical compositions for the use of the treatment and prevention of tumors.

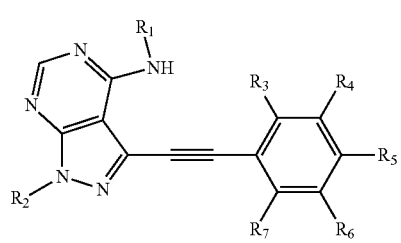

18 Claims, 4 Drawing Sheets

(56) References Cited

OTHER PUBLICATIONS

International Search Report for International Application No. PCT/CN2016/070725, dated Apr. 22, 2016, 3 pages.
Notification of Reasons for Refusal for JP Application No. 2017-554635, dated Jun. 5, 2018, 6 pages.
Extended European Search Report for EP Application No. 16737071.7, dated May 17, 2018, 5 pages.
Office Action for CA Application No. 2,973,247, dated May 18, 2018, 4 pages.

* cited by examiner

3-ACETYLENYL-PYRAZOLE-PYRIMIDINE DERIVATIVE, AND PREPARATION METHOD THEREFOR AND USES THEREOF

CROSS REFERENCE TO RELATED APPLICATIONS

This application is a continuation-in-part of International Application No. PCT/CN2016/070725, filed Jan. 12, 2016, which claims priority to CN Application No. 201510016197.2, filed Jan. 13, 2015, the entire disclosures of which are hereby incorporated by reference in their entirety.

FIELD OF THE INVENTION

The present invention relates to the field of chemical and medicine, more particularly, 3-ethynylpyrazolopyrimidine derivatives and their preparation methods and uses.

BACKGROUND OF THE INVENTION

Kinase is a class of important phosphotransferases whose function is to catalyze the transfer of the γ-phosphate group at the end of adenosine triphosphate to the amino acid residues of a particular substrate protein to phosphorylate the protein and thereby play its physiological biochemical function. Protein kinases are key components of cellular signal transduction pathways. Protein kinases are involved in the regulation of multiple cellular processes, including cell growth, energy metabolism, cell cycle, transcription, apoptosis, differentiation and so on. In addition, protein kinases play a vital role in maintaining intercellular relationships, homeostasis, immune system function and so on. The abnormal regulation of protein kinases is associated with the development of various diseases, especially tumors. Kinase has become important targets for disease treatment, it has attracted wide attention.

Since 2001 the first tyrosine protein kinase drug imatinib (Imatinib) listed, protein kinase drugs have become the fastest growing unit in the global drug market. As of 2014, more than 20 protein kinase drugs have been approved worldwide, including more than 10 antitumor drugs, such as Imatinib, Gefitinib, Erlotinib, Sorafenib, Sunitinib, Dasatinib, Nilotinib, Laptinib, Pazopanib, and Regorafenib. The successful development of protein kinases, especially the development of anti-tumor drugs targeting multiple protein kinases, has made it a hot research field for the scientific and pharmaceutical industry.

Although current research and development of protein-kinase drug has achieved great success, there is still a lot of room and potential for development. In particular, the development of novel protein kinase inhibitors for the treatment of refractory tumors, drug-resistant tumors, and highly metastatic tumors, such as triple-negative breast cancer, drug-resistant lung cancer, liver cancer, pancreatic cancer, melanoma, multiple leukemia and so on, is still the current research hotspot.

DETAILED DESCRIPTION OF THE INVENTION

The invention provides a 3-ethynylpyrazolopyrimidine derivative, and the structure is shown in Formula I:

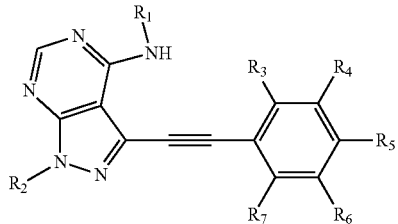

Wherein, $R_1$ is —H, $C_1$~$C_4$ alkyl,

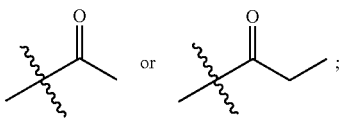

$R_2$ is —H, $C_1$~$C_8$ alkyl,

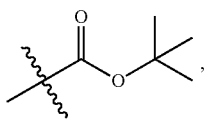 [SMILES: *C(=O)OC(C)(C)C]

$C_3$~$C_8$ cycloalkyl substituted with $R_8$,

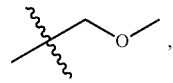 [SMILES: *COC]

$C_3$~$C_8$ epoxyalkyl,

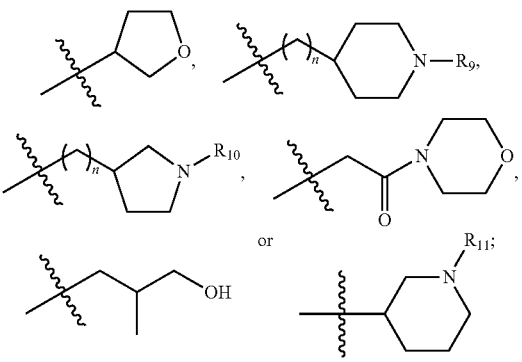

$R_3$~$R_7$ are independently selected from —H, $C_1$~$C_8$ alkyl, —OH, $C_1$~$C_8$ alkoxyl, halogen,

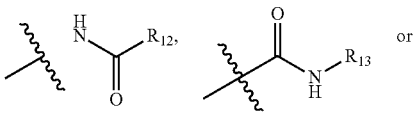

-continued

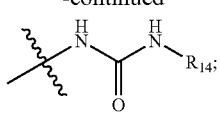

$R_8$~$R_{11}$ represent —H, $C_1$~$C_8$ alkyl, halogen, —OH,

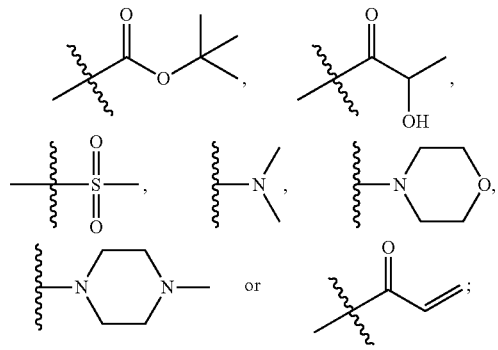

$R_{12}$~$R_{14}$ independently represent

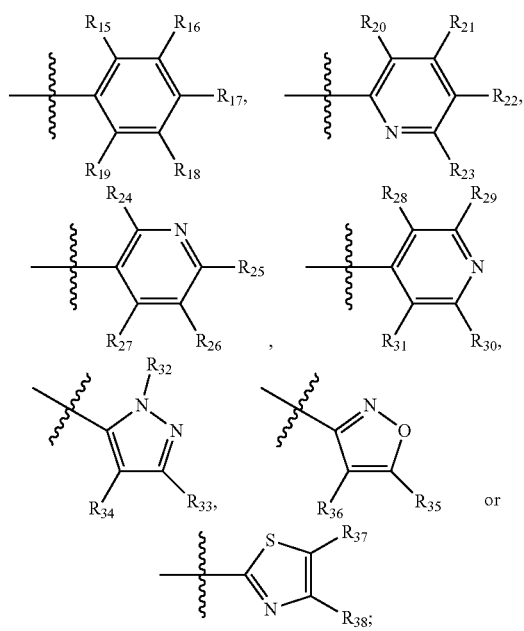

$R_{15}$~$R_{19}$ are independently selected from —H, $C_1$~$C_8$ alkyl, —OH, $C_1$~$C_8$ alkoxyl, halogen, —$CF_3$, —$OCF_3$,

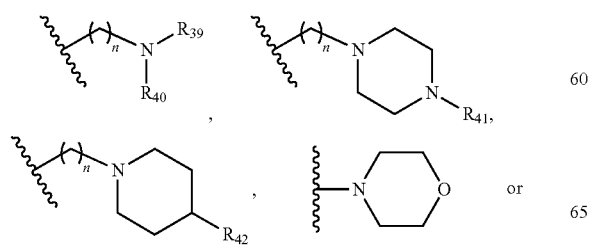

-continued

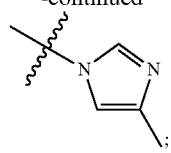

$R_{20}$~$R_{38}$ independently represent —H, halogen, $C_1$~$C_8$ alkyl, $C_1$~$C_8$ cycloalkyl, —$OCF_3$ or —$CF_3$;

$R_{39}$~$R_{42}$ are $C_1$~$C_8$ alkyl, $C_3$~$C_8$ cycloalkyl or $C_1$-$C_8$ hydroxyalkyl;

n=0~6.

In a preferred embodiment of the present invention, $R_1$ is —H or

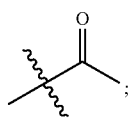

$R_2$ is —H, $C_1$~$C_4$ alkyl,

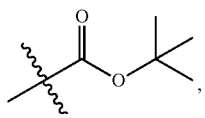 [SMILES: *C(=O)OC(C)(C)C]

$R_8$ substituted $C_3$~$C_8$ cycloalkyl,

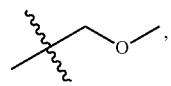 [SMILES: *COC]

$C_3$~$C_8$ epoxyalkyl,

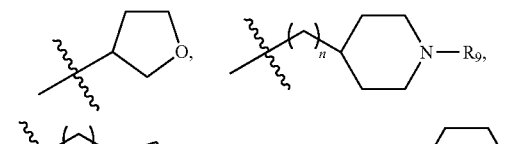

or

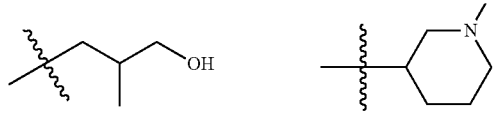

$R_3$~$R_7$ are independently selected from —H, $C_1$~$C_4$ alkyl, —OH, $C_1$~$C_4$ alkoxyl, halogen,

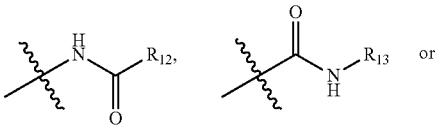

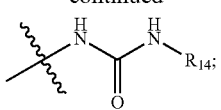

$R_8$~$R_{11}$ are —H, $C_1$~$C_4$ alkyl, halogen, —OH,

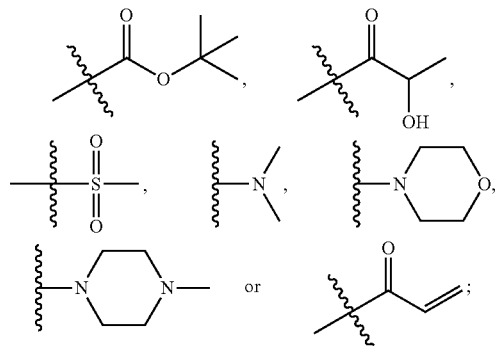

$R_{12}$~$R_{14}$ independently represent

[structures with $R_{15}$–$R_{19}$ phenyl; $R_{20}$–$R_{23}$ pyridyl; $R_{24}$–$R_{27}$ pyridyl; $R_{28}$–$R_{31}$ pyridyl; $R_{32}$–$R_{34}$ pyrazolyl; $R_{35}$–$R_{36}$ isoxazolyl; $R_{37}$–$R_{38}$ thiazolyl]

$R_{15}$~$R_{19}$ are independently selected from —H, $C_1$~$C_4$ alkyl, —OH, $C_1$~$C_4$ alkoxyl, halogen, —CF$_3$, —OCF$_3$,

[structures with $R_{39}$/$R_{40}$ amine; $R_{41}$ piperazinyl; $R_{42}$ piperidinyl; morpholino] or

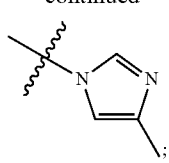

$R_{20}$~$R_{38}$ are —H, halogen, $C_1$~$C_4$ alkyl, $C_1$~$C_4$ cycloalkyl, —OCF$_3$ or —CF$_3$; $R_{39}$~$R_{42}$ independently represent $C_1$~$C_4$ alkyl, $C_3$~$C_8$ cycloalkyl or $C_1$~$C_4$ hydroxyalkyl; n=0~4.

Preferably, $R_1$ is —H or

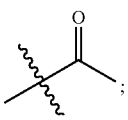

$R_2$ is —H, $C_1$~$C_4$ alkyl,

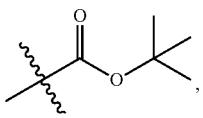 [SMILES: *C(=O)OC(C)(C)C]

$R_8$ substituted $C_3$~$C_8$ cycloalkyl,

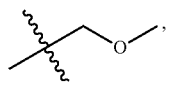 [SMILES: *COC]

$C_3$~$C_8$ epoxyalkyl,

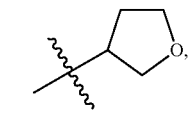 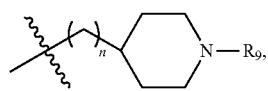

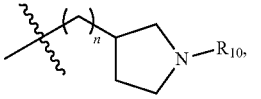

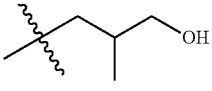 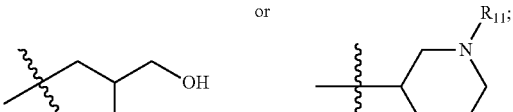

$R_3$~$R_7$ are independently selected from —H, $C_1$~$C_4$ alkyl, —OH, $C_1$~$C_4$ alkoxyl, halogen,

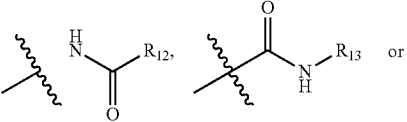 or

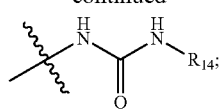

$R_8$~$R_{11}$ represent —H, $C_1$~$C_4$ alkyl, —OH,

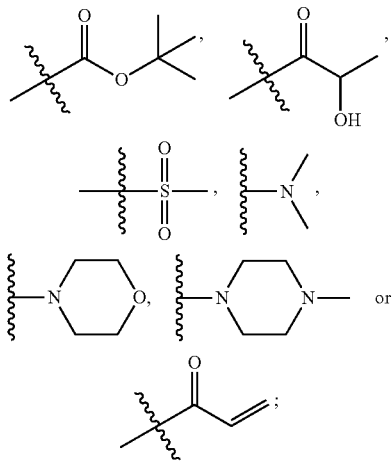

$R_{12}$~$R_{14}$ independently represent

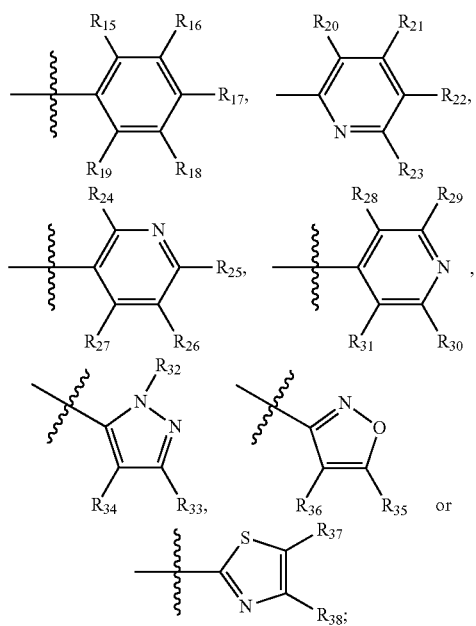

$R_{15}$~$R_{19}$ are independently selected from —H, $C_1$~$C_4$ alkyl, —OH, $C_1$~$C_4$ alkoxyl, halogen, —$CF_3$, —$OCF_3$,

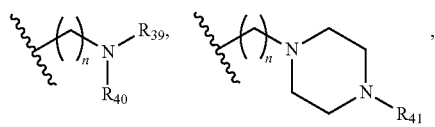

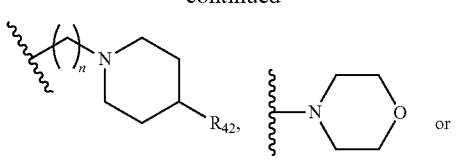

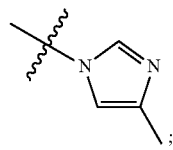

$R_{20}$~$R_{38}$ are —H, halogen, $C_1$~$C_4$ alkyl, $C_1$~$C_4$ cyloalkyl, —$OCF_3$ or —$CF_3$; $R_{39}$~$R_{42}$ independently represent $C_1$~$C_4$ alkyl, $C_3$~$C_8$ cyloalkyl or $C_1$~$C_4$ hydroxyalkyl; n=0~4.

Further preferably, $R_1$ is —H or

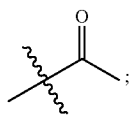 [SMILES: *C(C)=O]

$R_2$ is —H, $C_1$~$C_4$ alkyl,

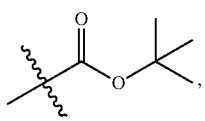 [SMILES: *C(=O)OC(C)(C)C]

$R_8$ substituted $C_3$~$C_8$ cycloalkyl,

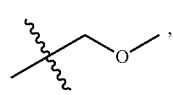 [SMILES: *COC]

$C_3$-$C_8$ epoxyalkyl,

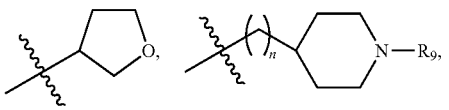

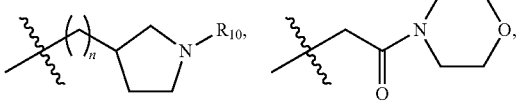

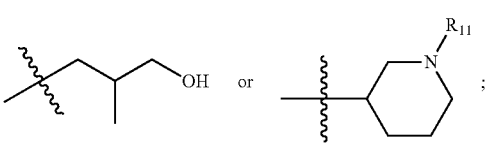

$R_3$~$R_7$ are independently selected from —H, $C_1$~$C_4$ alkyl, —OH, $C_1$~$C_4$ alkoxyl, halogen,

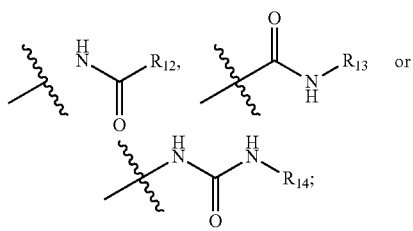

$R_8 \sim R_{11}$ are —H, $C_1 \sim C_4$ alkyl, —OH,

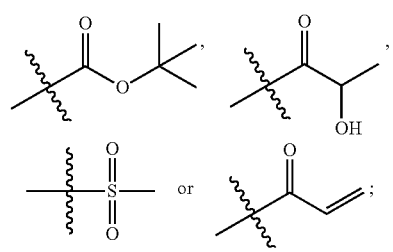

$R_{12} \sim R_{14}$ represent

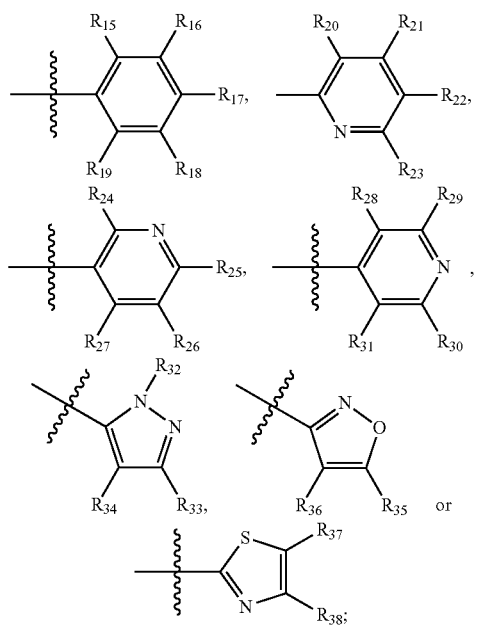

$R_{15} \sim R_{19}$ independently represent —H, $C_1 \sim C_4$ alkyl, —OH, $C_1 \sim C_4$ alkoxyl, halogen, —CF$_3$, —OCF$_3$,

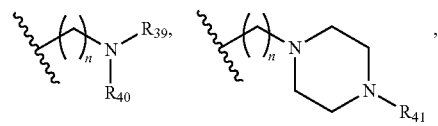

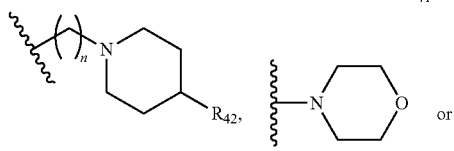

or

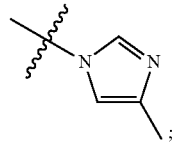

$R_{20} \sim R_{38}$ are independently selected from —H, halogen, $C_1 \sim C_4$ alkyl, $C_1 \sim C_4$ cycloalkyl, —OCF$_3$ or —CF$_3$; $R_{39} \sim R_{42}$ are $C_1 \sim C_4$ alkyl, $C_3$-$C_8$ cycloalkyl or $C_1 \sim C_4$ hydroxyalkyl; n=0~4.

More preferably, $R_1$ is —H or

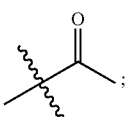

$R_2$ is —H, $C_1 \sim C_4$ alkyl,

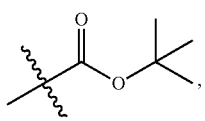 [SMILES: *C(=O)OC(C)(C)C]

$R_8$ substituted $C_3 \sim C_8$ cycloalkyl,

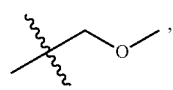 [SMILES: *COC]

$C_3 \sim C_8$ epoxyalkyl,

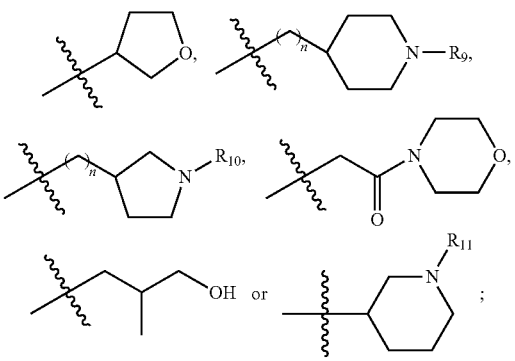

$R_3 \sim R_7$ are independently selected from —H, $C_1 \sim C_4$ alkyl, —OH, $C_1 \sim C_4$ alkoxyl, halogen,

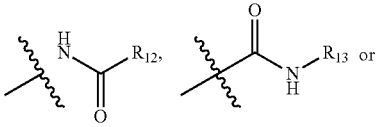

or

-continued

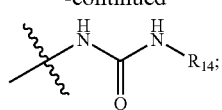

$R_8 \sim R_{11}$ are —H, $C_1 \sim C_4$ alkyl, —OH,

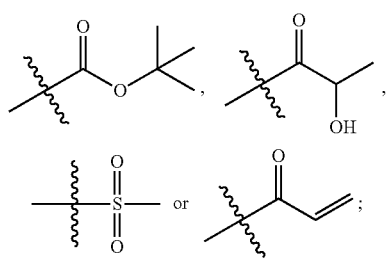

$R_{12} \sim R_{14}$ represent

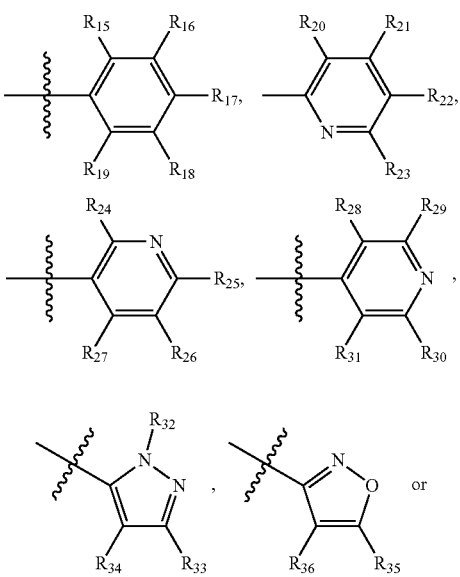

$R_{15} \sim R_{19}$ independently represent —H, $C_1 \sim C_4$ alkyl, —OH, $C_1 \sim C_4$ alkoxyl, halogen, —CF$_3$, —OCF$_3$,

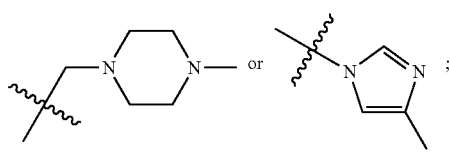

$R_{20} \sim R_{38}$ are independently selected from —H, halogen, $C_1 \sim C_4$ alkyl, $C_1 \sim C_4$ cycloalkyl, —OCF$_3$ or —CF$_3$; n=0~2.

Optimally, $R_1$ is —H or

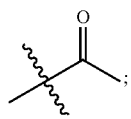 [SMILES: *C(C)=O]

$R_2$ is —H, $C_1 \sim C_4$ alkyl,

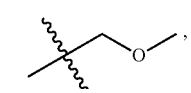

$R_8$ substituted $C_3 \sim C_8$ cycloalkyl,

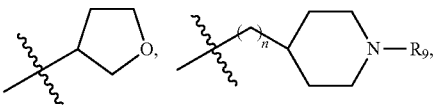

$C_3 \sim C_8$ epoxyalkyl,

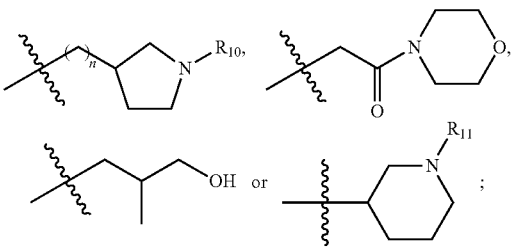

$R_3 \sim R_7$ are —H, $C_1 \sim C_4$ alkyl, —OH, $C_1 \sim C_4$ alkoxyl, —F, —Cl,

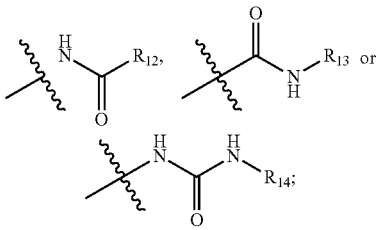

$R_8 \sim R_{11}$ represent —H, $C_1 \sim C_4$ alkyl, —OH,

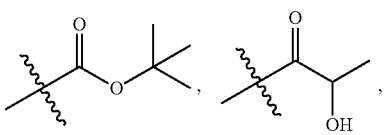

-continued

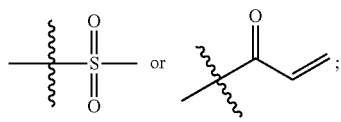

$R_{12}$~$R_{14}$ are

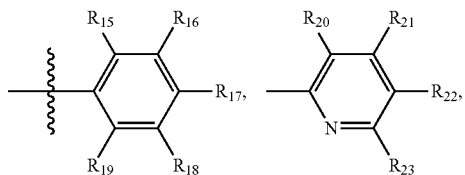

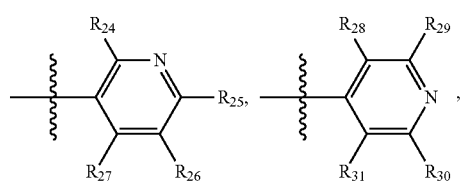

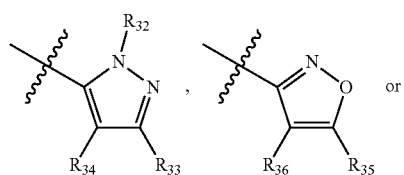

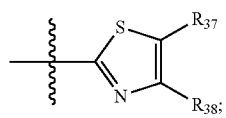

$R_{15}$~$R_{19}$ represent —H, $C_1$~$C_4$ alkyl, —OH, $C_1$~$C_4$ alkoxyl, —F, —Cl, —CF$_3$, —OCF$_3$,

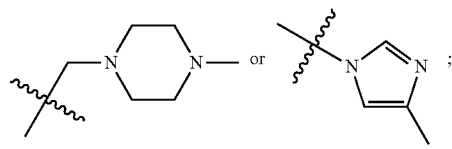

$R_{20}$~$R_{38}$ are —H, $C_1$~$C_4$ alkyl or —CF$_3$; n=0 or 1.

The 3-ethynylpyrazolopyrimidine derivatives described above, when $R_6$ is

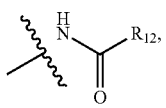

the structure is shown as formula II:

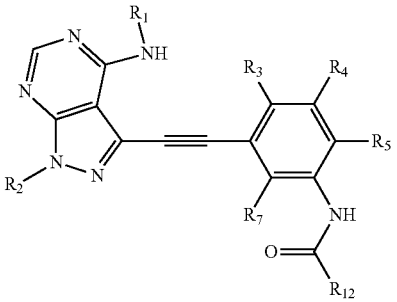

II

Wherein, $R_1$ is —H or

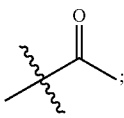 [SMILES: *C(C)=O]

$R_2$ is —H, $C_1$~$C_4$ alkyl,

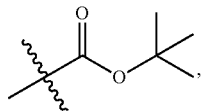 [SMILES: *C(=O)OC(C)(C)C]

$C_3$-$C_8$ cycloalkyl substituted with $R_8$,

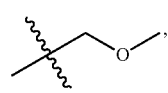 [SMILES: *COC]

$C_3$~$C_8$ epoxyalkyl,

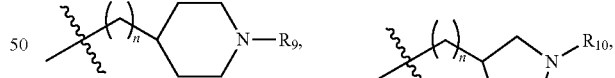

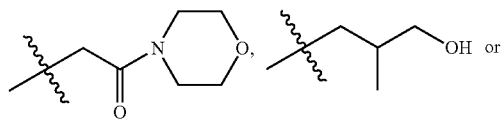

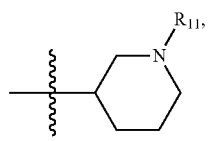

n=0~4; $R_3$~$R_5$, $R_7$ are —H, $C_1$~$C_4$ alkyl, —OH, $C_1$~$C_4$ alkoxyl or halogen; $R_8$~$R_{11}$ represent —H, $C_1$~$C_4$ alkyl, —OH,

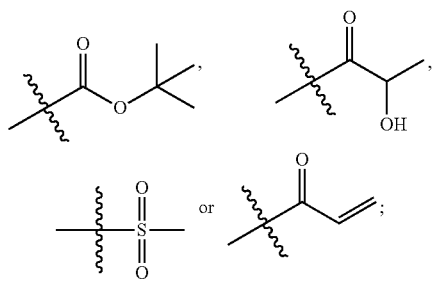
R$_{12}$ is
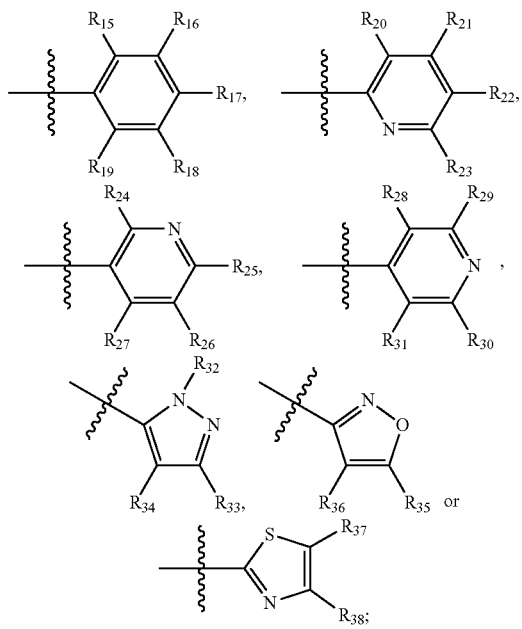
R$_{15}$~R$_{19}$ are —H, C$_1$~C$_4$ alkyl, —OH, C$_1$~C$_4$ alkoxyl, halogen, —CF$_3$, —OCF$_3$,
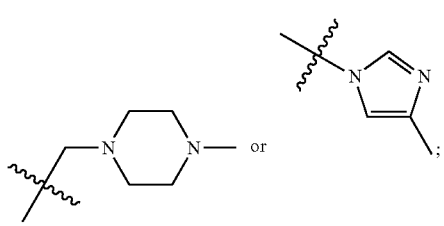
R$_{20}$~R$_{38}$ independently represent —H, C$_1$~C$_4$ alkyl or —CF$_3$.
Preferably, R$_1$ is —H or
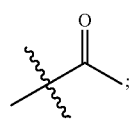
R$_2$ is —H, C$_1$~C$_4$ alkyl,
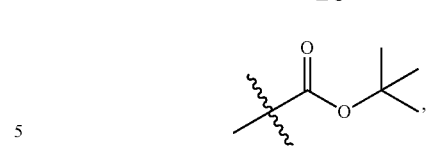
R$_8$ substituted C$_3$~C$_8$ cycloalkyl,
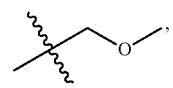
C$_3$~C$_8$ epoxyalkyl,
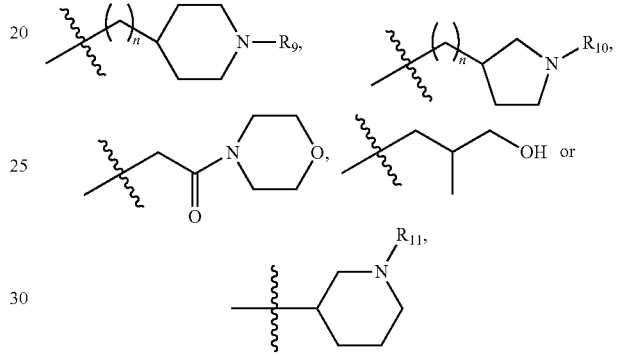
n=0~4; R$_3$~R$_5$, R$_7$ are —H, C$_1$~C$_4$ alkyl, —OH, C$_1$~C$_4$ alkoxyl or halogen; R$_8$~R$_{11}$ represent —H, C$_1$~C$_4$ alkyl, —OH,
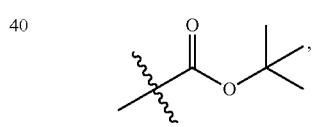
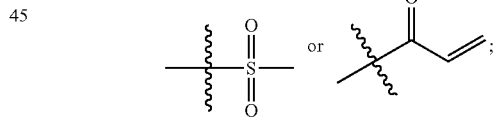
R$_{12}$ is
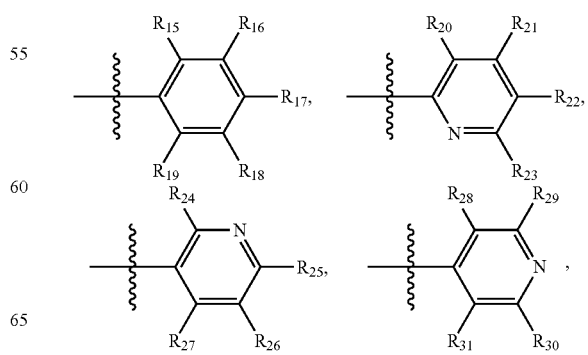

-continued

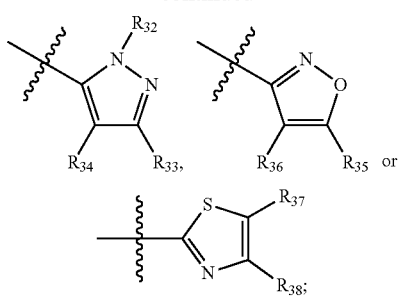

$R_{15}$~$R_{19}$ are —H, $C_1$~$C_4$ alkyl, —OH, $C_1$~$C_4$ alkoxyl, halogen, —$CF_3$, —$OCF_3$,

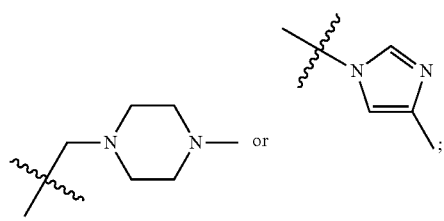 or $R_{20}$~$R_{38}$ independently represent —H, $C_1$~$C_4$ alkyl or —$CF_3$.

Preferably, $R_1$ is —H or

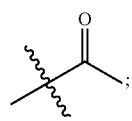 [SMILES: *C(C)=O]

$R_2$ is $C_1$~$C_4$ alkyl, $R_8$ substituted $C_3$~$C_8$ cycloalkyl,

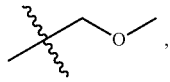 [SMILES: *COC], $C_3$~$C_8$ epoxyalkyl,

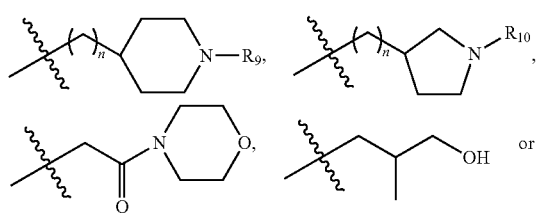

n=0~4; $R_8$~$R_{11}$ are —H, $C_1$~$C_4$ alkyl, —OH,

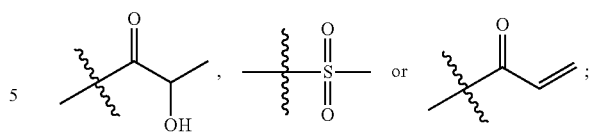

$R_3$~$R_5$, $R_7$ represent —H, $C_1$~$C_4$ alkyl, —OH, $C_1$~$C_4$ alkoxyl or halogen; $R_{12}$ is

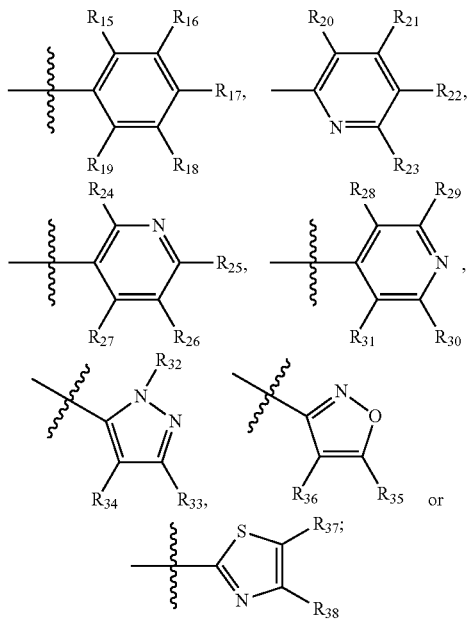

$R_{15}$~$R_{19}$ independently represent —H, $C_1$~$C_4$ alkyl, —OH, $C_1$~$C_4$ alkoxyl, halogen, —$CF_3$, —$OCF_3$,

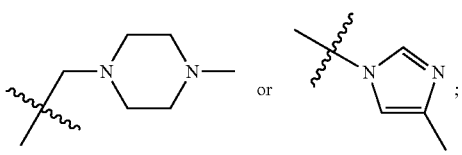

$R_{20}$~$R_{38}$ are independently selected from —H, $C_1$~$C_4$ alkyl or —$CF_3$.

Further preferably, $R_1$ is —H or

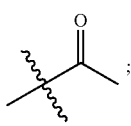

$R_2$ is $C_1$~$C_4$ alkyl, $R_8$ substituted $C_3$~$C_8$ cycloalkyl,

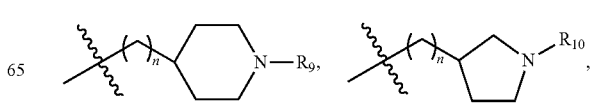

-continued

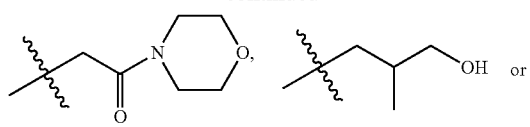

or 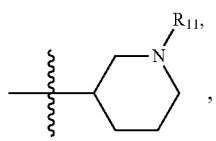

n=0~4; $R_8$~$R_{11}$ are —H, $C_1$~$C_4$ alkyl, —OH,

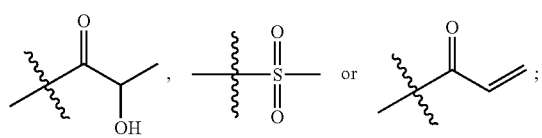

$R_3$~$R_5$, $R_7$ represent —H, $C_1$~$C_4$ alkyl, —OH, $C_1$~$C_4$ alkoxyl or halogen; $R_{12}$ is

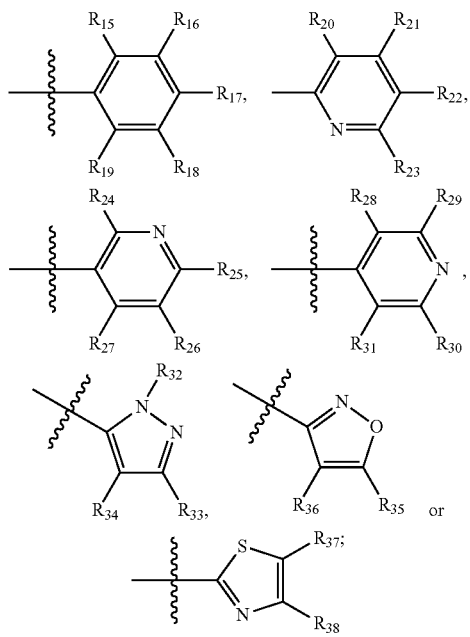

$R_{15}$~$R_{19}$ are —H, $C_1$~$C_4$ alkyl, —OH, $C_1$~$C_4$ alkoxyl, halogen, —CF$_3$, —OCF$_3$,

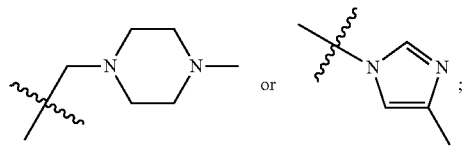

$R_{20}$~$R_{38}$ represent —H, $C_1$~$C_4$ alkyl or —CF$_3$.

More preferably, $R_1$ is —H or

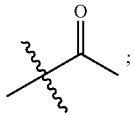

$R_2$ is $C_1$~$C_4$ alkyl, $R_8$ substituted $C_3$~$C_8$ cycloalkyl,

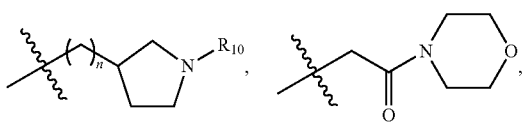

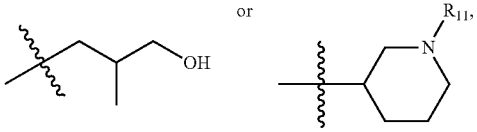

n=0~2; $R_8$~$R_{11}$ are —H, $C_1$~$C_4$ alkyl, —OH,

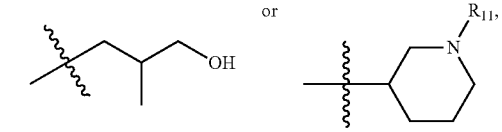

$R_3$~$R_5$, $R_7$ represent —H, $C_1$~$C_4$ alkyl, —OH, $C_1$~$C_4$ alkoxyl or halogen; $R_{12}$ is

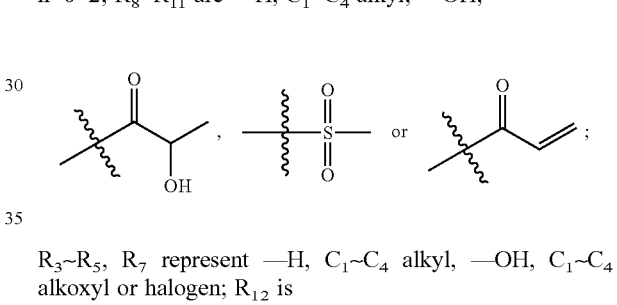

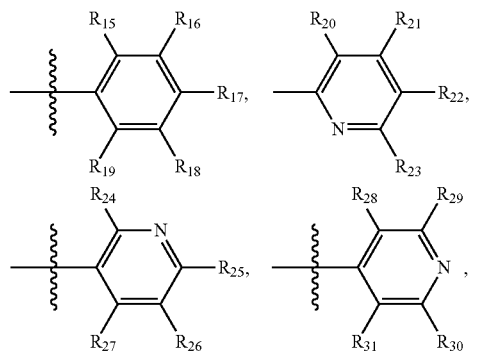

H, $C_1$~$C_4$ alkyl, —OH, $C_1$~$C_4$ alkoxyl, halogen, —CF$_3$, —OCF$_3$,

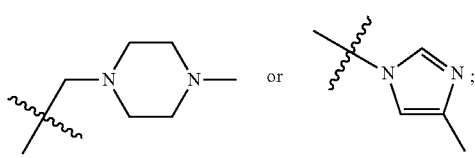 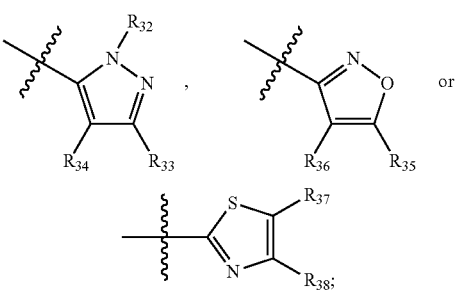

$R_{20} \sim R_{38}$ represent —H, $C_1 \sim C_4$ alkyl or —CF$_3$.

Further preferably, $R_1$ is —H or

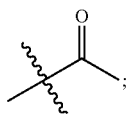 [SMILES: *C(C)=O]

$R_2$ is $C_1 \sim C_4$ alkyl, $R_8$ substituted $C_3$-$C_8$ cycloalkyl,

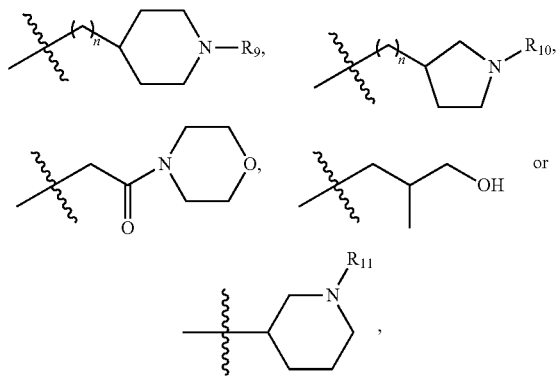

$R_{15} \sim R_{19}$ are —H, $C_1 \sim C_4$ alkyl, —OH, $C_1 \sim C_4$ alkoxyl, halogen, —CF$_3$, —OCF$_3$,

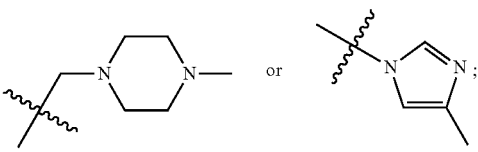

$R_{20} \sim R_{38}$ represent —H, $C_1 \sim C_4$ alkyl or —CF$_3$.

Preferably, $R_3 \sim R_5$, $R_7$ are —H, $C_1 \sim C_4$ alkyl or halogen; $R_1$ is —H or

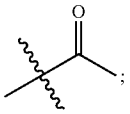

$R_2$ is —H, $C_1 \sim C_4$ alkyl,

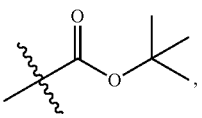

substituted $R_8$ $C_3 \sim C_8$ cycloalkyl,

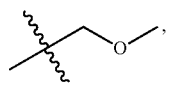

$C_3 \sim C_8$ epoxyalkyl,

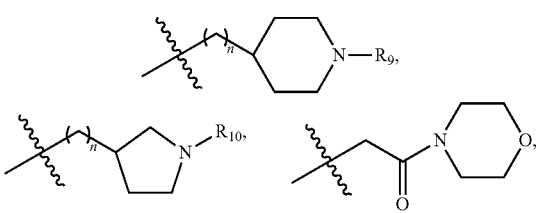

n=0 or 1; $R_8 \sim R_{11}$ are —H, $C_1 \sim C_4$ alkyl, —OH,

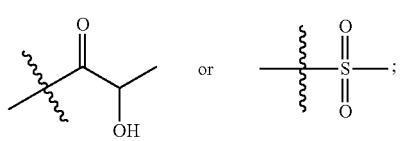

$R_3 \sim R_5$, $R_7$ are independently selected from —H, $C_1 \sim C_4$ alkyl, —OH, $C_1 \sim C_4$ alkoxyl or halogen; $R_{12}$ is

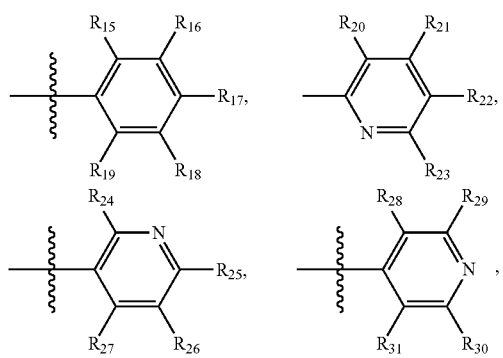

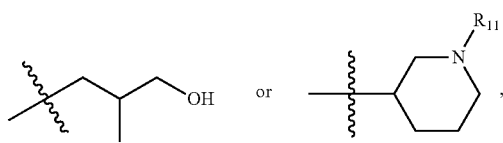
n=0~4; $R_8$~$R_{11}$ are —H, $C_1$~$C_4$ alkyl, —OH,
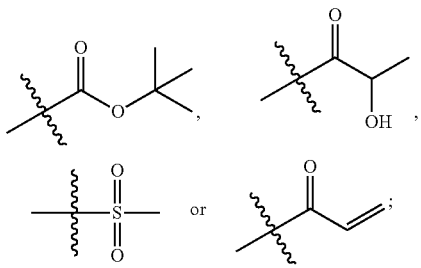
$R_{12}$ is
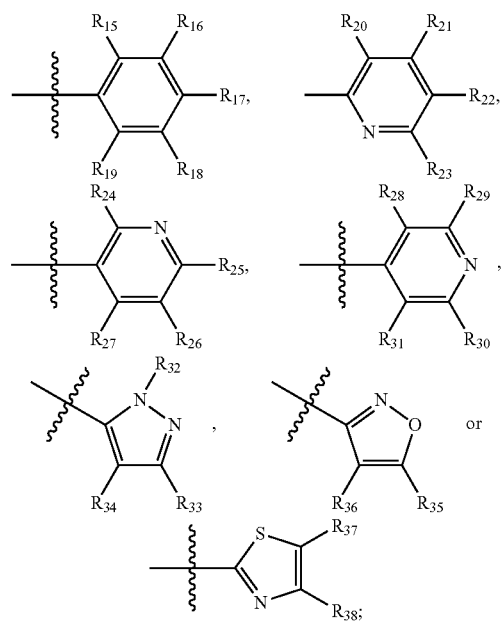
$R_{15}$~$R_{19}$ represent —H, $C_1$~$C_4$ alkyl, —OH, $C_1$~$C_4$ alkoxyl, halogen, —$CF_3$, —$OCF_3$,
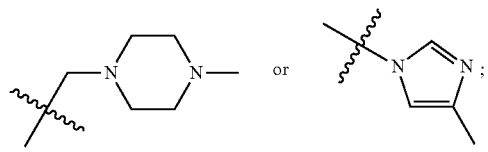
$R_{20}$~$R_{38}$ independently represent —H, $C_1$~$C_4$ alkyl or —$CF_3$.
Further preferably, $R_3$~$R_5$, $R_7$ are —H, $C_1$~$C_4$ alkyl, —F or —Cl; $R_1$ is —H or
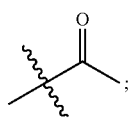 [SMILES: *C(C)=O]
$R_2$ is —H, $C_1$~$C_4$ alkyl,
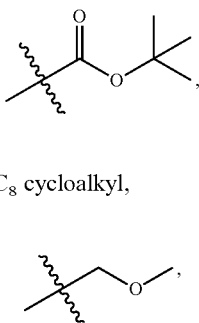
$R_8$ substituted $C_3$-$C_8$ cycloalkyl,
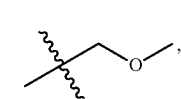 [SMILES: *COC]
$C_3$~$C_8$ epoxyalkyl,
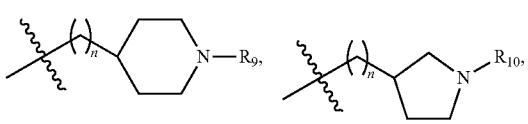
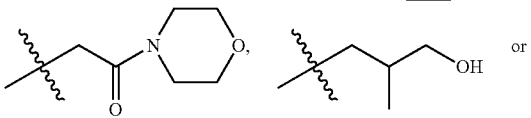
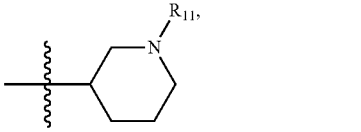
n=0~4; $R_8$~$R_{11}$ are —H, $C_1$~$C_4$ alkyl, —OH,
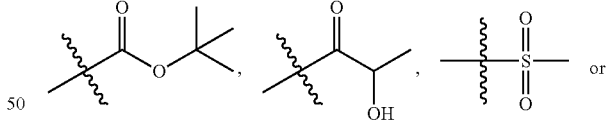
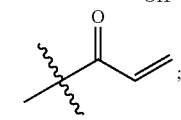
$R_{12}$ is
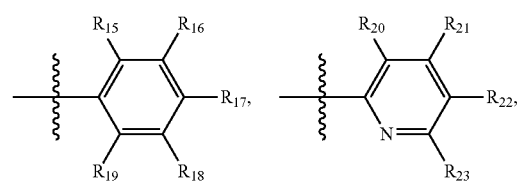

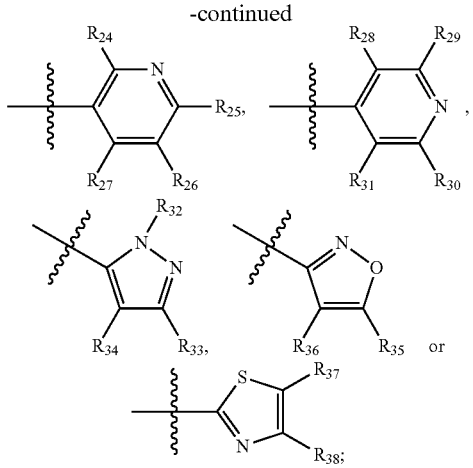

$R_{15}$~$R_{19}$ are —H, $C_1$~$C_4$ alkyl, —OH, $C_1$~$C_4$ alkoxyl, halogen, —$CF_3$, —$OCF_3$,

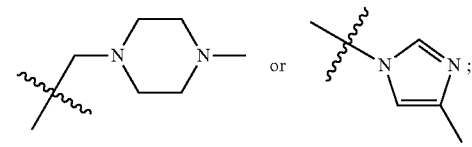

$R_{20}$~$R_{38}$ represent —H, $C_1$~$C_4$ alkyl or —$CF_3$.

Further preferably, $R_3$~$R_5$, $R_7$ are —H, methyl or —Cl; $R_1$≠H or

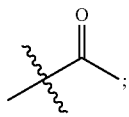 [SMILES: *C(C)=O]

$R_2$ is —H, $C_1$~$C_4$ alkyl,

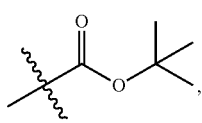

$R_8$ substituted $C_3$-$C_8$ cycloalkyl,

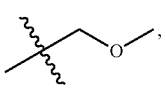 [SMILES: *COC]

$C_3$~$C_8$ epoxyalkyl,

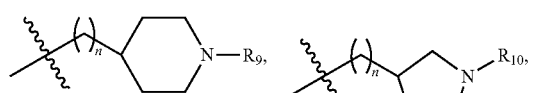

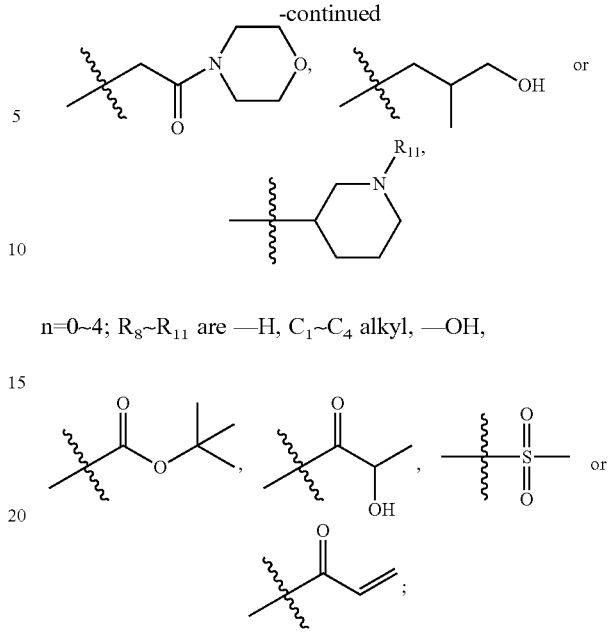

n=0~4; $R_8$~$R_{11}$ are —H, $C_1$~$C_4$ alkyl, —OH,

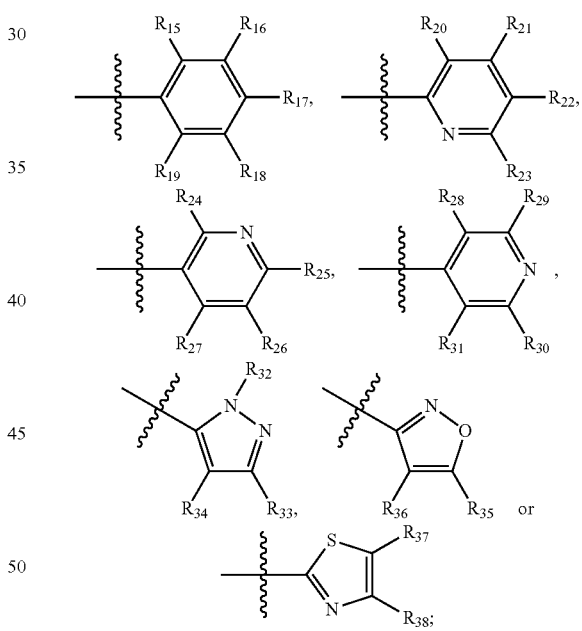

$R_{12}$ is

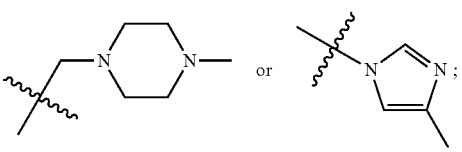

$R_{15}$~$R_{19}$ represent —H, $C_1$~$C_4$ alkyl, —OH, $C_1$~$C_4$ alkoxyl, halogen, —$CF_3$, —$OCF_3$, $R_{20}$~$R_{38}$ independently represent —H, $C_1$~$C_4$ alkyl or —$CF_3$.

Preferably, $R_{15}$~$R_{19}$ are independently selected from —H, $C_1$~$C_4$ alkyl, $C_1$~$C_4$ alkoxyl, halogen, —$CF_3$, —$OCF_3$ or

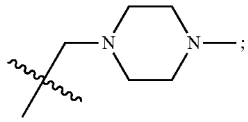 [SMILES: *CN1CCN(C)CC1]

$R_1$ is —H or

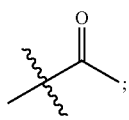 [SMILES: *C(C)=O]

$R_2$ is —H, $C_1$~$C_4$ alkyl,

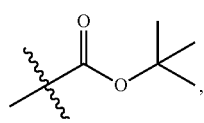

$R_8$ substituted $C_3$~$C_8$ cycloalkyl,

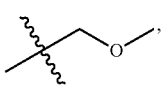

$C_3$~$C_8$ epoxyalkyl,

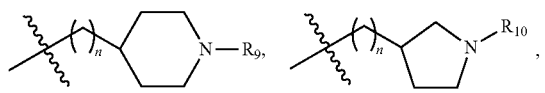

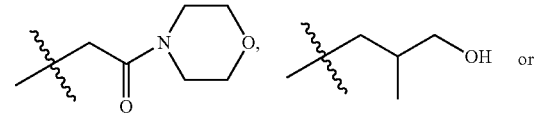

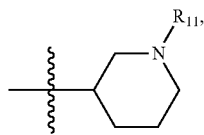

n=0~4; $R_3$~$R_5$, $R_7$ are —H, $C_1$~$C_4$ alkyl, —OH, $C_1$~$C_4$ alkoxyl or halogen; $R_8$~$R_1$ represent —H, $C_1$~$C_4$ alkyl, —OH,

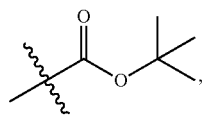 [SMILES: *C(=O)OC(C)(C)C] 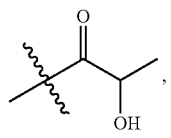

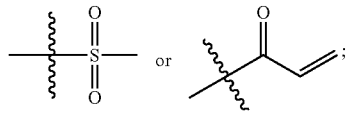

$R_{12}$ is

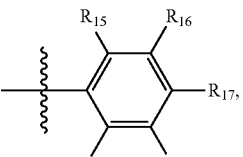 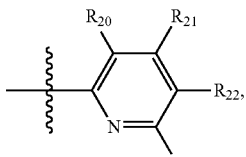

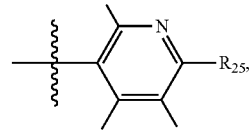 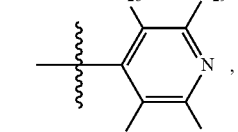

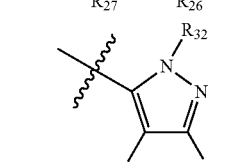 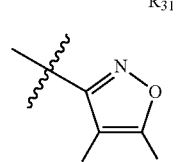

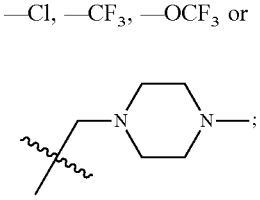

$R_{20}$~$R_{38}$ are —H, $C_1$~$C_4$ alkyl or —$CF_3$.

More preferably, $R_{15}$~$R_{19}$ are —H, $C_1$~$C_4$ alkyl, methoxyl, —F, —Cl, —$CF_3$, —$OCF_3$ or

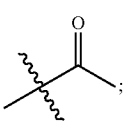

$R_1$ is —H or

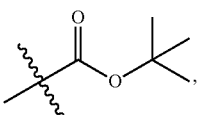

$R_2$ is —H, $C_1$~$C_4$ alkyl, $R_8$ substituted $C_3$~$C_8$ cyloalkyl,

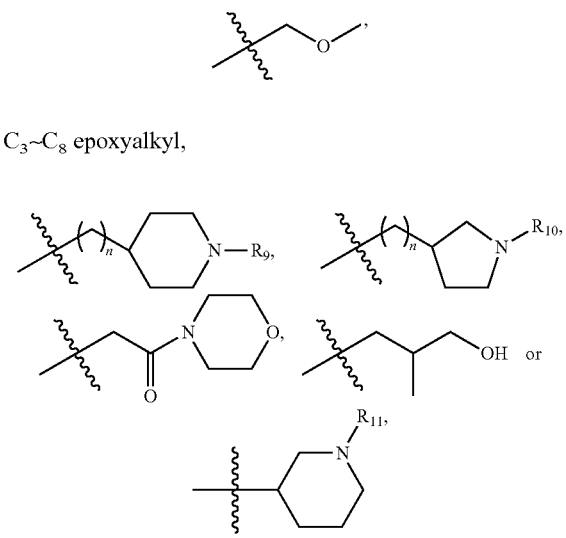

$C_3$~$C_8$ epoxyalkyl, n=0~4; $R_3$~$R_5$, $R_7$ are —H, $C_1$~$C_4$ alkyl, —OH, $C_1$~$C_4$ alkoxyl or halogen; $R_8$~$R_{11}$ independently represent —H, $C_1$~$C_4$ alkyl, —OH,

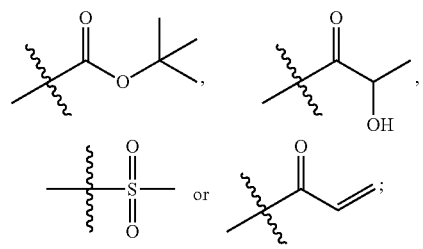

$R_{12}$ is

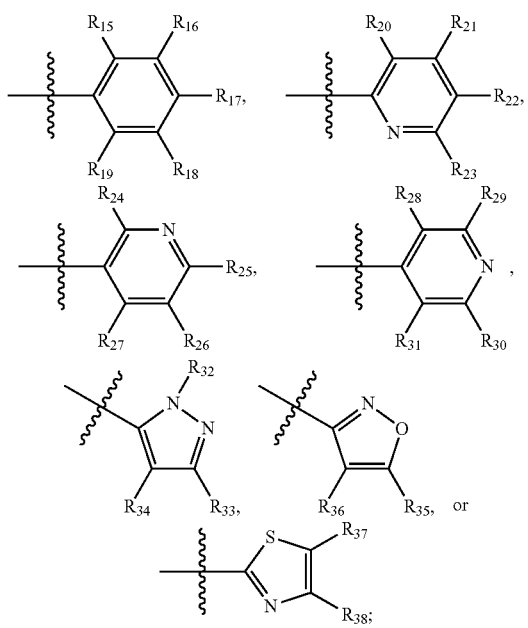

$R_{20}$~$R_{38}$ are —H, $C_1$~$C_4$ alkyl or —CF$_3$.

Optimally, $R_1$ is —H or

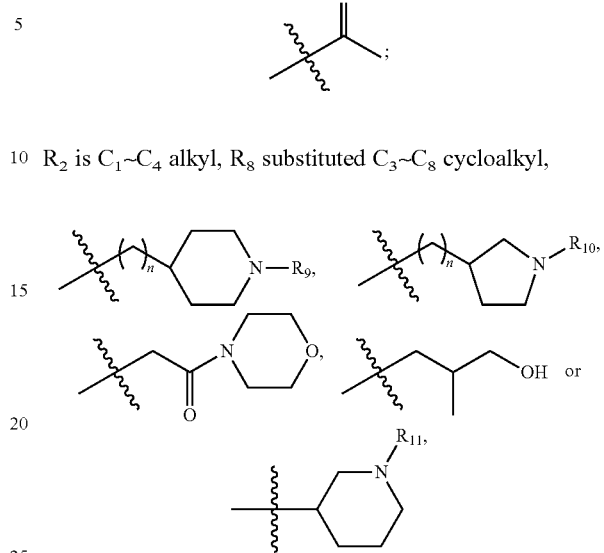

$R_2$ is $C_1$~$C_4$ alkyl, $R_8$ substituted $C_3$~$C_8$ cycloalkyl, n=0 or 1; $R_3$~$R_5$, $R_7$ are —H, methyl or —Cl; $R_8$~$R_{11}$ represent —H, $C_1$~$C_4$ alkyl, —OH,

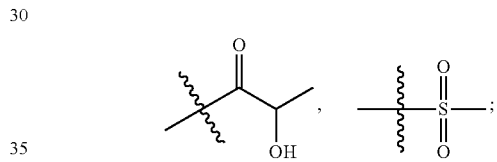

$R_{12}$ is

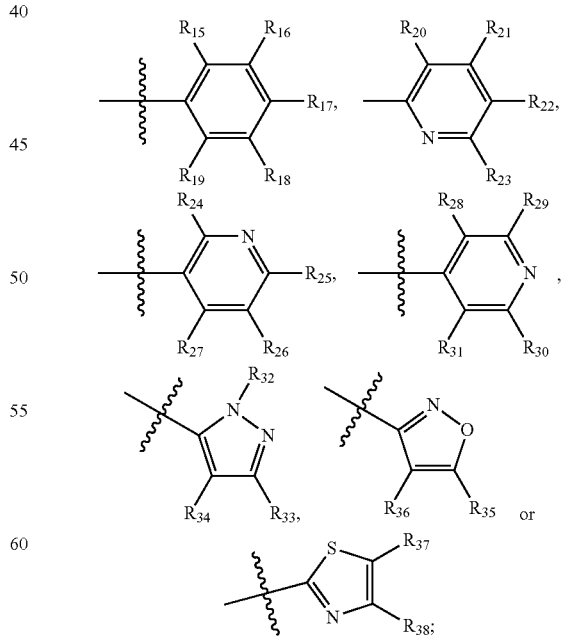

$R_{15}$~$R_{19}$ are —H, $C_1$~$C_4$ alkyl, methoxyl, —F, —Cl, —CF$_3$, —OCF$_3$ or

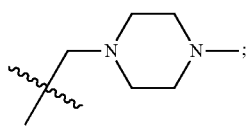 [SMILES: *CN1CCN(C)CC1]

$R_{20}$~$R_{38}$ represent —H, $C_1$~$C_4$ alkyl or —$CF_3$.

The 3-ethynylpyrazolopyrimidine derivatives described above, when $R_6$

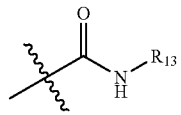

is, the structure is shown as formula III

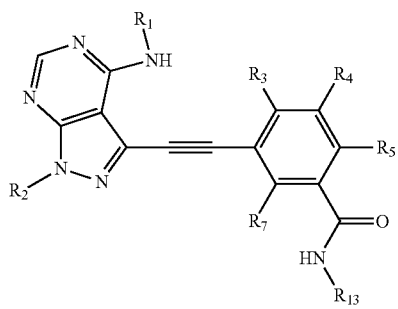

III

Wherein, $R_1$ is —H or

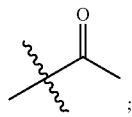 [SMILES: *C(C)=O]

$R_2$ is —H, $C_1$~$C_4$ alkyl,

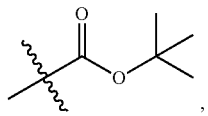 [SMILES: *C(=O)OC(C)(C)C]

$R_8$ substituted $C_3$~$C_8$ cycloalkyl,

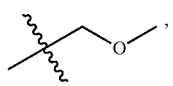 [SMILES: *COC]

$C_3$~$C_8$ epoxyalkyl,

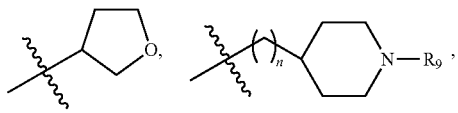

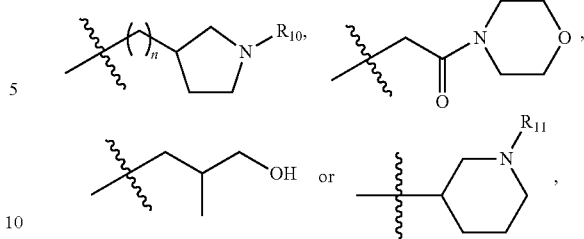

n=0~4; $R_3$~$R_5$, $R_7$ are —H, $C_1$~$C_4$ alkyl, —OH, $C_1$~$C_4$ alkoxyl or halogen; $R_8$~$R_{11}$ represent —H, $C_1$~$C_4$ alkyl, —OH,

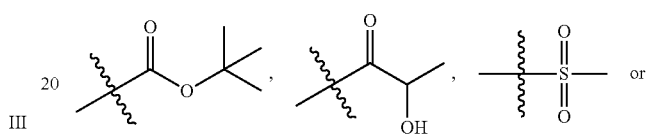

$R_{13}$ is

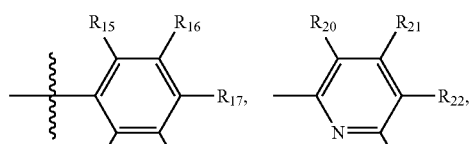

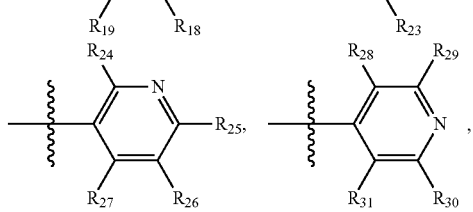

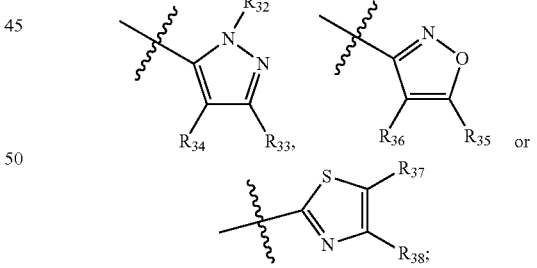

$R_{15}$~$R_{19}$ are —H, $C_1$~$C_4$ alkyl, —OH, $C_1$~$C_4$ alkoxyl, halogen, —$CF_3$, —$OCF_3$,

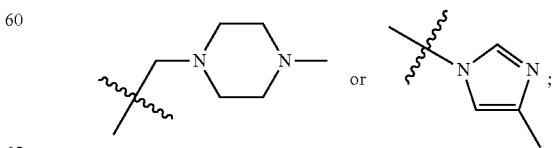

$R_{20}$~$R_{38}$ represent —H, $C_1$~$C_4$ alkyl or —$CF_3$.

Preferably, R₂ is $C_1\sim C_4$ alkyl,

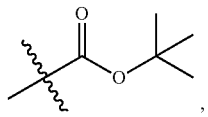 [SMILES: *C(=O)OC(C)(C)C]

$C_3\sim C_8$ cycloalkyl substituted with R₈,

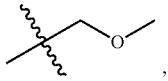 [SMILES: *COC]

$C_3\sim C_8$ epoxyalkyl,

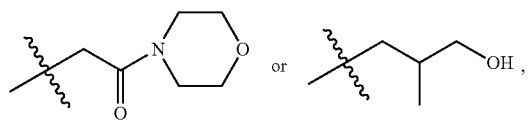

n=0~4; R₈, R₉ are —H, $C_1\sim C_4$ alkyl, —OH,

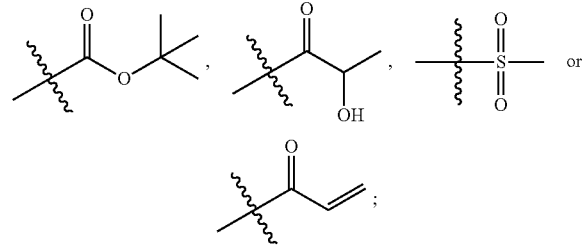

R₁ is —H or

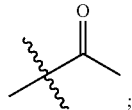

R₃~R₅, R₇ represent —H, $C_1\sim C_4$ alkyl, —OH, $C_1\sim C_4$ epoxyalkyl or halogen; R₁₃ is

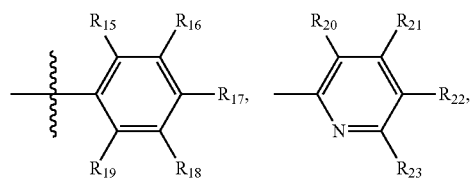

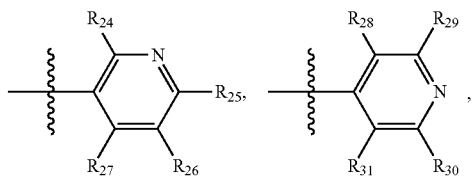

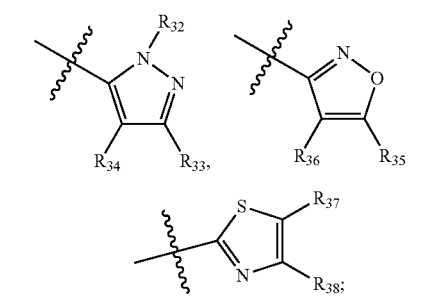

R₁₅~R₁₉ are —H, $C_1\sim C_4$ alkyl, —OH, $C_1\sim C_4$ alkoxyl, halogen, —CF₃, —OCF₃,

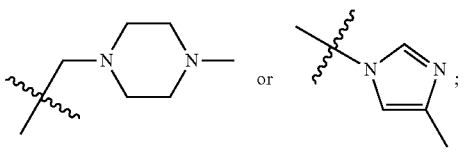

R₂₀~R₃₈ represent —H, $C_1\sim C_4$ alkyl or —CF₃.

More preferably, R₂ is $C_1\sim C_4$ alkyl, R₈ substituted $C_3\sim C_8$ cycloalkyl,

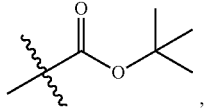 [SMILES: *C(=O)OC(C)(C)C]

R₈ substituted $C_3\sim C_8$ cycloalkyl,

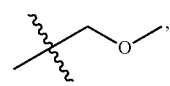 [SMILES: *COC]

$C_3\sim C_8$ epoxyalkyl,

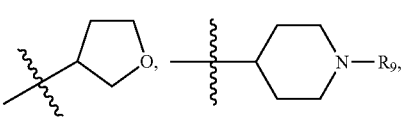

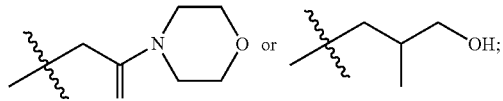

R₈, R₉ are —H, $C_1\sim C_4$ alkyl, —OH,

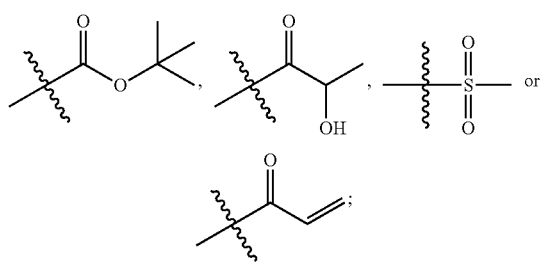

R₁ is —H or

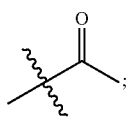 [SMILES: *C(C)=O]

R₃~R₅, R₇ are independently selected from —H, C₁~C₄ alkyl, —OH, C₁~C₄ alkoxyl or halogen; R₁₃ is

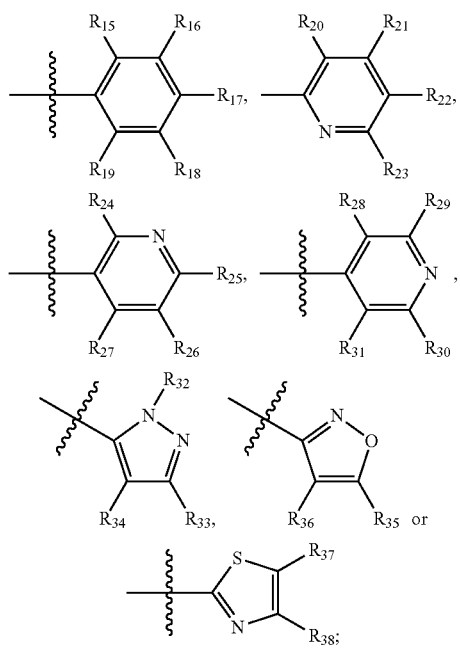

R₁₅~R₁₉ represent —H, C₁~C₄ alkyl, —OH, C₁~C₄ alkoxyl, halogen, —CF₃, —OCF₃,

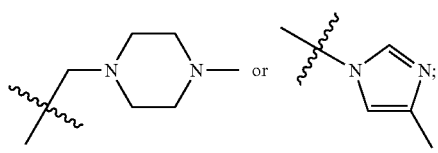

R₂₀~R₃₈ are —H, C₁~C₄ alkyl or —CF₃.

Further preferably, R₂ is C₁~C₄ alkyl, R₈ substituted C₃~C₈ cycloalkyl,

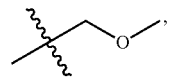 [SMILES: *COC]

C₃-C₈ epoxyalkyl,

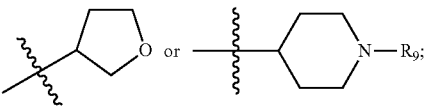

R₈, R₉ are —H, C₁~C₄ alkyl, —OH,

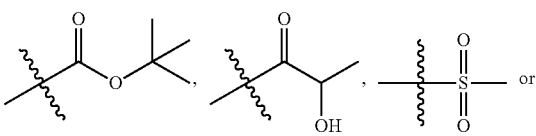

R₁ is

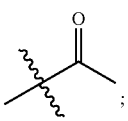 [SMILES: *C(C)=O]

R₃~R₅, R₇ represent —H, C₁~C₄ alkyl, —OH, C₁~C₄ alkoxyl or halogen; R₁₃ is

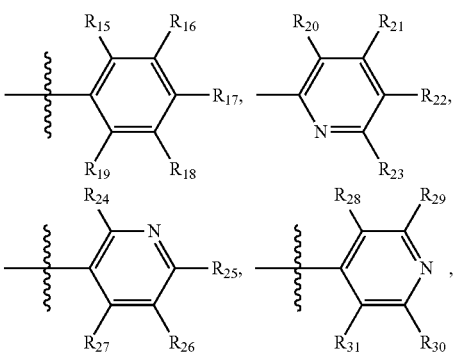

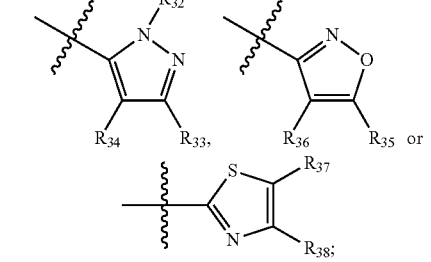

R₁₅~R₁₉ are —H, C₁~C₄ alkyl, —OH, C₁~C₄ alkoxyl, halogen, —CF₃, —OCF₃,

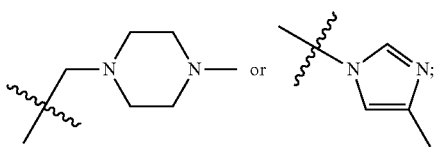

$R_{20}$~$R_{38}$ represent —H, $C_1$~$C_4$ alkyl or —$CF_3$.

Further preferably, $R_2$ is $C_1$~$C_4$ alkyl, $R_8$ substituted $C_3$~$C_8$ cycloalkyl,

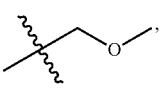 [SMILES: *COC]

$C_3$~$C_8$ epoxyalkyl,

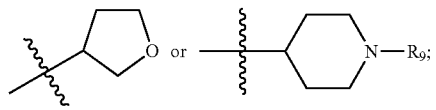

$R_8$, $R_9$ are —H, $C_1$~$C_4$ alkyl,

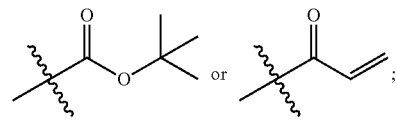

$R_1$ is —H or

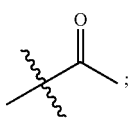

$R_3$~$R_5$, $R_7$ independently represent —H, $C_1$~$C_4$ alkyl, —OH, $C_1$~$C_4$ alkoxyl or halogen; $R_{13}$ is

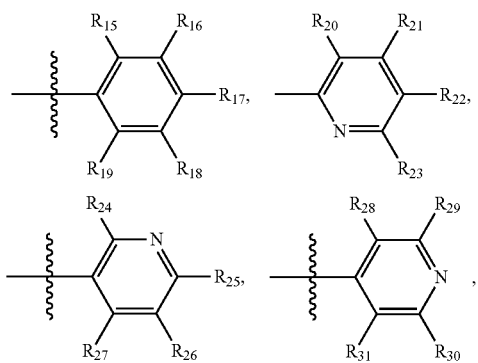

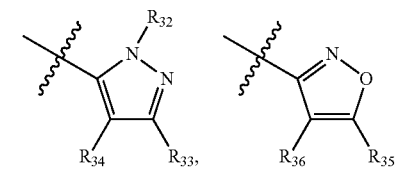

$R_{15}$~$R_{19}$ are —H, $C_1$~$C_4$ alkyl, —OH, $C_1$~$C_4$ alkoxyl, halogen, —$CF_3$, —$OCF_3$,

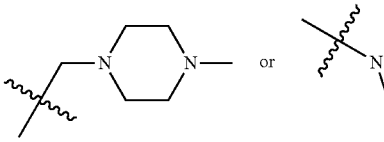

$R_{20}$~$R_{38}$ represent —H, $C_1$~$C_4$ alkyl or —$CF_3$.

Preferably, $R_3$~$R_5$, $R_7$ are independently selected from —H, $C_1$~$C_4$ alkyl, —OH or halogen; $R_1$ is —H or

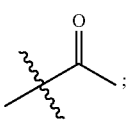 [SMILES: *C(C)=O]

$R_2$ is —H, $C_1$~$C_4$ alkyl,

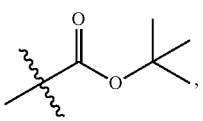 [SMILES: *C(=O)OC(C)(C)C]

$R_8$ substituted $C_3$~$C_8$ cycloalkyl,

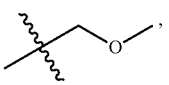 [SMILES: *COC]

$C_3$~$C_8$ epoxyalkyl,

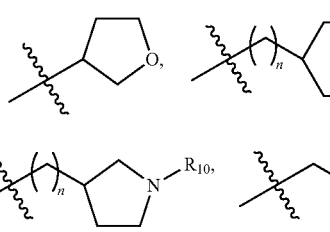

-continued

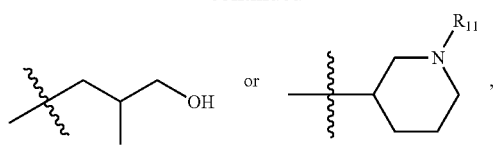

n=0~4; $R_8$~$R_{11}$ are —H, $C_1$~$C_4$ alkyl, —OH,

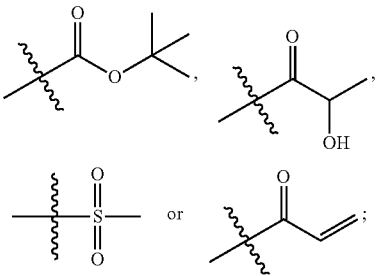

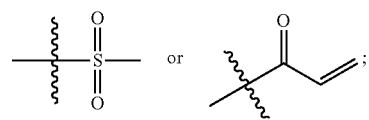

$R_{13}$ is

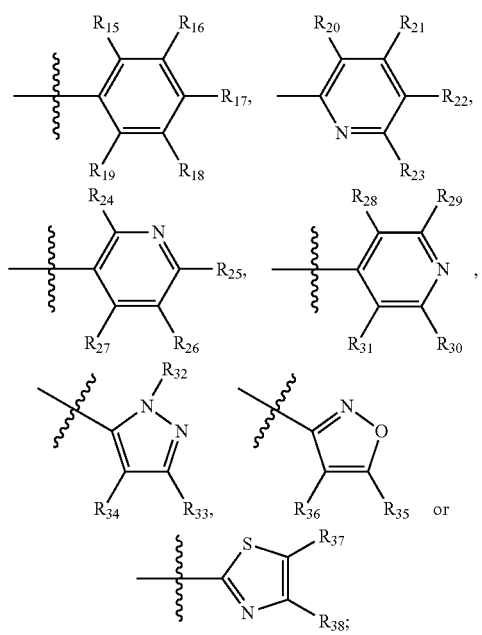

$R_{15}$~$R_{19}$ independently represent —H, $C_1$~$C_4$ alkyl, —OH, $C_1$~$C_4$ alkoxyl, halogen, —$CF_3$, —$OCF_3$,

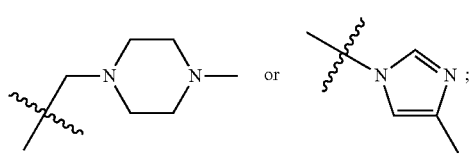

$R_{20}$~$R_{38}$ are —H, $C_1$~$C_4$ alkyl or —$CF_3$.

More preferably, $R_3$~$R_5$, $R_7$ are —H, $C_1$~$C_4$ alkyl, —OH or —Cl; $R_1$ is —H or

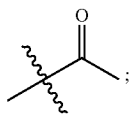 [SMILES: *C(C)=O]

$R_2$ is —H, $C_1$~$C_4$ alkyl,

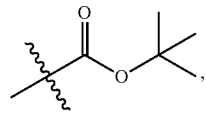 [SMILES: *C(=O)OC(C)(C)C]

$C_3$~$C_8$ cycloalkyl substituted with $R_8$,

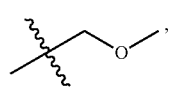 [SMILES: *COC]

$C_3$~$C_8$ epoxyalkyl,

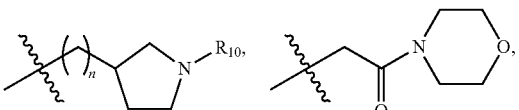

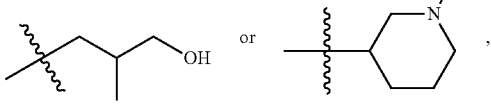

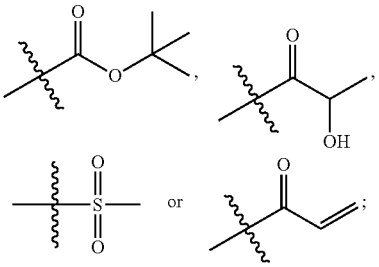

n=0~4; $R_8$~$R_{11}$ represent —H, $C_1$~$C_4$ alkyl, —OH

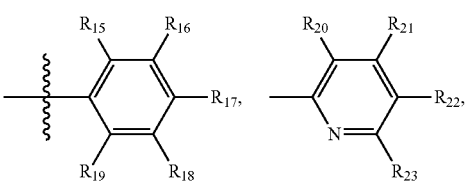

$R_{13}$ is

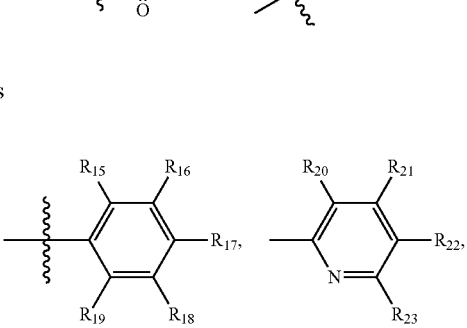

-continued

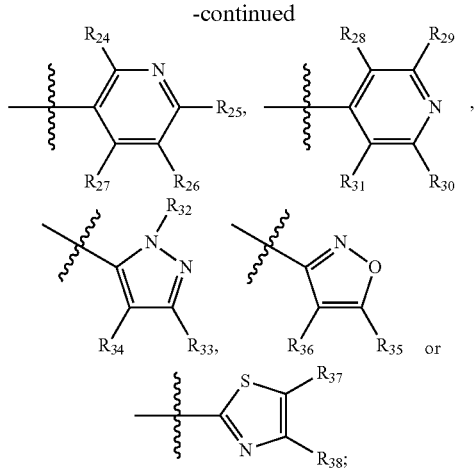

$R_{15}$~$R_{19}$ are —H, $C_1$~$C_4$ alkyl, —OH, $C_1$~$C_4$ alkoxyl, halogen, —$CF_3$, —$OCF_3$,

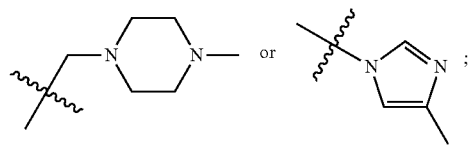

$R_{20}$~$R_{38}$ independently represent —H, $C_1$~$C_4$ alkyl or —$CF_3$.

Preferably, $R_{13}$ is

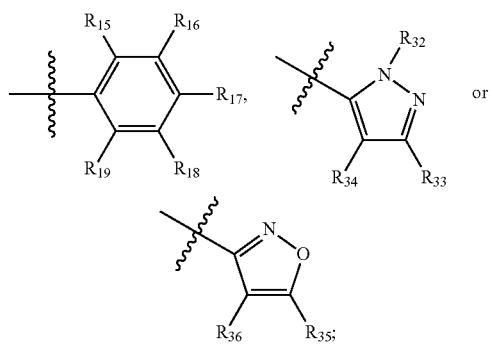

$R_1$ is —H or

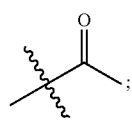 [SMILES: *C(C)=O]

$R_2$ is —H, $C_1$~$C_4$ alkyl,

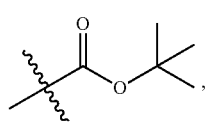 [SMILES: *C(=O)OC(C)(C)C]

$C_1$~$C_3$ cycloalkyl substituted with $R_8$,

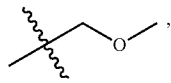 [SMILES: *COC]

$C_3$-$C_8$ epoxyalkyl,

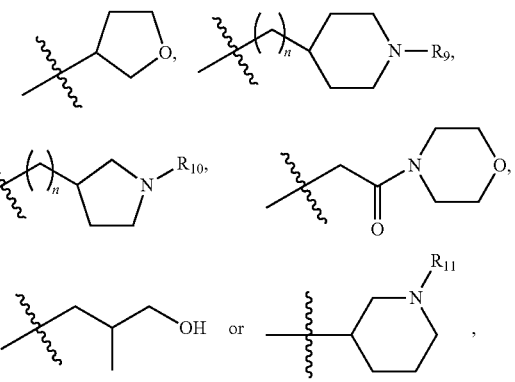

n=0~4; $R_3$~$R_5$, $R_7$ are —H, $C_1$~$C_4$ alkyl, —OH, $C_1$~$C_4$ alkoxyl or halogen; $R_8$~$R_{11}$ represent —H, $C_1$~$C_4$ alkyl, —OH,

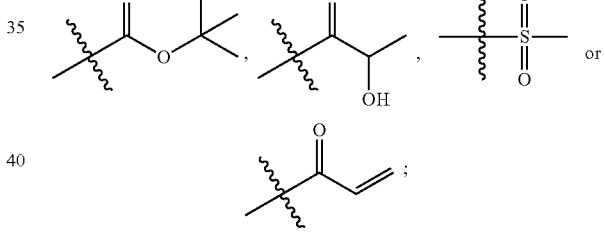

$R_{15}$~$R_{19}$ independently represent —H, $C_1$~$C_4$ alkyl, —OH, $C_1$~$C_4$ alkoxyl, halogen, —$CF_3$, —$OCF_3$,

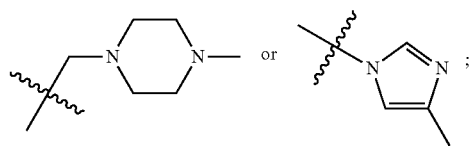

$R_{20}$~$R_{38}$ are —H, $C_1$~$C_4$ alkyl or —$CF_3$.

Preferably, $R_{15}$~$R_{19}$ are independently selected from —H, $C_1$~$C_4$ alkyl, $C_1$~$C_4$ alkoxyl, halogen, —$CF_3$ or

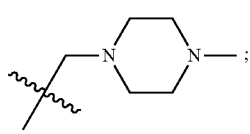 [SMILES: *CN1CCN(C)CC1]

R₁ is —H or

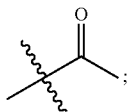 [SMILES: *C(C)=O]

R₂ is —H,
C₁~C₄ alkyl

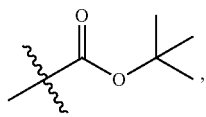 [SMILES: *C(=O)OC(C)(C)C]

C₃~C₈ cycloalkyl substituted with R₈,

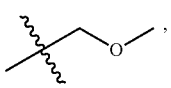 [SMILES: *COC]

C₃~C₈ epoxyalkyl,

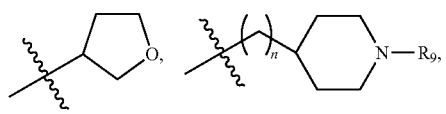

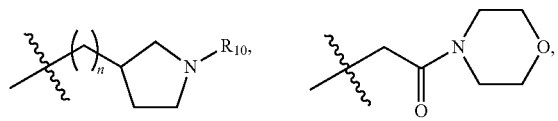

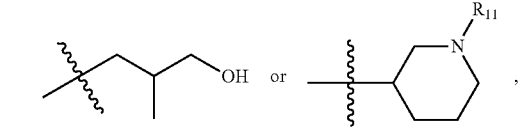

n=0~4; R₃~R₅, R₇ are —H, C₁~C₄ alkyl, —OH, C₁~C₄ alkoxyl or halogen; R₈~R₁₁ represent —H, C₁~C₄ alkyl, —OH,

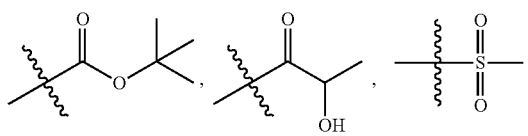

R₁₃ is

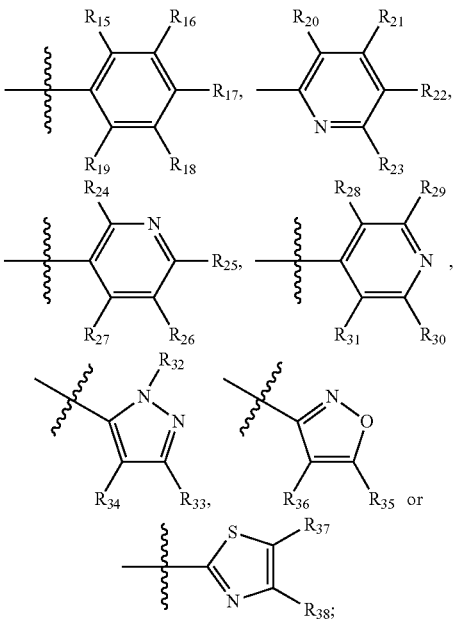

R₂₀~R₃₈ independently represent —H, C₁~C₄ alkyl or —CF₃.

More preferably, R₁₅~R₁₉ are from —H, C₁~C₄ alkyl, halogen, —CF₃ or

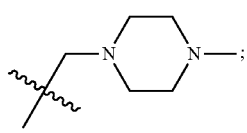 [SMILES: *CN1CCN(C)CC1]

R₁ is —H or

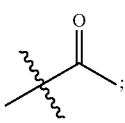 [SMILES: *C(C)=O]

R₂ is —H, C₁~C₄ alkyl,

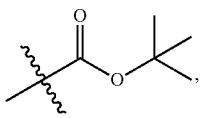

R₈ substituted C₃~C₈ cyloalkyl,

C₃~C₈ epoxyalkyl,

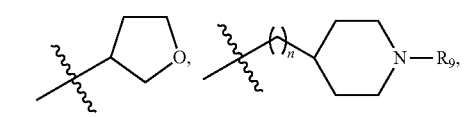

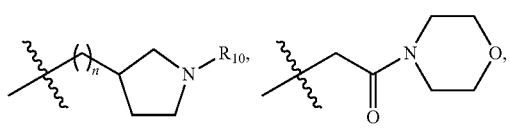

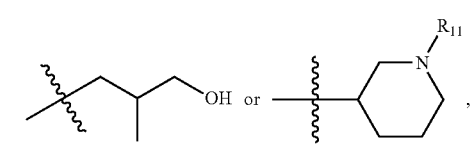

n=0~4; $R_3$~$R_5$, $R_7$ are —H, $C_1$~$C_4$ alkyl, —OH, $C_1$~$C_4$ alkoxyl or halogen; $R_8$~$R_{11}$ are —H, $C_1$~$C_4$ alkyl, —OH,

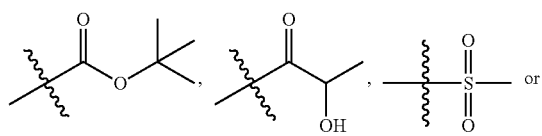

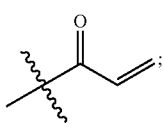

$R_{13}$ is

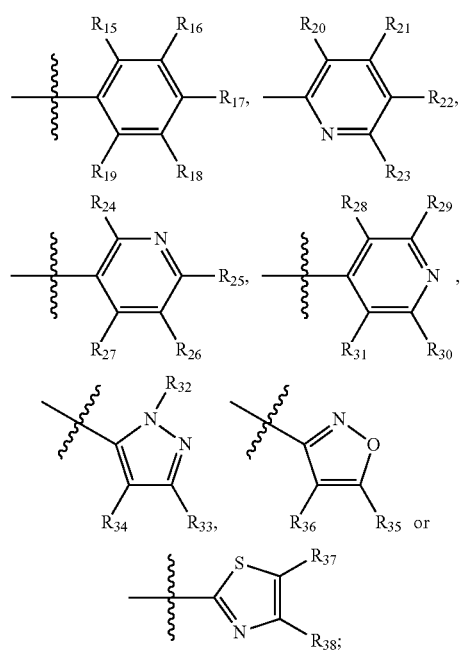

$R_{20}$~$R_{38}$ are —H, $C_1$~$C_4$ alkyl or —CF$_3$.

More preferably, $R_{15}$~$R_{19}$ are independently selected from —H, $C_1$~$C_4$ alkyl, —CF$_3$ or

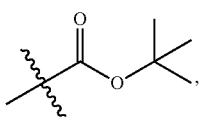 [SMILES: *C(=O)OC(C)(C)C]

$R_1$ is —H or

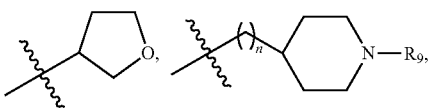

$R_2$ is —H, $C_1$~$C_4$ alkyl,

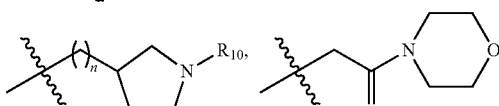

$R_8$ substituted $C_3$~$C_8$ cycloalkyl,

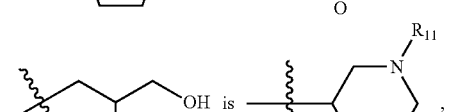

$C_3$~$C_8$ epoxyalkyl,

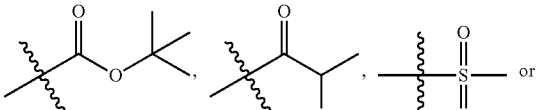

n=0~4; $R_3$~$R_5$, $R_7$ are —H, $C_1$~$C_4$ alkyl, —OH, $C_1$~$C_4$ alkoxyl or halogen; $R_8$~$R_{11}$ represent —H, $C_1$~$C_4$ alkyl, —OH,

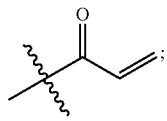

$R_{13}$ is

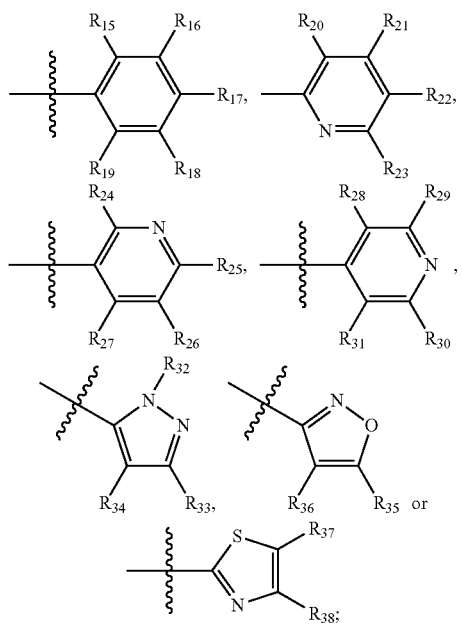

$R_{20}$~$R_{38}$ independently represent —H, $C_1$~$C_4$ alkyl or —$CF_3$.

Preferably, $R_{20}$~$R_{38}$ are —H or $C_1$~$C_4$ alkyl; $R_1$ is —H or

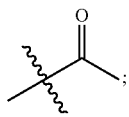 [SMILES: *C(C)=O]

$R_2$ is —H, $C_1$~$C_4$ alkyl,

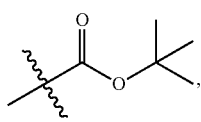 [SMILES: *C(=O)OC(C)(C)C]

$R_8$ substituted $C_3$~$C_8$ cycloalkyl,

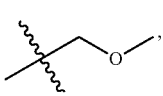

$C_3$~$C_8$ epoxyalkyl,

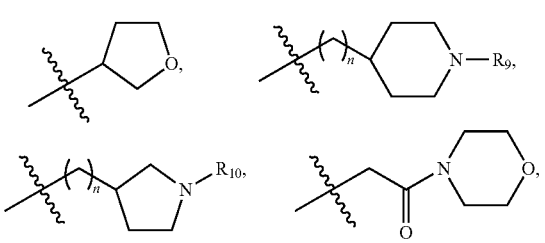

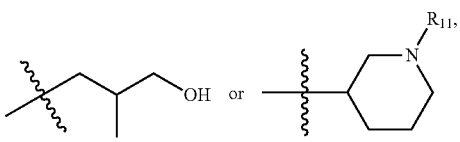

n=0~4; $R_3$~$R_5$, $R_7$ are —H, $C_1$~$C_4$ alkyl, —OH, $C_1$~$C_4$ alkoxyl or halogen; $R_8$~$R_{11}$ represent —H, $C_1$~$C_4$ alkyl, —OH,

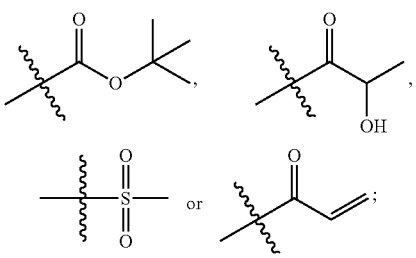

$R_{13}$ is

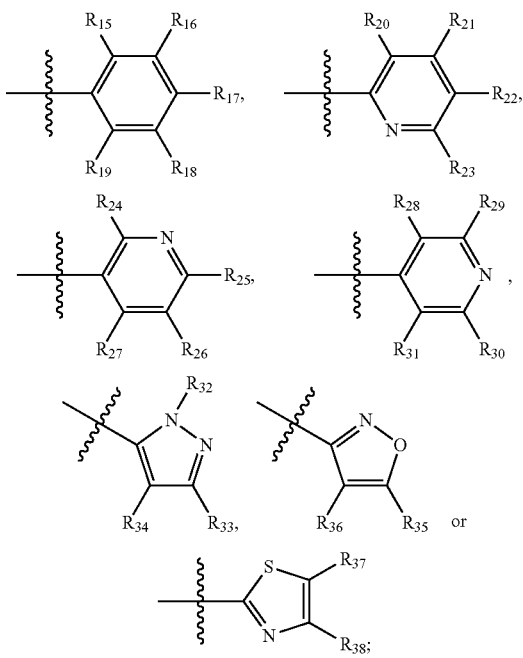

$R_{15}$~$R_{19}$ are —H, $C_1$~$C_4$ alkyl, —OH, $C_1$~$C_4$ alkoxyl, halogen, —$CF_3$, —$OCF_3$,

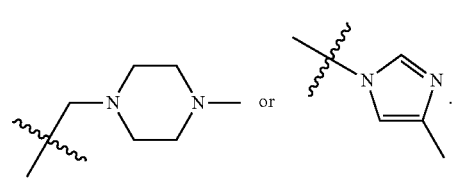

Optimally, $R_1$ is —H or

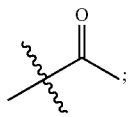 [SMILES: *C(C)=O];

$R_2$ is $C_1$~$C_4$ alkyl, $R_8$ substituted $C_3$~$C_8$ cycloalkyl,

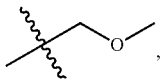 [SMILES: *COC], $C_3$~$C_8$ epoxyalkyl,

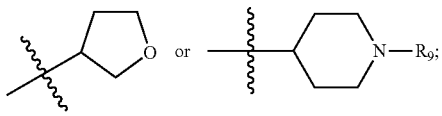;

$R_3$~$R_5$, $R_7$ are —H, $C_1$~$C_4$ alkyl, —OH or —Cl; $R_8$, $R_9$ represent —H, $C_1$~$C_4$ alkyl,

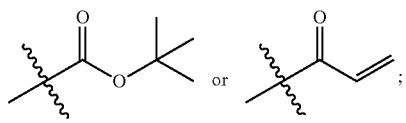;

$R_{13}$ is

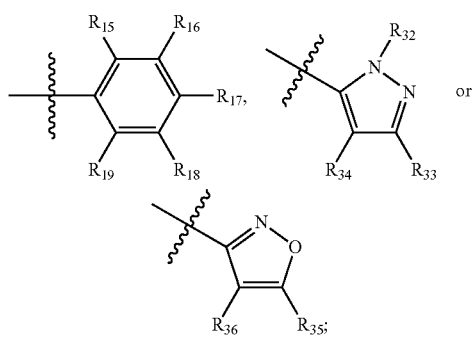

$R_{15}$~$R_{19}$ are —H, $C_1$~$C_4$ alkyl, —CF$_3$ or

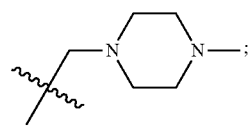;

$R_{20}$~$R_{38}$ are —H or $C_1$~$C_4$ alkyl.

The 3-ethynylpyrazolopyrimidine derivatives described above, when $R_6$ is

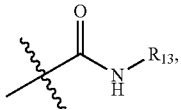

$R_{13}$ is

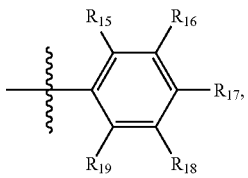

the structure is shown as formula IV:

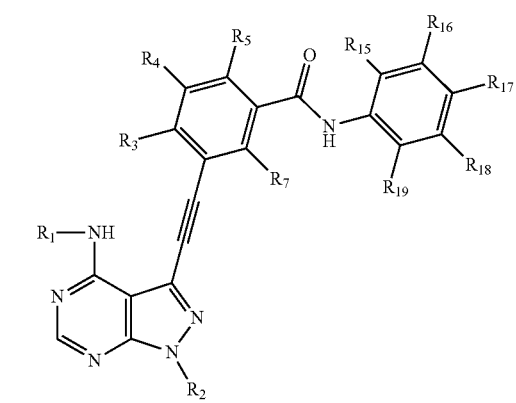

Wherein, $R_1$ is —H or

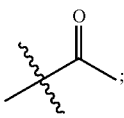;

$R_2$ is —H, $C_1$~$C_4$ alkyl,

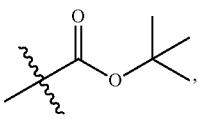 [SMILES: *C(=O)OC(C)(C)C], $C_3$-$C_8$ cycloalkyl substituted with $R_8$,

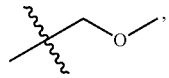 [SMILES: *COC], $C_3$~$C_8$ epoxyalkyl,

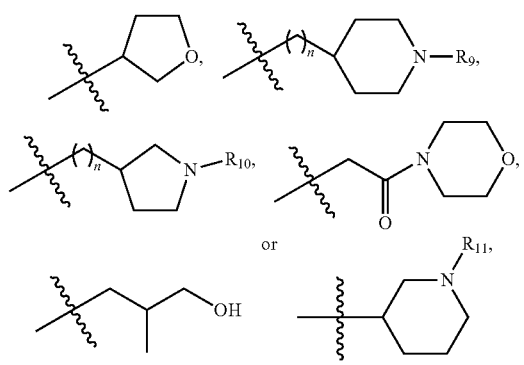

n=0~4; $R_3$~$R_5$, $R_7$ are —H, $C_1$~$C_4$ alkyl, —OH, $C_1$~$C_4$ alkoxyl or halogen; $R_8$~$R_{11}$ are —H, $C_1$~$C_4$ alkyl, —OH,

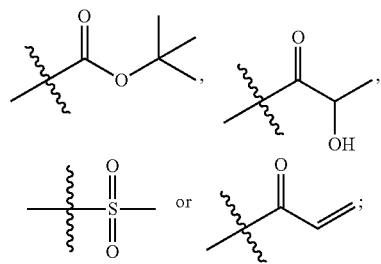

$R_{15}$~$R_{19}$ are —H, $C_1$~$C_4$ alkyl, —OH, $C_1$~$C_4$ alkoxyl, halogen, —$CF_3$, —$OCF_3$,

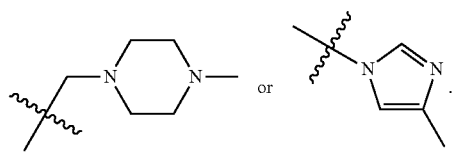

Preferably, $R_2$ is $C_1$~$C_4$ alkyl,

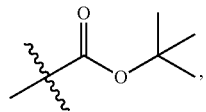

$R_8$ substituted $C_3$~$C_8$ cycloalkyl,

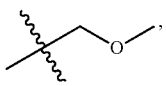 [SMILES: *COC]

$C_3$-$C_8$ epoxyalkyl,

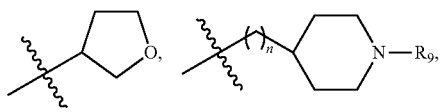

-continued

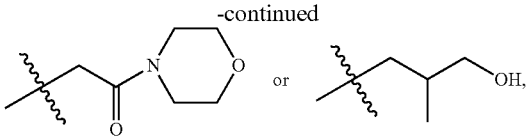

n=0~4; $R_8$, $R_9$ are —H, $C_1$~$C_4$ alkyl, —OH,

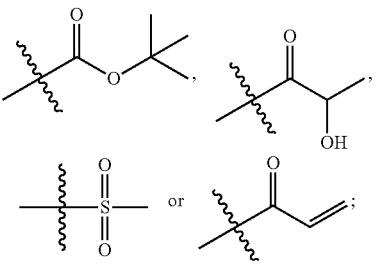

$R_1$ is —H or

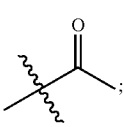

$R_3$~$R_5$, $R_7$ are —H, $C_1$~$C_4$ alkyl, —OH, $C_1$~$C_4$ alkoxyl or halogen; $R_{15}$~$R_{19}$ represent —H, $C_1$~$C_4$ alkyl, —OH, $C_1$~$C_4$ alkoxyl, halogen, —$CF_3$, —$OCF_3$,

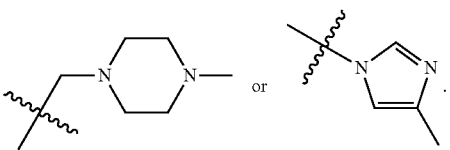

More preferably, $R_2$ is $C_1$~$C_4$ alkyl,

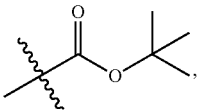 [SMILES: *C(=O)OC(C)(C)C]

$R_8$ substituted $C_3$-$C_8$ cycloalkyl,

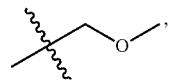 [SMILES: *COC]

$C_3$~$C_8$ epoxyalkyl,

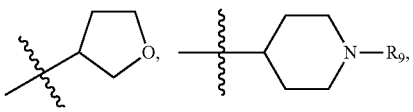

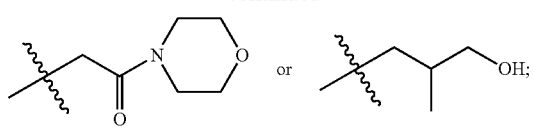 or 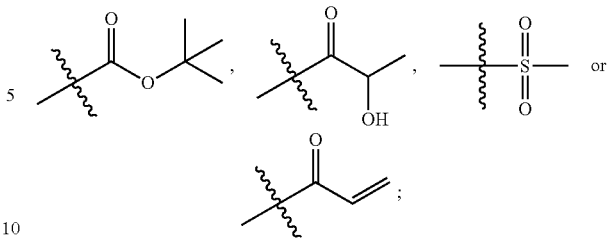

$R_8$, $R_9$ are —H, $C_1$~$C_4$ alkyl, —OH,

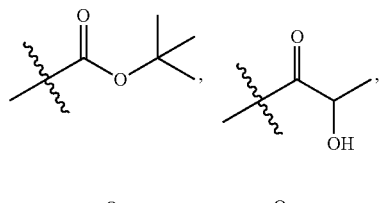

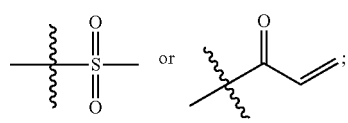 or 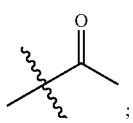

$R_1$ is —H or

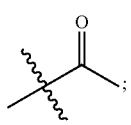 [SMILES: *C(C)=O]

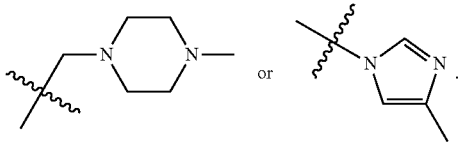;

$R_3$~$R_5$, $R_7$ are —H, $C_1$~$C_4$ alkyl, —OH, $C_1$~$C_4$ alkoxyl or halogen; $R_{15}$~$R_{19}$ represent —H, $C_1$~$C_4$ alkyl, —OH, $C_1$~$C_4$ alkoxyl, halogen, —CF$_3$, —OCF$_3$, $R_3$~$R_5$, $R_7$ represent —H, $C_1$~$C_4$alkyl, —OH, $C_1$~$C_4$ alkoxyl or halogen; $R_{15}$~$R_{19}$ are —H, $C_1$~$C_4$ alkyl, —OH, $C_1$~$C_4$ alkoxyl, halogen, —CF$_3$, —OCF$_3$,

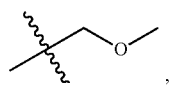

Still further preferably, $R_2$ is $C_1$~$C_4$ alkyl, $R_8$ substituted $C_3$~$C_8$ cycloalkyl,

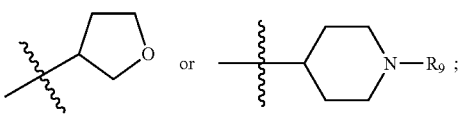, $C_3$-$C_8$ epoxyalkyl,

Further preferably, $R_2$ is $C_1$~$C_4$ alkyl, $R_8$ substituted $C_3$~$C_8$ cycloalkyl,

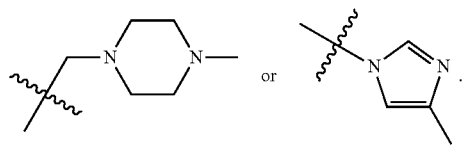

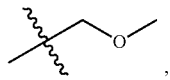 [SMILES: *COC], $C_3$~$C_8$ epoxyalkyl, $R_8$, $R_9$ are —H, $C_1$~$C_4$ alkyl,

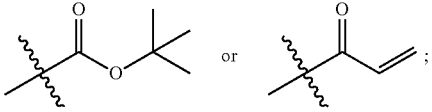;

$R_1$ is —H or

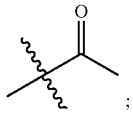;

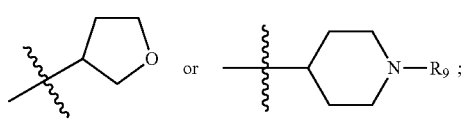

$R_8$, $R_9$ are —H, $C_1$~$C_4$ alkyl, —OH, $R_3\sim R_5$, $R_7$ represent —H, $C_1\sim C_4$ alkyl, —OH, $C_1\sim C_4$ alkoxyl or halogen; $R_{15}\sim R_{19}$ are —H, $C_1\sim C_4$ alkyl, —OH, $C_1\sim C_4$ alkoxyl, halogen, —$CF_3$, —$OCF_3$,

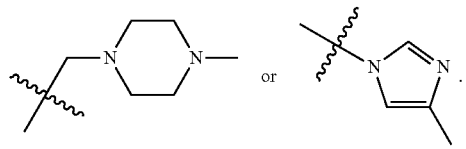

Preferably, $R_3\sim R_5$, $R_7$ are —H, $C_1\sim C_4$ alkyl, —OH or halogen; $R_1$ is —H or

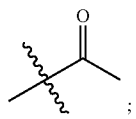 [SMILES: *C(C)=O]

$R_2$ is —H, $C_1\sim C_4$ alkyl,

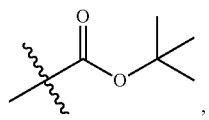 [SMILES: *C(=O)OC(C)(C)C]

$R_8$ substituted $C_3\sim C_8$ cycloalkyl,

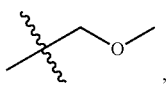 [SMILES: *COC]

$C_3\sim C_8$ epoxyalkyl,

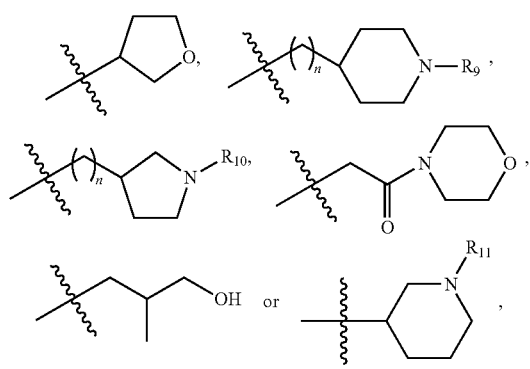

n=0~4; $R_8\sim R_{11}$ are —H, $C_1\sim C_4$ alkyl, —OH,

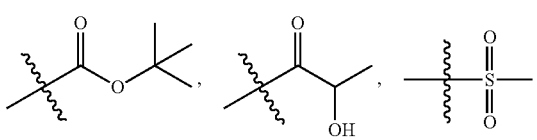

-continued

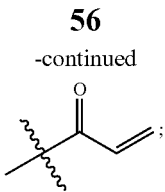

$R_{15}\sim R_{19}$ represent —H, $C_1\sim C_4$ alkyl, —OH, $C_1\sim C_4$ alkoxyl, halogen, —$CF_3$, —$OCF_3$,

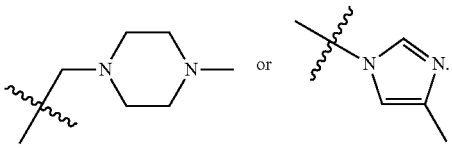

More preferably, $R_3\sim R_5$, $R_7$ are —H, $C_1\sim C_4$ alkyl, —OH or —Cl; $R_1$ is —H or

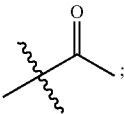

$R_2$ is —H, $C_1\sim C_4$ alkyl,

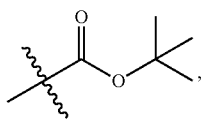

$R_8$ substituted $C_3$-$C_8$ cycloalkyl,

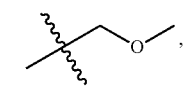 [SMILES: *COC]

$C_3\sim C_8$ epoxyalkyl,

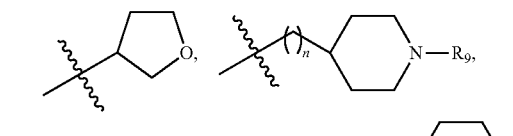

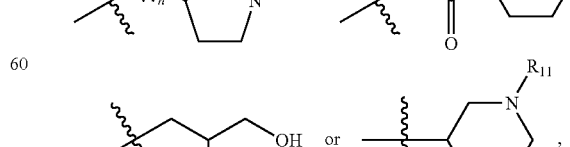

n=0~4; $R_8\sim R_{11}$ are —H, $C_1\sim C_4$ alkyl, —OH,

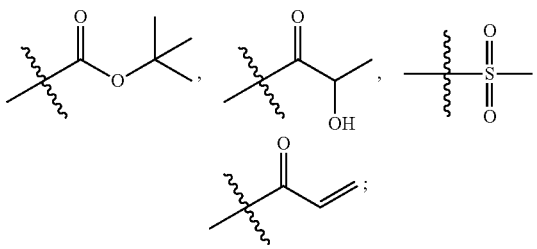 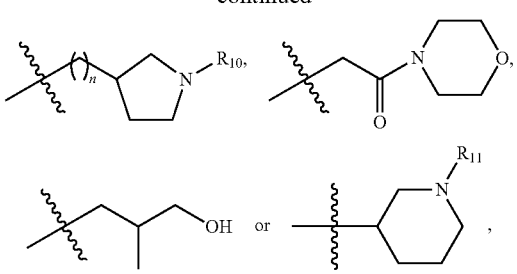

$R_{15}\sim R_{19}$ represent —H, $C_1\sim C_4$ alkyl, —OH, $C_1\sim C_4$ alkoxyl, halogen, —$CF_3$, —$OCF_3$, n=0~4; $R_3\sim R_5$, $R_7$ are —H, $C_1\sim C_4$ alkyl, —OH, $C_1\sim C_4$ alkoxyl or halogen; $R_8\sim R_{11}$ represent —H, $C_1\sim C_4$ alkyl, —OH,

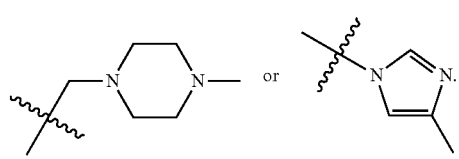 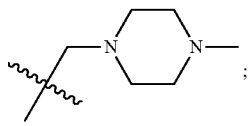

Preferably, $R_{15}\sim R_{19}$ are —H, $C_1\sim C_4$ alkyl, $C_1\sim C_4$ alkoxyl, halogen, —$CF_3$ or More preferably, $R_{15}\sim R_{19}$ are —H, $C_1\sim C_4$ alkyl, halogen, —$CF_3$ or

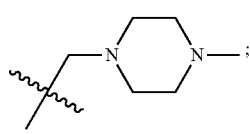 [SMILES: *CN1CCN(C)CC1]

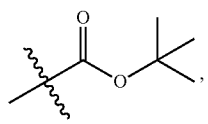

$R_1$ is —H or $R_1$ is —H or

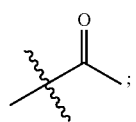 [SMILES: *C(C)=O]

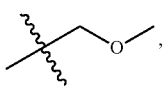

$R_2$ is —H, $C_1\sim C_4$ alkyl, $R_2$ is —H, $C_1\sim C_4$ alkyl,

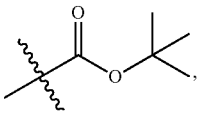 [SMILES: *C(=O)OC(C)(C)C]

$R_8$ substituted $C_3\sim C_8$ cyloalkyl, $R_8$ substituted $C_3\sim C_8$ cycloalkyl,

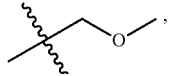

$C_3\sim C_8$ epoxyalkyl,

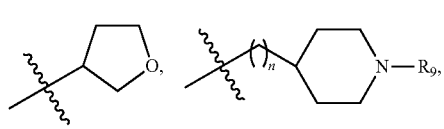

$C_3\sim C_8$ epoxyalkyl,

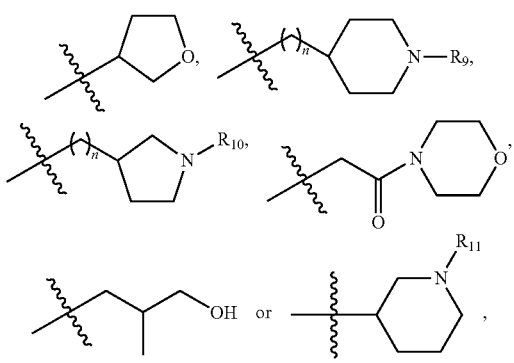

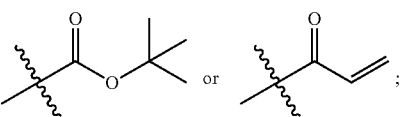

n=0~4; $R_3$~$R_5$, $R_7$ are —H, $C_1$~$C_4$ alkyl, —OH, $C_1$~$C_4$ alkoxyl or halogen; $R_8$~$R_{11}$ independently represent —H, $C_1$~$C_4$ alkyl, —OH,

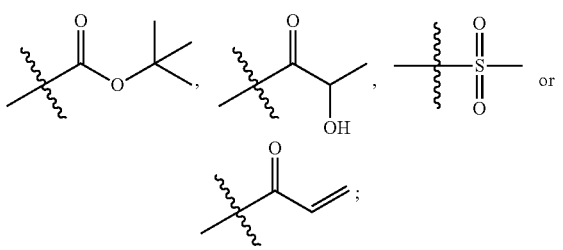

still more preferably, $R_{15}$~$R_{19}$ are —H, $C_1$~$C_4$ alkyl, —CF$_3$ or

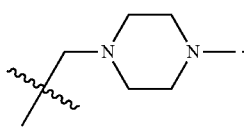 [SMILES: *CN1CCN(C)CC1]

Optimally, $R_1$ is —H or

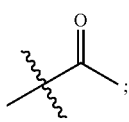 [SMILES: *C(C)=O]

$R_2$ is $C_1$~$C_4$ alkyl, $R_8$ substituted $C_3$~$C_8$ cycloalkyl,

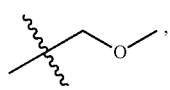 [SMILES: *COC]

$C_3$~$C_8$ epoxyalkyl,

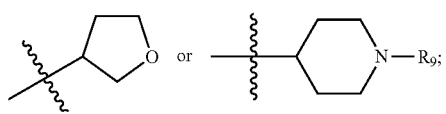

$R_3$~$R_5$, $R_7$ are —H, $C_1$~$C_4$ alkyl, —OH or —Cl; $R_8$, $R_9$ represent —H, $C_1$~$C_4$ alkyl,

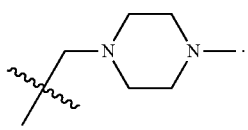 [SMILES: *CN1CCN(C)CC1]

$R_{15}$~$R_{19}$ are —H, $C_1$~$C_4$ alkyl, —CF$_3$ or

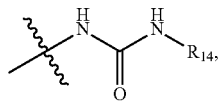

The 3-ethynylpyrazolopyrimidine derivatives above, when $R_6$ is

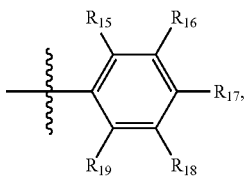

$R_{13}$ is

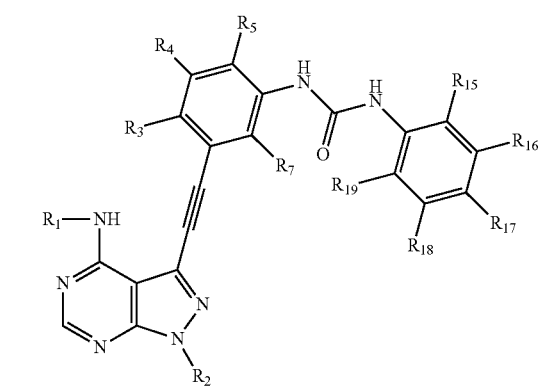

the structure is shown as formula V:

Wherein, $R_1$ is —H or

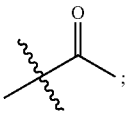

$R_2$ is —H, $C_1$~$C_4$ alkyl,

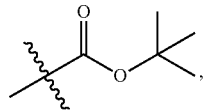

$R_8$ substituted $C_3$~$C_8$ cycloalkyl,

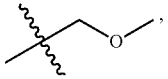

$C_3$~$C_8$ epoxyalkyl,

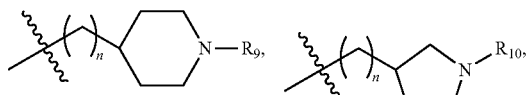

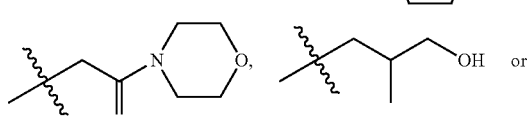


n=0~4; $R_3$~$R_5$, $R_7$ are —H, $C_1$~$C_4$ alkyl, —OH, $C_1$~$C_4$ alkoxyl, halogen; $R_8$~$R_{11}$ represent —H, $C_1$~$C_4$ alkyl, —OH,

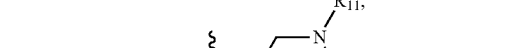

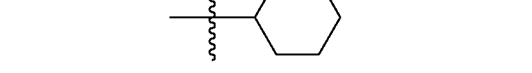

$R_{15}$~$R_{19}$ are —H, $C_1$~$C_4$ alkyl, —OH, $C_1$~$C_4$ alkoxyl, halogen, —$CF_3$, —$OCF_3$,

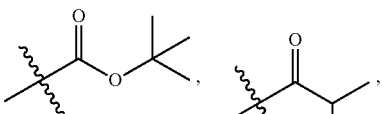

or

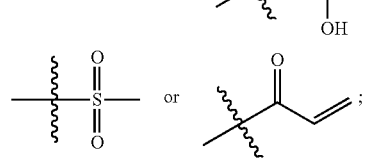

$R_{20}$~$R_{38}$ represent —H, $C_1$~$C_4$ alkyl or —$CF_3$.

Preferably, $R_1$ is —H or

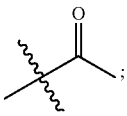 [SMILES: *C(C)=O]

$R_2$ is —H, $C_1$~$C_4$ alkyl,

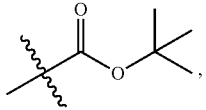

$R_8$ substituted $C_3$~$C_8$ cycloalkyl,

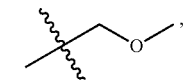 [SMILES: *COC]

$C_3$-$C_8$ epoxyalkyl,

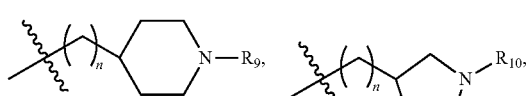

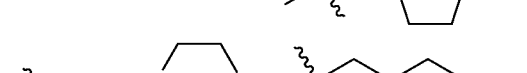

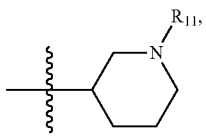

n=0~4; $R_3$~$R_5$, $R_7$ are —H, $C_1$~$C_4$ alkyl, —OH, $C_1$~$C_4$ alkoxyl or halogen; $R_8$-$R_{11}$ represent —H, $C_1$~$C_4$ alkyl, —OH

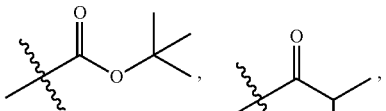

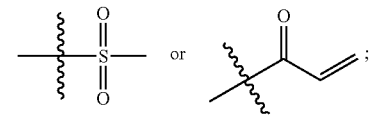

$R_{15}$~$R_{19}$ represent —H, $C_1$~$C_4$ alkyl, —OH, $C_1$~$C_4$ alkoxyl, halogen, —$CF_3$, —$OCF_3$,

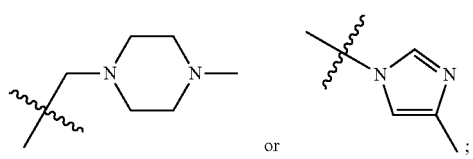

or $R_{20}$~$R_{38}$ represent —H, $C_1$~$C_4$ alkyl or —$CF_3$.
Preferably, $R_2$ is $C_1$~$C_4$ alkyl,

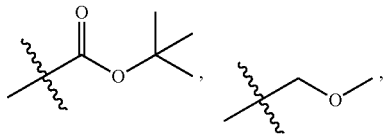

$C_3$~$C_8$ cycloalkyl,

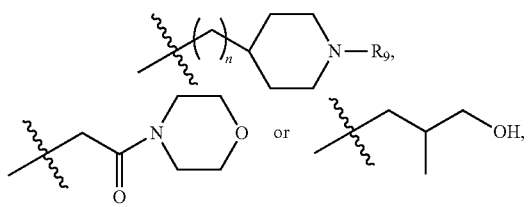

n=0 or 1; $R_9$ is $C_1$~$C_4$ alkyl, —OH,

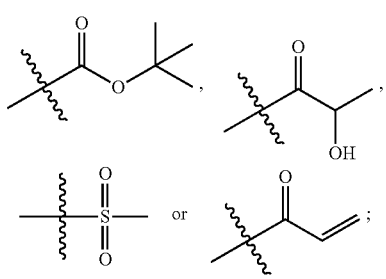

$R_1$ is —H or

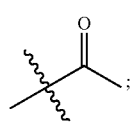 [SMILES: *C(C)=O]

$R_3$~$R_5$, $R_7$ are —H, $C_1$~$C_4$ alkyl, —OH, $C_1$~$C_4$ alkoxyl or halogen; $R_{15}$~$R_{19}$ represent —H, $C_1$~$C_4$ alkyl, —OH, $C_1$~$C_4$ alkoxyl, halogen, —$CF_3$, —$OCF_3$,

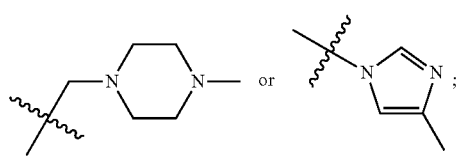

$R_{20}$~$R_{38}$ are —H, $C_1$~$C_4$ alkyl or —$CF_3$.

More preferably, $R_2$ is $C_1$~$C_4$ alkyl,

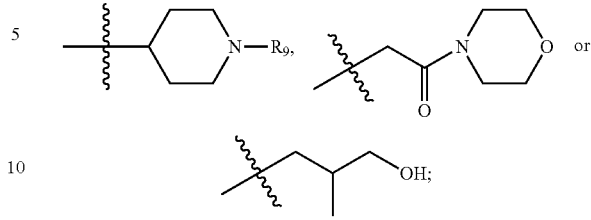

$R_9$ is $C_1$~$C_4$ alkyl, —OH or

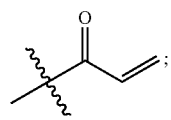 [SMILES: *C(=O)C=C]

$R_1$ is —H or

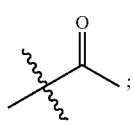 [SMILES: *C(C)=O]

$R_3$~$R_5$, $R_7$ are —H, $C_1$~$C_4$alkyl, —OH, $C_1$~$C_4$ alkoxyl or halogen; $R_{15}$~$R_{19}$ represent —H, $C_1$~$C_4$ alkyl, —OH, $C_1$~$C_4$ alkoxyl, halogen, —$CF_3$, —$OCF_3$,

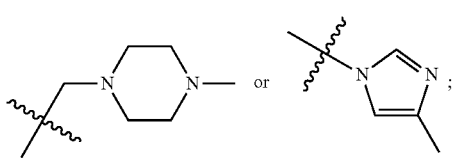

$R_{20}$~$R_{38}$ independently represent —H, $C_1$~$C_4$ alkyl or —$CF_3$.

Further preferably, $R_2$ is $C_1$~$C_4$ alkyl or

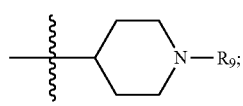

$R_9$ is $C_1$~$C_4$ alkyl; $R_1$ is —H or

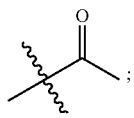 [SMILES: *C(C)=O]

$R_3$~$R_5$, $R_7$ are —H, $C_1$~$C_4$ alkyl, —OH, $C_1$~$C_4$ alkoxyl or halogen; $R_{15}$~$R_{19}$ represent —H, $C_1$~$C_4$ alkyl, —OH, $C_1$~$C_4$ alkoxyl, halogen, —$CF_3$, —$OCF_3$,

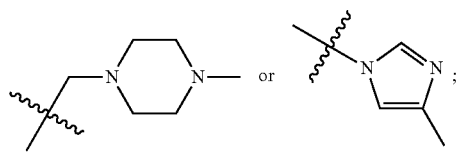 or 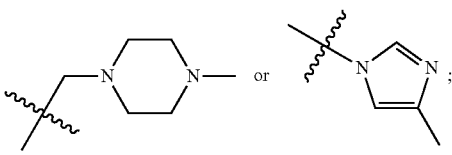;

$R_{20}$~$R_{38}$ are —H, $C_1$~$C_4$ alkyl or —$CF_3$.

Preferably, $R_3$~$R_5$, $R_7$ are —H, $C_1$~$C_4$ alkyl, —OH or halogen; $R_1$ is —H or

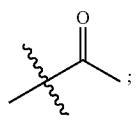 [SMILES: *C(C)=O];

$R_2$ is —H, $C_1$~$C_4$ alkyl,

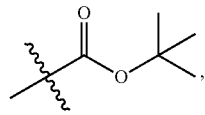 [SMILES: *C(=O)OC(C)(C)C], $R_8$ substituted with $C_3$~$C_8$ cycloalkyl,

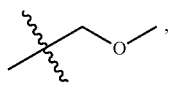 [SMILES: *COC], $C_3$-$C_8$ epoxyalkyl,

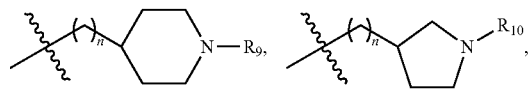

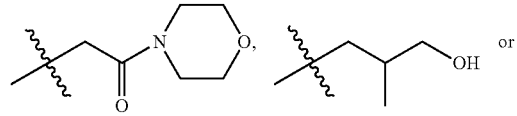

n=0~4; $R_8$~$R_{11}$ are —H, $C_1$~$C_4$ alkyl, —OH,

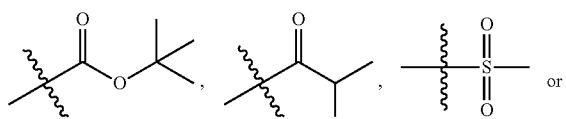 or

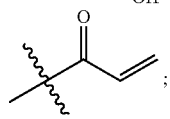;

$R_{15}$~$R_{19}$ represent —H, $C_1$~$C_4$ alkyl, —OH, $C_1$~$C_4$ alkoxyl, halogen, —$CF_3$, —$OCF_3$,

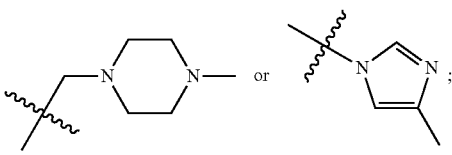;

$R_{20}$~$R_{38}$ independently represent —H, $C_1$~$C_4$ alkyl or —$CF_3$.

More preferably, $R_3$~$R_5$, $R_7$ are independently selected from —H, $C_1$~$C_4$ alkyl or halogen; $R_1$ is —H or

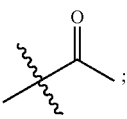 [SMILES: *C(C)=O];

$R_2$ is —H, $C_1$~$C_4$ alkyl,

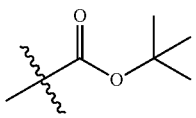, $C_3$~$C_8$ cyclopropyl substituted with $R_8$,

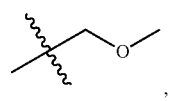, $C_3$~$C_8$ epoxyalkyl

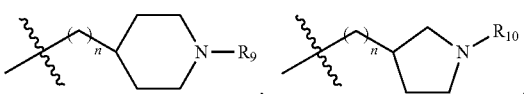

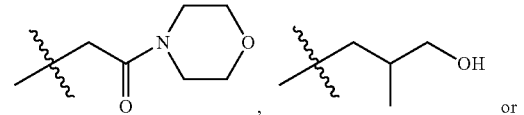

n=0~4; $R_8$~$R_{11}$ are —H, $C_1$~$C_4$ alkyl, —OH,

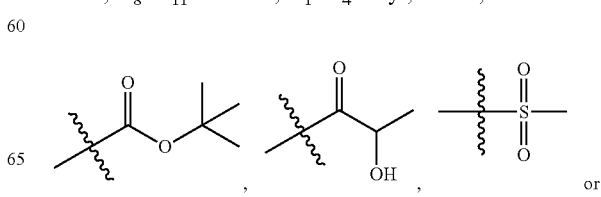

or

-continued

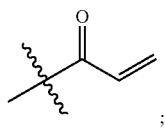
;

$R_{15}$~$R_{19}$ are —H, $C_1$~$C_4$ alkyl, —OH, $C_1$~$C_4$ alkoxyl, halogen, —$CF_3$, —$OCF_3$,

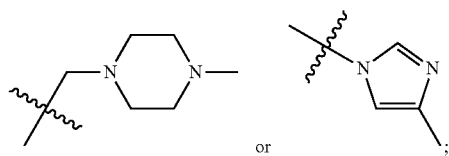

$R_{20}$~$R_{38}$ are —H, $C_1$~$C_4$ alkyl or —$CF_3$.

Further preferably, $R_3$~$R_5$, $R_7$ are —H, $C_1$~$C_4$ alkyl or —Cl; $R_1$ is —H or

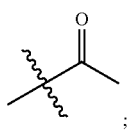 [SMILES: *C(C)=O]
;

$R_2$ is —H, $C_1$~$C_4$ alkyl,

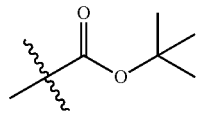
, $R_8$ substituted $C_3$~$C_8$ cyclopropyl,

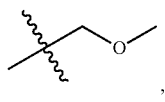 [SMILES: *COC]
, $C_3$~$C_8$ epoxyalkyl,

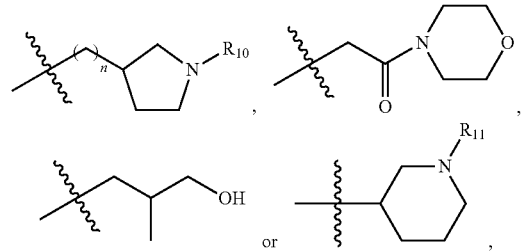

n=0~4; $R_8$~$R_{11}$ are —H, $C_1$~$C_4$ alkyl, —OH,

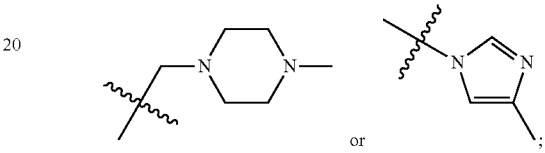
;

$R_{15}$~$R_{19}$ are —H, $C_1$~$C_4$ alkyl, —OH, $C_1$~$C_4$ epoxyalkyl, halogen, —$CF_3$, —$OCF_3$,

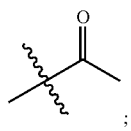

$R_{20}$~$R_{38}$ represent —H, $C_1$~$C_4$ alkyl or —$CF_3$.

Preferably, $R_{15}$~$R_{19}$ are —H, $C_1$~$C_4$ alkyl, —OH, $C_1$~$C_4$ alkoxyl, halogen or —$CF_3$; $R_1$ is —H or

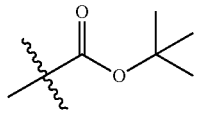
;

$R_2$ is —H, $C_1$~$C_4$ alkyl,

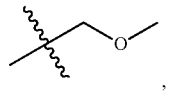 [SMILES: *COC]
, $R_8$ substituted $C_3$~$C_8$ cycloalkyl, $C_3$-$C_8$ epoxyalkyl,

-continued

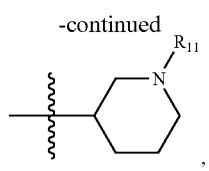

n=0~4; R$_3$~R$_5$, R$_7$ are —H, C$_1$~C$_4$ alkyl, —OH, C$_1$~C$_4$ alkoxyl or halogen; R$_8$~R$_{11}$ represent —H, C$_1$~C$_4$ alkyl, —OH,

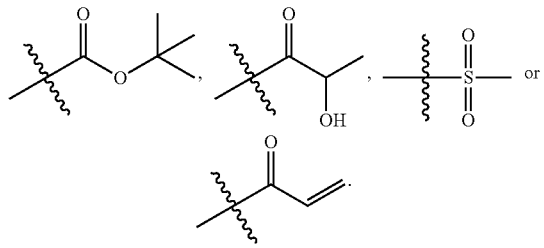

More preferably, R$_{15}$~R$_{19}$ represent —H, C$_1$~C$_4$ alkyl, halogen or —CF$_3$; R$_1$ is —H or

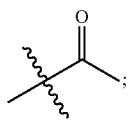

R$_2$ is —H, C$_1$~C$_4$ alkyl,

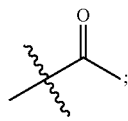

C$_3$~C$_8$ cyclopropyl substituted with R$_8$,

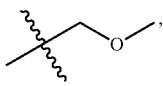 [SMILES: *COC]

C$_3$~C$_8$ epoxyalkyl,

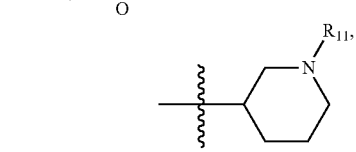

n=0~4; R$_3$~R$_5$, R$_7$ are independently selected from —H, C$_1$~C$_4$ alkyl, —OH, C$_1$~C$_4$ alkoxyl or halogen; R$_8$~R$_{11}$ represent —H, C$_1$~C$_4$ alkyl, —OH,

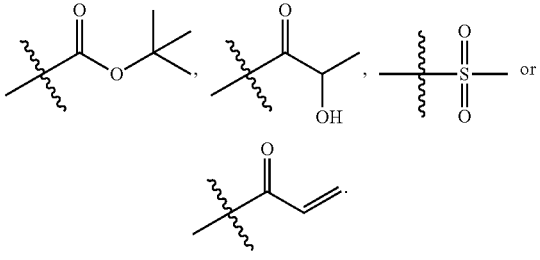

Further preferably, R$_{15}$~R$_{19}$ are independently selected from —H or —CF$_3$; R$_1$ is —H or

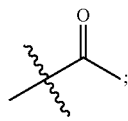

R$_2$ is —H, C$_1$~C$_4$ alkyl,

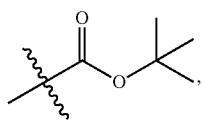 [SMILES: *C(=O)OC(C)(C)C]

C$_3$~C$_8$ cycloalkyl substituted with R$_8$,

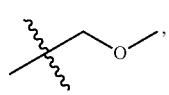 [SMILES: *COC]

C$_3$~C$_8$ epoxyalkyl,

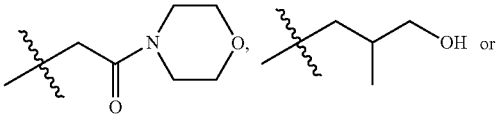

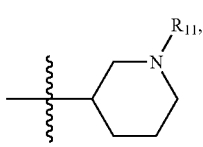

n=0~4; R$_3$~R$_5$, R$_7$ independently represent —H, C$_1$~C$_4$ alkyl, —OH, C$_1$~C$_4$ alkoxyl or halogen; R$_8$~R$_{11}$ are independently selected from —H, C$_1$~C$_4$ alkyl, —OH,

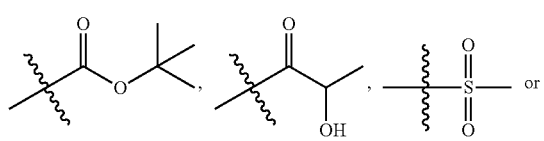
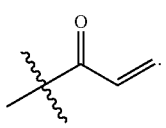
Optimally, R₁ is —H; R₂ is $C_1$~$C_4$ alkyl or
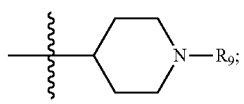
$R_3$~$R_5$, $R_7$ are —H, $C_1$~$C_4$ alkyl or —Cl; $R_9$ is $C_1$~$C_4$ alkyl; $R_{15}$~$R_{19}$ are independently selected —H or —CF₃.
The structure of 3-ethynylpyrazolopyrimidine derivatives above is shown as:
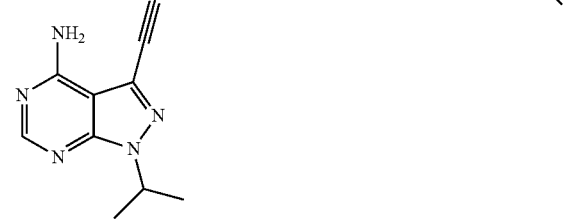
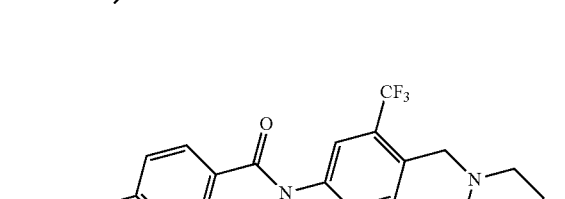
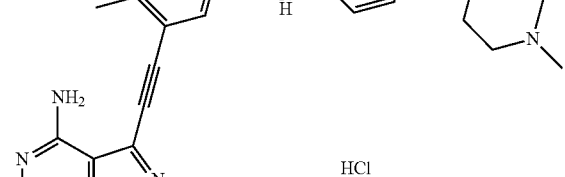
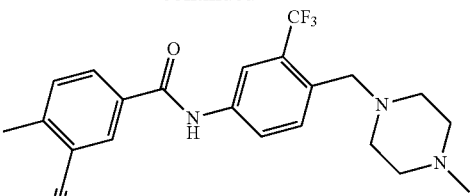
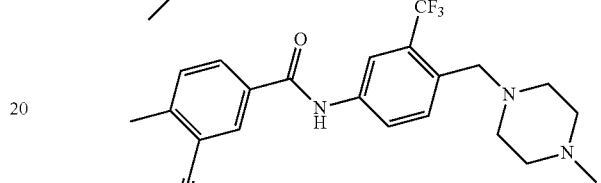
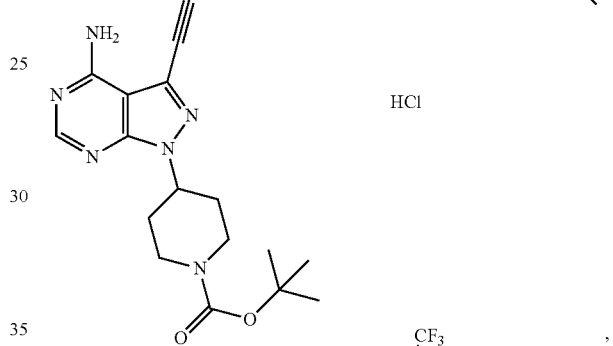
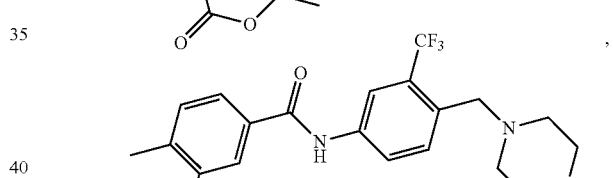
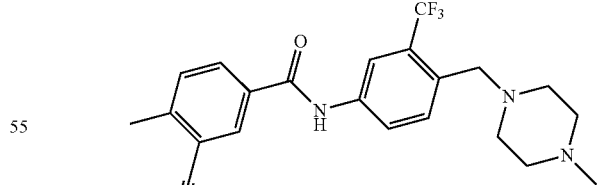
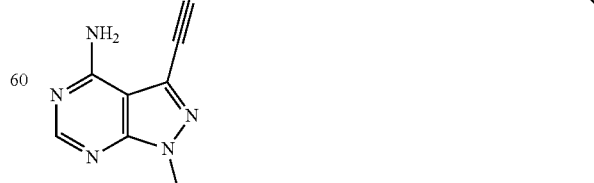

73
-continued
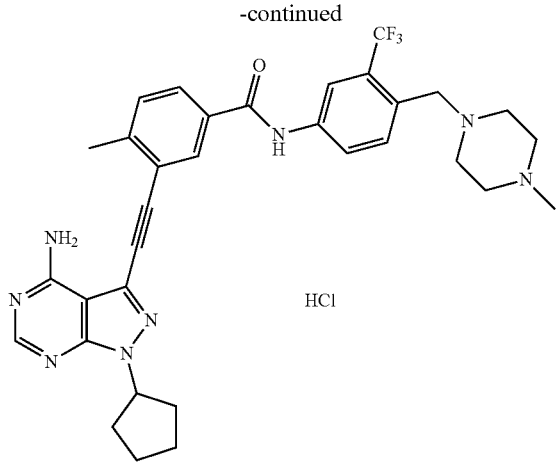
HCl
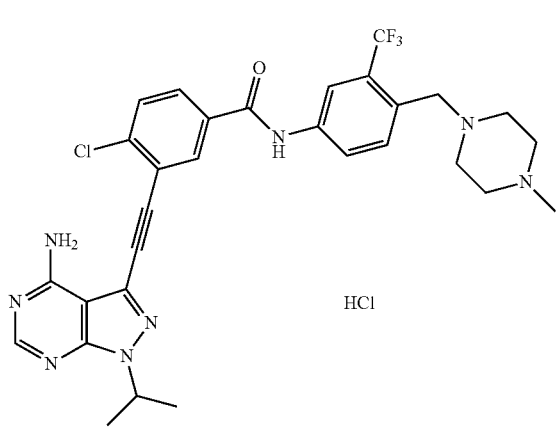
HCl
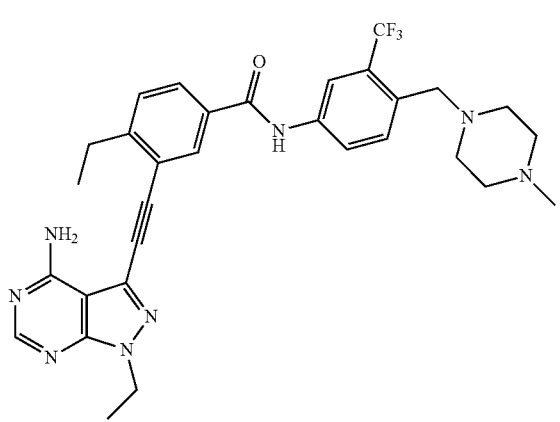
74
-continued
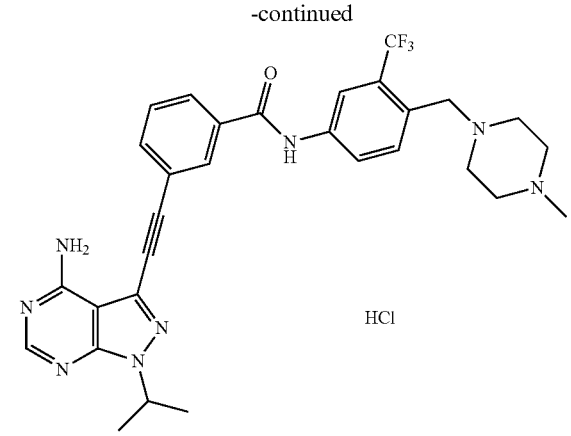
HCl
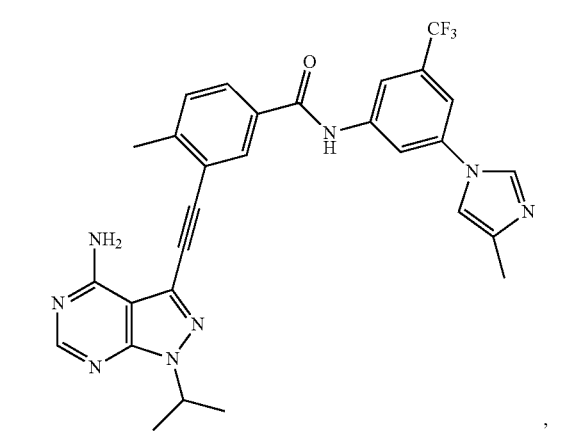
,
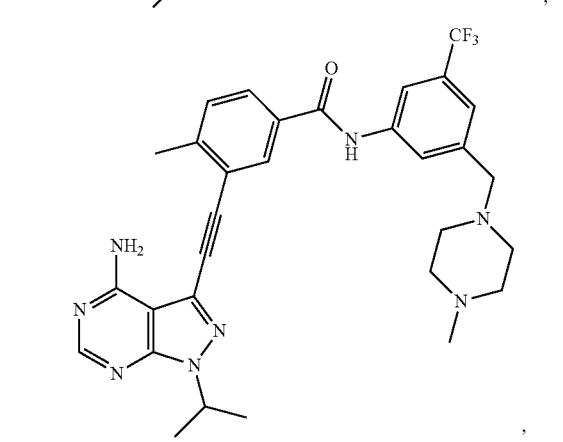
,
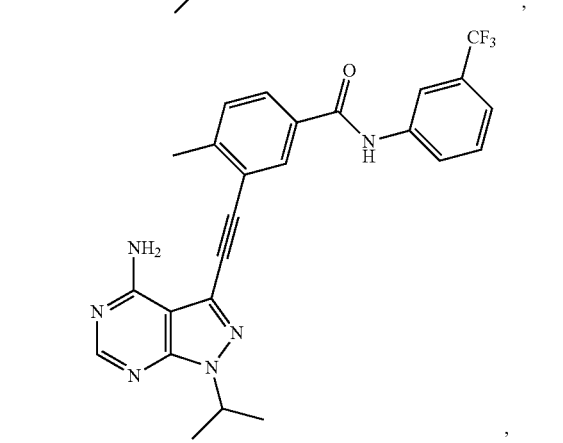
, 75
-continued
76
-continued
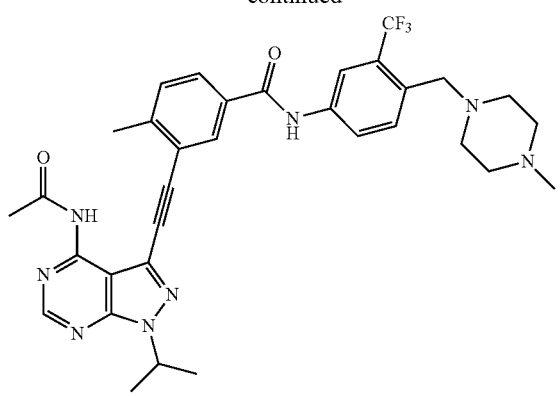
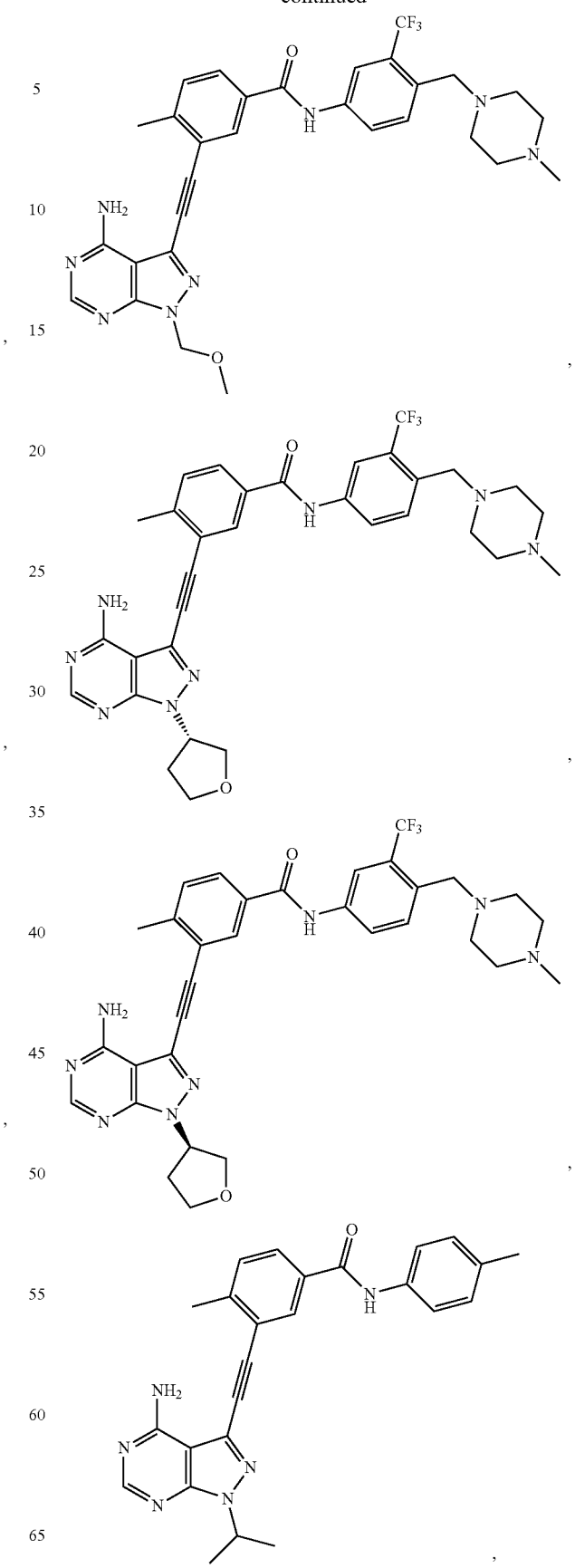

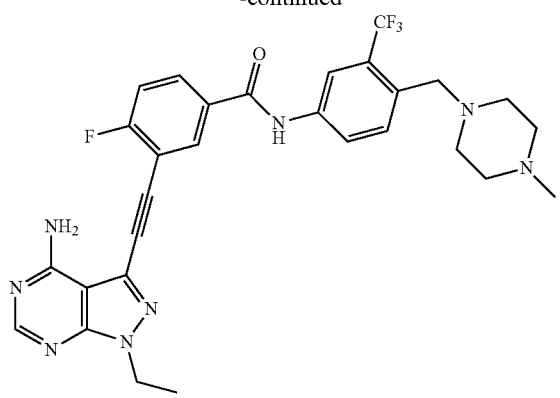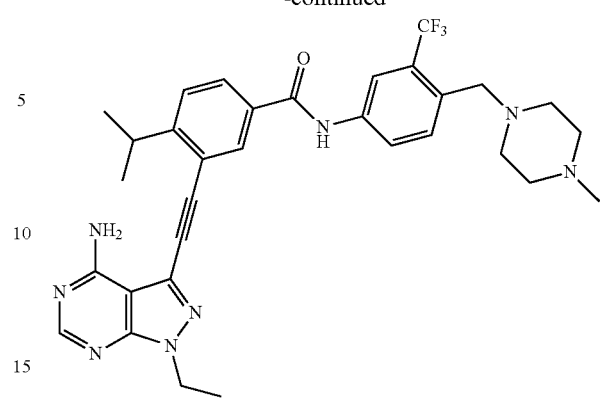

79
-continued
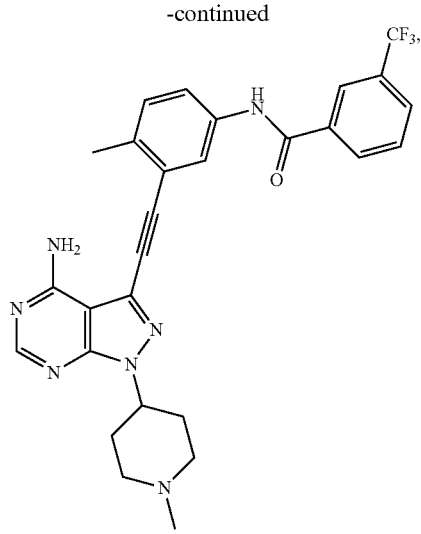
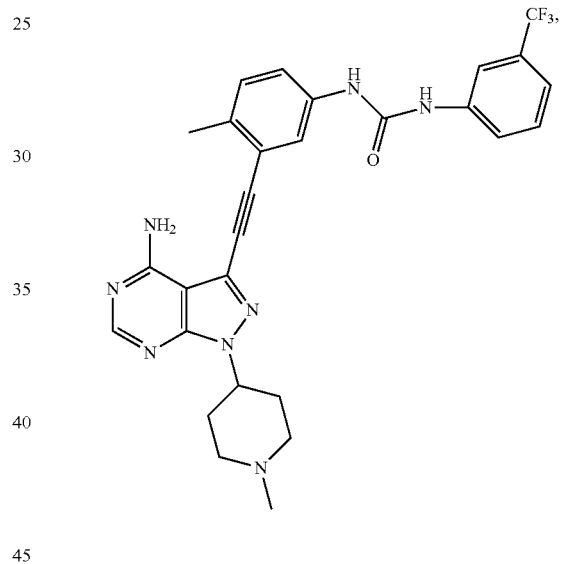
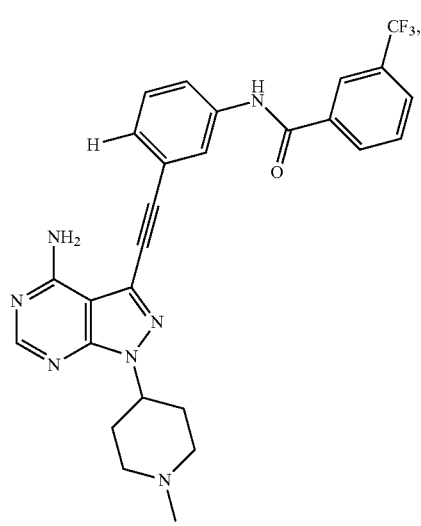
80
-continued
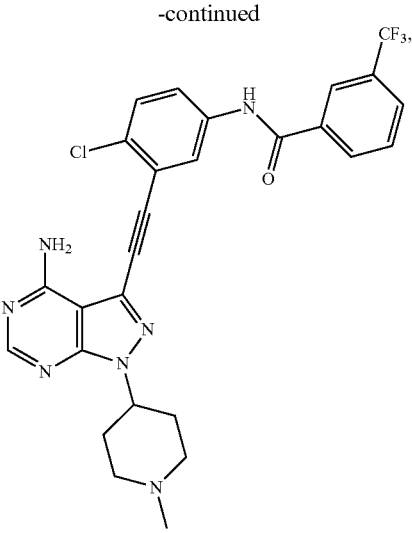
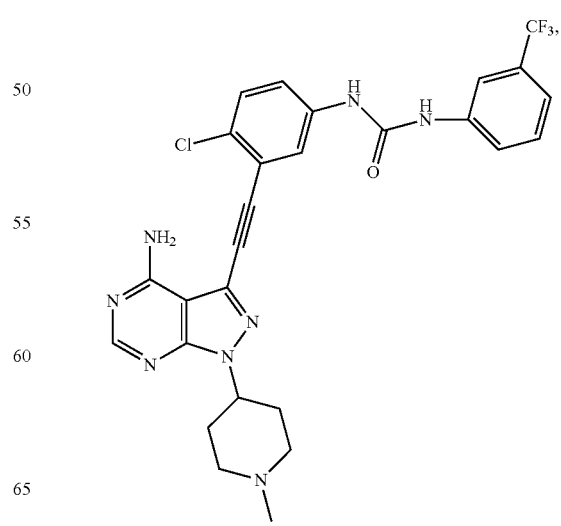

81
-continued
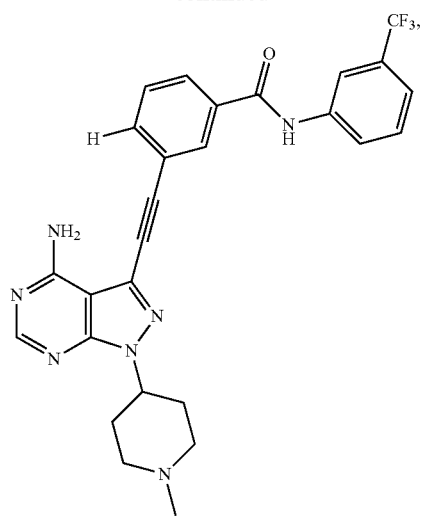
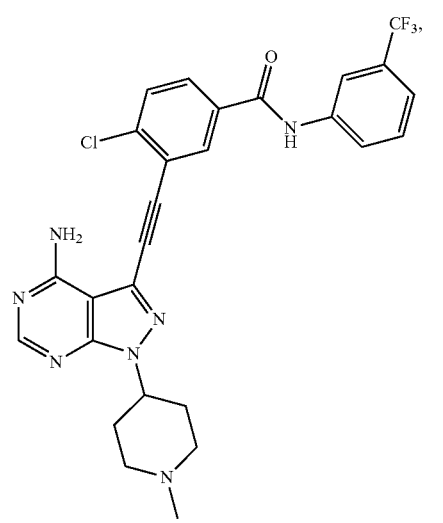
82
-continued
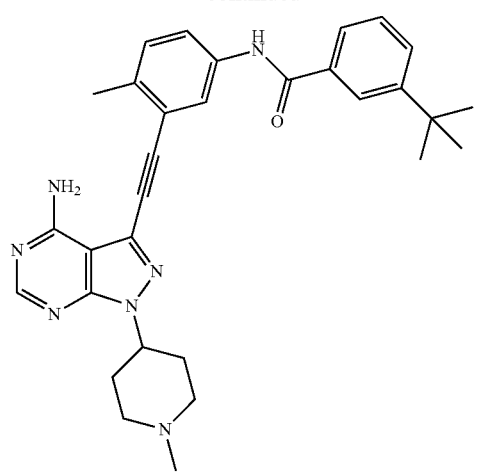
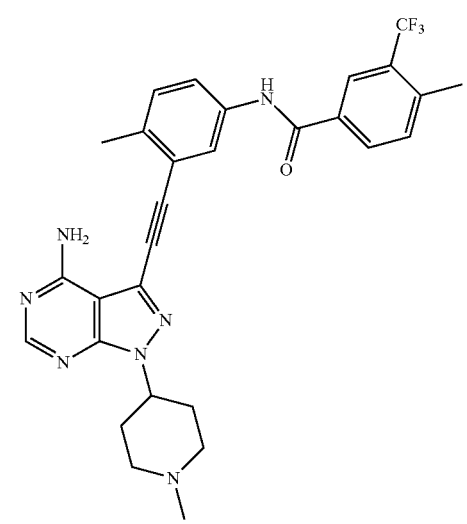

83
-continued
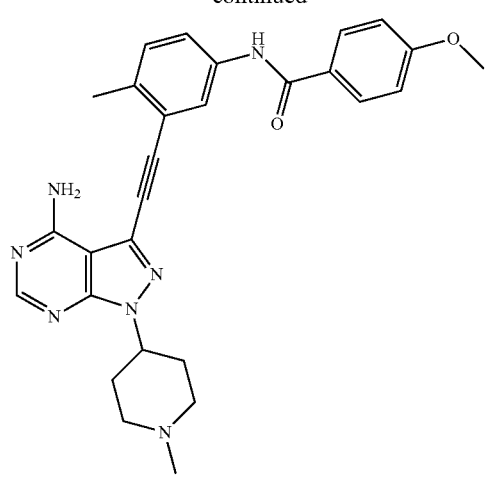
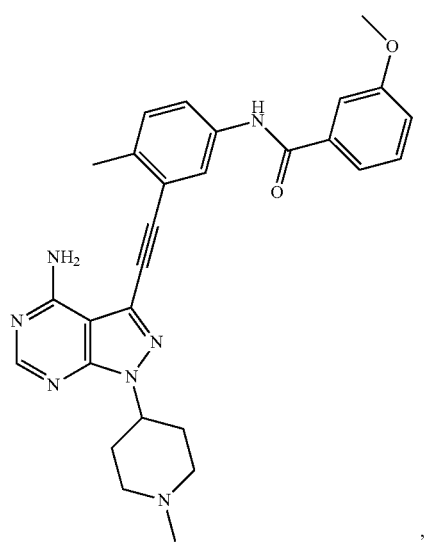
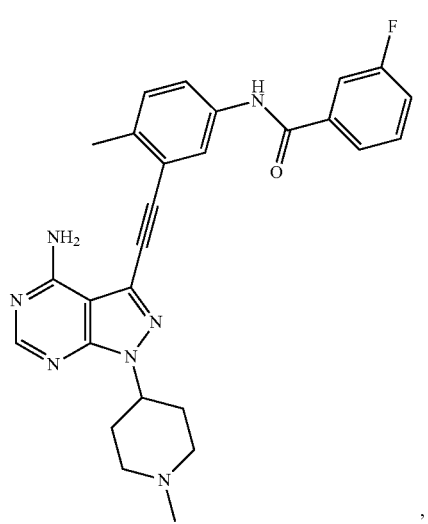
84
-continued
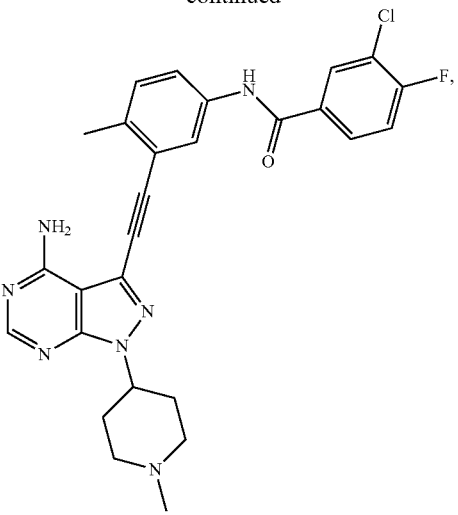
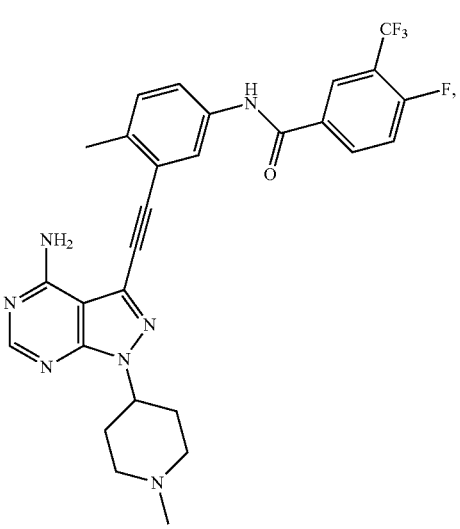
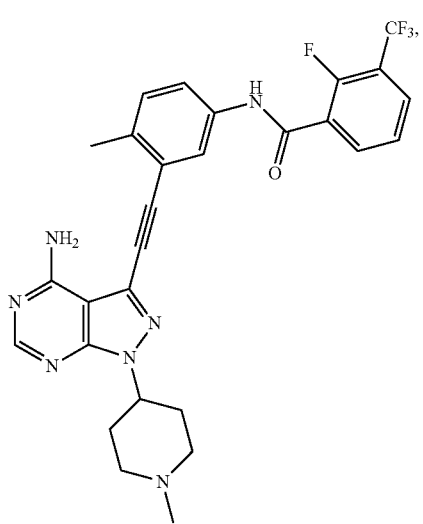

85
-continued
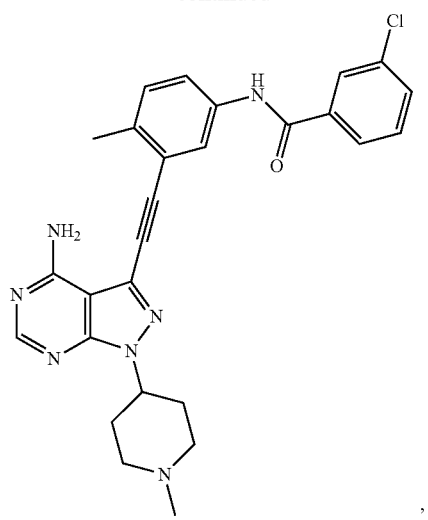
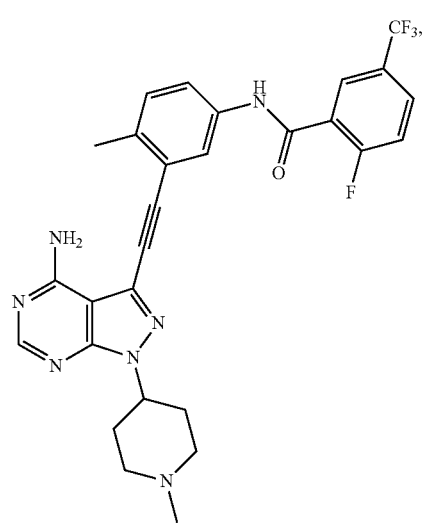
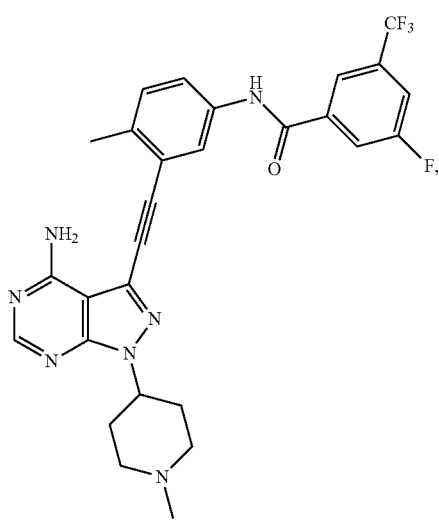
86
-continued
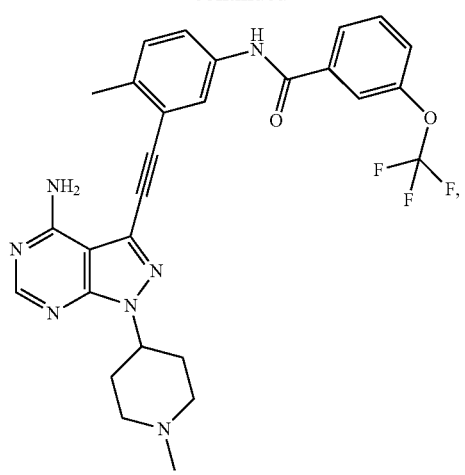
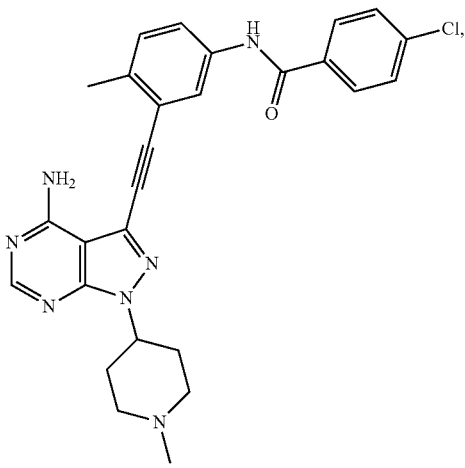

87
-continued
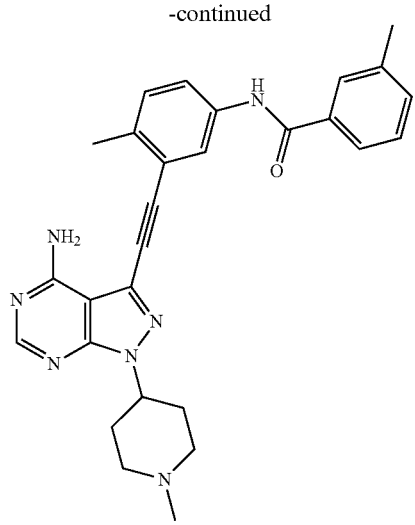
,
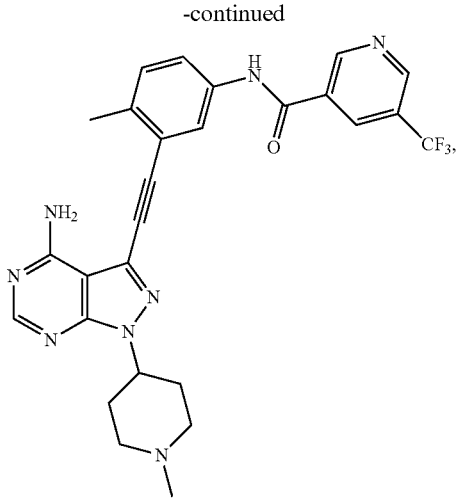
88
-continued
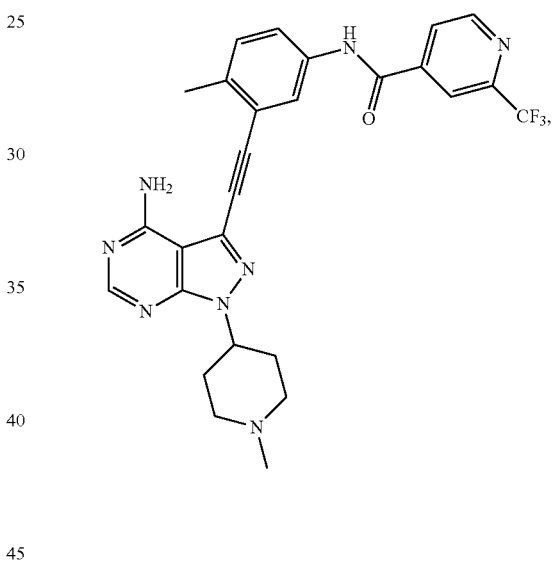
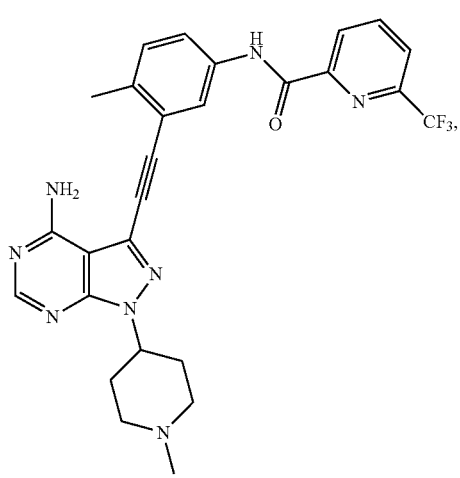
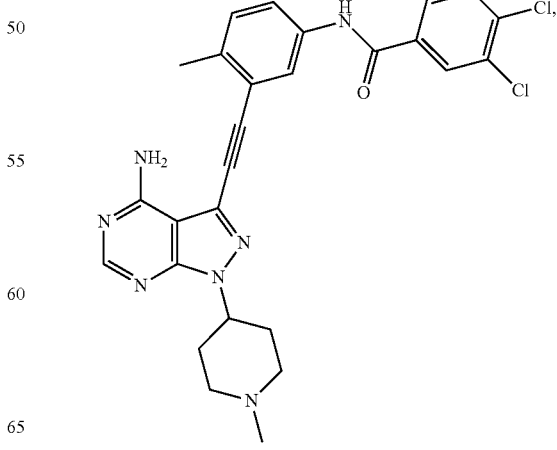

89
-continued
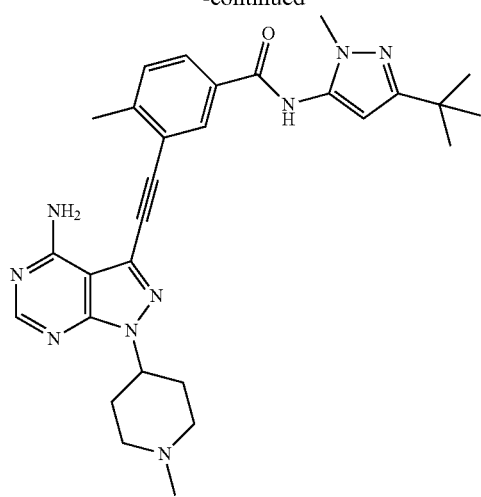
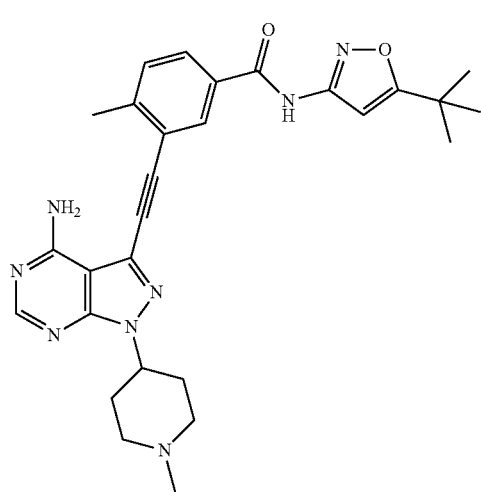
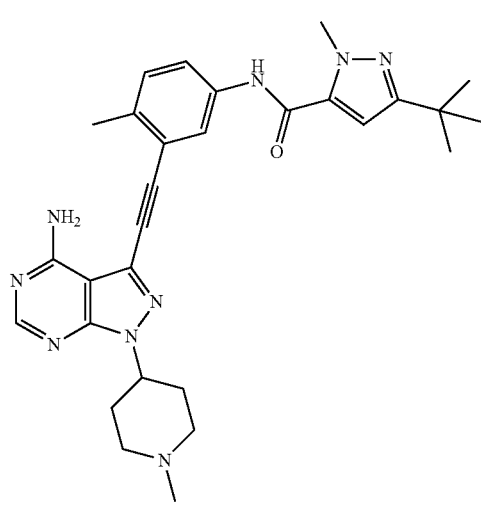
90
-continued
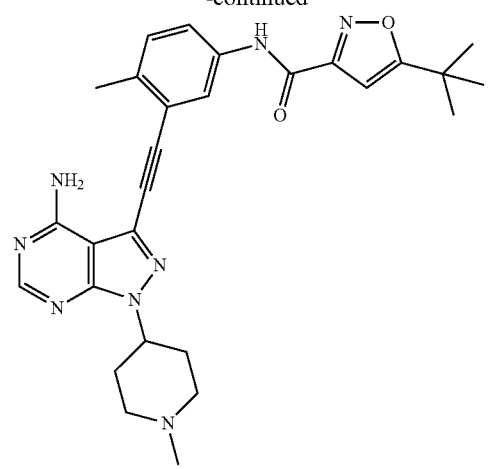
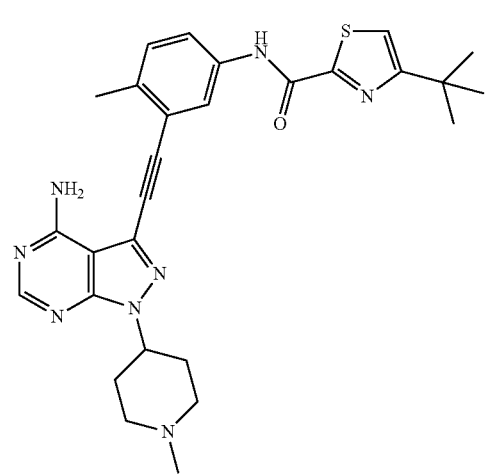
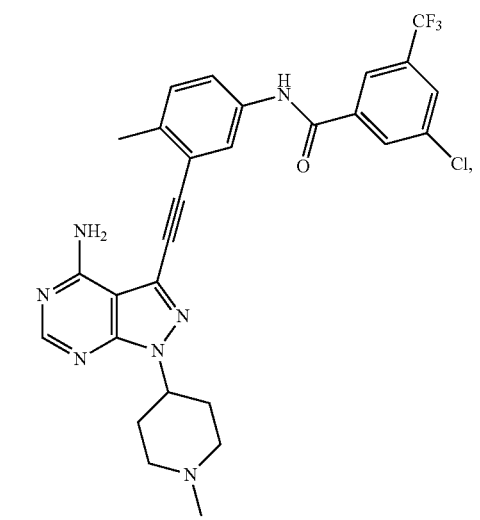

91
-continued
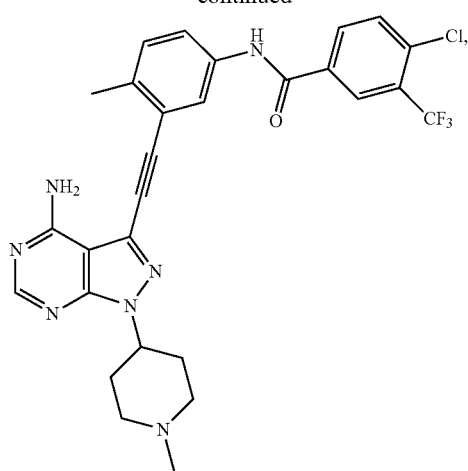
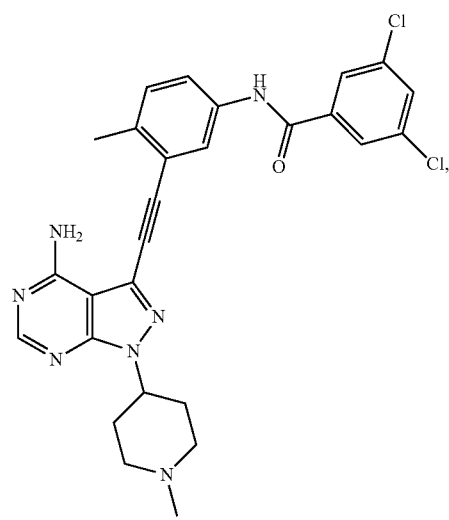
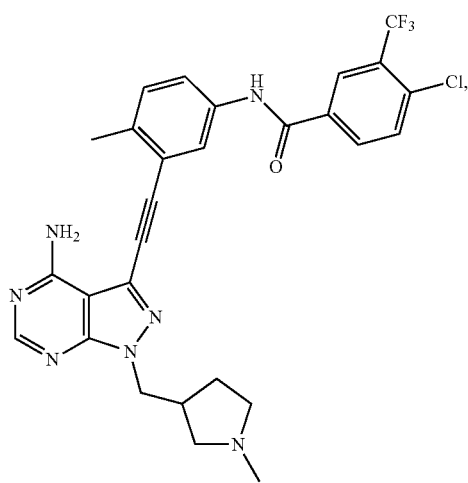
92
-continued
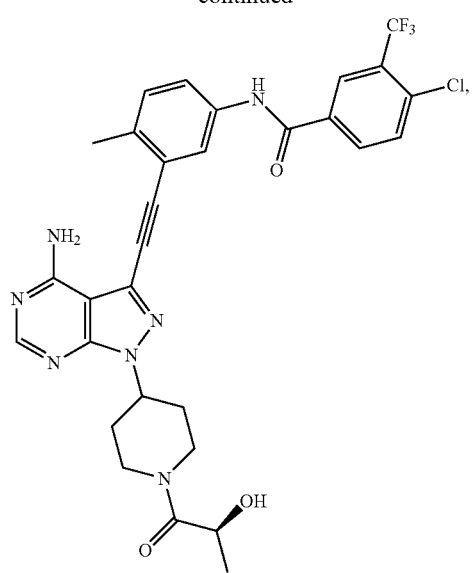
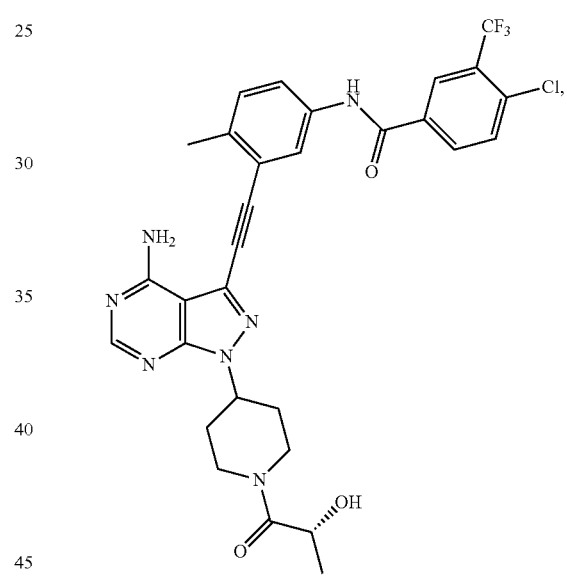
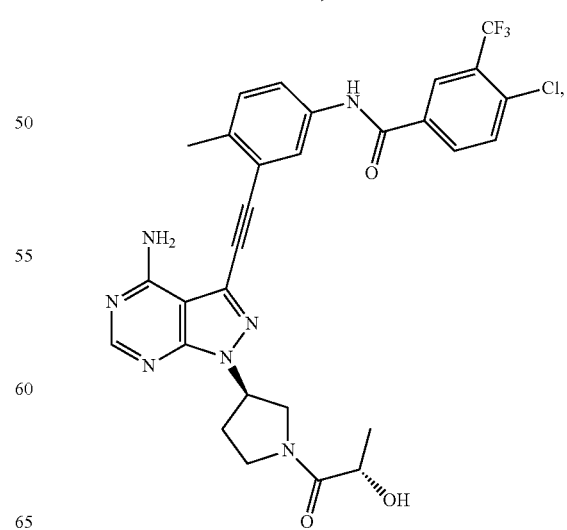

93
-continued
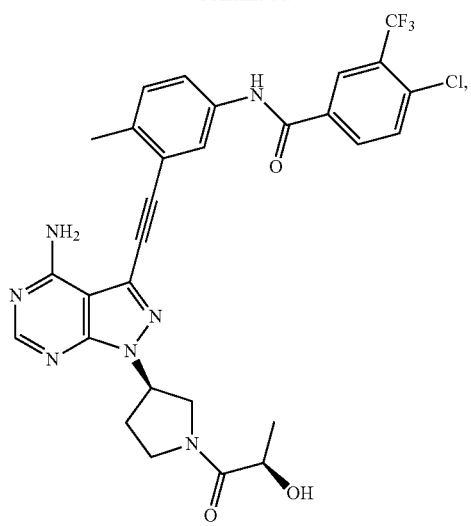
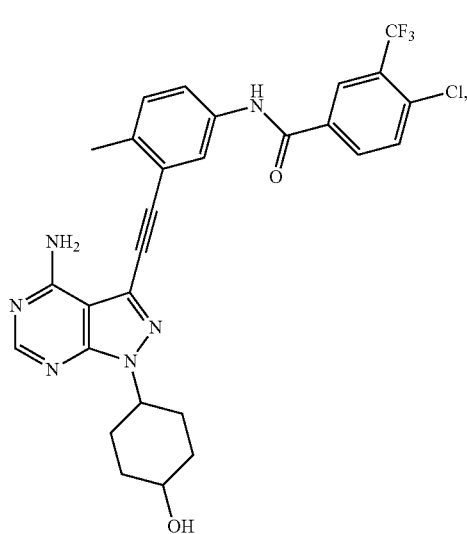
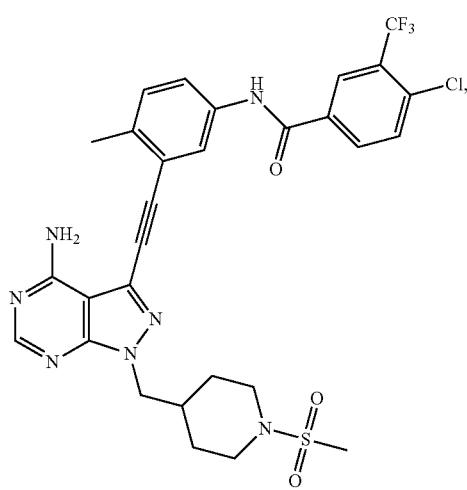
94
-continued
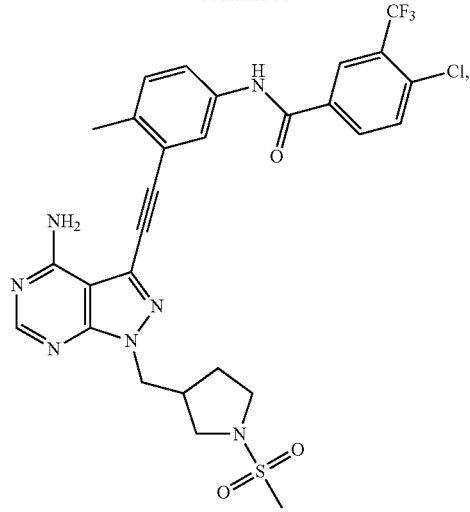
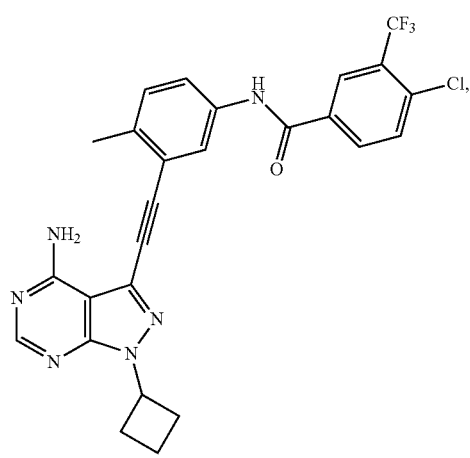
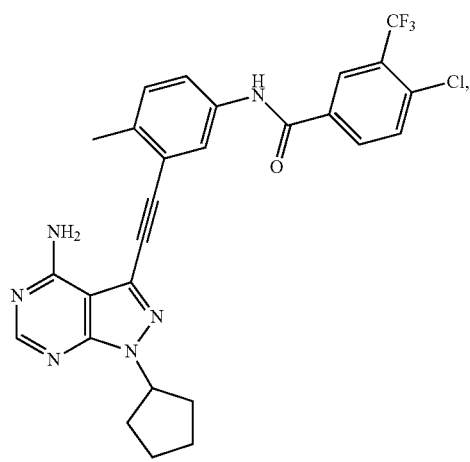

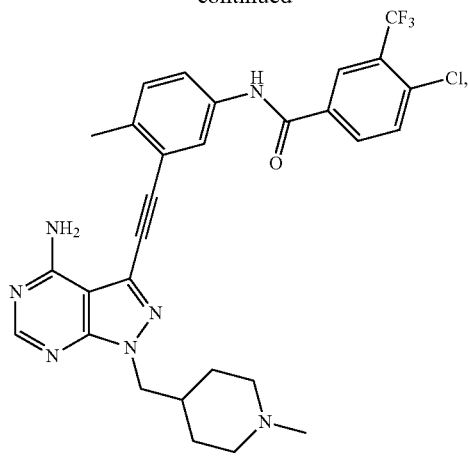
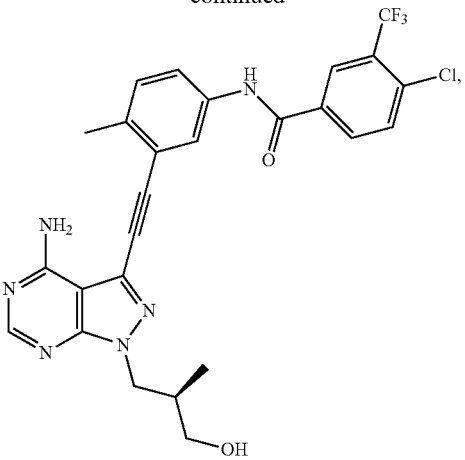
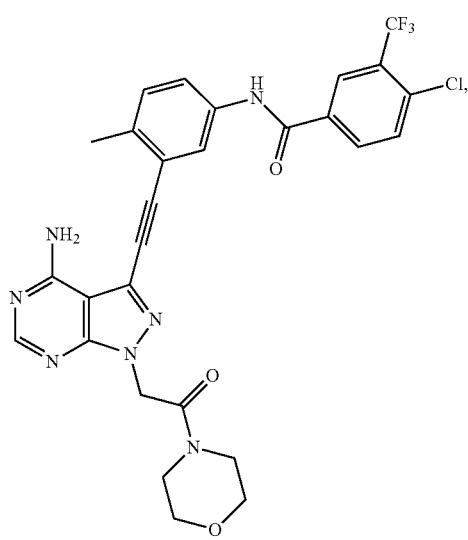
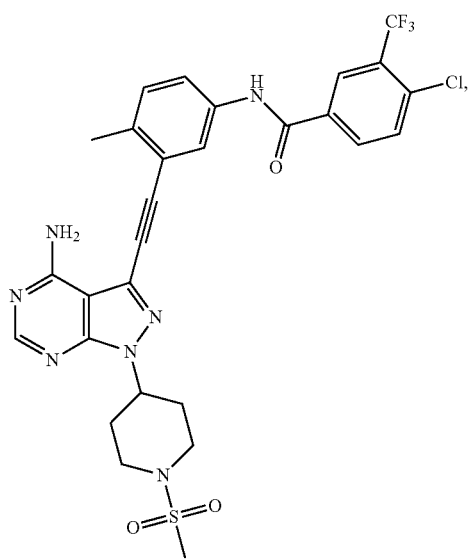
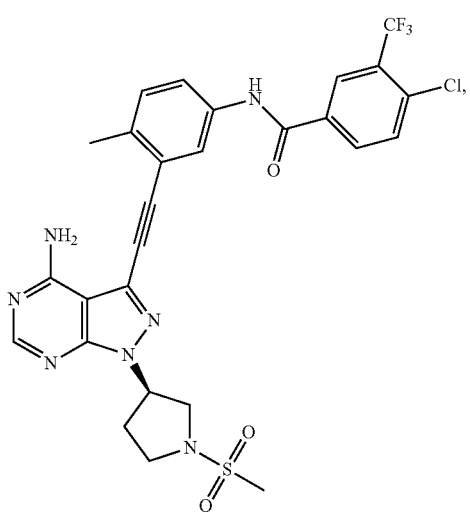

97
-continued
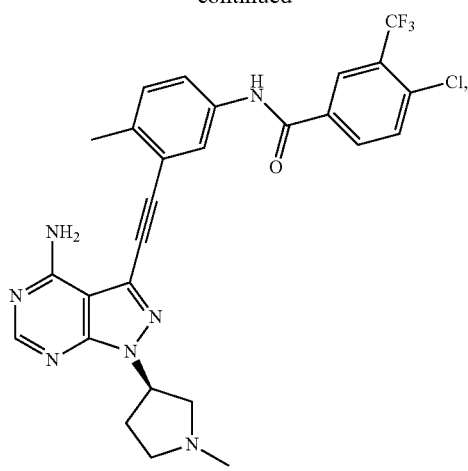
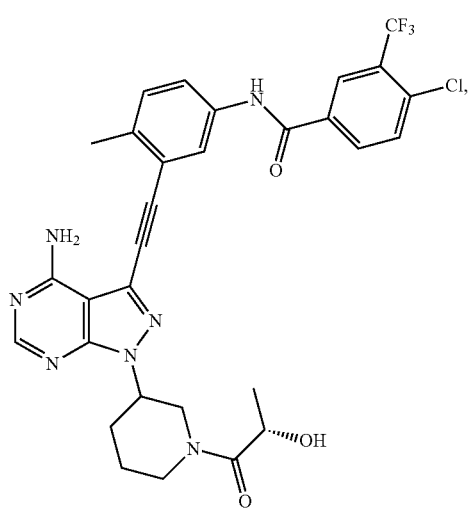
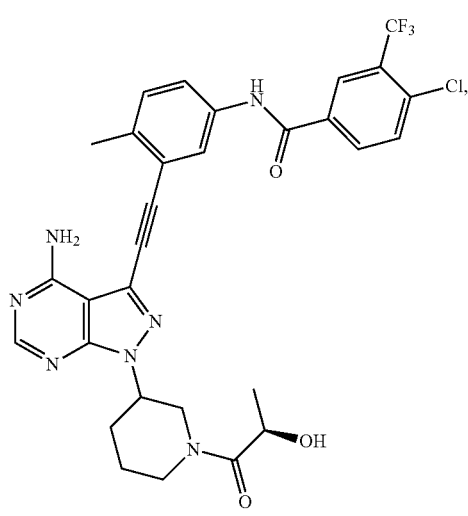
98
-continued
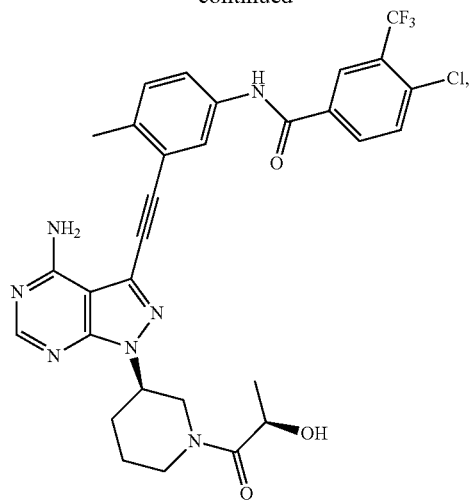
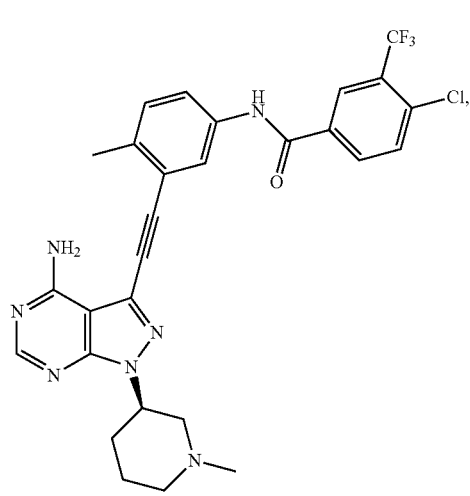
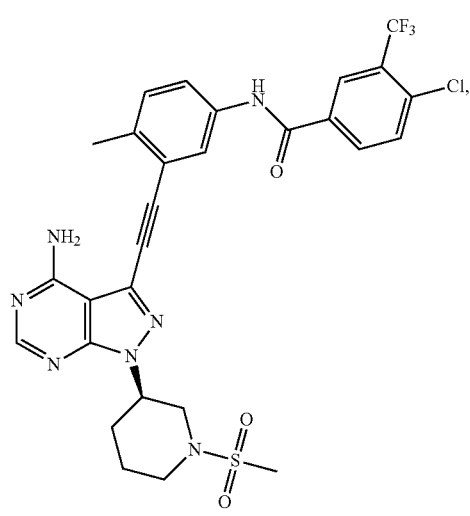

99
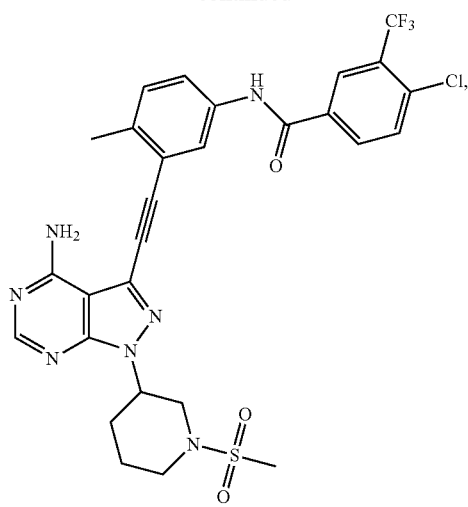
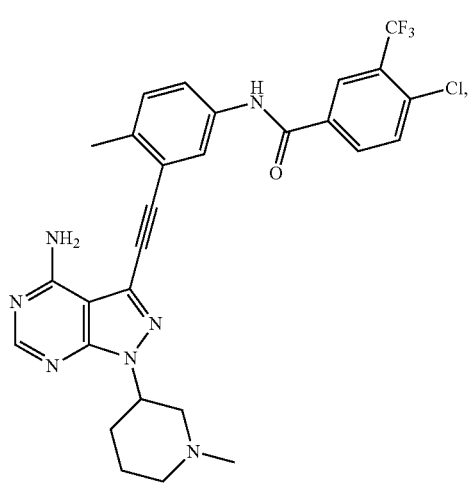
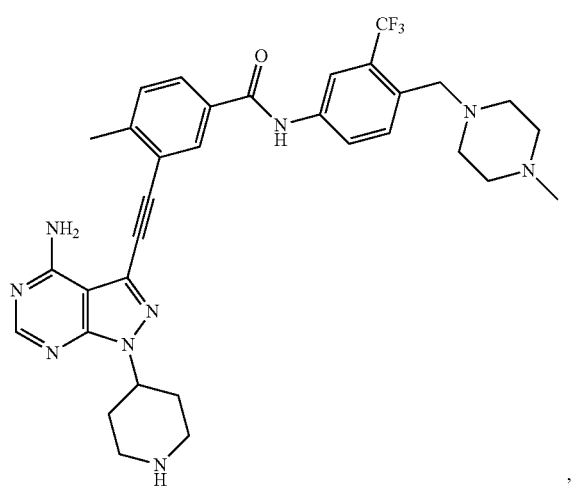
100
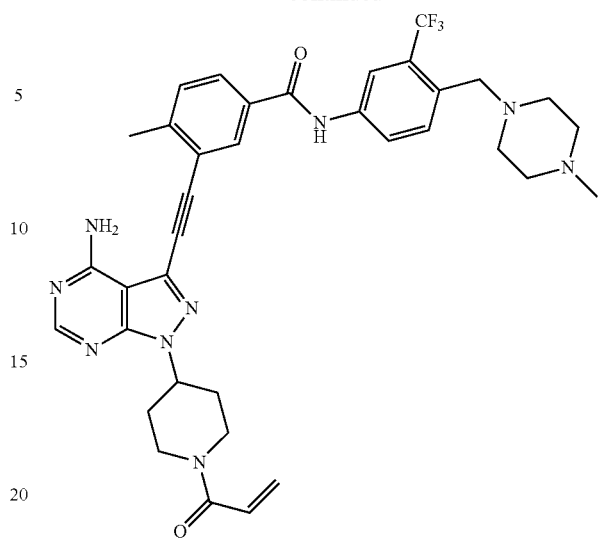
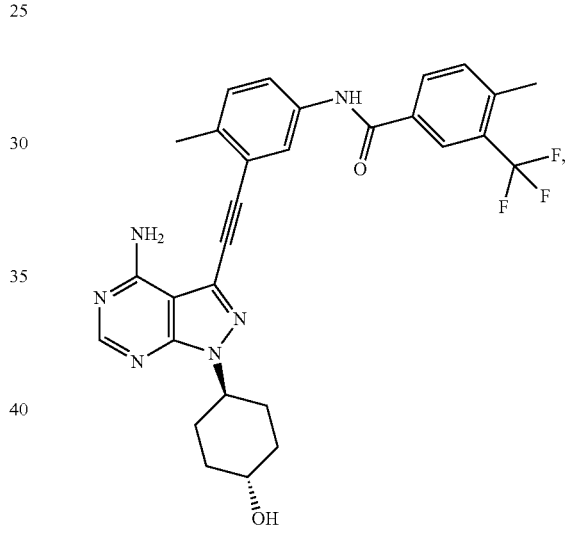
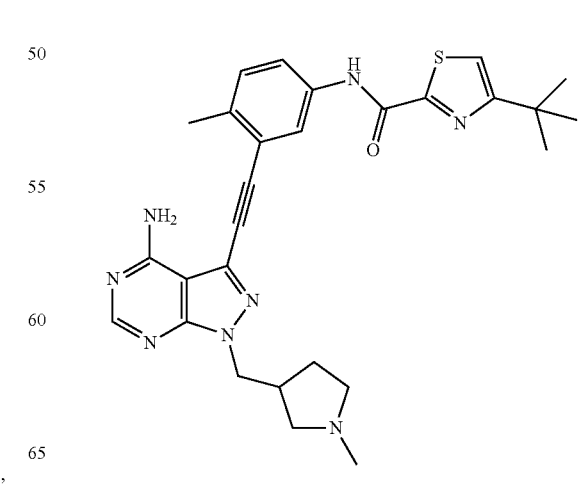

101
-continued
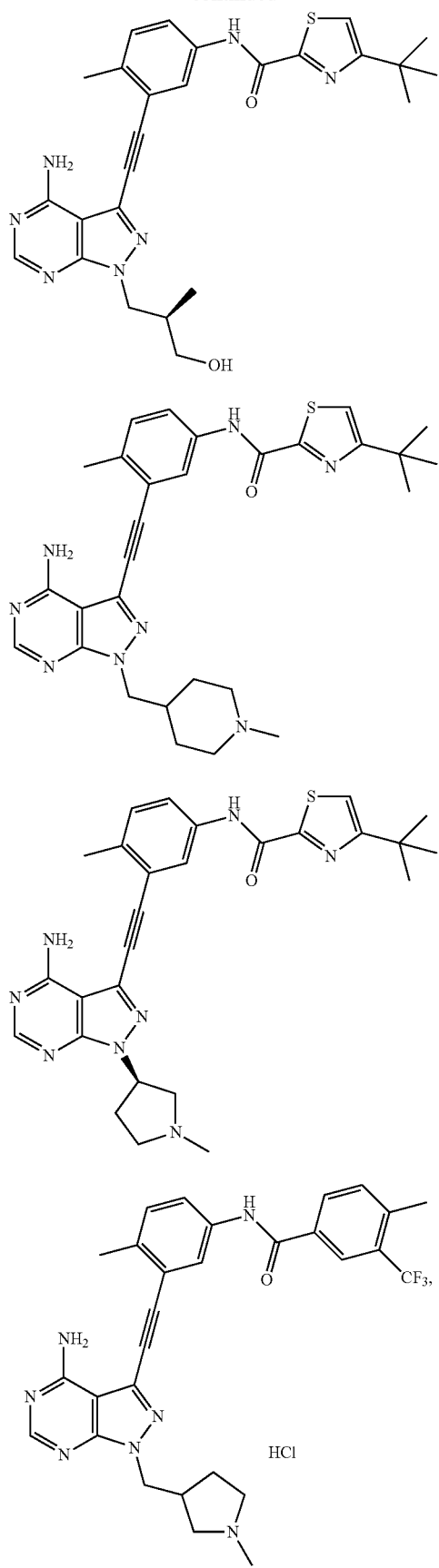
102
-continued
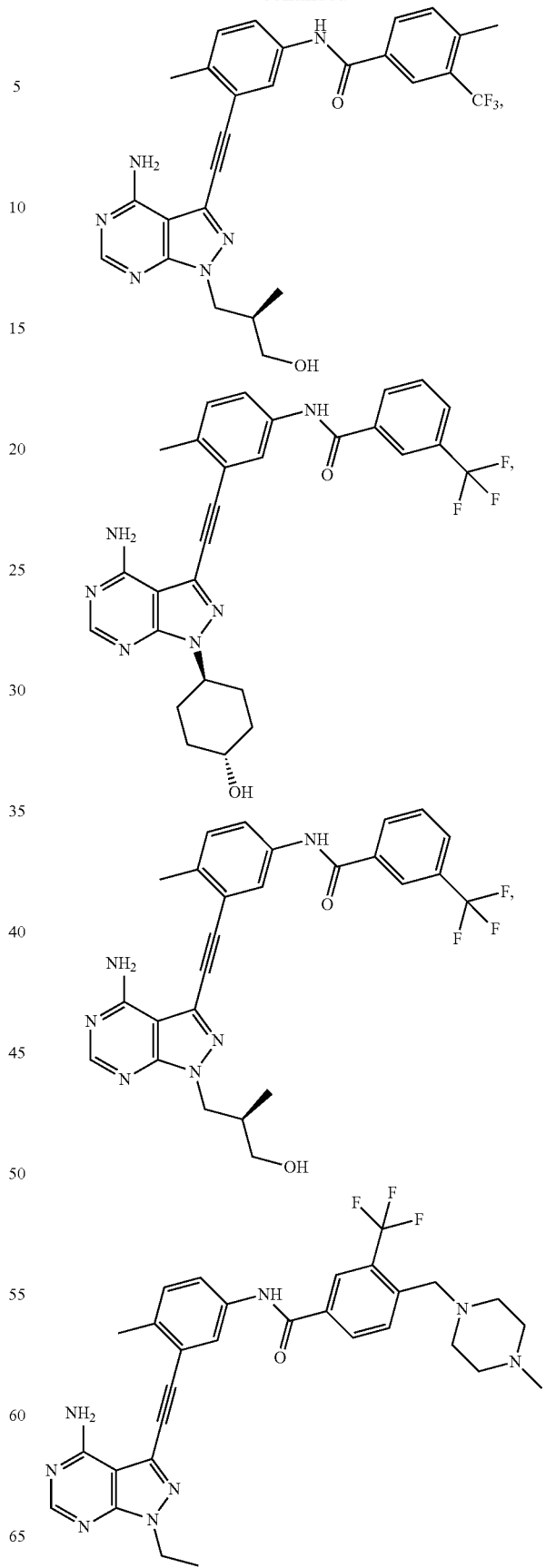

103
-continued
104
-continued
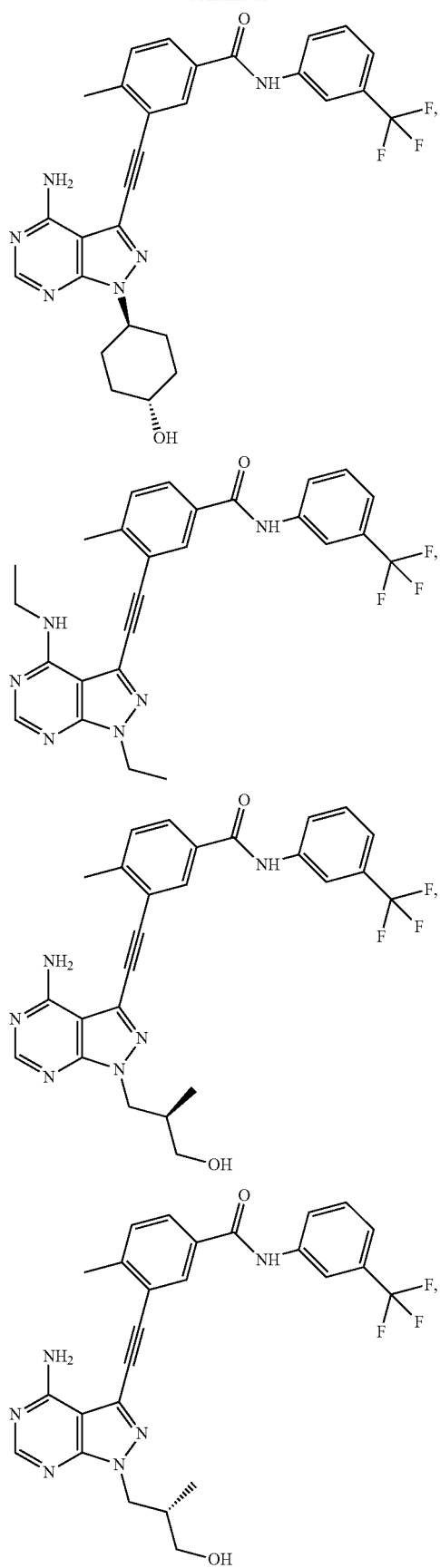
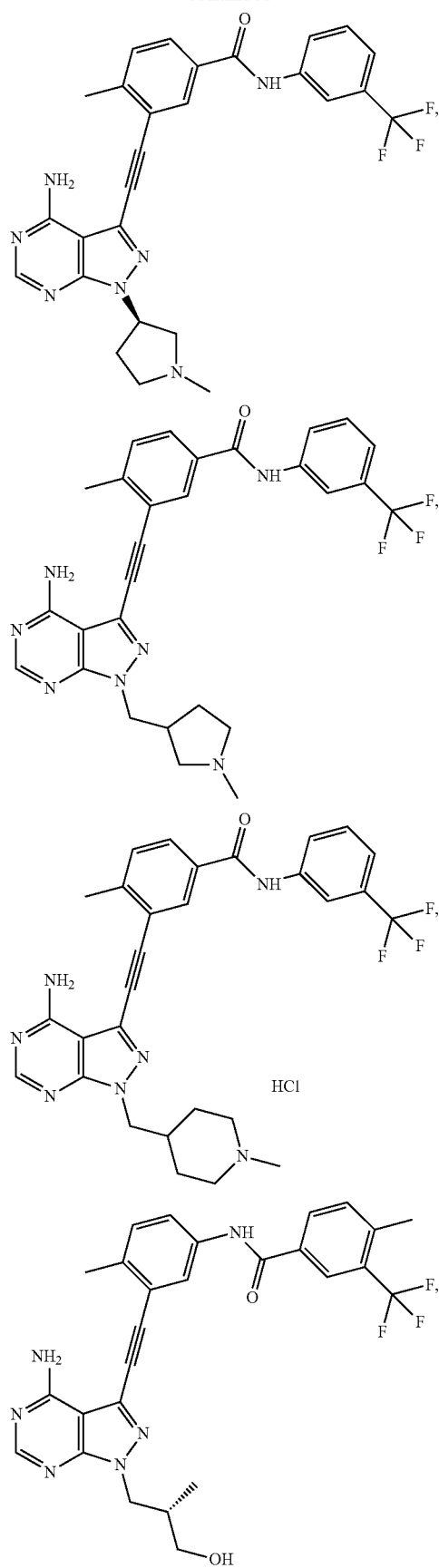

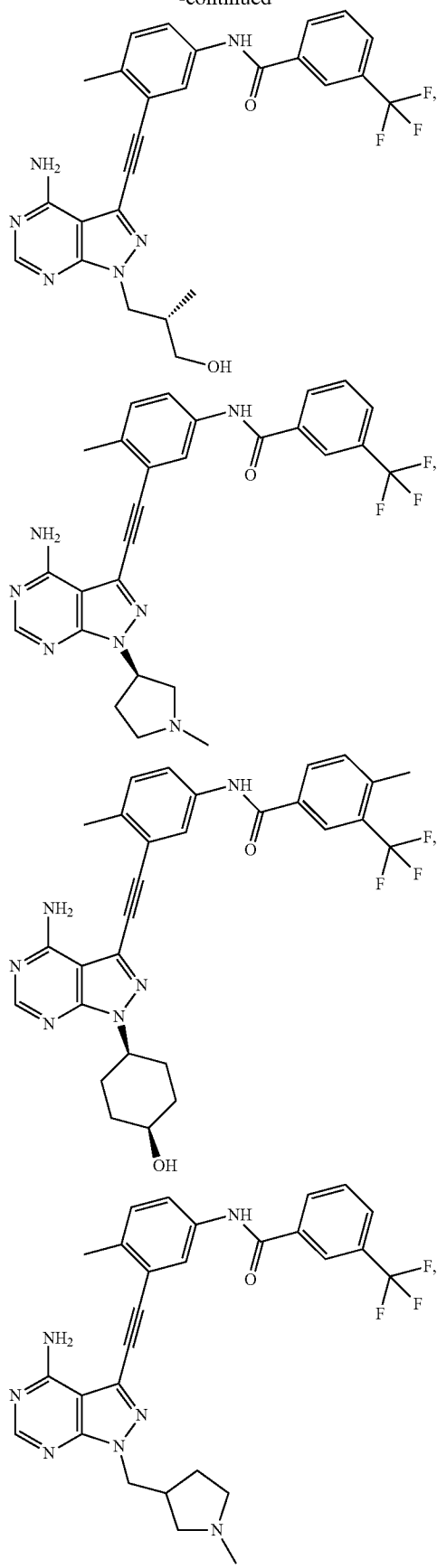
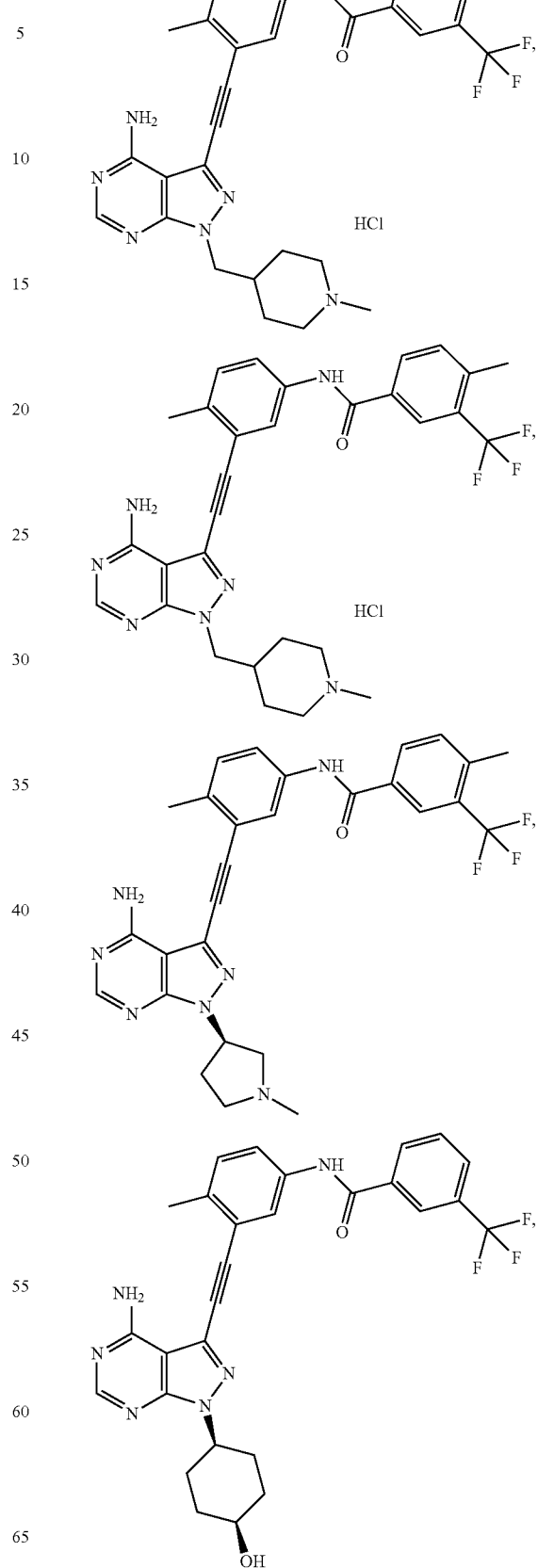

107
-continued
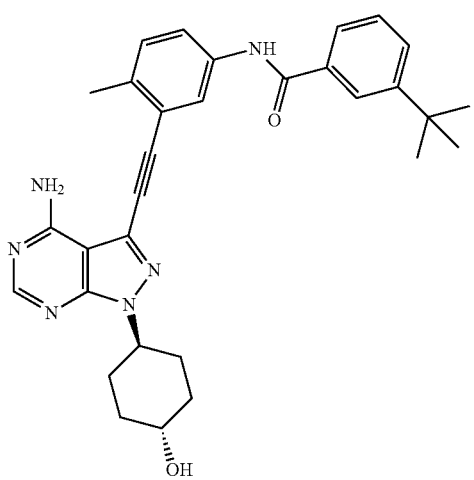
or
108
-continued
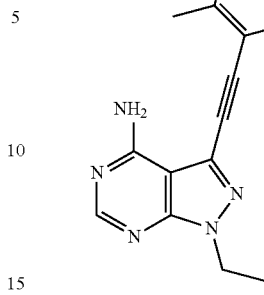
The present invention also provides a process for the preparation of the 3-ethynylpyrazolopyrimidine derivatives described above:
When $R_6$ is
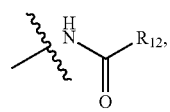
the synthetic route of the compound of formula II is shown as:
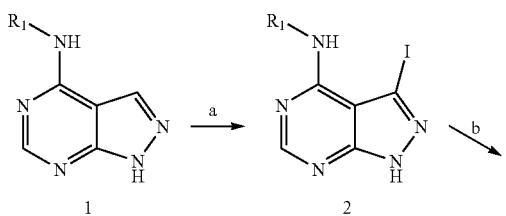
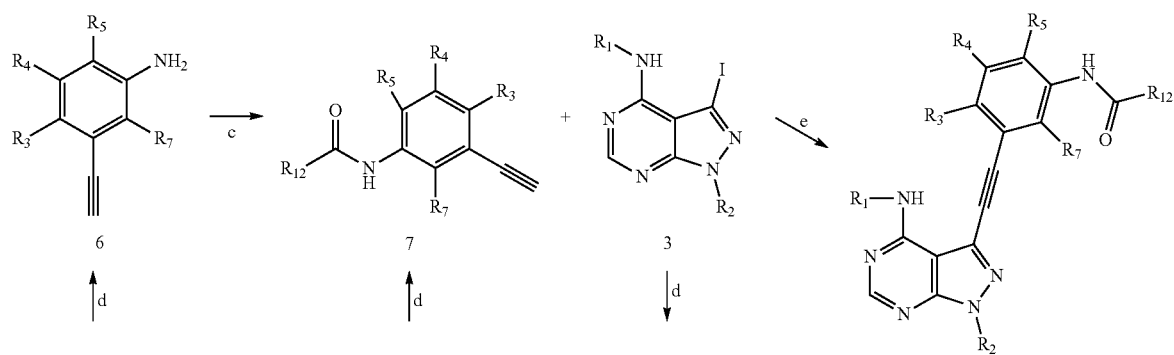
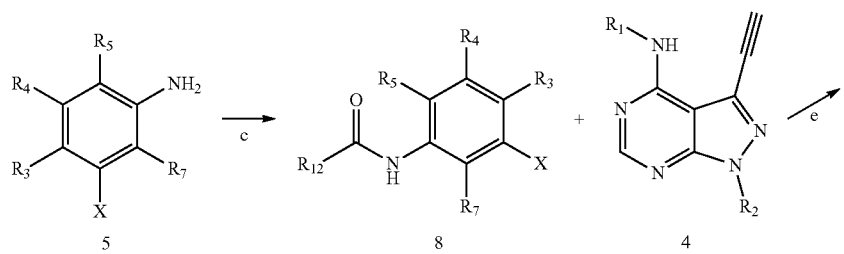

When R$_6$ is
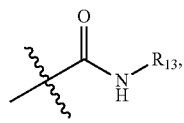
R$_{13}$ is
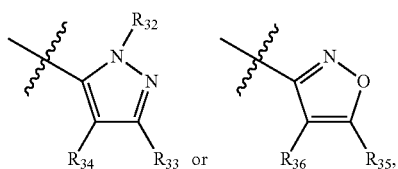
the synthetic route of the compound of formula III is shown as:
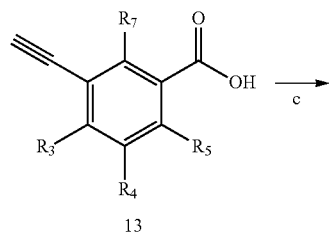
13
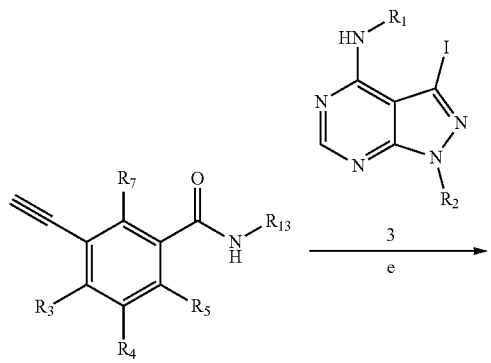
10
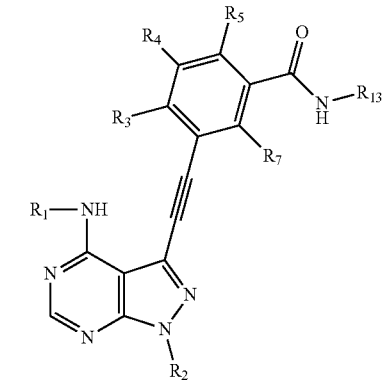
When R$_6$ is
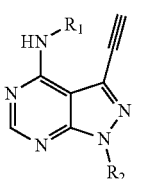
R$_{13}$ is
the synthetic route of the compound of formula IV is shown as:
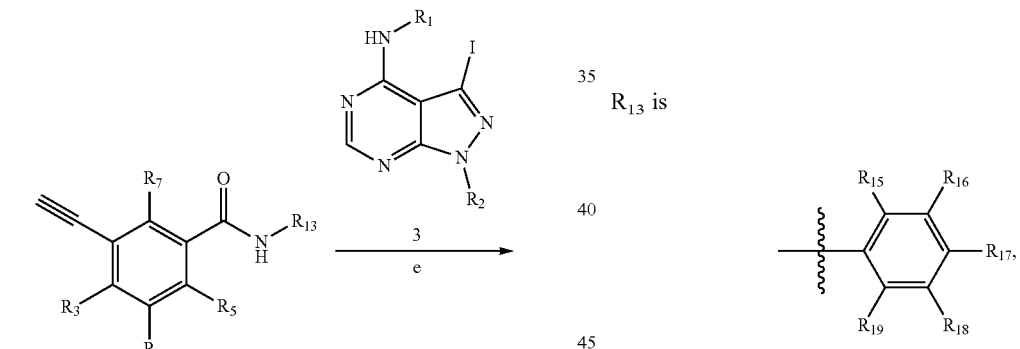
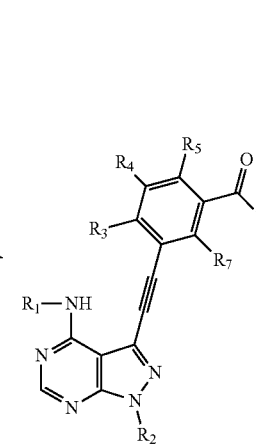

111 112
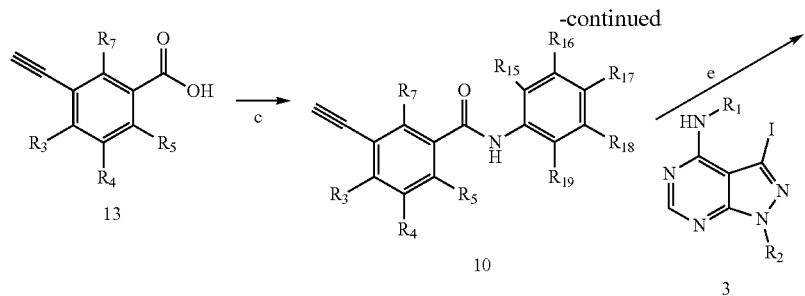
When R₆ is
R₁₄ is
the synthetic route of the compound in formula V is shown as:
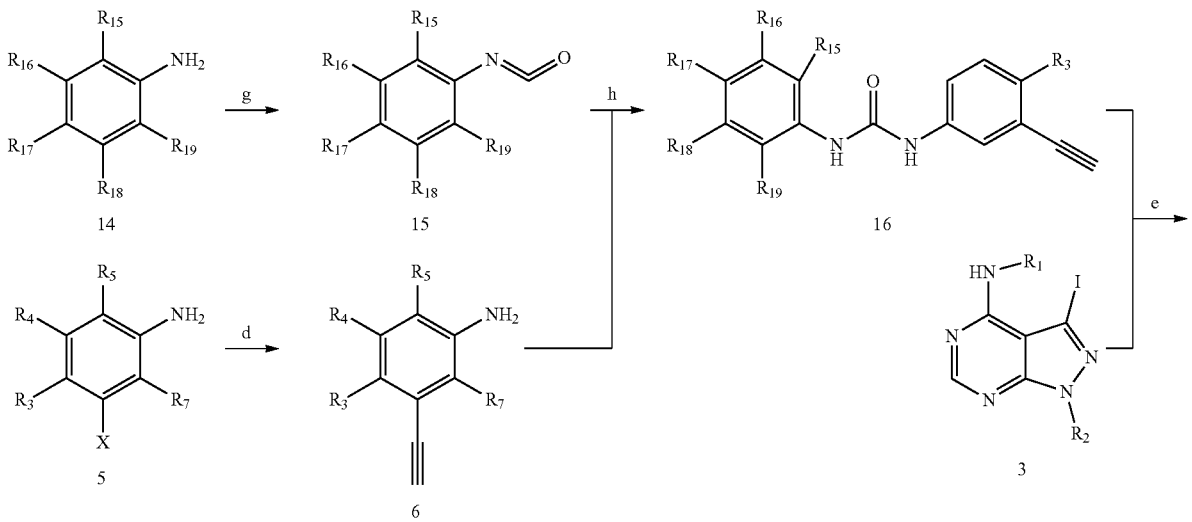
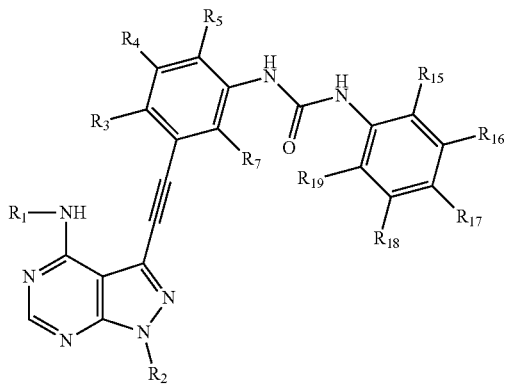

The conditions of the reaction scheme described above are shown as:

a, Compound 1 react with common halogenated reagents (such as NIS (N-iodosuccinimide), NBS (N-bromosuccinimide), Br₂, I₂, ICl, IBr) to form compound 2.
b, Haloalkane of $R_2$ (bromide or iodide) or the corresponding sulfonate (methanesulfonate, p-toluenesulfonate, p-nitrobenzenesulfonate and so on) is substituted with compound 2 under basic conditions (such as KOH, NaOH, $K_2CO_3$, $Na_2CO_3$, $Cs_2CO_3$, NaH) to give compound 3.
c, The corresponding compound containing carboxyl group is condensed with the corresponding compound containing amino group under normal condensation conditions (such as a condensing agent method, a mixed acid anhydride method, an activation method) to give the corresponding compound 7 to 10 linked with amide bonds.
d, the corresponding intermediate is coupled with an alkyne reagent with a protecting group at one end under the transition metal to obtain the corresponding intermediate and then the protecting group is deprotected to obtain the corresponding compound 4, the compound 6, the compound 7, the compound 10 and compound 13 containing the alkynyl group.
e, The corresponding intermediates containing halogens are coupled with the intermediates containing with alkynyl under the catalysis of the transition metal to give compounds of the general formulas II, III, IV and V. The coupling reaction is carried out using palladium catalyst ($Pd_4(PPh_3)_4$, $PdAc_2$, $Pd_2(dba)_3$, $PdPPh_3Cl_2$ and so on), a copper salt (CuCl, CuBr, CuI) and a suitable organic base or inorganic base (triethylamine (TEA), diisopropylamine (DIPEA), $K_2CO_3$, $NaCO_3$, $NaHCO_3$ an so on) in a suitable solvent (THF (tetrahydrofuran), toluene, DMF (N, N-dimethylformamide), 1,4-dioxane and so on) at 20 to 150° C.
f, The compound 12 is catalyzed with concentrated sulfuric acid in the corresponding alcoholic solution (methanol, ethanol, etc.) to afford the corresponding esterified intermediate.
g, The Compound 14 is reacted with triphosgene in the presence of a suitable base (TEA, DIPEA, etc.), solvent (ethyl acetate (EA), THF, dichloromethane (DCM), etc.), at the temperature (0-50° C.) to give compound 15.
h, Compound 15 and compound 6 in a suitable solvent (EA (ethyl acetate) THF, DCM, dichloromethane, toluene, DMF, etc.) at 20 to 120° C. afford compound 16.

Wherein, $R_1$ is —H, $C_1$~$C_4$ alkyl,

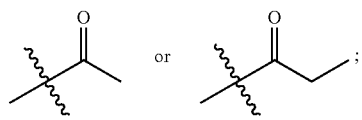

$R_2$ is —H, $C_1$~$C_8$ alkyl,

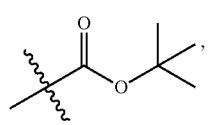 [SMILES: *C(=O)OC(C)(C)C]

$C_3$~$C_8$ alkyl substituted with $R_8$,

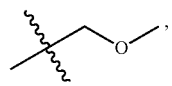 [SMILES: *COC]

$C_3$~$C_8$ epoxyalkyl,

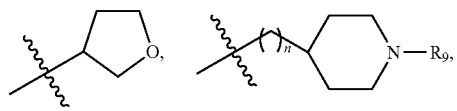

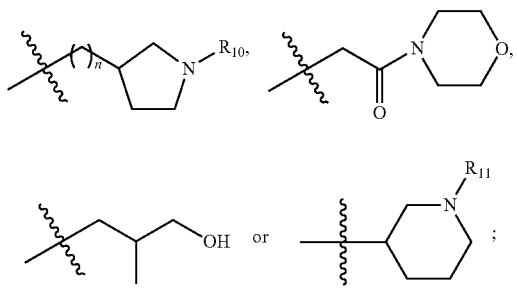

$R_3$~$R_7$ are independently selected from —H, $C_1$~$C_8$ alkyl, —OH, $C_1$~$C_8$ alkoxyl, halogen,

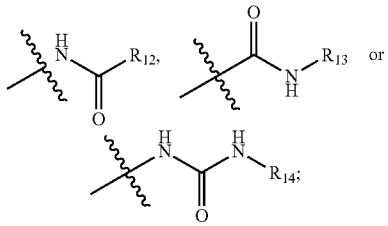

$R_8$~$R_{11}$ independently represent —H, $C_1$~$C_8$ alkyl, halogen, —OH,

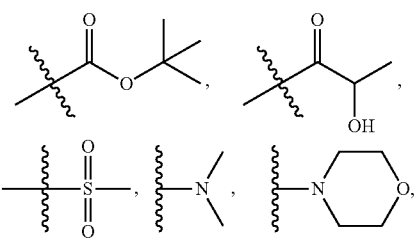

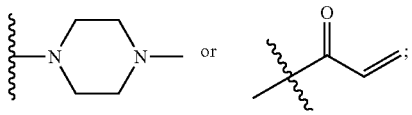

$R_{12}$~$R_{14}$ are

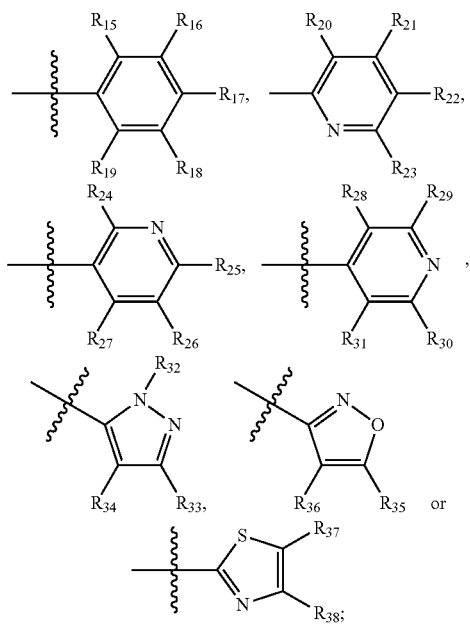

$R_{15}$~$R_{19}$ are independently selected from —H, $C_1$~$C_8$ alkyl, —OH, $C_1$~$C_8$ alkoxyl, halogen, —$CF_3$, —$OCF_3$,

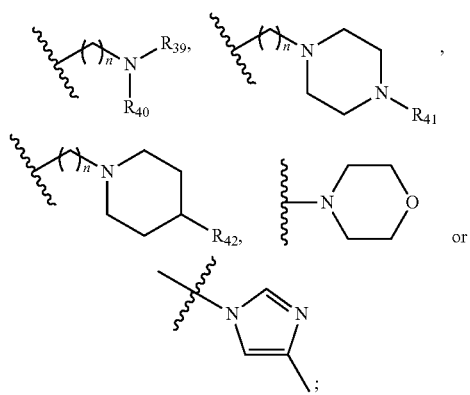

$R_{20}$~$R_{38}$ independently represent —H, halogen, $C_1$~$C_8$ alkyl, $C_1$~$C_8$ cyloalkyl, —$OCF_3$ or —$CF_3$; $R_{39}$~$R_{42}$ are independently selected from $C_1$~$C_8$ alkyl, $C_3$-$C_8$ cycloalkyl $C_1$~$C_8$ hydroxyalkyl; n=0≠6.

3-ethynylpyrazolopyrimidine derivatives previously described of the invention include their isotopic compounds, racemates, optically active isomers, polymorphic forms or mixtures thereof.

The present invention also provides pharmaceutically acceptable salts of the 3-ethynylpyrazolopyrimidine derivatives described above.

The present invention also provides prodrugs of the compounds of the present invention the prodrugs, according to the present invention, are derivatives of the above compounds which may themselves have weak activity or even no activity, and change into a corresponding bioactive form under physiological conditions (e.g., by metabolizing, solvent decomposition or otherwise) after administration.

The present invention also provides pharmaceutically acceptable hydrates of the 3-ethynylpyrazolopyrimidine derivatives described above.

The present invention also provides a pharmaceutical composition prepared by adding pharmaceutically acceptable auxiliary ingredients into 3-ethynylpyrazolopyrimidine derivatives in the present invention. The structure of the 3-ethynylpyrazolopyrimidine derivatives provided by the present invention is shown in Formulas I to V.

The present invention also provides the use of the above 3-ethynyl-pyrazolopyrimidine derivative, its salt or hydrate thereof in the manufacture of kinase inhibitors.

Further, the above-described kinase inhibitors are agents that inhibit at least one kinase in kinases such as SRC family tyrosine kinase (Blk protein tyrosine kinase, Fgr tyrosine protein kinase, Frk protein tyrosine kinase, Fyn protein tyrosine kinase, Hck tyrosine kinase, Lck protein tyrosine kinase, Lyn protein tyrosine kinase, c-SRC tyrosine protein kinase, YES tyrosine kinase), Of FLT3 (human FMS-like tyrosine kinase 3), Abl (Abl tyrosine kinase), VEGFR1 (vascular endothelial growth factor receptor 1), VEGFR2 (vascular endothelial growth factor receptor 2), VEGFR3 (vascular endothelial growth factor receptor 3), RET (RET receptor tyrosine kinase), C-RAF (c-RAF serine/threonine protein kinase), B-RAF (B-RAF serine/threonine protein kinase), c-KIT (tyrosine kinase KIT), PDGFα(platelet-derived growth factor receptor α), PDGFβ (platelet-derived growth factor receptor β), FGFR1 (fibroblast growth factor receptor 1), FGFR2 (fibroblast growth factor receptor 2), FGFR3 (fibroblast growth factor receptor 3), EphA2 (EphA2 tyrosine kinase), EphB2 (EphB2 tyrosine kinase), EphB4 (EphB4 tyrosine kinase), ALK (anaplastic lymphoma kinase), Met (Met tyrosine kinase) DDR1 (DDR1 tyrosine kinase), DDR2 (DDR2 tyrosine kinase), Btk (Btk tyrosine kinase), BMX (BMX tyrosine kinase), TAK1 (transforming growth factor kinase 1), Arg (Arg tyrosine kinase), BRK (BRK tyrosine kinase), CSK (CSK tyrosine kinase), EGFR (T790M) (T790M mutant epidermal growth factor receptor tyrosine kinase), EGFR (T790M, L858R) (T790M, L958R double mutant epidermal growth factor receptor tyrosine kinase), Flt1 (FLT1 tyrosine kinase), Flt4 (Flt4 tyrosine kinase), of LIMK1 (single human serine protein kinase 1), Mer (Mer tyrosine kinase), PTK5 (PTK5 tyrosine kinase), Pyk2 (Pyk2 tyrosine kinase), Ret (Ret tyrosine kinase), SAPK2b (stress-activated protein kinase-2b), Tie2 (Tie2 tyrosine kinase), Txk (Txk tyrosine kinase).

The present invention also provides the use of the above 3-ethynylpyrazolopyrimidine derivatives, salts or hydrates thereof for the preparation of antitumor agents.

Furthermore, the above tumors are leukemia or solid tumors.

Further, the above-mentioned solid tumors are at least one of lung cancer, breast cancer, pancreatic cancer, melanoma, glioma, liver cancer, thyroid tumor, cervical cancer, gastric cancer or colorectal cancer. Among them, the above-mentioned leukemia is acute myeloid leukemia or mixed leukemia.

The 3-ethynylpyrazolopyrimidine derivatives provided by the present invention have a good inhibitory effect on tumors such as human breast cancer, human lung cancer, human pancreatic cancer, human malignant melanoma and human leukemia.

DETAIL DESCRIPTION

Example 1

Figure 1:
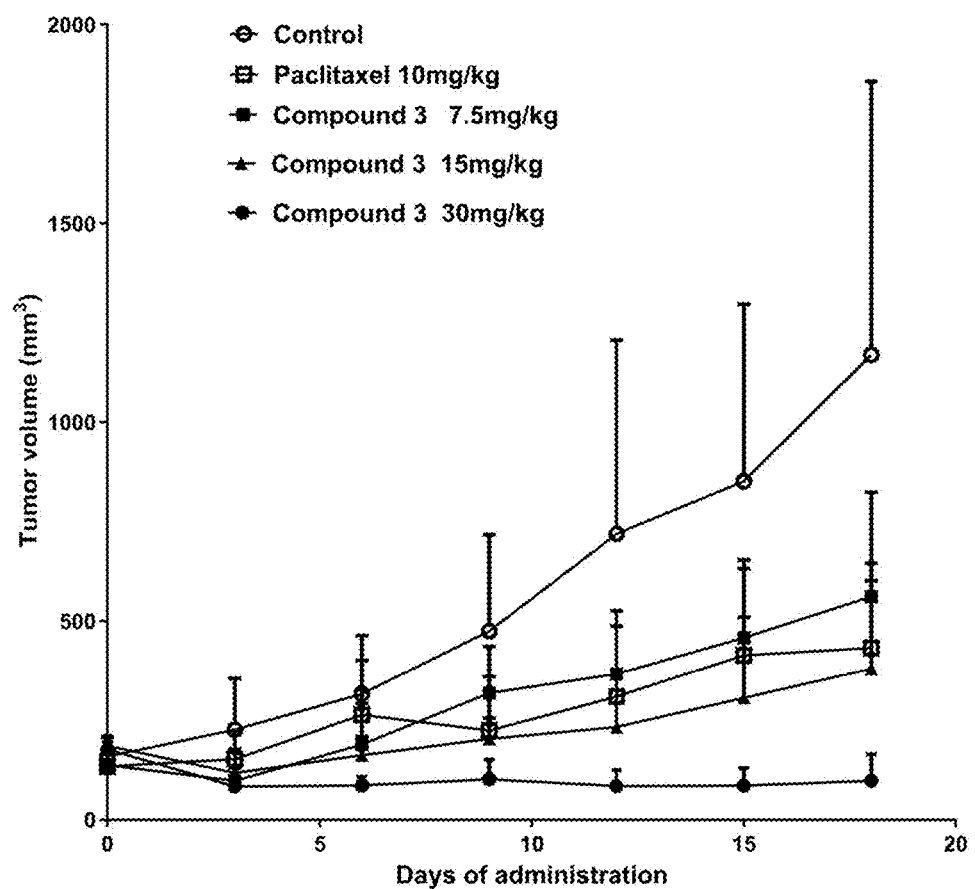
FIG. 1: In vivo pharmacodynamics experiments of Compound 3 against nude mice.

Preparation of 3-ethynyl-1-isopropyl-1H-pyrazolo [3, 4-d]pyrimidin-4-amine (Intermediate 1)

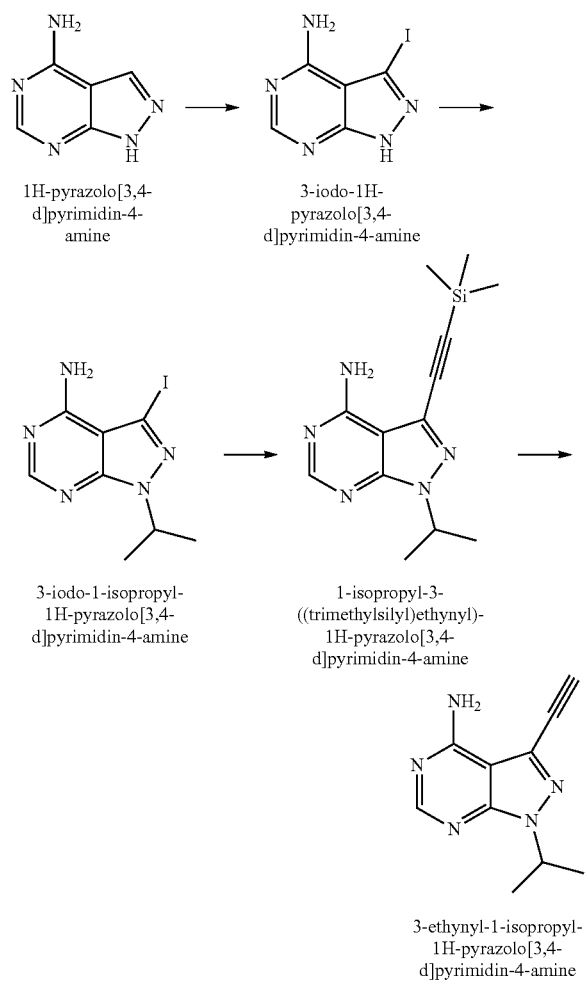

Step 1: Preparation of 3-iodo-1H-pyrazolo [3, 4-d] pyrimidin-4-amine 1H-pyrazolo [3, 4-d] pyrimidin-4-amine (20 g, 148.0 mmol, 1.0 eq) was placed in a three-necked flask. To the flask was added 150 mL of DMF (N, N-dimethylformamide), and the mixture was stirred and replaced with nitrogen 3 times. NIS (N-iodosuccinimide) (50 g, 222.0 mmol, 1.5 eq) was added and the solution was heated at 80° C. The reaction monitored by TLC was completed after 22 h, stopped and the DMF was concentrated to the remaining half of the solution. The mixture was stirred at 150 mL of saturated aqueous $Na_2S_2O_3$ and filtered under reduced pressure. The filter cake was washed successively with saturated aqueous $Na_2S_2O_3$ and water to colorless. The product was dried in vacuo to give the title product as a light yellow powder (33.9 g, 87.8% yield). $^1$H NMR (400 MHz, DMSO-$d_6$) δ 8.17 (s, 1H). MS m/z (ESI): 262.1 [M+H].

Step 2: Preparation of 3-iodo-1-isopropyl-1H-pyrazolo [3, 4-d] pyrimidin-4-amine 3-iodo-1H-pyrazolo [3, 4-d] pyrimidin-4-amine (5 g, 19.2 mmol, 1.0 eq) was placed in a three-necked flask. To the flask was added 40 mL of DMF and potassium carbonate (5.3 g, 38.4 mmol, 2.0 eq), and the mixture was replaced with nitrogen 3 times, then 2-bromopropane (1.9 mL, 20.1 mmol, 1.05 eq) was added and the solution was heated to 80° C. The reaction monitored by TLC was completed after 4 h, and stopped. DMF was then distilled off under reduced pressure, and the residue was extracted with a mixed solvent of DCM (methylene chloride) and water 3 times, then the combined DCM layer was evaporated to dryness, and the product was recrystallized from a mixed solvent of EA (ethyl acetate)/PE (petroleum ether) (1:3 by volume ratio) to give the desired product as yellowish powder. The desired product in recrystallization mother liquor was also obtained by column chromatography (5.4 g, 92.8% yield). $^1$H NMR (400 MHz, DMSO-$d_6$) δ 8.19 (s, 1H), 4.99-4.93 (m, 1H), 1.42 (d, J=6.7 Hz, 6H). MS m/z (ESI): 304.0 [M+H].

Step 3: Preparation of 1-isopropyl-3-((trimethylsilyl) ethynyl)-1H-pyrazolo [3, 4-d]pyrimidin-4-amine 3-iodo-1-isopropyl-1H-pyrazolo [3, 4-d] pyrimidin-4-amine (5.4 g, 17.8 mmol, 1.0 eq) was placed in a three-necked flask. To the flask was added 40 mL of DMF, CuI (339 mg, 1.78 mmol, 0.1 eq) Pd(PPh$_3$)$_4$ (1 g, 0.89 mmol, 0.05 eq) and the solution was raised to 80° C. for 2.5 h. The reaction monitored TLC was completed, and then the DMF was distilled off under reduced pressure and the remaining residue was separated by column chromatography to give the desired product directly for the next step reaction. MS m/z (ESI): 274.2 [M+H].

Step 4: Preparation of 3-ethynyl-1-isopropyl-1H-pyrazolo [3, 4-d] pyrimidin-4-amine 1-isopropyl-3-((trimethylsilyl)ethynyl)-1H-pyrazolo[3,4-d]pyrimidin-4-amine in 20 mL MeOH (methanol), to the solution was added potassium carbonate (4.9 g, 35.6 mmol, 2.0 eq), and the mixture was stirred at room temperature for 10 min. The reaction monitored by TLC was completed, and MeOH was distilled off under reduced pressure and the mixture was dispersed in water. The aqueous layer was washed with DCM 3 times, and the DCM layers were combined and evaporated to dryness. The intermediate 1 was isolated by column chromatography as a light gray powder (1.6 g, yield 44.7%) $^1$H NMR (400 MHz, DMSO-d$_6$) δ 8.22 (s, 1H), 5.02-4.98 (m, 1H), 4.62 (s, 1H), 1.44 (d, J=6.7 Hz, 6H). MS m/z (ESI): 202.1 [M+H].

Example 2

Preparation of Intermediates 2 to 10

The following intermediates 2 to 10 were obtained, using different halogenated alkanes reaction with 1H-pyrazolo [3,4-d] pyrimidin-4-amine, by adding cesium carbonate, potassium carbonate, DIPEA (diisopropylethylamine) or other inorganic or organic base, PdCl$_2$(PPh$_3$)$_2$ or Pd(PPh$_3$)$_4$, by a method similar to the preparation of intermediate 1.

| No. | Structure | $^1$H-NMR | ESI$^+$ [M + H] |
|---|---|---|---|
| Intermediate 2 | 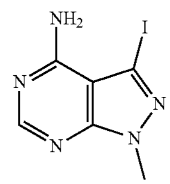 | $^1$H NMR (400 MHz, DMSO-d$_6$) δ 8.21 (s, 1H), 3.88 (s, 3H). | 275.9 |
| Intermediate 3 | 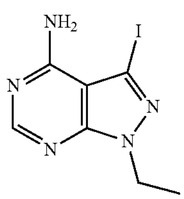 | $^1$H NMR (400 MHz, DMSO-d$_6$) δ 8.20 (s, 1H), 4.30 (q, J = 7.2 Hz, 2H), 1.35 (t, J = 7.2 Hz, 3H). | 290.0 |
| Intermediate 4 | 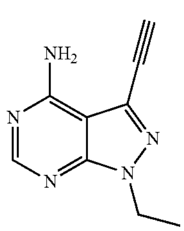 | $^1$H NMR (400 MHz, DMSO-d$_6$) δ 8.23 (s, 1H), 4.63 (s, 1H), 4.32 (q, J = 6.8 Hz, 2H), 1.37 (t, J = 6.8 Hz, 3H). | 188.2 |
| Intermediate 5 | 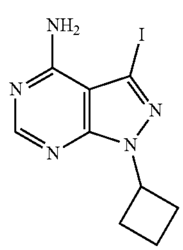 [SMILES: Nc1ncnc2c1c(I)nn2C1CCC1] | $^1$H NMR (400 MHz, DMSO-d$_6$) δ 8.19 (s, 1H), 5.32-5.13 (m, 1H), 2.71-2.54 (m, 2H), 2.36 (d, J = 4.7 Hz, 2H), 1.93-1.76 (m, 2H). | 316.1 |
| Intermediate 6 | 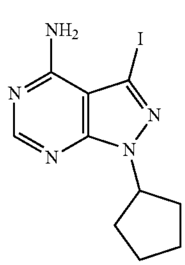 [SMILES: Nc1ncnc2c1c(I)nn2C1CCCC1] | $^1$H NMR (400 MHz, DMSO-d$_6$) δ 8.19 (s, 1H), 5.28-4.97 (m, 1H), 2.09-2.00 (m, 2H), 1.99-1.88 (m, 2H), 1.88-1.78 (m, 2H), 1.72-1.59 (m, 2H). | 330.1 |
| Intermediate 7 | | $^1$H NMR (400 MHz, DMSO-d$_6$) δ 8.26 (s, 1H), 5.54 (s, 2H), 3.26 (s, 3H). | 306.0 |
| Intermediate 8 | | $^1$H NMR (400 MHz, DMSO-d$_6$) δ 8.20 (s, 1H), 4.64 (t, J = 5.3 Hz, 1H), 4.31-4.26 (m, 1H), 4.13-4.08 (m, 1H), 3.30 (t, J = 5.6 Hz, 2H), 2.19-2.14 (m, 1H), 0.75 (d, J = 6.8 Hz, 3H). | 334.4 |
| Intermediate 9 | | $^1$H NMR (400 MHz, DMSO-d$_6$) δ 8.20 (s, 1H), 4.64 (t, J = 5.3 Hz, 1H), 4.34-4.26 (m, 1H), 4.13-4.08 (m, 1H), 3.30 (t, J = 5.6 Hz, 2H), 2.20-2.12 (m, 1H), 0.75 (d, J = 6.8 Hz, 3H). | 334.3 |
| Intermediate 10 | | $^1$H NMR (400 MHz, DMSO-d$_6$) δ 8.18 (s, 1H), 5.29 (s, 2H), 3.65 (s, 2H), 3.57 (s, 4H), 3.41 (s, 2H). | 389.1 |

Example 3

Preparation of 3-iodo-1-(1-(methylsulfonyl)piperidin-3-yl)-1H-pyrazolo[3,4-d]pyrimidin-4-amine (Intermediate 11)

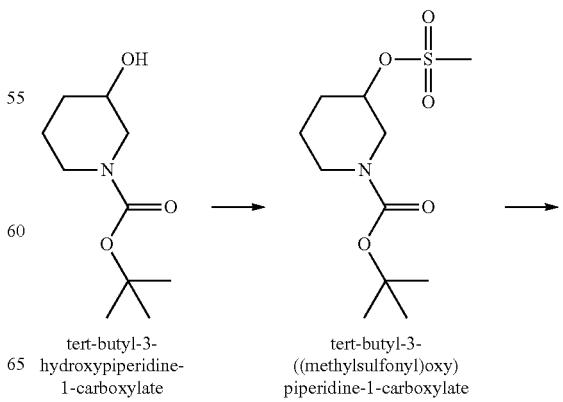

tert-butyl-3-hydroxypiperidine-1-carboxylate tert-butyl-3-((methylsulfonyl)oxy)piperidine-1-carboxylate -continued

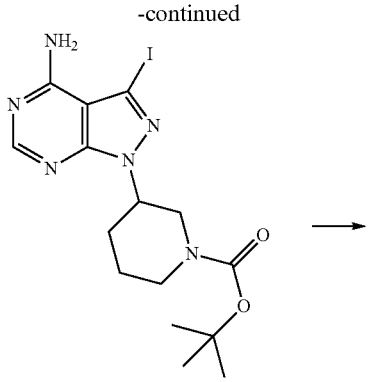

tert-butyl 3-(4-amino-3-iodo-1H-pyrazolo[3,4-d]pyrimidin-1-yl)piperidine-1-carboxylate

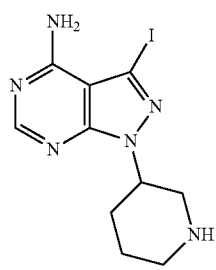

3-iodo-1-(piperidin-3-yl)-1H-pyrazolo[3,4-d]pyrimidin-1-amine

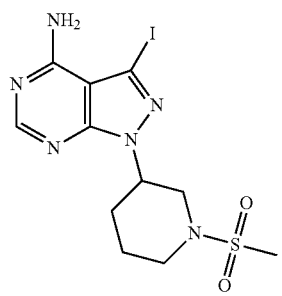

3-iodo-1-(1-(methylsulfonyl)piperidin-3-yl)-1H-pyrazolo[3,4-d]pyrimidin-4-amine

Step 1: Preparation of tert-butyl 3-((methylsulfonyl) oxy) piperidine-1-carboxylate The solution of N-Boc-3-hydroxypiperidine (2.1 g, 10 mmol, 1.0 eq) and DIPEA (2.1 mL, 15 mmol, 1.5 eq) in 20 mL DCM was stirred. To the solution was slowly added dropwise methanesulfonyl chloride (1.0 mL, 13 mmol, 1.3 eq) after cooling to 0° C., and mixture was allowed to raise to room temperature. Then the reaction mixture was washed successively with a 1 M HCl solution, saturated aqueous sodium bicarbonate solution, saturated aqueous sodium chloride solution and water. The obtained DCM layer was dried over anhydrous magnesium sulfate, filtered and evaporated to dryness to give the product as a yellow solid (2.65 g, 95.1% yield). MS m/z (ESI): 280.1 [M+H].

Step 2: Preparation of tert-butyl 3-(4-amino-3-iodo-1H-pyrazolo [3, 4-d]pyrimidin-1-yl)-piperidine-1-carboxylate 3-iodo-pyrazolo [3, 4-d]pyrimidin-4-amine (2.4 g, 9.2 mmol, 1.0 eq), tert-butyl 3-((methanesulfonyl) oxo) piperidine-1-carboxylate (3.1 g, 11 mmol, 1.2 eq), cesium carbonate (6.0 g, 18.4 mmol, 2.0 eq) in 50 mL of DMF was purged with nitrogen for 3 times and the solution was heated to 80° C. for 3 h. the reaction was monitored by TLC, and the residue obtained was evaporated to dryness. To the residue water was added and the aqueous layer was extracted with DCM until no product. The combined DCM layers were evaporated to dryness, and the product was purified by column chromatography as a light yellow solid (2.9 g, 73.4% yield). $^1$H NMR (400 MHz, CDCl$_3$) δ 8.31 (s, 1H), 6.12 (s, 2H), 4.78-4.70 (m, 1H), 4.31 (br.s, 1H), 4.12 (br.s, 1H), 3.36 (br.s, 1H), 2.83 (t, J=12.0 Hz, 1H), 2.30-1.94 (m, 2H), 1.87 (d, J=13.0 Hz, 1H), 1.74-1.54 (m, 1H), 1.44 (s, 9H). MS m/z (ESI): 445.1 [M+H].

Step 3: Preparation of 3-iodo-1-(piperidin-3-yl)-1H-pyrazolo[3,4-d]pyrimidin-4-amine (4-amino-3-iodo-1H-pyrazolo [3, 4-d] pyrimidin-1-yl) piperidine-1-carboxylate (2.9 g) was dissolved in 35 mL of methanol. To the solution 4M HCl dioxane solution 35 mL was added, and the mixture was stirred at room temperature for 8 h then precipitated. The reaction solution was cooled to 0° C. and filtered under reduced pressure. Filter cake was dispersed in water, and the pH was adjusted to 8. The solid was obtained under vacuum filtration, washed with water, evaporated to dryness in ethanol under reduced pressure and dried in vacuo to give the desired product (2.2 g, 93.1% yield). MS m/z (ESI): 345.1 [M+H].

Step 4: Preparation of 3-iodo-1-(1-(methylsulfonyl) piperidin-3-yl)-1H-pyrazolo [3, 4-d]-pyrimidin-4-amine 3-iodo-1-(piperidin-3-yl)-1H-pyrazolo [3,4-d]pyrimidin-4-amine (172.1 mg, 0.5 mmol, 1.0 eq) in 4 mL DCM was added DIPEA ((0.7.3 mg, 0.5 mmol, 1.0 eq), and the mixture was stirred at 0° C. Methanesulfonyl chloride (57.3 mg, 0.5 mmol, 1.0 eq) was slowly added dropwise and the reaction was monitored by TLC, washed successively with saturated aqueous sodium bicarbonate solution, saturated aqueous sodium chloride solution and water. The DCM layer was dried over anhydrous magnesium sulfate, filtered and evaporated to dryness to afford intermediate 11 as a white powder (197.8 mg, 93.7% yield). $^1$H NMR (400 MHz, DMSO-d$_6$) δ 8.23 (s, 1H), 4.83-4.65 (m, 1H), 3.69 (d, J=7.2 Hz, 1H), 3.59 (d, J=11.1 Hz, 1H), 3.07 (t, J=10.9 Hz, 1H), 2.91 (s, 3H), 2.80 (t, J=10.9 Hz, 1H), 2.45-2.00 (m, 2H), 1.95 (d, J=13.6 Hz, 1H), 1.76-1.59 (m, 1H). MS m/z (ESI): 423.0 [M+H].

Example 4

Preparation of Intermediate 12~19

The following intermediates 12 to 19 were obtained by a method similar to the preparation of intermediate 11 using different alkyl alcohol or alkyl sulfonate reaction with 1H-pyrazolo [3,4-d] pyrimidin-4-amine, by adding cesium carbonate, potassium carbonate or other inorganic or organic base, methanesulfonyl chloride or p-nitromethanesulfonyl chloride, HCl ethanol solution, HCl ether solution, trifluoroacetic acid and other raw materials.

| No. | Structure | ¹H-NMR | ESI⁺ [M + H] |
|---|---|---|---|
| Intermediate 12 | 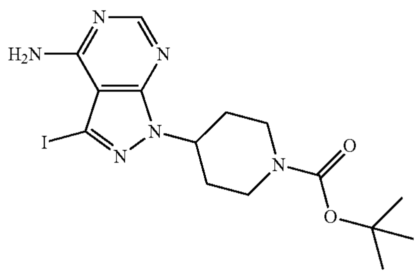 [SMILES: CC(C)(C)OC(=O)N1CCC(n2nc(I)c3c(N)ncnc32)CC1] | ¹H NMR (400 MHz, DMSO-d₆) δ 8.20 (s, 1H), 4.87-4.75 (m, 1H), 4.06 (d, J = 10.8 Hz, 2H), 2.95 (br.s, 2H), 1.99-1.81 (m, 4H), 1.43 (s, 9H). | 445.3 |
| Intermediate 13 | 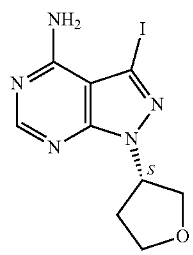 | ¹H NMR (400 MHz, DMSO-d₆) δ 8.21 (s, 1H), 5.50-5.28 (m, 1H), 4.10-3.96 (m, 2H), 3.92-3.80 (m, 2H), 2.43-2.23 (m, 2H). | 332.1 |
| Intermediate 14 | 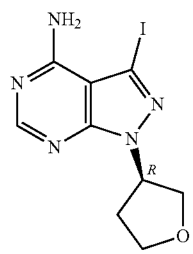 | ¹H NMR (400 MHz, DMSO-d₆) δ 8.21 (s, 1H), 5.60-5.28 (m, 1H), 4.15-3.96 (m, 2H), 3.94-3.76 (m, 2H), 2.44-2.22 (m, 2H). | 332.1 |
| Intermediate 15 | 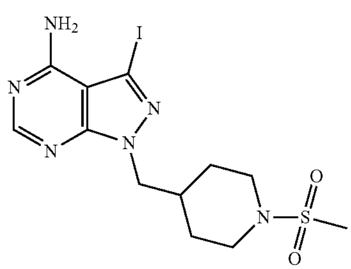 [SMILES: CS(=O)(=O)N1CCC(Cn2nc(I)c3c(N)ncnc32)CC1] | ¹H NMR (400 MHz, DMSO-d₆) δ 8.20 (s, 1H), 4.21 (d, J = 7.0 Hz, 2H), 3.46-3.56 (m, 2H), 2.82 (s, 3H), 2.58-2.72 (m, 2H), 1.94-2.10 (m, 1H), 1.50-1.64 (m, 2H), 1.14-1.34 (m, 2H). | 437.1 |
| Intermediate 16 | 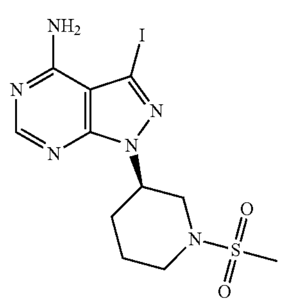 [SMILES: CS(=O)(=O)N1CCC[C@@H](n2nc(I)c3c(N)ncnc32)C1] | ¹H NMR (400 MHz, DMSO-d₆) δ 8.23 (s, 1H), 4.84-4.64 (m, 1H), 3.70 (dd, J = 11.0, 4.0 Hz, 1H), 3.59 (d, J = 11.4 Hz, 1H), 3.18-3.00 (m, 1H), 2.91 (s, 3H), 2.85-2.76 (m, 1H), 2.17-2.01 (m, 2H), 2.01-1.91 (m, 1H), 1.77-1.64 (m, 1H). | 423.0 |
| Intermediate 17 | 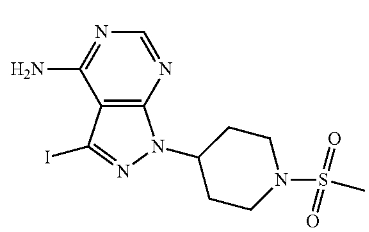 [SMILES: CS(=O)(=O)N1CCC(n2nc(I)c3c(N)ncnc32)CC1] | ¹H NMR (400 MHz, DMSO-d₆) δ 8.21 (s, 1H), 4.83-4.68 (m, 1H), 3.69 (d, J = 11.9 Hz, 2H), 3.06-2.95 (m, 2H), 2.93 (s, 3H), 2.16-2.01 (m, 2H), 2.00 (d, J = 9.5 Hz, 2H). | 423.0 |

| No. | Structure | ¹H-NMR | ESI⁺ [M + H] |
|---|---|---|---|
| Intermediate 18 | 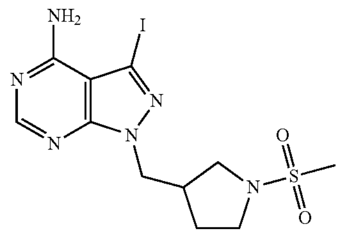 [SMILES: CS(=O)(=O)N1CCC(Cn2nc(I)c3c(N)ncnc32)C1] | ¹H NMR (400 MHz, DMSO-d₆) δ 8.14 (s, 1H), 4.25 (dd, J = 7.1, 2.6 Hz, 2H), 3.27-3.18 (m, 2H), 3.13 (t, J = 8.8 Hz, 1H), 2.96 (dd, J = 10.0, 7.1 Hz, 1H), 2.81 (s, 3H), 2.68 (dd, J = 14.6, 7.4 Hz, 1H), 1.87-1.75 (m, 1H), 1.62-1.52 (m, 1H). | 423.0 |
| Intermediate 19 | 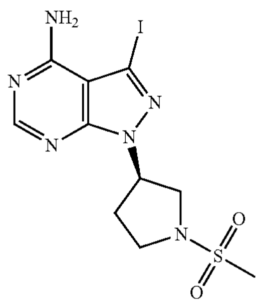 [SMILES: CS(=O)(=O)N1CC[C@@H](n2nc(I)c3c(N)ncnc32)C1] | ¹H NMR (400 MHz, DMSO-d₆) δ 8.23 (s, 1H), 5.51-5.37 (m, 1H), 3.81-3.77 (m, 1H), 3.61-3.49 (m, 2H), 3.48-3.43 (m, 1H), 2.96 (s, 3H), 2.46-2.28 (m, 2H). | 409.0 |

Example 5

Preparation of (R)-3-iodo-1-(1-methylpiperidin-3-yl)-1H-pyrazolo [3, 4-d]pyrimidin-4-amine (Intermediate 20)

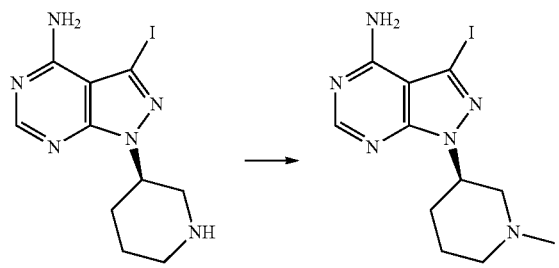 [SMILES: Nc1ncnc2c1c(I)nn2[C@@H]1CCCNC1 ; CN1CCC[C@@H](n2nc(I)c3c(N)ncnc32)C1]

(R)-3-iodo-1-(piperidin-3-yl)-1H-pyrazolo [3,4-d] pyrimidin-4-amine (750 mg, 2 mmol, 1.0 eq) was dissolved in 18 mL mixed solvent of dichloroethane/methanol (8:1 by volume ratio). Aqueous formaldehyde solution (37%, 0.82 mL, 10 mmol, 5.0 eq) was added dropwise and the mixture was stirred at room temperature for 10 min, and NaBH₃CN (502.7 mg, 8 mmol, 4.0 eq) was added in two batches. After 10 min the reaction monitored by was completed TLC. To the solution 3 mL water was added dropwise. After the addition, the solvent was evaporated to dryness under reduced pressure. The obtained residue was dispersed in water, and the pH was adjusted to alkaline. Then the solid was filtered, washed with water and evaporated to dryness under reduced pressure in ethanol. The residue obtained was recrystallized to give intermediate 20 as a white powder (500 mg, 70.0% yield). ¹H NMR (400 MHz, DMSO-d₆) δ 8.20 (s, 1H), 4.73-4.66 (m, 1H), 4.41 (t, J=4.8 Hz, 1H), 3.48-3.41 (m, 1H), 2.88 (dd, J=11.1, 3.7 Hz, 1H), 2.77 (d, J=11.1 Hz, 1H), 2.21 (s, 3H), 1.97-1.72 (m, 3H), 1.71-1.61 (m, 1H). MS m/z (ESI): 359.1 [M+H].

Example 6

Preparation of Intermediate 21~24

The following intermediates 21 to 24 were obtained by a method similar to the preparation of intermediate 20 using different secondary amines containing aryl groups reaction with 1H-pyrazolo[3,4-d] pyrimidin-4-amine with addition alkyl aldehydes or aryl aldehydes and so on.

| No. | Structure | ¹H-NMR | ESI⁺ [M + H] |
|---|---|---|---|
| Intermediate 21 | 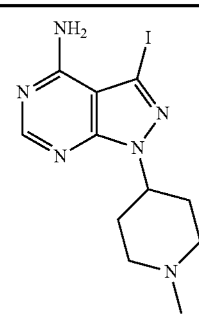 | ¹H NMR (400 MHz, CDCl₃) δ 8.31 (s, 1H), 4.76-4.58 (m, 1H), 3.03 (d, J = 11.5 Hz, 2H), 2.43-2.32 (m, 5H), 2.23 (t, J = 11.2 Hz, 2H), 2.00 (d, J = 11.2 Hz, 2H). | 359.1 |
| Intermediate 22 | 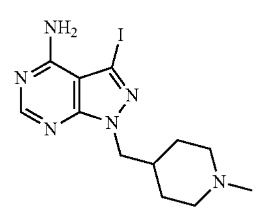 [SMILES: CN1CCC(Cn2nc(I)c3c(N)ncnc32)CC1] | ¹H NMR (400 MHz, DMSO-d₆) δ 8.20 (s, 1H), 4.16 (d, J = 6.9 Hz, 2H), 2.69 (d, J = 10.9 Hz, 2H), 2.11 (s, 3H), 1.90-1.65 (m, 3H), 1.42 (d, J = 11.5 Hz, 2H), 1.30-1.12(m, 2H). | 373.1 |

-continued

| No. | Structure | ¹H-NMR | ESI⁺ [M + H] |
|---|---|---|---|
| Intermediate 23 | ![structure] | ¹H NMR (400 MHz, DMSO-d₆) δ 8.20 (s, 1H), 4.22 (d, J = 7.4 Hz, 2H), 2.74-2.62 (m, 1H), 2.51-2.44 (m, 1H), 2.39-2.24 (m, 3H), 2.19 (s, 3H), 1.84-1.72 (m, 1H), 1.52-1.40 (m, 1H). | 359.1 |
| Intermediate 24 | ![structure] | ¹H NMR (400 MHz, DMSO-d₆) δ 8.21 (s, 1H), 5.35-5.22 (m, 1H), 2.96 (t, J = 8.5 Hz, 1H), 2.74-2.61 (m, 3H), 2.38-2.24 (m, 4H), 2.25-2.11 (m, 1H). | 345.1 |

Example 7

Preparation of N, 1-diethyl-3-iodo-1H-pyrazolo [3,4-d] pyrimidin-4-amine (Intermediate 25)

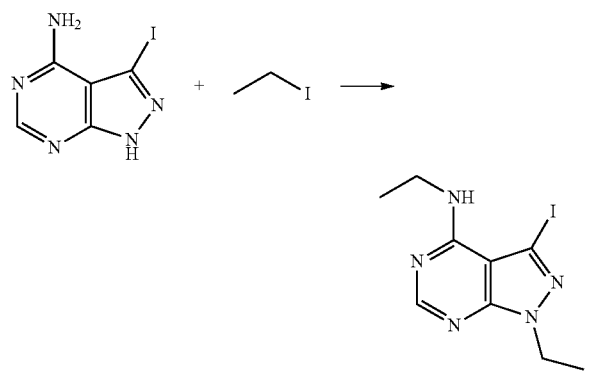

3-iodo-1H-pyrazolo [3,4-d] pyrimidin-4-amine (2.6 g, 10 mmol, 1.0 eq) placed in a three-neck flask, and to the flask 35 mL DMF and cesium carbonate (9.8 g, 30 mmol, 3.0 eq) was added. The mixture was replaced with nitrogen for 3 times, and ethyl iodine (2.0 mL, 25 mmol, 2.5 eq) was added. The mixture heated to 100° C. for 10 h. The reaction monitored by TLC was completed, stopped and the DMF was distilled off under reduced pressure. The residue obtained was extracted with mixed solvent of DCM (dichloromethane) and water 3 times. The DCM layer combined was evaporated to dryness, and separated by column chromatography to give intermediate 25 as an off-white powder (1.75 g, 55.1% yield). MS m/z (ESI): 318.0 [M+H].

Example 8

Preparation of (R)-1-((R)-3-(4-amino-3-iodo-1H-pyrazolo[3,4-d]pyrimidin-1-yl)piperidin-1-yl)-2-Hydroxypropan-1-one (Intermediate 26)

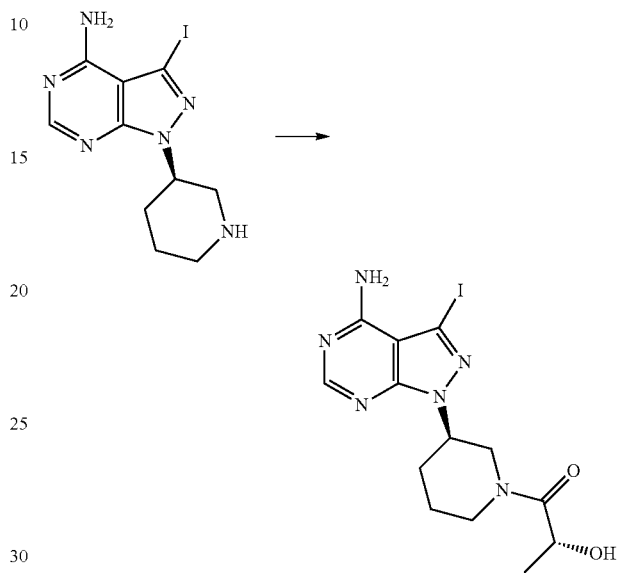

D-2-hydroxypropionic acid (157 mg, 1.74 mmol, 1.2 eq), HOBT (1-hydroxybenzotriazole) (235.1 mg, 1.74 mmol, 1.2 eq), and EDCI (1-ethyl-3-(3-dimethylaminopropyl) carbodiimide hydrochloride) (417 mg, 2.2 mmol, 1.5 eq) was dissolved in DMF. To the solution triethylamine (0.61 mL, 4.35 mmol, 3.0 eq) was added, and the mixture was stirred at room temperature for 0.5 h. To the solution (R)-3-iodo-1-(piperidin-3-yl)-1H-pyrazolo[3,4-d]pyrimidin-4-amine (500 mg, 1.45 mmol, 1.0 eq) was added and stirred at room temperature for about 5 h. The DMF was distilled off, and the residue was extracted with saturated aqueous sodium bicarbonate solution and methylene chloride twice. The organic layer was combined and evaporated, and the residue was separated by column chromatography to give intermediate 26 as a white solid (442 mg, yield 73.3%). ¹H NMR (400 MHz, DMSO-d₆) δ 8.22 (s, 1H), 5.04-4.94 (m, 1H), 4.77-4.51 (m, 1H), 4.50-4.44 (m, 1H), 4.40-4.26 (m, 1H), 4.19-4.03 (m, 1H), 3.13-2.98 (m, 1H), 2.76 (t, J=12.1 Hz, 1H), 2.25-2.11 (m, 1H), 2.06-2.04 (m, 1H), 1.86 (t, J=13.8 Hz, 1H), 1.62-1.49 (m, 1H), 1.24-1.13 (m, 3H). MS m/z (ESI): 417.1 [M+H].

Example 9

Preparation of Intermediate 27~32

The following intermediates 27 to 32 were obtained by a method similar to the preparation of intermediate 25 using different secondary amines with aryl groups and different configurations of lactic acids.

| No. | Structure | ¹H-NMR | ESI⁺ [M + H] |
|---|---|---|---|
| Intermediate 27 | (structure) | ¹H NMR (400 MHz, DMSO-d₆) δ 8.22 (s, 1H), 5.09-4.81 (m, 1H), 4.78-4.53 (m, 1H), 4.52-4.42 (m, 1H), 4.42-4.31 (m, 1H), 4.30-3.88 (m, 1H), 3.22-3.04 (m, 1H), 2.83-2.58 (m, 1H), 2.29-2.11 (m, 1H), 2.05 (d, J = 11.8 Hz, 1H), 1.93-1.76 (m, 1H), 1.71-1.41 (m, 1H), 1.29-1.19 (m, 3H). | 417.1 |
| Intermediate 28 | (structure) | ¹H NMR (400 MHz, DMSO-d₆) δ 8.22 (d, J = 4.9 Hz, 1H), 4.96-4.87 (m, 1H), 4.74-4.51 (m, 1H), 4.49-4.44 (m, 1H), 4.37 (t, J = 9.5 Hz, 1H), 4.18-3.97 (m, 1H), 3.16-3.09 (m, 1H), 2.79-2.62 (m, 1H), 2.22-2.14 (m, 1H), 2.06 (d, J = 7.0 Hz, 1H), 1.91-1.84 (m, 1H), 1.69-1.49 (m, 1H), 1.21 (t, J = 7.3 Hz, 3H). | 417.1 |
| Intermediate 29 | (structure) | ¹H NMR (400 MHz, DMSO-d₆) δ 8.21 (s, 1H), 4.95-4.87 (m, 2H), 4.48 (s, 2H), 4.15 (t, J = 15.2 Hz, 1H), 3.26-3.18 (m, 1H), 2.86-2.79 (m, 1H), 2.08-1.99 (m, 1H), 1.92 (br.s, 3H), 1.24-1.19 (m, 3H). | 417.1 |
| Intermediate 30 | (structure) | ¹H NMR (400 MHz, DMSO-d₆) δ 8.21 (s, 1H), 5.04-4.82 (m, 2H), 4.48 (s, 2H), 4.25-4.05 (m, 1H), 3.28-3.12 (m, 1H), 2.87-2.73 (m, 1H), 2.13-1.98 (m, 1H), 1.92 (s, 3H), 1.26-1.14 (m, 3H). | 417.1 |
| Intermediate 31 | (structure) | ¹H NMR (400 MHz, DMSO-d₆) δ 8.22 (d, J = 2.5 Hz, 1H), 5.48-5.32 (m, 1H), 4.95-4.88 (m, 1H), 4.38-4.17 (m, 1H), 4.00-3.88 (m, 1H), 3.85-3.58 (m, 3H), 2.45-2.38 (m, 1H), 2.38-2.23 (m, 1H), 1.23-1.16 (m, 3H). | 403.2 |
| Intermediate 32 | (structure) | ¹H NMR (400 MHz, DMSO-d₆) δ 8.23 (d, J = 1.5 Hz, 1H), 5.52-5.27 (m, 1H), 4.95-4.91 (m, 1H), 4.36-4.28 (m, 1H), 4.11-4.06 (m, 1H), 3.94-3.75 (m, 1H), 3.75-3.62 (m, 1H), 3.60-3.49 (m, 1H), 2.43-2.38 (m, 1H), 2.35-2.30 (m, 1H), 1.22-1.15 (m, 3H). | 403.2 |

Example 10

Preparation of cis/trans-4-(4-amino-3-iodo-1H-pyrazolo [3, 4-d]pyrimidin-1-yl)cyclohexane-1-ol (Intermediates 33 and 34)

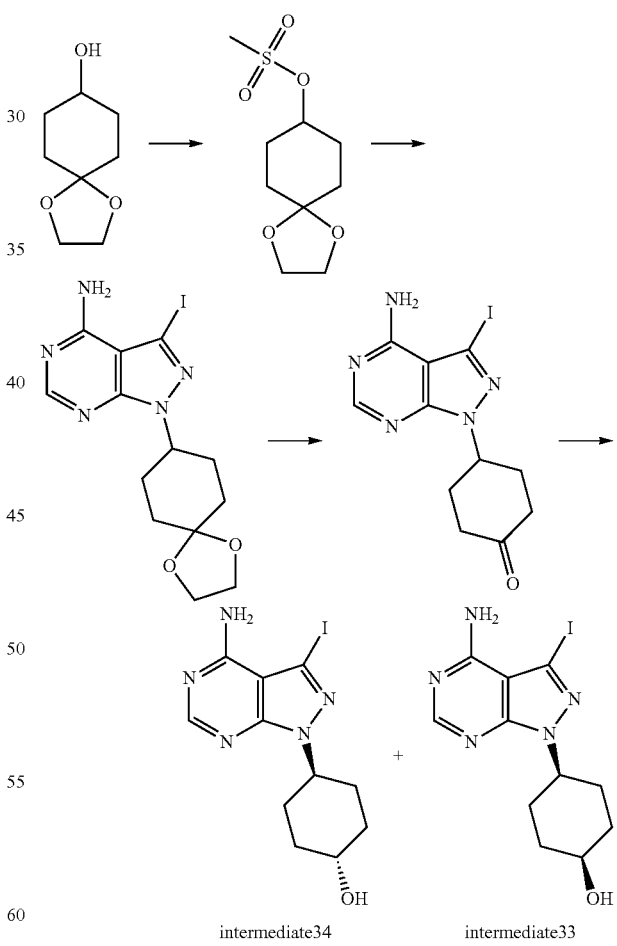

intermediate34   intermediate33

Step 1

The target product was synthesized using 4-hydroxycyclohexanone ethylene glycol acetal and methylsulfonyl chloride as the starting material by referring to the method described in Step 1 of Example 3. MS m/z (ESI): 236.1 [M+H].

Step 2: Preparation of 3-iodo-1-(1,4-dioxaspiro [4.5] decan-8-yl) 1H-pyrazolo[3,4-d]pyrimidin-4-amine The target product was synthesized using 1,4-dioxaspiro [4.5] decan-8-yl methanesulfonate and 3-iodo-1H-pyrazolo [3, 4-d] pyrimidine-4-amine as the starting material by referring to the method described in Step 2 of Example 3. $^1$H NMR (400 MHz, DMSO-d$_6$) δ 8.19 (s, 1H), 4.79-4.63 (m, 1H), 3.98-3.82 (m, 4H), 2.19-2.11 (m, 2H), 1.91-1.64 (m, 6H). MS m/z (ESI): 402.2 [M+H].

Step 3: Preparation of 4-(4-amino-3-iodo-1H-pyrazolo [3,4-d] pyrimidin-1-yl) cyclohexane-1-one To a solution of 3-iodo-1-(1,4-dioxaspiro[4.5]decan-8-yl)-1H-pyrazolo[3,4-d] pyrimidin-4-amine (1.94 g, 4.84 mmol) in 40 mL of acetone was added 20 mL 1M HCl, and the solution was stirred at 70° C. for 3 h, and cooled to room temperature overnight. Acetone was distilled off under reduced pressure and the remaining aqueous solution was adjusted to pH 10. A large amount of precipitated solid was filtered and dried to give the desired product as a white solid (1.68 g, 97.1% yield). $^1$H NMR (400 MHz, DMSO-d$_6$) δ 8.27 (s, 1H), 5.21-5.15 (m, 1H), 2.75-2.61 (m, 2H), 2.37-2.26 (m, 4H), 2.20-2.17 (m, 2H). MS m/z (ESI): 358.1 [M+H].

Step 4: Preparation of 4-(4-amino-3-iodo-1H-pyrazolo[3,4-d]pyrimidin-1-yl) cyclohexane-1-ol 4-(4-amino-3-iodo-1H-pyrazolo[3,4-d] pyrimidin-1-yl) cyclohexane-1-one (1.68 g, 4.7 mmol, 1.0 eq) in methanol at 0° C., was added sodium borohydride (183 mg, 4.7 mmol, 1.0 eq) in portions, and the reaction was allowed to warm to room temperature. The reaction was completed 1 h later. After addition of 5 mL of water, the mixture was stirred for 5 min and evaporated to dryness. The residue obtained was extracted with methylene chloride and saturated aqueous sodium bicarbonate and the intermediate was obtained by column chromatography. The front point (Rf=0.63, DCM/MeOH=8) cis-4-(4-amino-3-iodo-1H-pyrazolo [3, 4-d]pyrimidin-1-yl) cyclohexane-1-ol as a white solid (375 mg, 22.2% yield). $^1$H NMR (400 MHz, DMSO-d$_6$) δ 8.19 (s, 1H), 4.64-4.60 (m, 1H), 4.49 (d, J=2.4 Hz, 1H), 3.88 (s, 1H), 2.41-2.20 (m, 2H), 1.87-1.69 (m, 2H), 1.66-1.57 (m, 4H). MS m/z (ESI): 360.2 [M+H]. The rear point (Rf=0.55, DCM/MeOH=8) intermediate 34 trans-4-(4-amino-3-iodo-1H-pyrazolo [3,4-d] pyrimidin-1-yl) cyclohexane-1-ol, a white solid (844 mg, 50.1% yield). $^1$H NMR (400 MHz, DMSO-d$_6$) δ 8.19 (s, 1H), 4.68 (d, J=4.3 Hz, 1H), 4.62-4.50 (m, 1H), 3.56-3.49 (m, 1H), 2.03-1.79 (m, 5H), 1.46-1.29 (m, 3H). MS m/z (ESI): 360.2 [M+H].

Example 11

Preparation of N-(3-iodo-4-methylphenyl)-4-((4-methylpiperazin-1-yl)methyl)-3-(trifluoromethyl) benzamide (Intermediate 35)

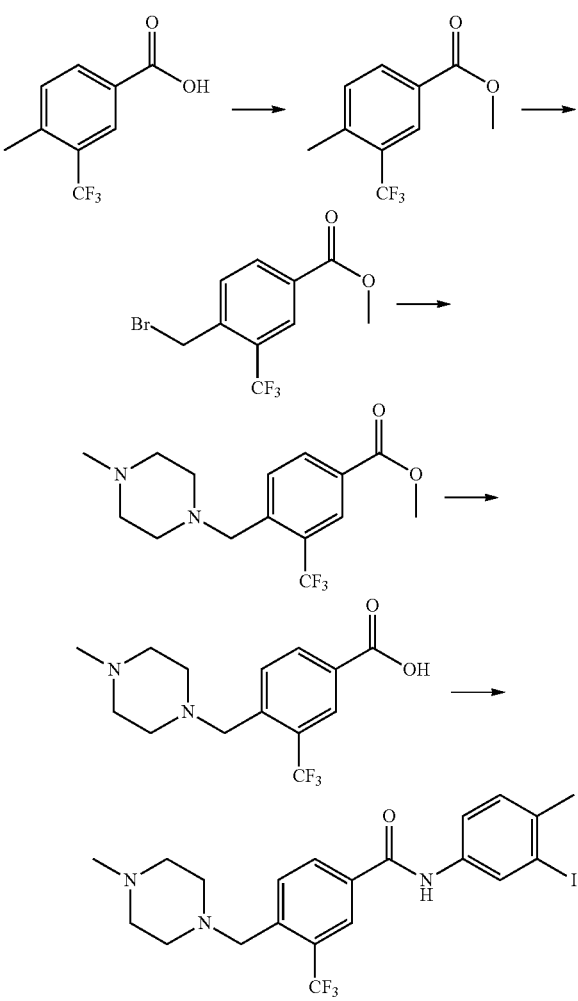

Step 1: Preparation of 4-methyl-3-benzoate 4-methyl-3-(trifluoromethyl) benzoic acid (2.04 g, 10 mmol, 1.0 eq) in 25 mL of MeOH was added 2 mL of concentrated sulfuric acid. And the reaction monitored by TLC was completed after 24 hours under reflux with stirring. MeOH was distilled off and DCM was added to dissolved the residue. The solution was washed successively with saturated aqueous sodium bicarbonate solution, saturated aqueous sodium chloride solution and water. The obtained organic layer was dried over anhydrous magnesium sulfate, filtered and evaporated to dryness to give the product (1.85 g, 84.8% yield) for the next step.

Step 2: Preparation of 4-bromomethyl-3-trifluoromethyl-benzoic acid methyl ester To a solution of methyl-3-(trifluoromethyl)benzoate was dissolved in 1, 2-dichloroethane (DCE) was added NBS (N-bromosuccinimide) (1.81 g of (0.78 mmol, 1.2 eq), AIBN (azobisisobutyronitrile) (0.139 g, 0.848 mmol, 0.1 eq) with stirring. The mixture was purged with nitrogen at 80° C. for 30 h, washed with saturated aqueous sodium bicarbonate, aqueous solution of sodium chloride and water. The DCE layer was dried over magnesium sulfate and evaporated to dryness. The product 80% yield estimated was directly used for the next step.

Step 3: Preparation of methyl 4-(4-methylpiperazin-1-ylmethyl)-3-trifluoromethylbenzoate A solution of 4-bromomethyl-3-trifluoromethyl-benzoic acid methyl ester (6.78 mmol, 1.0 eq), triethylamine (1.03 g, 10.2 mmol, 1.5 eq), N-methylpiperazine (0.681 g, 6.8 mmol, 1.0 eq) in chloroform was stirred for 1 h. The reaction was completed, and the mixture was washed successively with saturated sodium bicarbonate solution, saturated aqueous sodium chloride solution and water. The chloroform layer was evaporated to dryness and the residue was separated by column chromatography to give the title product as a light yellow oil. MS m/z (ESI): 317.2 [M+H].

Step 4: Preparation of 4-(4-methylpiperazin-1-ylmethyl)-3-trifluoromethylbenzoic acid To a solution of Methyl-4-(4-methylpiperazin-1-ylmethyl)-3-trifluoromethyl-benzoic acid methyl ester (1.72 g, 5.4 mmol) in 20 mL of ethanol was added 3 mL of 5 M aqueous solution of NaOH and the mixture was stirred at room temperature overnight. The pH of the solution was adjusted to 6. And the solution was concentrated under reduced pressure. To the residue tetrahydrofuran was added. The mixture obtained was filtrated under reduced pressure, and the filtrate was evaporated to give the desired product as a light yellow powder (1.47 g, 89.9% yield).

Step 5: Preparation of N-(3-iodo-4-methylphenyl)-4-((4-methylpiperazin-1-yl) methyl)-3-(trifluoromethyl) benzamide 4-(4-methylpiperazin-1-yl-methyl)-3-trifluoromethylbenzoic acid (0.755 g, 2.5 mmol, 1.0 eq), HATU (O-(7-azabenzotriazol-1-oxo)-N, N, N', N'-tetramethyluronium hexafluorophosphate) (1.14 g, 3 mmol, 1.2 eq), DIPEA (1.29 g, 10 mmol, 4.0 eq) was dissolved in methylene chloride. The mixture was stirred at room temperature for 0.5 h and to the solution 3-iodo-4-methylaniline (582.6 mg, 2.5 mmol, 1.0 eq) was added. Then the mixture was stirred at 45° C. overnight, evaporated to dryness after the completion of the reaction, extracted with saturated aqueous sodium bicarbonate and methylene chloride 3 times. The organic layer was combined and concentrated under reduced pressure. The residue obtained was isolated by column chromatography to give the title product as a light yellow solid (892 mg, 69.0% yield). $^1$H NMR (400 MHz, CDCl$_3$) 8.10 (s, 1H), 8.08 (d, J=2 Hz, 1H), 8.08-8.05 (m, 1H), 8.0 (s, 1H), 7.95 (s, 1H), 7.55 (dd, J=4, 2 Hz, 1H), 7.20 (d, J=8 Hz, 1H), 3.75 (s, 2H) 2.60-2.41 (m, 8H), 2.40 (s, 3H), 2.30 (s, 3H). MS m/z (ESI): 518.1 [M+H].

Example 12

Preparation of N-(3-iodo-4-methylphenyl)-4-((4-methylpiperazin-1-yl) methyl)benzamide (Intermediate 36)

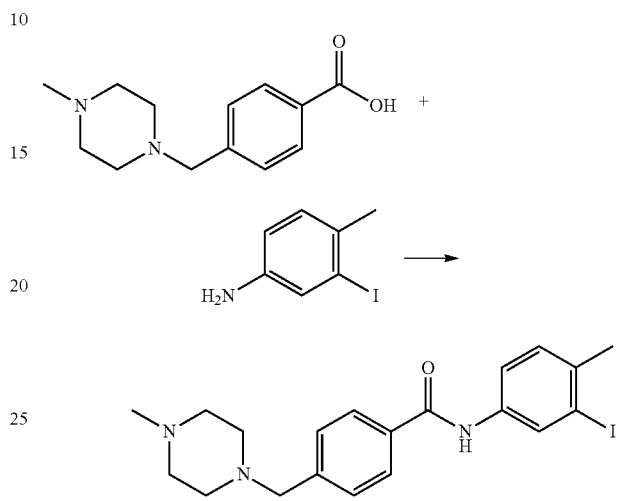

Intermediate 36 was obtained as a pale yellow solid (532 mg, hydrochloride, 76.7% yield) by a similar condensation procedure as described in Step 5 of intermediate 35. $^1$H NMR (400 MHz, DMSO-d$_6$) δ 10.35 (br.s, 1H), 10.26 (s, 1H), 8.34 (s, 1H), 7.95 (d, J=7.6 Hz, 2H), 7.72 (d, J=8.3 Hz, 1H), 7.47 (d, J=7.6 Hz, 2H), 7.30 (d, J=8.3 Hz, 1H), 3.64 (s, 2H), 3.39 (br.s, 2H), 3.01 (br.s, 2H), 2.87 (br.s, 2H), 2.73 (s, 3H), 2.42 (br.s, 2H), 2.34 (s, 3H). MS m/z (ESI): 450.1 [M+H].

Preparation of N-(3-ethynyl-4-methylphenyl)-4-((4-methylpiperazin-1-yl) methyl)-3-(trifluoromethyl) benzamide (Intermediate 37)

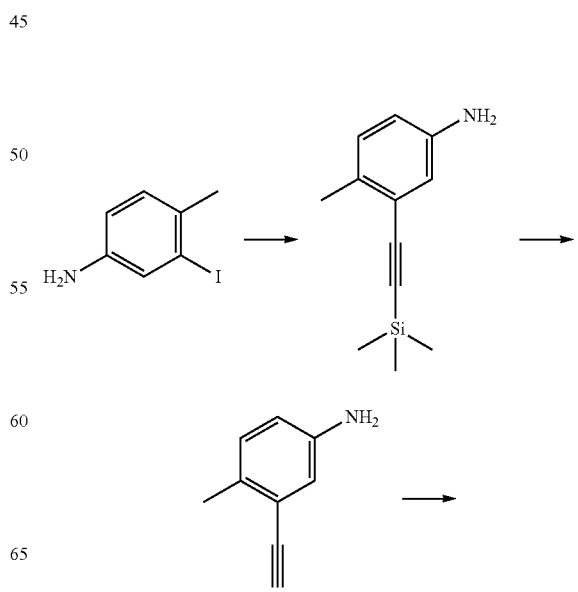

135

-continued

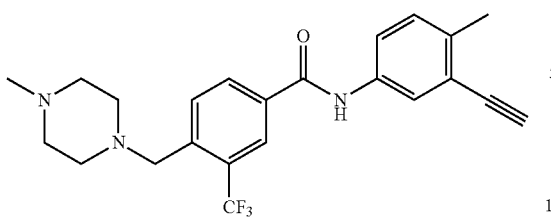

Step 1: Preparation of 3-trimethylsilylethynyl-4-methylaniline

A mixture of 3-iodo-4-methylaniline (11.65 g, 50 mmol, 1.0 eq), cuprous iodide (0.9 g, 4.7 mmol, 0.1 eq), bis(triphenylphosphine) palladium dichloride (1.75 g, 2.5 mmol, 0.05 eq) was dissolved in dioxane. The solution was replaced with nitrogen 3 times, and to the solution DIPEA (1.29 g, 100 mmol, 2.0 eq), trimethylsilylacetylene (6.4 g, 65 mmol, 1.3 eq) was added. Then the solution was heated to 75° C. for 17 h, evaporated under reduced pressure. The residue obtained was separated by column chromatography to afford the title product used directly in the next step.

Step 2: Preparation of 3-ethynyl-4-methylaniline 3-trimethylsilyl ethynyl-4-methylaniline was dissolved in methanol and to the solution potassium carbonate (3.45 g, 25 mmol, 0.5 eq) was added. The solution was stirred at room temperature for 10 min and the reaction was completed. The solvent was evaporated to dryness under reduced pressure and the residue obtained was extracted with DCM and water 3 times. And the DCM layer was dried and evaporated to dryness to give oil. The oil was isolated by column chromatography to give the product 3-ethynyl-4-methylaniline as a yellowish brown oil (4.0 g, 61.0% yield). $^1$H NMR (400 MHz, CDCl$_3$) δ 6.99 (d, J=8.1 Hz, 1H), 6.81 (s, 1H), 6.61 (d, J=8.1 Hz, 1H), 3.44 (s, 2H), 3.23 (s, 1H), 2.34 (s, 3H). MS m/z (ESI): 132.2 [M+H].

Step 3: Preparation of N-(3-ethynyl-4-methylphenyl)-4-((4-methylpiperazin-1-yl) methyl)-3-(trifluoromethyl) benzamide Intermediate 37 was obtained as a light yellow solid (1.2 g, hydrochloride, yield 71.7%) by a similar condensation procedure as described in Step 5 of intermediate 35. $^1$H NMR (400 MHz, DMSO-d$_6$) δ 11.24 (br.s, 1H), 10.58 (s, 1H), 8.33 (d, J=6.4 Hz, 2H), 8.14 (s, 1H), 7.92 (s, 1H), 7.72 (d, J=8.3 Hz, 1H), 7.28 (d, J=8.3 Hz, 1H), 4.39 (s, 1H), 4.06 (s, 2H), 3.47 (d, J=10.9 Hz, 2H), 3.22 (br.s, 2H), 3.13 (br.s, 2H), 2.89 (br.s, 2H), 2.77 (s, 3H), 2.36 (s, 3H). MS m/z (ESI): 416.3 [M+H].

136

Example 14

Preparation of N-(3-ethynyl-4-methylphenyl)-6-(trifluoromethyl) methylpyridine amide Intermediate 38

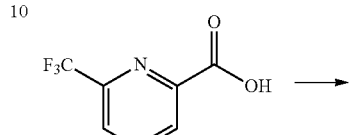

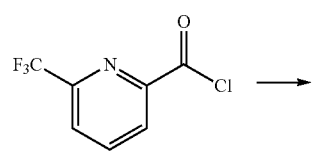

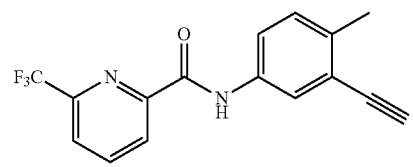

The solution of 6-trifluoromethyl-pyridine-2-carboxylic acid (229.33 mg, 1.2 mmol, 1.2 eq) in thionyl chloride was refluxed for 80° C. 3 h, and thionyl chloride was evaporated to dryness under reduced pressure to give 6-(trifluoromethyl Methyl) pyridine-2-carboxylic acid chloride as colorless oil which was dissolved in DCM. A mixture of 3-ethynyl-4-methylaniline (131.17 mg, 1.0 mmol, 1.0 eq) and triethylamine (202.4 mg, 2.0 mmol, 2.0 eq) were dissolved in DCM and cooled to −5° C. To the solution methyl-pyridine-2-formyl chloride in DCM was slowly added dropwise. After the addition, the mixture was allowed to warm to room temperature without heat. The reaction was completed 15 min later. To the reaction solution an aqueous solution of sodium hydroxide was added, and the mixture was extracted with DCM twice. The DCM layer was combined and washed successively with dilute hydrochloric acid and water, dried over anhydrous magnesium sulfate and evaporated to dryness to afford the intermediate 38 as a white solid (225 mg, yield 73.9%). $^1$H NMR (400 MHz, DMSO-d$_6$) δ 10.47 (s, 1H), 8.08-8.05 (m, 2H), 7.93 (dd, J=7.3, 1.4 Hz, 1H), 7.76 (d, J=2.2 Hz, 1H), 7.54 (dd, J=8.3, 2.2 Hz, 1H), 7.06 (d, J=8.3 Hz, 1H), 4.16 (s, 1H), 2.13 (s, 3H). MS m/z (ESI): 305.1 [M+H].

Example 15

Preparation of Intermediate 39~64

The following intermediates 39 to 64 were obtained, using arylcarboxylic acid, aryl acid chloride, pentaheterocyclic acid chloride and aniline containing different substituents as starting materials, in a similar manner to that described for the preparation of the intermediate 38.

| No. | Structure | ¹H-NMR | ESI⁺ [M + H] |
|---|---|---|---|
| Intermediate 39 | 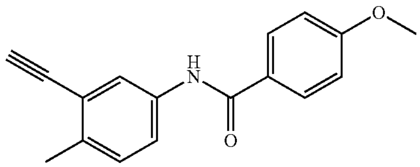 [SMILES: C#Cc1cc(NC(=O)c2ccc(OC)cc2)ccc1C] | ¹H NMR (400 MHz, DMSO-d₆) δ 10.22 (s, 1H), 7.90 (d, J = 2.2 Hz, 1H), 7.70 (dd, J = 8.3, 2.2 Hz, 1H), 7.53 (d, J = 7.7 Hz, 1H), 7.48 (d, J = 2.2 Hz, 1H), 7.45 (t, J = 7.7 Hz, 1H), 7.27 (d, J = 8.1 Hz, 1H), 7.16 (dd, J = 8.1, 2.0 Hz, 1H), 4.38 (s, 1H), 3.84 (s, 3H), 2.35 (s, 3H). | 266.2 |
| Intermediate 40 | 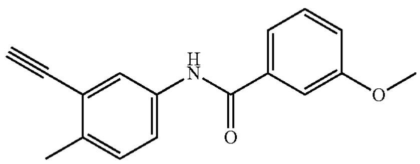 [SMILES: C#Cc1cc(NC(=O)c2cccc(OC)c2)ccc1C] | ¹H NMR (400 MHz, DMSO-d₆) δ 10.09 (s, 1H), 7.98-7.93 (m, 2H), 7.90 (d, J = 2.2 Hz, 1H), 7.69 (dd, J = 8.3, 2.2 Hz, 1H), 7.25 (d, J = 8.3 Hz, 1H), 7.09-7.04 (m, 2H), 4.37 (s, 1H), 3.85 (s, 3H), 2.35 (s, 3H). | 266.2 |
| Intermediate 41 | 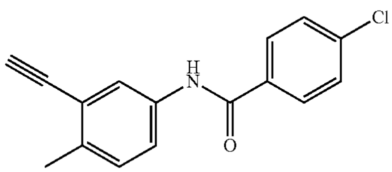 [SMILES: C#Cc1cc(NC(=O)c2ccc(Cl)cc2)ccc1C] | ¹H NMR (400 MHz, DMSO-d₆) δ 10.07 (s, 1H), 7.77-7.71 (m, 2H), 7.66 (d, J = 2.2 Hz, 1H), 7.44 (dd, J = 8.3, 2.2 Hz, 1H), 7.40-7.35 (m, 2H), 7.03 (d, J = 8.3 Hz, 1H), 4.15 (s, 1H), 2.12 (s, 3H). | 270.1 |
| Intermediate 42 | 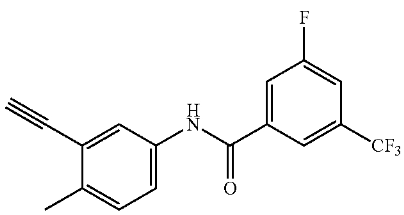 [SMILES: C#Cc1cc(NC(=O)c2cc(F)cc(C(F)(F)F)c2)ccc1C] | ¹H NMR (400 MHz, DMSO-d₆) δ 10.50 (s, 1H), 8.17 (s, 1H), 8.11 (d, J = 9.2 Hz, 1H), 7.98 (d, J = 8.4 Hz, 1H), 7.89 (d, J = 2.1 Hz, 1H), 7.68 (dd, J = 8.4, 2.1 Hz, 1H), 7.30 (d, J = 8.4 Hz, 1H), 4.41 (s, 1H), 2.37 (s, 3H). | 322.1 |
| Intermediate 43 | 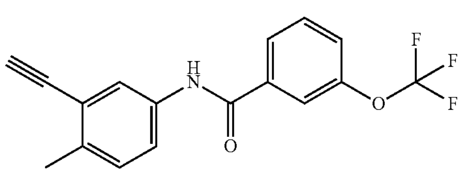 [SMILES: C#Cc1cc(NC(=O)c2cccc(OC(F)(F)F)c2)ccc1C] | ¹H NMR (400 MHz, DMSO-d₆) δ 10.39 (s, 1H), 8.01 (d, J = 7.7 Hz, 1H), 7.94-7.87 (m, 2H), 7.72-7.66 (m, 2H), 7.66-7.59 (m, 1H), 7.29 (d, J = 8.4 Hz, 1H), 4.40 (s, 1H), 2.37 (s, 3H). | 320.1 |
| Intermediate 44 | 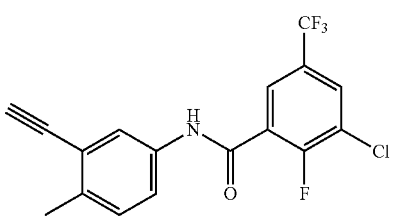 [SMILES: C#Cc1cc(NC(=O)c2cc(C(F)(F)F)cc(Cl)c2F)ccc1C] | ¹H NMR (400 MHz, DMSO-d₆) δ 10.47 (s, 1H), 8.08 (dd, J = 6.1, 1.9 Hz, 1H), 7.84 (dd, J = 5.2, 1.9 Hz, 1H), 7.60 (d, J = 2.1 Hz, 1H), 7.34 (dd, J = 8.3, 2.1 Hz, 1H), 7.06 (d, J = 8.3 Hz, 1H), 4.18 (s, 1H), 2.13 (s, 3H). | 356.1 |
| Intermediate 45 | 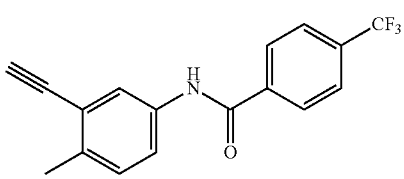 [SMILES: C#Cc1cc(NC(=O)c2ccc(C(F)(F)F)cc2)ccc1C] | ¹H NMR (400 MHz, DMSO-d₆) δ 10.47 (s, 1H), 8.15 (d, J = 8.1 Hz, 2H), 7.93 (d, J = 8.1 Hz, 3H), 7.70 (dd, J = 8.4, 2.2 Hz, 1H), 7.29 (d, J = 8.4 Hz, 1H), 4.40 (s, 1H), 2.37 (s, 3H). | 304.1 |
| Intermediate 46 | 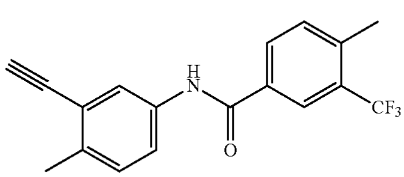 [SMILES: C#Cc1cc(NC(=O)c2ccc(C)c(C(F)(F)F)c2)ccc1C] | ¹H NMR (400 MHz, DMSO-d₆) δ 10.39 (s, 1H), 8.24 (s, 1H), 8.15 (d, J = 8.0 Hz, 1H), 7.89 (d, J = 2.2 Hz, 1H), 7.69 (dd, J = 8.3, 2.2 Hz, 1H), 7.63 (d, J = 8.0 Hz, 1H), 7.28 (d, J = 8.3 Hz, 1H), 4.39 (s, 1H), 2.53 (d, J = 1.3 Hz, 3H), 2.36 (s, 3H). | 318.1 |

| No. | Structure | ¹H-NMR | ESI⁺ [M + H] |
|---|---|---|---|
| Intermediate 47 | 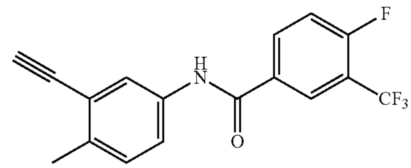 [SMILES: C#Cc1cc(NC(=O)c2ccc(F)c(C(F)(F)F)c2)ccc1C] | ¹H NMR (400 MHz, DMSO-d₆) δ 10.46 (s, 1H), 8.41-8.29 (m, 2H), 7.88 (d, J = 2.2 Hz, 1H), 7.76-7.63 (m, 2H), 7.29 (d, J = 8.4 Hz, 1H), 4.40 (s, 1H), 2.36 (s, 3H). | 322.1 |
| Intermediate 48 | 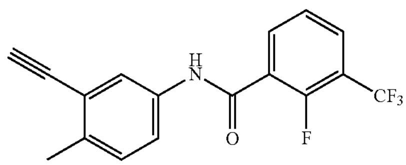 [SMILES: C#Cc1cc(NC(=O)c2cccc(C(F)(F)F)c2F)ccc1C] | ¹H NMR (400 MHz, DMSO-d₆) δ 10.65 (s, 1H), 8.06-7.92 (m, 2H), 7.85 (d, J = 2.2 Hz, 1H), 7.64-7.50 (m, 2H), 7.29 (d, J = 8.4 Hz, 1H), 4.41 (s, 1H), 2.36 (s, 3H). | 322.1 |
| Intermediate 49 | 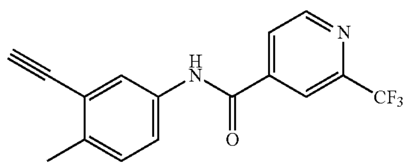 [SMILES: C#Cc1cc(NC(=O)c2ccnc(C(F)(F)F)c2)ccc1C] | ¹H NMR (400 MHz, DMSO-d₆) δ 10.63 (s, 1H), 8.95 (d, J = 5.0 Hz, 1H), 8.31 (s, 1H), 8.14 (d, J = 4.7 Hz, 1H), 7.85 (d, J = 2.0 Hz, 1H), 7.64 (dd, J = 8.4, 2.0 Hz, 1H), 7.27 (d, J = 8.4 Hz, 1H), 4.37 (s, 1H), 2.32 (s, 3H). | 305.1 |
| Intermediate 50 | 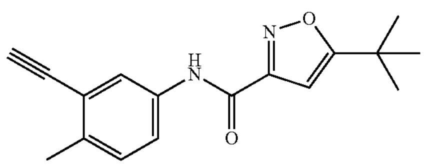 [SMILES: C#Cc1cc(NC(=O)c2cc(C(C)(C)C)on2)ccc1C] | ¹H NMR (400 MHz, CDCl₃) δ 8.47 (s, 1H), 7.73 (d, J = 2.3 Hz, 1H), 7.57 (dd, J = 8.3, 2.3 Hz, 1H), 7.20 (d, J = 8.3 Hz, 1H), 6.49 (s, 1H), 3.29 (s, 1H), 2.43 (s, 3H), 1.39 (s, 9H). | 283.2 |
| Intermediate 51 | 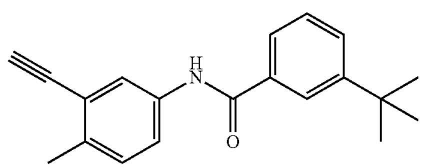 [SMILES: C#Cc1cc(NC(=O)c2cccc(C(C)(C)C)c2)ccc1C] | ¹H NMR (400 MHz, CDCl₃) δ 7.91 (s, 1H), 7.75 (s, 1H), 7.70 (d, J = 2.2 Hz, 1H), 7.65-7.55 (m, 3H), 7.41 (t, J = 7.8 Hz, 1H), 7.21 (d, J = 8.3 Hz, 1H), 3.28 (s, 1H), 2.43 (s, 3H), 1.37 (s, 9H). | 292.2 |
| Intermediate 52 | 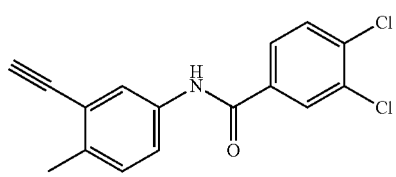 | ¹H NMR (400 MHz, CDCl₃) δ 7.94 (d, J = 2.0 Hz, 1H), 7.76 (br.s, 1H), 7.68-7.66 (m, 2H), 7.58-7.48 (m, 2H), 7.20 (d, J = 8.3 Hz, 1H), 3.28 (s, 1H), 2.43 (s, 3H). | 304.1 |
| Intermediate 53 | 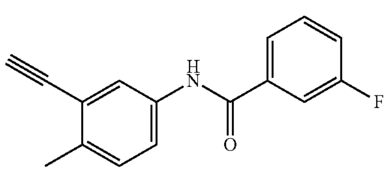 [SMILES: C#Cc1cc(NC(=O)c2cccc(F)c2)ccc1C] | ¹H NMR (400 MHz, DMSO-d₆) δ 10.26 (s, 1H), 7.85 (d, J = 2.1 Hz, 1H), 7.76 (d, J = 7.8 Hz, 1H), 7.73-7.70 (m, 1H), 7.64 (dd, J = 8.3, 2.2 Hz, 1H), 7.57-7.52 (m, 1H), 7.41 (td, J = 8.4, 2.4 Hz, 1H), 7.23 (d, J = 8.4 Hz, 1H), 4.34 (s, 1H), 2.31 (s, 3H). | 254.1 |
| Intermediate 54 | 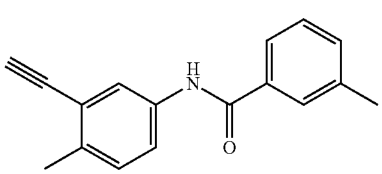 [SMILES: C#Cc1cc(NC(=O)c2cccc(C)c2)ccc1C] | ¹H NMR (400 MHz, DMSO-d₆) δ 10.21 (s, 1H), 7.91 (d, J = 2.1 Hz, 1H), 7.76 (s, 1H), 7.75-7.73 (m, 1H), 7.69 (dd, J = 8.3, 2.1 Hz, 1H), 7.47-7.37 (m, 2H), 7.26 (d, J = 8.3 Hz, 1H), 4.38 (s, 1H), 2.40 (s, 3H), 2.36 (s, 3H). | 250.1 |
| Intermediate 55 | 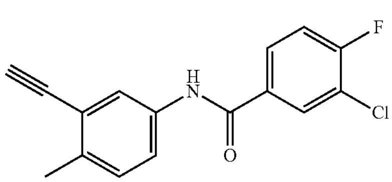 [SMILES: C#Cc1cc(NC(=O)c2ccc(F)c(Cl)c2)ccc1C] | ¹H NMR (400 MHz, DMSO-d₆) δ 10.35 (s, 1H), 8.21 (d, J = 5.6 Hz, 1H), 8.08-7.94 (m, 1H), 7.89 (s, 1H), 7.68 (d, J = 8.2 Hz, 1H), 7.61 (t, J = 8.9 Hz, 1H), 7.29 (d, J = 8.4 Hz, 1H), 4.40 (s, 1H), 2.36 (s, 3H). | 288.1 |

| No. | Structure | ¹H-NMR | ESI⁺ [M + H] |
|---|---|---|---|
| Intermediate 56 | 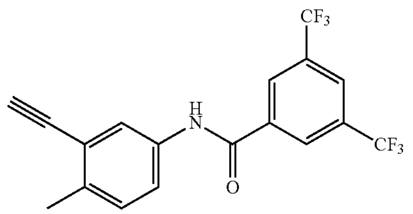 [SMILES: C#Cc1cc(NC(=O)c2cc(C(F)(F)F)cc(C(F)(F)F)c2)ccc1C] | ¹H NMR (400 MHz, DMSO-d₆) δ 10.66 (s, 1H), 8.61 (s, 2H), 8.38 (s, 1H), 7.89 (d, J = 2.0 Hz, 1H), 7.70 (dd, J = 8.3, 2.0 Hz, 1H), 7.31 (d, J = 8.3 Hz, 1H), 4.41 (s, 1H), 2.37 (s, 3H). | 372.1 |
| Intermediate 57 | 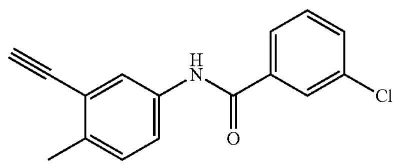 [SMILES: C#Cc1cc(NC(=O)c2cccc(Cl)c2)ccc1C] | ¹H NMR (400 MHz, DMSO-d₆) δ 10.35 (s, 1H), 8.01 (t, J = 1.7 Hz, 1H), 7.91 (t, J = 4.7 Hz, 2H), 7.75-7.63 (m, 2H), 7.58 (t, J = 7.9 Hz, 1H), 7.28 (d, J = 8.4 Hz, 1H), 4.39 (s, 1H), 2.36 (s, 3H). | 270.1 |
| Intermediate 58 | 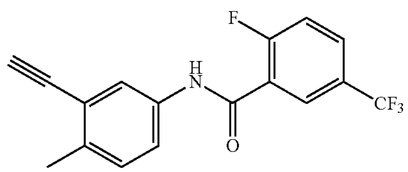 [SMILES: C#Cc1cc(NC(=O)c2cc(C(F)(F)F)ccc2F)ccc1C] | ¹H NMR (400 MHz, DMSO-d₆) δ 10.61 (s, 1H), 8.07 (d, J = 4.4 Hz, 1H), 8.03-7.95 (m, 1H), 7.85 (d, J = 1.6 Hz, 1H), 7.70-7.53 (m, 2H), 7.29 (d, J = 8.4 Hz, 1H), 4.40 (s, 1H), 2.36 (s, 3H). | 322.1 |
| Intermediate 59 | 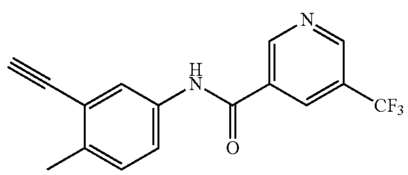 [SMILES: C#Cc1cc(NC(=O)c2cncc(C(F)(F)F)c2)ccc1C] | ¹H NMR (400 MHz, DMSO-d₆) δ 10.61 (s, 1H), 9.37 (s, 1H), 9.19 (s, 1H), 8.68 (s, 1H), 7.90 (d, J = 1.9 Hz, 1H), 7.68 (dd, J = 8.3, 1.9 Hz, 1H), 7.31 (d, J = 8.3 Hz, 1H), 4.41 (s, 1H), 2.37 (s, 3H). | 305.1 |
| Intermediate 60 | 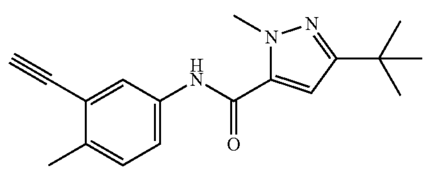 [SMILES: C#Cc1cc(NC(=O)c2cc(C(C)(C)C)nn2C)ccc1C] | ¹H NMR (400 MHz, DMSO-d₆) δ 10.13 (s, 1H), 7.87 (d, J = 2.1 Hz, 1H), 7.64 (dd, J = 8.3, 2.1 Hz, 1H), 7.27 (d, J = 8.3 Hz, 1H), 6.95 (s, 1H), 4.39 (s, 1H), 4.03 (s, 3H), 2.36 (s, 3H), 1.29 (s, 9H). | 296.2 |
| Intermediate 61 | 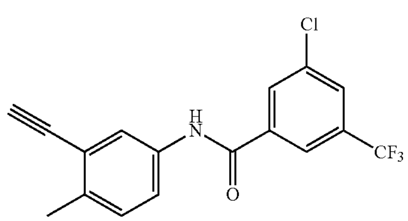 [SMILES: C#Cc1cc(NC(=O)c2cc(Cl)cc(C(F)(F)F)c2)ccc1C] | ¹H NMR (400 MHz, CDCl₃) δ 8.03 (s, 1H), 7.98 (s, 1H), 7.79 (s, 1H), 7.73 (s, 1H), 7.69 (d, J = 2.2 Hz, 1H), 7.56 (dd, J = 8.3, 2.2 Hz, 1H), 7.23 (d, J = 8.3 Hz, 1H), 3.30 (s, 1H), 2.44 (s, 3H). | 338.1 |
| Intermediate 62 | 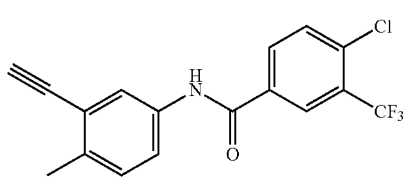 | ¹H NMR (400 MHz, CDCl₃) δ 8.16 (d, J = 1.5 Hz, 1H), 7.96 (dd, J = 8.3, 2.1 Hz, 1H), 7.85 (s, 1H), 7.66 (d, J = 2.1 Hz, 1H), 7.62 (d, J = 8.3 Hz, 1H), 7.54 (dd, J = 8.3, 2.0 Hz, 1H), 7.20 (d, J = 8.3 Hz, 1H), 3.28 (s, 1H), 2.43 (s, 3H). | 338.1 |
| Intermediate 63 | 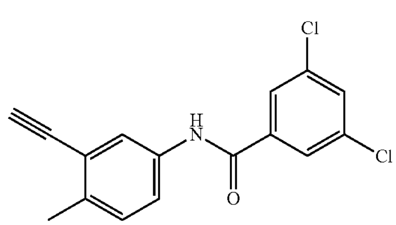 [SMILES: C#Cc1cc(NC(=O)c2cc(Cl)cc(Cl)c2)ccc1C] | ¹H NMR (400 MHz, DMSO-d₆) δ 10.40 (s, 1H), 7.97 (s, 2H), 7.87 (d, J = 6.1 Hz, 2H), 7.67 (s, 1H), 7.28 (s, 1H), 4.38 (s, 1H), 2.35 (s, 3H). | 304.1 |

| No. | Structure | ¹H-NMR | ESI⁺ [M + H] |
|---|---|---|---|
| Intermediate 64 | 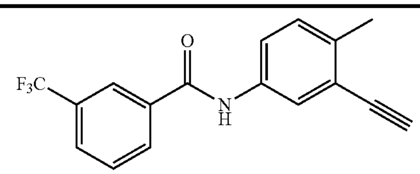 | ¹H NMR (400 MHz, CDCl₃) δ 8.09 (s, 1H), 8.02 (d, J = 6.4 Hz, 2H), 7.78 (d, J = 7.7 Hz, 1H), 7.67 (s, 1H), 7.58 (t, J = 8.0 Hz, 1H), 7.55 (d, J = 8.5 Hz, 1H), 7.17 (d, J = 8.3 Hz, 1H), 3.27 (s, 1H), 2.42 (s, 3H). | 304.1 |

Example 16

Preparation of 2-tert-butyl-N-(3-ethynyl-4-methylphenyl) thiazole-5-carboxamide (Intermediate 65)

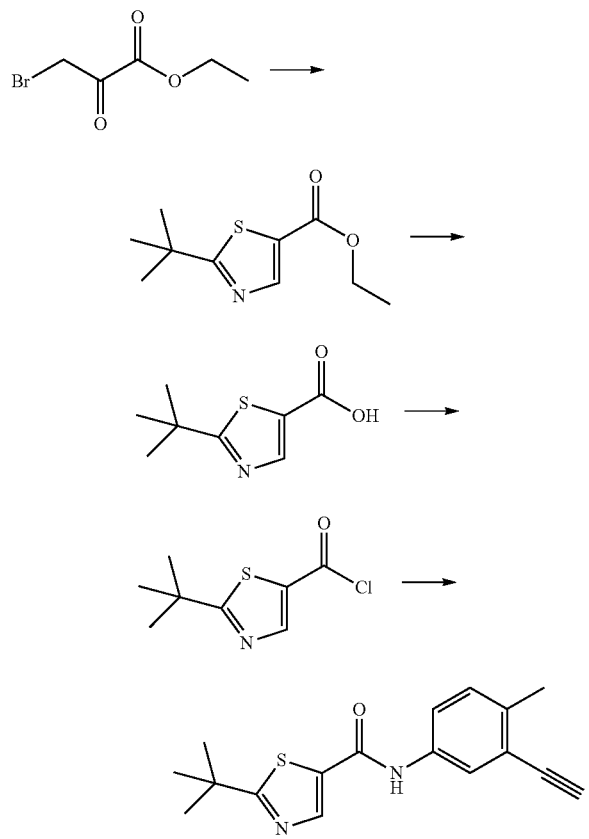

Step 1: Preparation of 2-tert-butyl-thiazole-5-carboxylic acid ethyl ester

A solution of ethyl 3-bromopyruvate (1.95 g, 10 mmol, 1.0 eq) and 2, 2, 2-trimethyl-thioacetamide (1.17 g, 10 mmol, 1.0 eq) in 20 mL of ethanol was stirred at room temperature for 48 h. The solvent was evaporated under reduced pressure, and the residue was extracted with aqueous sodium bicarbonate and DCM. The DCM layer was dried over anhydrous magnesium sulfate and evaporated to dryness. The residue was separated by column chromatography to give 2-tert-butyl-thiazole-5-carboxylic acid ethyl ester as a colorless oil (1.15 g, 55.0% yield). ¹H NMR (400 MHz, CDCl₃) δ 8.01 (s, 1H), 4.38 (q, J=7.1 Hz, 2H), 1.46 (s, 9H), 1.37 (t, J=7.1 Hz, 3H). MS m/z (ESI): 214.0 [M+H].

Step 2: Preparation of 2-tert-butyl-thiazole-5-carboxylic acid

To a 2-tert-butyl-thiazole-5-carboxylate in 10 mL of THF, 5 mL of lithium hydroxide (0.45 g, 10.9 mmol, 1.1 eq) aqueous solution was added and the obtained solution was stirred at room temperature for about 16 h. The solvent was evaporated under reduced pressure, and the residue was dissolved in 5 mL of water. The pH was adjusted to about 3 with 2M HCl, and a large amount of white flocculent solid was precipitated. The filter cake was washed with water (2×5 mL) to give 2-Tert-butyl-thiazole-5-carboxylic acid as a white solid (0.55 g, 55.0% yield). MS m/z (ESI): 184.0 [M−H].

Step 3: Preparation of 2-tert-butyl-thiazole-5-carbonyl chloride

A solution of 2-tert-butyl-thiazole-5-carboxylic acid (203.7 mg, 1.1 mmol) in 3 mL thionyl chloride was refluxed for 2 h at 80° C. The solvent was evaporated to dryness under reduced pressure to afford the product directly used for the next step.

Step 4: Preparation of 2-tert-butyl-N-(3-ethynyl-4-methylphenyl) thiazole-5-carboxamide To the solution of 3-ethynyl-4-methyl-aniline (131.2 mg, 1.0 mmol, 1.0 eq) in 4 mL DCM, triethylamine (151.8 mg, 1.5 mmol, 1.5 eq) was added. After the solution cooling to 0° C. 2-tert-butyl-thiazole-5-carbonyl chloride in dichloromethane (4 mL) of Step 3 was added slowly dropwise. The mixture was allowed to warm to room temperature for 10 min without heat. And the mixture obtained was washed successively with saturated aqueous solution of ammonium chloride, saturated aqueous sodium bicarbonate. The organic layer was dried over anhydrous magnesium sulfate, filtered and evaporated in vacue. The residue was washed with 3 mL of petroleum ether to give the desired product as a light yellow powder (253.6 mg, 85.1% yield). ¹H NMR (400 MHz, DMSO-d₆) δ 9.95 (s, 1H), 8.30 (s, 1H), 7.95 (d, J=2.0 Hz, 1H), 7.76 (dd, J=8.3, 2.0 Hz, 1H), 7.28 (d, J=8.3 Hz, 1H), 4.39 (s, 1H), 2.37 (s, 3H), 1.47 (s, 9H). MS m/z (ESI): 299.1 [M+H].

Example 17

Preparation of N-(4-chloro-3-ethynylphenyl)-3-(trifluoromethyl) benzamide (Intermediate 66)

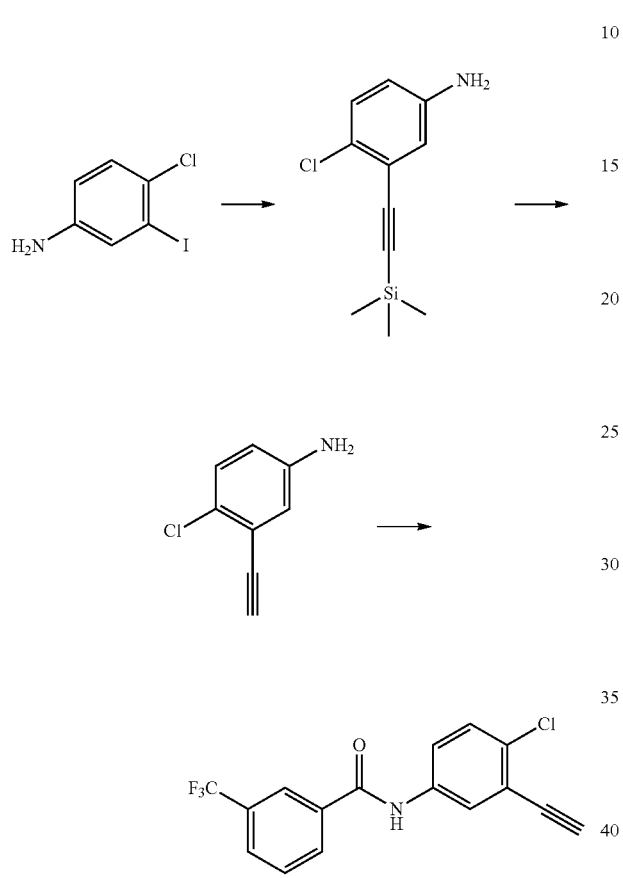

Step 1 and 2: Preparation of 3-ethynyl-4-chloroaniline

The target product was obtained as a light yellow oil using 3-iodo-4-chloroaniline as starting material according to the method described in Steps 1 and 2 of intermediate 37 (2.1 g, 77.8% yield). $^1$H NMR (400 MHz, DMSO-d$_6$) δ 7.12 (d, J=8.7 Hz, 1H), 6.75 (d, J=2.8 Hz, 1H), 6.60 (dd, J=8.7, 2.8 Hz, 1H), 5.39 (s, 2H), 4.34 (s, 1H). MS m/z (ESI): 518.3 [M+H].

Step 3: Preparation of N-(4-chloro-3-ethynylphenyl)-3-(trifluoromethyl) benzamide Intermediate 66 was obtained as a light yellow powder in a similar to that described in the preparation of intermediate 38 (291 mg, 90.1% yield). $^1$H NMR (400 MHz, DMSO-d$_6$) δ 10.64 (s, 1H), 8.30 (s, 1H), 8.26 (d, J=8.0 Hz, 1H), 8.07 (d, J=2.5 Hz, 1H), 8.00 (d, J=8.0 Hz, 1H), 7.89-7.82 (m, 1H), 7.82-7.75 (m, 1H), 7.57 (d, J=8.8 Hz, 1H), 4.61 (s, 1H). MS m/z (ESI): 324.1 [M+H].

Example 18

Preparation of 3-methyl-N-(4-((4-methylpiperazin-1-yl) methyl)-3-(trifluoromethyl) phenyl) benzamide (Intermediate 67)

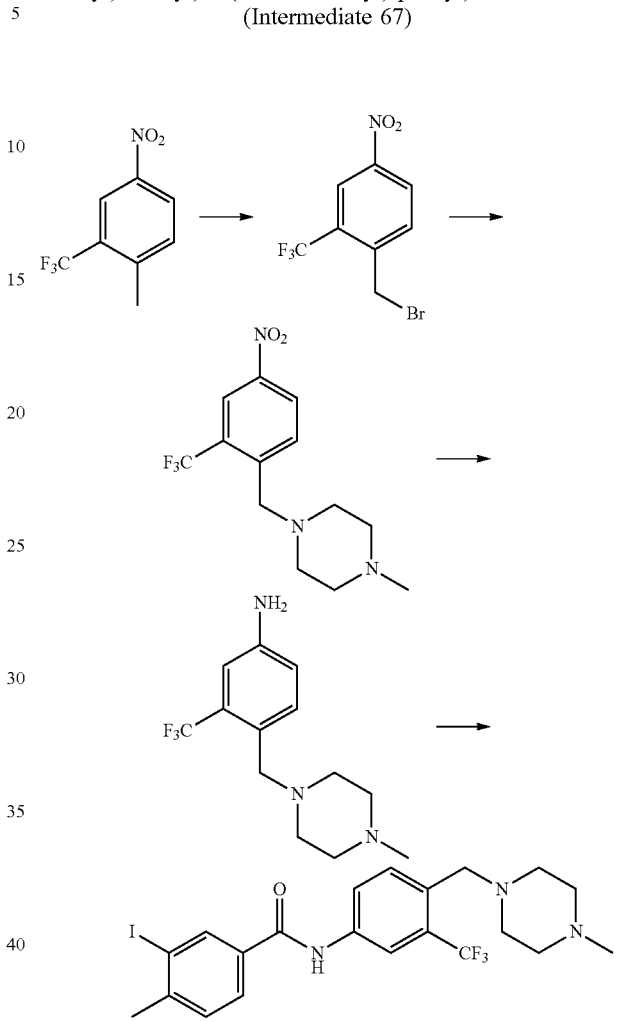

Step 1: Preparation of 1-bromomethyl-4-nitro-2-trifluoromethylbenzene

To a solution of 1-methyl-4-nitro-2-trifluoromethyl-benzene (5.62 g, 27.4 mmol, 1.0 eq) in 50 mL of 1, 2-dichloroethane, N-bromosuccinimide (5.85 g, 32.8 mmol, 1.2 eq) and AIBN (450 mg, 2.7 mmol, 0.1 eq) was added. The mixture was refluxed overnight, then cooled to room temperature, washed successively with saturated sodium bicarbonate solution, saturated sodium chloride solution and water, dried over anhydrous magnesium sulfate, filtered and concentrated under reduced pressure to give the title product used directly in the next step.

Step 2: Preparation of 1-methyl-4-(4-nitro-2-(trifluoromethyl) benzyl) piperazine To a solution of 1-bromo-4-nitro-2-trifluoromethyl-phenyl (20.55 mmol) in step 2 in 50 mL DCM, triethylamine (3.1 g, 30.8 mmol, 1.5 eq) and N-methyl piperazine (4.12 g, 41.1 mmol, 2.0 eq) was added. The mixture was stirred room temperature, concentrated under reduced pressure after completion of the reaction. The residue obtained was dissolved in DCM, washed with saturated sodium bicarbonate solution, saturated sodium chloride solution and water, dried over anhydrous magnesium sulfate, filtered and concentrated under reduced pressure. The residue was isolated by column chromatography to give the title product as a yellow solid. MS m/z (ESI): 304.2 [M+H].

Step 3: Preparation of 4-((4-methyl-piperazin-1-yl) methyl)-3-(trifluoromethyl) aniline To a solution of 1-methyl-4-(4-nitro-2-(trifluoromethyl) benzyl) piperazine (5 g) in 65 mL of 75% ethanol, 0.5 g of 10% palladium on carbon was added. Then the reaction solution was stirred under hydrogen atmosphere at room temperature for 5 h. After competition of the reaction, the reaction mixture was filtered under reduced pressure, evaporated to dryness to afford the desired product as a light yellow solid. MS m/z (ESI): 274.2 [M+H].

Step 4: Preparation of 3-iodo-4-methyl-N-(4-((4-methyl-piperazin-1-yl) methyl)-3-(trifluoromethyl) phenyl) benzamide Intermediate 67 was obtained as a light yellow solid (2.2 g, yield 74.3%) according to a similar condensation procedure as described in Step 5 of intermediate 35. $^1$H NMR (400 MHz, DMSO-$d_6$) δ 10.49 (s, 1H), 8.43 (s, 1H), 8.18 (d, J=1.5 Hz, 1H), 8.04 (d, J=8.5 Hz, 1H), 7.92 (d, J=8.0 Hz, 1H), 7.70 (d, J=8.5 Hz, 1H), 7.50 (d, J=8.0 Hz, 1H), 3.56 (s, 2H), 2.45 (s, 3H), 2.36 (d, J=20.7 Hz, 8H), 2.16 (s, 3H). MS m/z (ESI): 518.3 [M+H].

Example 19

Preparation of Intermediate 68~73

The following intermediates 68-73 were obtained using benzoic acid and aniline containing different substituents by analogous procedures described for intermediate 67.

| No. | Structure | $^1$H-NMR | ESI$^+$ [M + H] |
|---|---|---|---|
| Intermediate 68 | 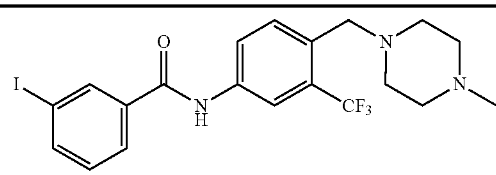 | $^1$H NMR (400 MHz, DMSO-$d_6$) δ 10.57 (s, 1H), 8.32 (s, 1H), 8.18 (s, 1H), 8.04 (d, J = 8.5 Hz, 1H), 7.98 (d, J = 7.9 Hz, 2H), 7.71 (d, J = 8.5 Hz, 1H), 7.36 (t, J = 7.9 Hz, 1H), 3.57 (s, 2H), 2.40 (br.s, 8H), 2.17 (s, 3H). | 504.1 |
| Intermediate 69 | 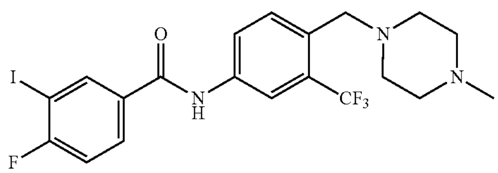 [SMILES: CN1CCN(Cc2ccc(NC(=O)c3ccc(F)c(I)c3)cc2C(F)(F)F)CC1] | $^1$H NMR (400 MHz, DMSO-$d_6$) δ 10.56 (s, 1H), 8.46 (d, J = 5.7 Hz, 1H), 8.17 (s, 1H), 8.03 (d, J = 8.3 Hz, 2H), 7.71 (d, J = 8.6 Hz, 1H), 7.45 (t, J = 8.2 Hz, 1H), 3.58 (s, 2H), 2.43 (br.s, 8H), 2.24 (s, 3H). | 522.1 |
| Intermediate 70 | HCl | $^1$H NMR (400 MHz, DMSO-$d_6$) δ 10.76 (s, 1H), 8.54 (s, 1H), 8.24 (s, 1H), 8.13 (d, J = 8.3 Hz, 1H), 8.01 (d, J = 8.3 Hz, 1H), 7.89 (br.s, 1H), 7.77 (d, J = 8.3 Hz, 1H), 3.90 (br.s, 2H), 3.47 (br.s, 2H), 3.16 (br.s, 4H), 2.78 (s, 3H), 2.71 (br.s, 2H). | 538.1 |
| Intermediate 71 | 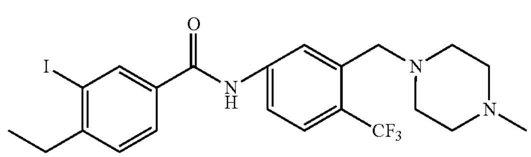 [SMILES: CCc1ccc(C(=O)Nc2ccc(C(F)(F)F)c(CN3CCN(C)CC3)c2)cc1I] | $^1$H NMR (400 MHz, CDCl$_3$), δ 8.29 (s, 1H), 8.16 (s, 1H), 7.88-7.85 (m, 2H), 7.78 (d, J = 8.0 Hz, 1H), 7.74 (d, J = 8.4 Hz, 1H), 7.29 (d, J = 8.0 Hz, 1H), 3.62 (s, 2H), 2.77 (q, J = 7.6 Hz, 2H), 2.51 (br.s, 8H), 2.41 (s, 3H), 1.22 (t, J = 7.6 Hz, 3H). | 532.1 |
| Intermediate 72 | 1HCl | $^1$H NMR (400 MHz, DMSO-$d_6$) δ 10.43 (s, 1H), 9.62 (br.s, 1H), 8.43 (d, J = 1.9 Hz, 1H), 8.19 (s, 1H), 8.14-7.97 (m, 2H), 7.69 (d, J = 8.5 Hz, 1H), 7.16 (d, J = 8.5 Hz, 1H), 3.92 (s, 3H), 3.65 (s, 2H), 3.15 (br.s, 4H), 2.75 (s, 3H), 2.67 (br.s, 4H). | 534.1 |
| Intermediate 73 | 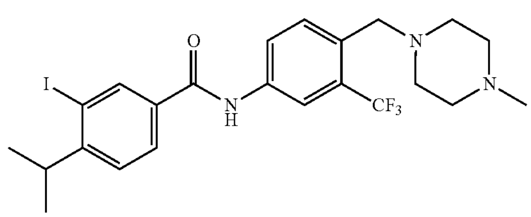 [SMILES: CC(C)c1ccc(C(=O)Nc2ccc(CN3CCN(C)CC3)c(C(F)(F)F)c2)cc1I] | $^1$H NMR (400 MHz, CDCl$_3$) δ 8.37 (s, 1H), 8.31 (s, 1H), 7.95 (d, J = 7.0 Hz, 2H), 7.90 (d, J = 8.1 Hz, 1H), 7.57 (d, J = 7.0 Hz, 1H), 7.36 (d, J = 8.1 Hz, 1H), 3.73 (s, 2H), 3.30-3.20 (m, 1H), 3.04 (br.s, 4H), 2.87 (s, 4H), 2.74 (s, 3H), 1.26 (d, J = 6.8 Hz, 6H). | 546.1 |

Example 20

Preparation of 3-ethynyl-4-methyl-N-(4-((4-methyl-piperazin-1-yl) methyl)-3-(trifluoromethyl)phenyl) benzamide (Intermediate 74)

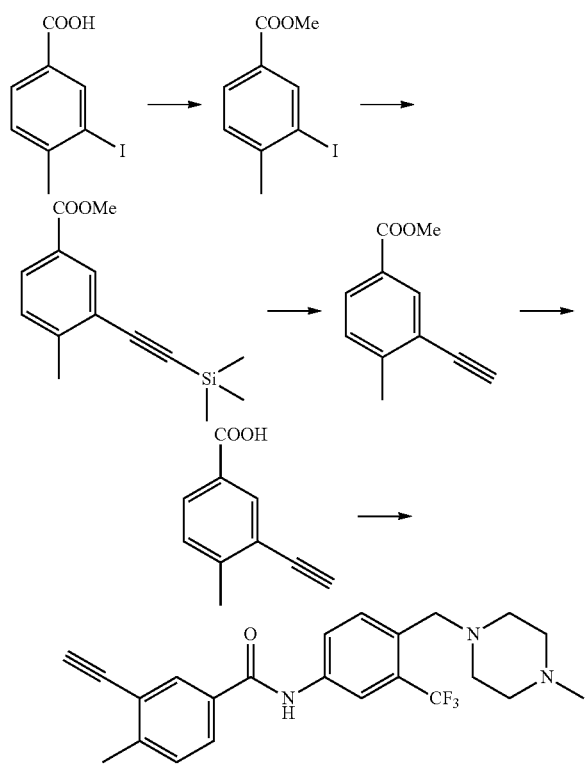

Step 1: Preparation of methyl 3-iodo-4-methylbenzoate

To a solution of 3-iodo-4-methylbenzoic acid (15 g, 57.14 mmol) in methanol, concentrated sulfuric acid was slowly added dropwise. The reaction solution was allowed to exotherm. After addition, the solution was heated to 70° C. the reaction monitored by TLC was completed 48 h later. The methanol was evaporated under reduced pressure to give brown oil which was slowly poured into 200 mL of water, and the mixture was milk white with heat emission. The aqueous phase was extracted with DCM twice. The DCM layer combined was washed successively with aqueous sodium bicarbonate solution, saturated aqueous sodium chloride solution, water once. The DCM layer was dried over anhydrous sodium sulfate and evaporated to dryness under reduced pressure to give the title product as a yellowish brown oil.

Step 2: Preparation of 3-trimethyl-silicone-4-methylbenzoate

To the oil of Step 1 in THF, copper iodide (1.1 g, 5.74 mmol, 0.1 eq) and tetrakis (triphenylphosphine) palladium (3.3 g, 2.86 mmol, 0.05 eq) was added. The solution was purged with nitrogen 3 times. To the solution triethylamine (11.57 g, 114.28 mmol, 2.0 eq) and trimethylsilylacetylene (8.4 g, 85.71 mmol, 1.5 eq) was added. Then the solution obtained was stirred at room temperature for 24 hours, evaporated to dryness under reduced pressure and the title product was isolated by column chromatography as a yellow oil.

Step 3: Preparation of 3-ethynyl-4-methylbenzoate

To the oil in the previous step methanol, potassium carbonate (3.95 g, 28.57 mmol, 0.5 eq) was added. The reaction was carried out after stirred at room temperature for 10 min. The solvent was evaporated to dryness under reduced pressure. To the residue DCM was added, and the solution was washed with aqueous sodium bicarbonate, saturated sodium chloride aqueous solution, and water once. The DCM layer was dried over anhydrous sodium sulfate and separated by column chromatography to give the title product as a light yellow oil.

Step 4: Preparation of 3-ethynyl-4-methylbenzoic acid

The product obtained in the previous step was dissolved in methanol, and to the solution 10 mL saturated sodium hydroxide aqueous solution was added, and the solution afforded was stirred at room temperature overnight. After completion of the reaction, the solvent was evaporated under reduced pressure, and to the solution about 20 mL water was added. The pH was adjusted to about 3 with hydrochloric acid. Then a large amount of white solid was precipitated and the solution was extracted with DCM 3 times. The DCM layer combined was washed with water once, dried anhydrous sodium sulfate, and the product was evaporated to dryness to afford the product 3-ethynyl-4-methylbenzoic acid as a light yellow solid (8.0 g, total yield 87.2%). $^1$H NMR (400 MHz, DMSO-$d_6$) δ 13.04 (br.s, 1H), 7.93 (s, 1H), 7.85 (d, J=8.0 Hz, 1H), 7.43 (d, J=8.0 Hz, 1H), 4.48 (s, 1H), 2.45 (s, 3H). MS m/z (ESI): 159.0 [M−H].

Step 5: Preparation of 3-ethynyl-4-methyl-N-(4-((4-methyl-piperazin-1-yl)methyl)-3-(trifluoromethyl) phenyl) benzamide To a solution of 3-ethynyl-4-methylbenzoic acid (500 mg, 3.12 mmol, 1.05 eq) in DCM, HATU (1.42 g, 3.74 mmol, 1.2 eq) and DIPEA (806 mg, 6.24 mmol, 2.0 eq) was added. The mixture was stirred at room temperature for 30 min or so. Then to the solution 3-trifluoromethyl-4-[(4-methylpiperazin-1-yl) methyl]aniline (812 mg, 2.97 mmol, 1.0 eq) was added and the temperature was raised to 45° C. The reaction is completed after 20 h and the solvent was evaporated to dryness under reduced pressure to afford the residue extracted twice with DCM and saturated sodium bicarbonate aqueous solution. The DCM layer was evaporated to dryness to afford yellow oil which was purified by column chromatogram to give intermediate 74 as a yellowish brown solid (807 mg, 65.4% yield). $^1$H NMR (400 MHz, CDCl$_3$) δ 8.33 (s, 1H), 7.91 (s, 1H), 7.86 (d, J=13.7 Hz, 2H), 7.73 (t, J=7.1 Hz, 2H), 7.28 (s, 1H), 3.60 (s, 2H), 3.32 (s, 1H), 2.48 (br.s, 11H), 2.30 (s, 3H). MS m/z (ESI): 416.3 [M+H].

Example 21

Preparation of Intermediate 75~79

The following intermediates 75 to 79 were obtained, using aniline or arylamine containing different substituents as starting materials, by using the similar method as described for intermediate 74.

| No. | Structure | ¹H-NMR | ESI⁺ [M + H] |
|---|---|---|---|
| Intermediate 75 | 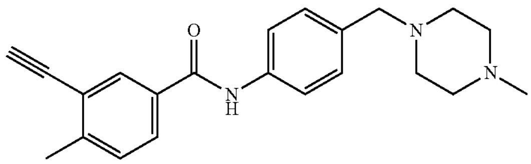 [SMILES: C#Cc1cc(C(=O)Nc2ccc(CN3CCN(C)CC3)cc2)ccc1C] | ¹H NMR (400 MHz, CDCl₃) δ 7.91 (d, J = 10.3 Hz, 2H), 7.76 (d, J = 7.7 Hz, 1H), 7.57 (d, J = 7.7 Hz, 2H), 7.31 (d, J = 7.7 Hz, 3H), 3.49 (s, 2H), 3.35 (s, 1H), 2.51 (s, 3H), 2.48 (br.s, 8H), 2.32 (s, 3H). | 348.2 |
| Intermediate 76 | 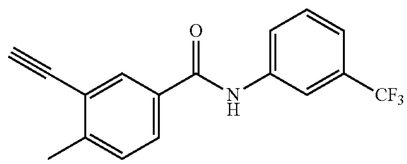 [SMILES: C#Cc1cc(C(=O)Nc2cccc(C(F)(F)F)c2)ccc1C] | ¹H NMR (400 MHz, DMSO-d₆) δ 10.55 (s, 1H), 8.25 (s, 1H), 8.11 (s, 1H), 8.07 (d, J = 8.4 Hz, 1H), 7.92 (d, J = 8.0 Hz, 1H), 7.60 (d, J = 8.0 Hz, 1H), 7.47 (t, J = 8.8 Hz, 2H), 4.54 (s, 1H), 2.47 (s, 3H). | 304.1 |
| Intermediate 77 | 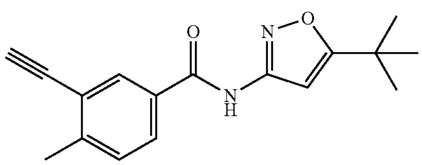 [SMILES: C#Cc1cc(C(=O)Nc2cc(C(C)(C)C)on2)ccc1C] | ¹H NMR (400 MHz, DMSO-d₆) δ 11.40 (s, 1H), 8.15 (s, 1H), 7.98 (d, J = 8.0 Hz, 1H), 7.50 (d, J = 8.0 Hz, 1H), 6.77 (s, 1H), 4.55 (s, 1H), 2.50 (s, 3H), 1.37 (s, 9H). | 283.2 |
| Intermediate 78 | 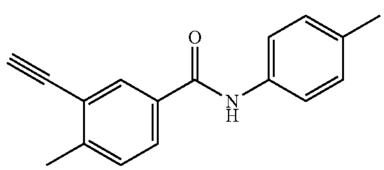 [SMILES: C#Cc1cc(C(=O)Nc2ccc(C)cc2)ccc1C] | ¹H NMR (400 MHz, CDCl₃) δ 7.93 (s, 1H), 7.76 (d, J = 8.0 Hz, 2H), 7.51 (d, J = 8.0 Hz, 2H), 7.32 (d, J = 8.0 Hz, 1H), 7.17 (d, J = 8.0 Hz, 2H), 3.34 (s, 1H), 2.51 (s, 3H), 2.34 (s, 3H). | 250.1 |
| Intermediate 79 | 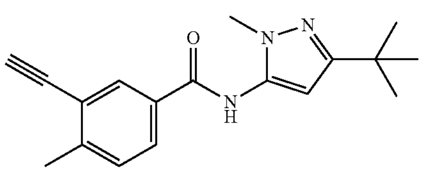 [SMILES: C#Cc1cc(C(=O)Nc2cc(C(C)(C)C)nn2C)ccc1C] | ¹H NMR (400 MHz, DMSO-d₆) δ 10.25 (s, 1H), 8.06 (d, J = 1.2 Hz, 1H), 7.89 (dd, J = 8.0, 1.2 Hz, 1H), 7.47 (d, J = 8.0 Hz, 1H), 6.11 (s, 1H), 4.51 (s, 1H), 3.63 (s, 3H), 2.47 (s, 3H), 1.24 (s, 9H). | 296.2 |

Example 22

Preparation of 3-ethynyl-4-methyl-N-(3-(4-methyl-1H-imidazol-1-yl)-5-(trifluoromethyl) phenyl) benzamide (Intermediate 80)

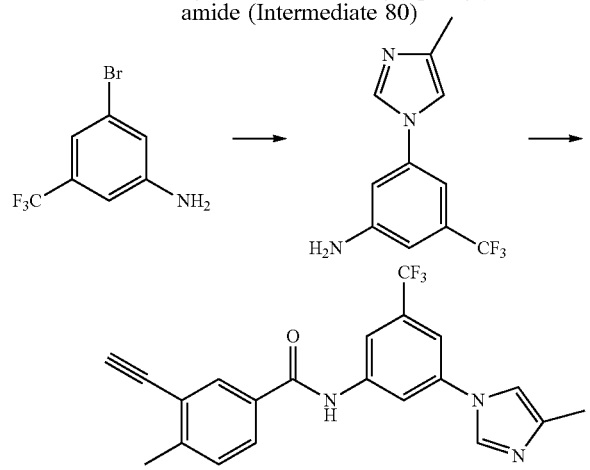

Step 1: Preparation of 3-(4-methyl-imidazol-1-yl)-5-trifluoromethyl-aniline

To the solution of Bromo-5-trifluoromethyl-phenylamine (500 mg, 2.1 mmol, 1.0 eq), 4-methyl-1H-imidazole (20.5 mg, 2.5 mmol, 1.2 eq), cuprous iodide (0.14 eq) and 8-hydroxyquinoline (44 mg, 0.3 mmol, 0.14 eq) in 3 mL dimethylsulfoxide was purged with nitrogen 3 times and the solution was heated to 120° C., the mixture was diluted with water after completion of the reaction. Then the organic layer was washed successively with dilute aqueous ammonia solution and saturated aqueous sodium chloride solution, dried over anhydrous magnesium sulfate, filtered and concentrated under reduced pressure. The residue was isolated by column chromatography to give the title product as a yellow solid (392 mg, 77.3% yield). ¹H NMR (400 MHz, CDCl₃) δ7.73 (s, 1H), 6.98 (s, 1H), 6.92 (s, 1H), 6.83 (s, 1H), 6.77 (s, 1H), 4.14 (s, 2H), 2.27 (s, 3H). MS m/z (ESI): 242.1 [M+H].

Step 2: Preparation of 3-ethynyl-4-methyl-N-(3-(4-methyl-1H-imidazol-1-yl)-5-(trifluoromethyl) phenyl)benzamide Intermediate 80 was obtained as light yellow solid (350 mg, 65.7% yield) using the similar condensation procedure described in Step 5 of intermediate 5. ¹H NMR (400 MHz, DMSO-d₆) δ 10.68 (s, 1H), 8.29 (s, 1H), 8.22 (s, 1H), 8.16 (s, 1H), 8.12 (s, 1H), 7.93 (d, J=8.0 Hz, 1H), 7.74 (s, 1H), 7.51 (d, J=9.0 Hz, 2H), 4.56 (s, 1H), 2.48 (s, 3H), 2.19 (s, 3H). MS m/z (ESI): 384.1 [M+H].

Example 23

Preparation of 3-ethynyl-4-methyl-N-(3-((4-methyl-piperazin-1-yl)methyl)-5-(trifluoromethyl) phenyl) benzamide (Intermediate 81)

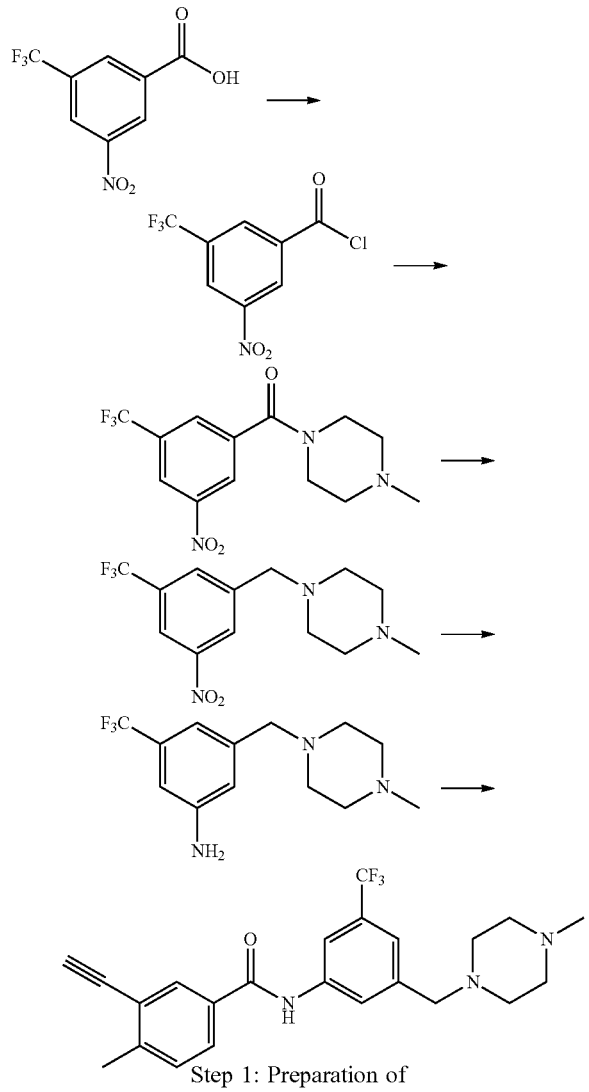

Step 1: Preparation of 3-nitro-5-trifluoromethylbenzoyl chloride

To a solution of 3-nitro-5-trifluoromethylbenzoic acid (3.52 g, 14.97 mmol, 1.0 eq) in 20 mL thionyl chloride and the solution was refluxed at 80° C. for 2 h. After completion of the reaction, the solvent was evaporated under reduced pressure to afford the remaining residue as the target product directly used for the next step.

Step 2: Preparation of (4-methylpiperazin-1-yl) (3-nitro-5-(trifluoromethyl)phenyl) methanone A solution of N-methylpiperazine (1.5 g, 15 mmol, 1.05 eq), triethylamine (2.2 g, 22.4 mmol, 1.5 mmol) in 20 mL DCM, 3-nitro-5-trifluoromethylbenzoyl chloride in the previous step dissolved in 6 mL DCM was slowly added. The mixture was stirred at room temperature for 0.5 h. then washed with saturated sodium bicarbonate solution, saturated sodium chloride solution and water after competition of the reaction, dried over anhydrous magnesium sulfate drying, filtrated and distilled in vacuum to afford the residue directly for the next step reaction. MS m/z (ESI): 318.1 [M+H].

Step 3: Preparation of 1-methyl-4-(3-nitro-5-(trifluoromethyl) benzyl) piperazine To a (4-methylpiperazin-1-yl) (3-nitro-5-(trifluoromethyl)phenyl) methanone (14.97 mmol) in anhydrous tetrahydrofuran under nitrogen atmosphere cooled to 0° C. 2 mol/L borane dimethyl sulfide (22.5 mL, 45 mmol, 3.0 eq) diluted to 50 mL with anhydrous tetrahydrofuran was slowly added dropwise. After addition, the temperature was raised to 65° C. overnight. Then the solution was cooled to 0° C., and to the solution 6M HCl 22.5 mL was added. The solution was heated to 65° C. for 1 h, and then cooled to 0° C. 4M NaOH aqueous solution was slowly added dropwise to the solution to adjust the pH to 9, and the reaction solution was extracted with ethyl acetate 3 times. The organic layer combined was dried over anhydrous magnesium sulfate, filtered under reduced pressure and evaporated to dryness and the residue was isolated by column chromatography to afford the title product as a light yellow oil (2.4 g, yield 53.2%). MS m/z (ESI): 304.1 [M+H].

Step 4: Preparation of 3-((4-methylpiperazin-1-yl) methyl)-5-(trifluoromethyl)

To a solution of 1-methyl-4-(3-nitro-5-(trifluoromethyl) benzyl) piperazine (2.4 g, 7.96 mmol) in 75% ethanol, 10% palladium on carbon (240 mg, 10% eq) was added. The solution afforded was replaced with nitrogen 3 times and the reaction proceeded at 50° C. After completion of the reaction, the solution was filtered under reduced pressure, evaporated to dryness to obtain the desired product as a white solid (2.1 g, 96.1% yield). MS m/z (ESI): 274.1 [M+H].

Step 5: Preparation of 3-ethynyl-4-methyl-N-(3-((4-methyl-piperazin-1-yl) methyl)-5-(trifluoromethyl) phenyl) benzamide Intermediate 81 was obtained as light yellow solid using the similar condensation procedure described in Step 5 of intermediate 5 (260 mg, hydrochloride, 61.7% yield). $^1$H NMR (400 MHz, DMSO-d$_6$) δ 10.55 (s, 1H), 9.28 (br.s, 1H), 8.10 (s, 3H), 7.91 (d, J=8.1 Hz, 1H), 7.49 (d, J=8.1 Hz, 1H), 7.41 (s, 1H), 4.56 (s, 1H), 3.66 (s, 2H), 3.39 (d, J=11.1 Hz, 2H), 3.14-2.99 (m, 2H), 2.94 (d, J=12.5 Hz, 2H), 2.80 (s, 3H), 2.47 (s, 3H), 2.33 (t, J=11.9 Hz, 2H). MS m/z (ESI): 416.3 [M+H].

Example 24

3-ethynyl-N-(3-(trifluoromethyl) phenyl) benzamide (Intermediate 82)

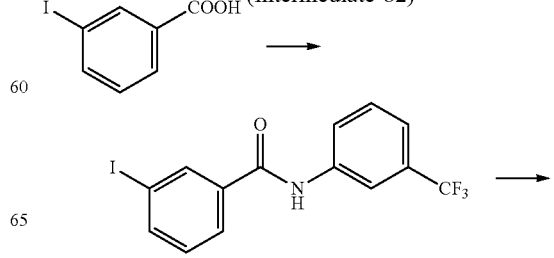

155

-continued

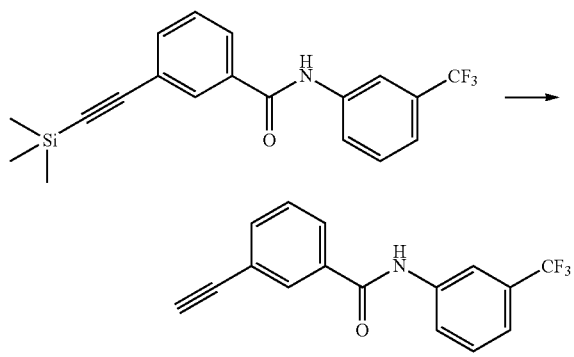

Step 1: Preparation of 3-iodo-N-(3-(trifluoromethyl) phenyl) benzamide:

A solution of m-iodobenzoic acid (1.29 g, 5.2 mmol, 1.05 eq), TBTU (O-(benzotriazol-1-oxide)-N, N, N', N'-tetramethyluronium hexafluorophosphate salt) (1.03 g, 10 mmol, 2.0 eq) and triethylamine in DCM was stirred at room temperature for 0.5 h. M-trifluoromethylaniline (805 mg, 5.0 mmol, 1.0 eq) was added and the temperature was raised to 45° C. for 12 h. the solvent was evaporated under reduced pressure, extracted with mixed solution of saturated sodium bicarbonate aqueous solution and DCM once. The DCM layer was evaporated to afford the target product isolated by column chromatography. $^1$H NMR (400 MHz, DMSO-$d_6$) δ 10.60 (s, 1H), 8.33 (s, 1H), 8.22 (s, 1H), 8.05 (d, J=8.0 Hz, 1H), 7.99 (dd, J=7.8, 1.2 Hz, 2H), 7.61 (t, J=8.0 Hz, 1H), 7.47 (d, J=7.8 Hz, 1H), 7.37 (t, J=8.0 Hz, 1H). MS m/z (ESI): 392.0 [M+H].

Step 2: Preparation of N-(3-(trifluoromethyl) phenyl)-3-((trimethylsilyl) ethynyl) benzamide To the product from the previous step in THF (tetrahydrofuran), copper iodide (95.23 mg, 0.5 mmol, 0.1 eq) and bis (triphenylphosphine) palladium dichloride (175.5 mg, 0.25 mmol, 0.05 eq) was added. The solution was replaced with nitrogen, and to the solution DIPEA (1.29 g, 10 mmol, 2.0 eq) and trimethylsilylacetylene (737 mg, 7.5 mmol, 1.5 eq) was added. The solution was stirred at room temperature for 4 h. The reaction was stopped and the target product was isolated by column chromatography and used directly in the next step. MS m/z (ESI): 362.2 [M+H].

Step 3: Preparation of
3-ethynyl-N-(3-(trifluoromethyl) phenyl) benzamide

To the product from the previous step in methanol, potassium carbonate (345.5 mg, 2.5 mmol, 0.5 eq) was added. And the mixture was stirred at room temperature. The reaction was completed after 10 min, and the solvent was evaporated to dryness to afford the residue that was separated by column chromatography to give intermediate 82 as a light yellow solid (875.0 mg, about 60.5% yield). $^1$H NMR (400 MHz, DMSO-$d_6$) δ 10.61 (s, 1H), 8.25 (s, 1H), 8.10 (s, 1H), 8.06 (d, J=8.3 Hz, 1H), 8.00 (d, J=7.9 Hz, 1H), 7.72 (d, J=7.7 Hz, 1H), 7.63-7.56 (m, 2H), 7.47 (d, J=7.9 Hz, 1H), 4.35 (s, 1H). MS m/z (ESI): 290.1 [M+H].

156

Example 25

Preparation of 4-chloro-3-ethynyl-N-(3-(trifluoromethyl) phenyl) benzamide (Intermediate 83)

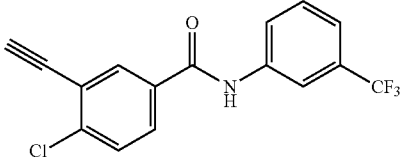

intermediate 83

Intermediate 83 was obtained, using intermediate 4-chloro-3-iodobenzoic acid and 3-trifluoromethylaniline as the starting material, by the analogous procedure described for intermediate 82. $^1$H NMR (400 MHz, CDCl$_3$) δ 7.98 (s, 1H), 7.91 (s, 1H), 7.85 (d, J=7.6 Hz, 1H), 7.77 (d, J=7.2 Hz, 1H), 7.46 (d, J=8.4 Hz, 2H), 7.44-7.39 (m, 2H), 3.43 (s, 1H). MS m/z (ESI): 324.1 [M+H].

Example 26

Preparation of 1-(3-ethynylphenyl)-3-(3-(trifluoromethyl) phenyl) urea (Intermediate 84)

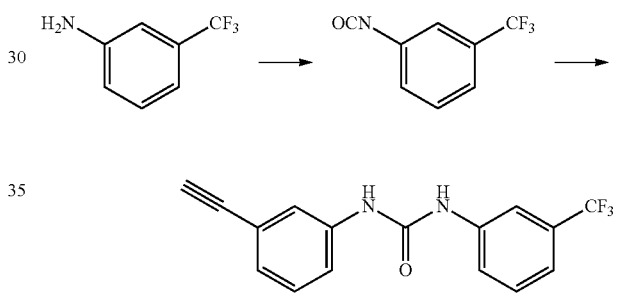

A solution of triphosgene (1.79 g, 6.0 mmol, 1.5 eq) in EA was stirred at room temperature. Trifluoromethylaniline (967 mg, 6.0 mmol, 1.5 eq) in EA was slowly added dropwise to the triphosgene EA solution over 30 min. Then to the solution triethylamine (1.2 g, 12 mmol, 2.0 eq) was added slowly and a large amount of white solid was precipitated and the reaction proceeded at room temperature for 2 h. The solvent was evaporated under reduced pressure, and to the residue EA was added. Then the insoluble solid was filtered off, and the filtrate was collected. M-ethynylaniline (469 mg, 4.0 mmol, 1.0 eq) was added to the filtrate to afford solid. The reaction was monitored by TLC, and after completion the solvent was evaporated under reduced pressure to afford the crude product recrystallized from ether: petroleum ether=1:1 to give intermediate 84 as a white solid (543 mg, about 44.6% yield). $^1$H NMR (400 MHz, DMSO-$d_6$) δ 9.35 (s, 1H), 9.15 (s, 1H), 8.01 (s, 1H), 7.68 (s, 1H), 7.59 (d, J=8.4 Hz, 1H), 7.52 (t, J=7.9 Hz, 1H), 7.44 (d, J=8.2 Hz, 1H), 7.31 (d, J=7.8 Hz, 2H), 7.10 (d, J=7.6 Hz, 1H), 4.17 (s, 1H). MS m/z (ESI): 304.2 [M+H].

Example 27

Preparation of Intermediate 85~86

The following intermediates 85 to 86 were obtained, using anilines containing different substituents as starting materials, by an analogous procedure described for intermediate 84.

| No. | Structure | ¹H-NMR | ESI⁺ [M + H] |
|---|---|---|---|
| Intermediate 85 | 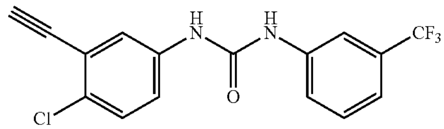 [SMILES: C#Cc1cc(NC(=O)Nc2cccc(C(F)(F)F)c2)ccc1Cl] | ¹H NMR (400 MHz, DMSO-d₆) δ 9.40 (s, 1H), 9.29 (s, 1H), 8.00 (s, 1H), 7.79 (s, 1H), 7.59 (d, J = 8.2 Hz, 1H), 7.52 (t, J = 7.9 Hz, 1H), 7.46 (d, J = 1.2 Hz, 2H), 7.33 (d, J = 7.7 Hz, 1H), 4.56 (s, 1H). | 339.1 |
| Intermediate 86 | 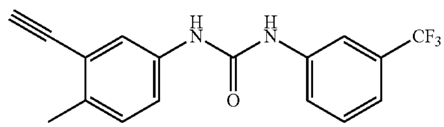 [SMILES: C#Cc1cc(NC(=O)Nc2cccc(C(F)(F)F)c2)ccc1C] | ¹H NMR (400 MHz, DMSO-d₆) δ 9.06 (s, 1H), 8.79 (s, 1H), 8.01 (s, 1H), 7.63 (d, J = 2.0 Hz, 1H), 7.57 (d, J = 8.3 Hz, 1H), 7.51 (t, J = 7.9 Hz, 1H), 7.33 (dd, J = 10.8, 4.7 Hz, 2H), 7.20 (d, J = 8.4 Hz, 1H), 4.35 (s, 1H), 2.33 (s, 3H). | 319.1 |

Example 28

Preparation of N-(3-((4-amino-1-isopropyl-1H-pyrazolo [3,4-d] pyrimidin-3-yl) ethynyl)-4-methylphenyl)-4-(4-methylpiperazin-1-yl) methyl) benzamide (Compound 1)

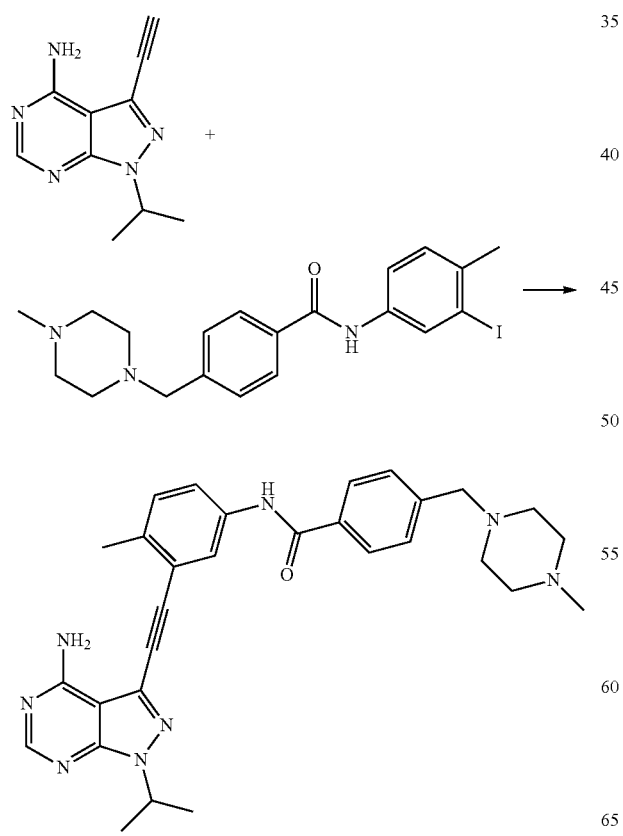

To the mixture of N-(3-iodo-4-methylphenyl)-4-((4-methylpiperazin-1-yl) methyl) benzamide (intermediate 36) (118 mg, 0.263 mmol, 1.0 eq), 3-ethynyl-1-isopropyl-1H-pyrazolo [3,4-d]pyrimidin-4-amine (intermediate 1) (55.57 mg, 0.276 mmol, 1.05 eq), PdCl₂(PPh₃)₂ (21.06 mg, 0.03 mmol, 0.1 eq), CuI (5.7 mg, 0.03 mmol, 0.1 eq) in a three-necked flask, 2 mL DMF was added. Then the solution afforded was replaced with nitrogen 3 times, and triethylamine (53.23 mg, 0.526 mmol, 2.0 eq) was added to afford the solution stirred at 80° C. overnight. The reaction monitored by TLC was completed, and DMF was distilled off under reduced pressure to afford the residue purified by column chromatography to give Compound 1 as a light yellow solid (62 mg, 45.1% yield). ¹H NMR (400 MHz, DMSO-d₆) δ 10.33 (s, 1H), 8.27 (s, 1H), 8.10 (s, 1H), 7.94 (d, J=7.6 Hz, 2H), 7.75 (d, J=8.2 Hz, 1H), 7.47 (d, J=7.6 Hz, 2H), 7.34 (d, J=8.2 Hz, 1H), 5.20-4.93 (m, 1H), 3.56 (s, 2H), 2.58 (br.s, 8H), 2.47 (s, 3H), 2.34 (s, 3H), 1.49 (d, J=6.4 Hz, 6H). MS m/z (ESI): 523.2930 [M+H].

Example 29

Preparation of Compound 2119

Compound 2~119 were obtained using aryl acetylene and halide with different substituents by a method analogous procedure described in Example 28.

| Compound | Structure | ¹H-NMR | ESI⁺ [M + H] |
|---|---|---|---|
| 2 | 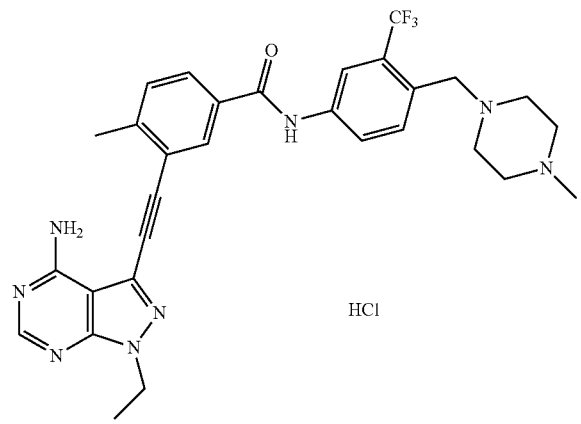 [SMILES: CCn1nc(C#Cc2cc(C(=O)Nc3ccc(CN4CCN(C)CC4)c(C(F)(F)F)c3)ccc2C)c2c(N)ncnc21 ; Cl] HCl | ¹H NMR (400 MHz, DMSO-d₆) δ 11.11 (br.s, 1H), 10.83 (s, 1H), 9.14 (br.s, 1H), 8.50 (s, 2H), 8.36 (s, 1H), 8.22 (d, J = 8.4 Hz, 1H), 8.03 (d, J = 8.2 Hz, 1H), 7.98 (br.s, 1H), 7.57 (d, J = 8.2 Hz, 1H), 4.44 (q, J = 7.2 Hz, 2H), 4.07 (br.s, 2H), 3.50 (br.s, 2H), 3.24 (br.s, 4H), 2.94 (br.s, 2H), 2.79 (s, 3H), 2.59 (s, 3H), 1.45 (t, J = 7.2 Hz, 3H). | 577.2652 |
| 3 | 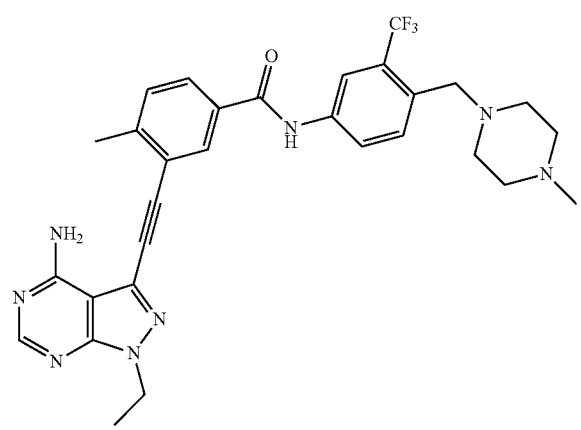 [SMILES: CCn1nc(C#Cc2cc(C(=O)Nc3ccc(CN4CCN(C)CC4)c(C(F)(F)F)c3)ccc2C)c2c(N)ncnc21] | ¹H NMR (400 MHz, DMSO-d₆) δ 10.56 (s, 1H), 8.34 (s, 1H), 8.27 (s, 1H), 8.22 (d, J = 1.7 Hz, 1H), 8.07 (d, J = 8.5 Hz, 1H), 7.97 (d, J = 8.1 Hz, 1H), 7.72 (d, J = 8.5 Hz, 1H), 7.55 (d, J = 8.1 Hz, 1H), 4.38 (q, J = 7.2 Hz, 2H), 3.57 (s, 2H), 2.58 (s, 3H), 2.39 (br.s, 8H), 2.16 (s, 3H), 1.42 (t, J = 7.2 Hz, 3H). | 577.2652 |
| 4 | 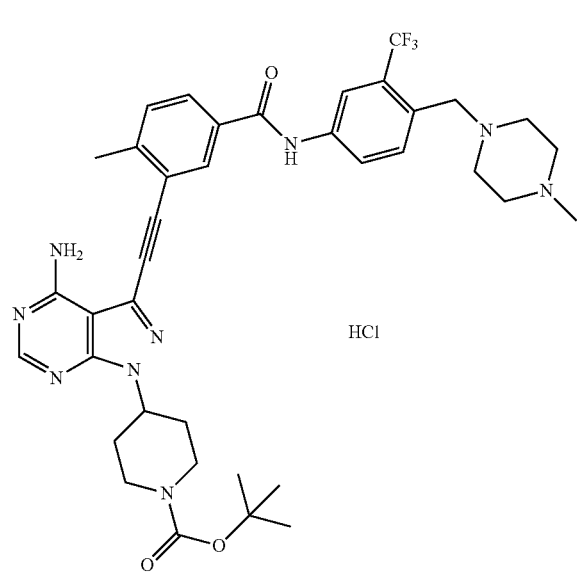 [SMILES: Cc1ccc(C(=O)Nc2ccc(CN3CCN(C)CC3)c(C(F)(F)F)c2)cc1C#CC(=N)c1c(N)ncnc1NC1CCN(C(=O)OC(C)(C)C)CC1 ; Cl] HCl | ¹H NMR (400 MHz, DMSO-d₆) δ 11.72 (br.s, 1H), 10.93 (s, 1H), 9.32 (br.s, 1H), 8.55 (d, J = 12.3 Hz, 2H), 8.42 (s, 1H), 8.25 (d, J = 8.2 Hz, 1H), 8.13 (br.s, 1H), 8.04 (d, J = 8.2 Hz, 1H), 7.55 (d, J = 8.0 Hz, 1H), 5.12 (t, J = 11.1 Hz, 1H), 5.04-4.89 (m, 1H), 4.24 (br.s, 2H), 4.09 (d, J = 11.0 Hz, 2H), 3.83-3.73 (m, 1H), 3.56 (br.s, 2H), 3.40 (br.s, 4H), 3.26-3.10 (m, 2H), 3.06 (s, 1H), 3.00 (br.s, 1H), 2.79 (s, 3H), 2.57 (s, 3H), 2.43-2.34 (m, 1H), 2.14 (d, J = 12.9 Hz, 1H), 1.43 (s, 9H). | 732.3598 |

-continued
| Compound | Structure | ¹H-NMR | ESI⁺ [M + H] |
|---|---|---|---|
| 5 | 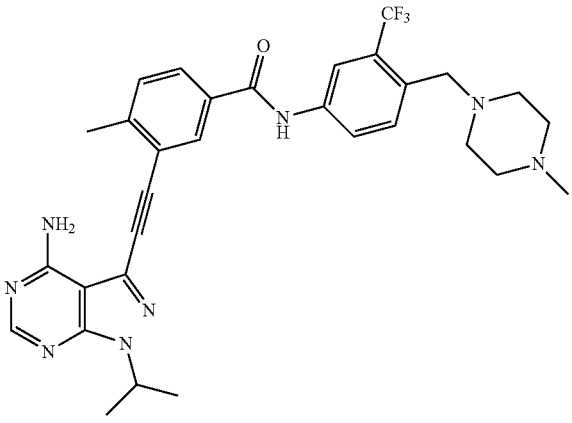 [SMILES: Cc1ccc(C(=O)Nc2ccc(CN3CCN(C)CC3)c(C(F)(F)F)c2)cc1C#CC(=N)c1c(N)ncnc1NC(C)C] | ¹H NMR (400 MHz, DMSO-d$_6$) δ 10.58 (s, 1H), 8.29 (s, 1H), 8.18 (s, 2H), 8.05 (d, J = 8.3 Hz, 1H), 7.91 (d, J = 8.0 Hz, 1H), 7.64 (d, J = 8.3 Hz, 1H), 7.46 (d, J = 8.0 Hz, 1H), 5.01-4.95 (m, 1H), 3.58 (s, 2H), 3.04 (br.s, 4H), 2.62 (s, 3H), 2.56 (br.s, 4H), 2.43 (s, 3H), 1.40 (d, J = 6.6 Hz, 6H). | 591.2808 |
| 6 | 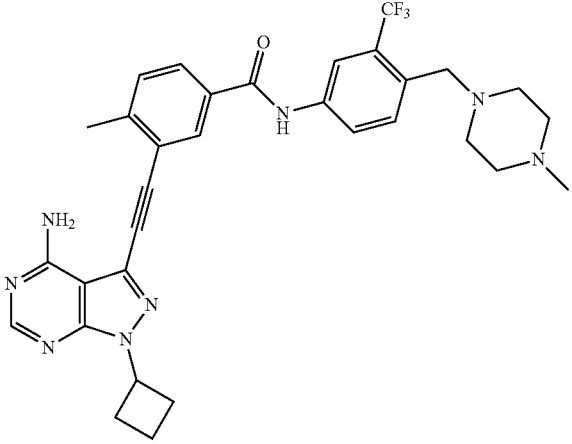 [SMILES: Cc1ccc(C(=O)Nc2ccc(CN3CCN(C)CC3)c(C(F)(F)F)c2)cc1C#Cc1nn(C2CCC2)c2ncnc(N)c12] | ¹H NMR (400 MHz, DMSO-d$_6$) δ 10.56 (s, 1H), 8.35 (s, 1H), 8.26 (s, 1H), 8.22 (s, 1H), 8.08 (d, J = 8.5 Hz, 1H), 7.97 (d, J = 8.0 Hz, 1H), 7.72 (d, J = 8.5 Hz, 1H), 7.55 (d, J = 8.0 Hz, 1H), 5.38-5.29 (m, 1H), 3.57 (s, 2H), 2.76-2.62 (m, 2H), 2.59 (s, 3H), 2.41 (br.s, 10H), 2.18 (s, 3H), 1.95-1.80 (m, 2H). | 603.2808 |
| 7 | 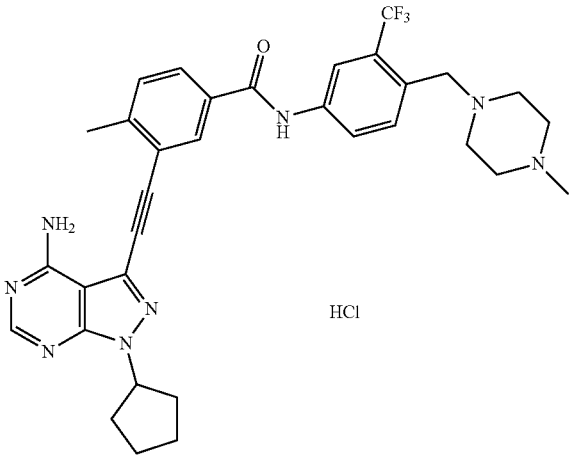 [SMILES: Cc1ccc(C(=O)Nc2ccc(CN3CCN(C)CC3)c(C(F)(F)F)c2)cc1C#Cc1nn(C2CCCC2)c2ncnc(N)c12 ; Cl] | ¹H NMR (400 MHz, DMSO-d$_6$) δ 11.56 (br.s, 1H), 10.90 (s, 1H), 9.35 (br.s, 1H), 8.53 (s, 2H), 8.40 (s, 1H), 8.24 (d, J = 8.5 Hz, 1H), 8.08 (br.s, 1H), 8.04 (d, J = 8.1 Hz, 1H), 7.57 (d, J = 8.1 Hz, 1H), 5.29 (q, J = 7.0 Hz, 1H), 4.18 (br.s, 2H), 3.54 (br.s, 2H), 3.34 (br.s, 4H), 3.16 (br.s, 2H), 2.80 (s, 3H), 2.58 (s, 3H), 2.16 (dt, J = 12.4, 7.2 Hz, 2H), 2.01 (td, J = 13.1, 6.6 Hz, 2H), 1.95-1.82 (m, 2H), 1.77-1.64 (m, 2H). | 617.2968 |

-continued

| Compound | Structure | ¹H-NMR | ESI⁺ [M + H] |
|---|---|---|---|
| 8 | (structure) HCl | ¹H NMR (400 MHz, DMSO-d₆) δ 11.80 (br.s, 1H), 11.00 (s, 1H), 9.52 (br.s, 1H), 8.62 (s, 1H), 8.56 (s, 1H), 8.45 (s, 1H), 8.28 (d, J = 8.4 Hz, 1H), 8.15 (br.s, 1H), 8.04 (d, J = 8.0 Hz, 1H), 7.55 (d, J = 8.0 Hz, 1H), 4.27 (br.s, 2H), 4.02 (s, 3H), 3.57 (br.s, 2H), 3.40 (br.s, 4H), 3.05 (br.s, 2H), 2.79 (s, 3H), 2.56 (s. 3H). | 563.2497 |
| 9 | (structure) HCl | ¹H NMR (400 MHz, DMSO-d₆) δ 10.92 (s, 1H), 9.00 (br.s, 1H), 8.62 (s, 1H), 8.46 (s, 1H), 8.32 (s, 1H), 8.19 (d, J = 8.1 Hz, 1H), 8.11 (d, J = 8.3 Hz, 1H), 7.89 (br.s, 1H), 7.86 (d, J = 8.3 Hz, 1H), 7.66 (br.s, 1H), 5.24-5.01 (m, 1H), 3.98 (br.s, 2H), 3.47 (br.s, 2H), 3.18 (br.s, 4H), 2.81 (br.s, 2H), 2.79 (s, 3H), 1.51 (d, J = 6.4 Hz, 6H). | 611.2268 |
| 10 | (structure) | ¹H NMR (400 MHz, DMSO-d₆) δ 10.62 (s, 1H), 8.35 (s, 1H), 8.28 (s, 1H), 8.24 (s, 1H), 8.09 (d, J = 8.3 Hz, 1H), 8.00 (d, J = 8.0 Hz, 1H), 7.72 (d, J = 8.3 Hz, 1H), 7.56 (d, J = 8.0 Hz, 1H), 4.38 (q, J = 7.6 Hz, 2H), 3.60 (s, 2H), 2.95 (q, J = 7.2 Hz, 2H), 2.51 (br.s, 8H), 2.34 (s, 3H), 1.42 (t, J = 7.6 Hz, 3H), 1.29 (t, J = 7.2 Hz, 3H). | 591.2805 |

-continued
| Compound | Structure | ¹H-NMR | ESI⁺ [M + H] |
|---|---|---|---|
| 11 | 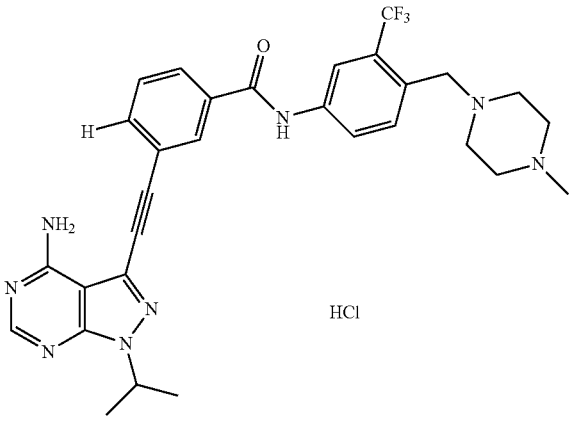 [SMILES: CC(C)n1nc(C#Cc2cccc(C(=O)Nc3ccc(CN4CCN(C)CC4)c(C(F)(F)F)c3)c2)c2c(N)ncnc21 ; Cl] HCl | ¹H NMR (400 MHz, DMSO-d₆) δ 11.45 (br.s, 1H), 10.95 (s, 1H), 9.37 (br.s, 1H), 8.53 (s, 2H), 8.39 (s, 1H), 8.23 (d, J = 8.3 Hz, 1H), 8.12 (d, J = 7.8 Hz, 1H), 8.08 (s, 1H), 8.02 (d, J = 7.8 Hz, 1H), 7.68 (t, J = 7.8 Hz, 1H), 5.15-5.08 (m, 1H), 4.16 (br.s, 2H), 3.53 (br.s, 2H), 3.32 (br.s, 4H), 3.08 (br.s, 2H), 2.80 (s, 3H), 1.51 (d, J = 6.6 Hz, 6H). | 577.2650 |
| 12 | 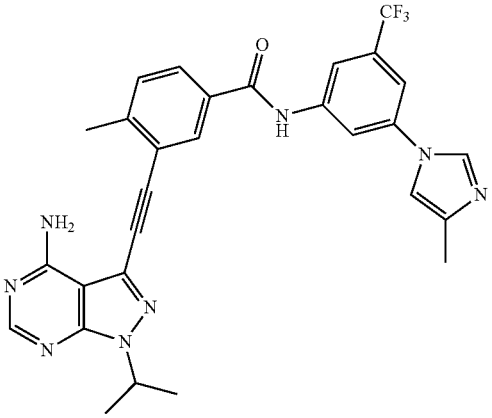 [SMILES: Cc1cn(-c2cc(NC(=O)c3ccc(C)c(C#Cc4nn(C(C)C)c5ncnc(N)c45)c3)cc(C(F)(F)F)c2)cn1] | ¹H NMR (400 MHz, DMSO-d₆) δ 10.74 (s, 1H), 8.37 (s, 1H), 8.31 (s, 1H), 8.27 (s, 1H), 8.23 (s, 1H), 8.18 (s, 1H), 7.99 (d, J = 7.9 Hz, 1H), 7.75 (s, 1H), 7.58 (d, J = 7.9 Hz, 1H), 7.52 (s, 1H), 5.17-4.96 (m, 1H), 2.60 (s, 3H), 2.19 (s, 3H), 1.49 (d, J = 6.4 Hz, 6H). | 559.2178 |
| 13 | 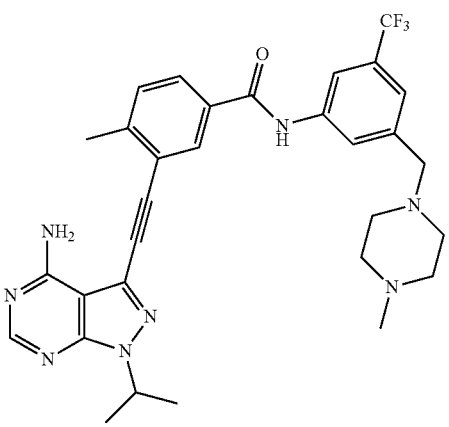 [SMILES: Cc1ccc(C(=O)Nc2cc(CN3CCN(C)CC3)cc(C(F)(F)F)c2)cc1C#Cc1nn(C(C)C)c2ncnc(N)c12] | ¹H NMR (400 MHz, DMSO-d₆) δ 10.59 (s, 1H), 8.36 (s, 1H), 8.27 (s, 1H), 8.20 (s, 1H), 8.04 (s, 1H), 7.97 (d, J = 8.0 Hz, 1H), 7.55 (d, J = 8.0 Hz, 1H), 7.37 (s, 1H), 5.09-5.03 (m, 1H), 3.56 (s, 2H), 2.59 (s, 3H), 2.42 (br.s, 8H), 2.20 (s, 3H), 1.49 (d, J = 6.6 Hz, 6H). | 591.2809 |

-continued

| Compound | Structure | ¹H-NMR | ESI⁺ [M + H] |
|---|---|---|---|
| 14 | 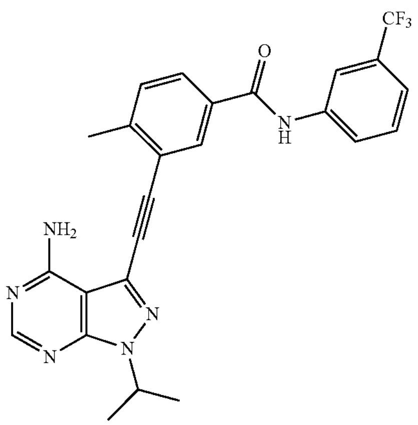 [SMILES: Cc1ccc(C(=O)Nc2cccc(C(F)(F)F)c2)cc1C#Cc1nn(C(C)C)c2ncnc(N)c12] | ¹H NMR (400 MHz, DMSO-d₆) δ 10.63 (s, 1H), 8.36 (s, 1H), 8.26 (s, 2H), 8.09 (d, J = 7.9 Hz, 1H), 7.97 (d, J = 7.7 Hz, 1H), 7.61 (t, J = 7.9 Hz, 1H), 7.54 (d, J = 7.9 Hz, 1H), 7.46 (d, J = 7.7 Hz, 1H), 5.20-4.92 (m, 1H), 2.58 (s, 3H), 1.48 (d, J = 6.4 Hz, 6H). | 479.1813 |
| 15 | 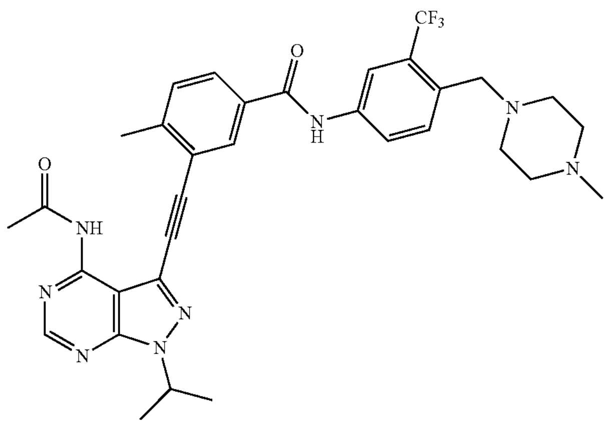 [SMILES: CC(=O)Nc1ncnc2c1c(C#Cc1cc(C(=O)Nc3ccc(CN4CCN(C)CC4)c(C(F)(F)F)c3)ccc1C)nn2C(C)C] | ¹H NMR (400 MHz, DMSO-d₆) δ 10.84 (s, 1H), 10.57 (s, 1H), 8.80 (s, 1H), 8.22 (s, 2H), 8.07 (d, J = 8.5 Hz, 1H), 7.97 (d, J = 8.1 Hz, 1H), 7.72 (d, J = 8.5 Hz, 1H), 7.55 (d, J = 8.1 Hz, 1H), 5.28-5.14 (m, 1H), 3.57 (s, 2H), 2.58 (s, 3H), 2.40 (br.s, 8H), 2.20 (s, 3H), 2.18 (s, 3H), 1.54 (d, J = 6.6 Hz, 6H). | 633.2914 |
| 16 | 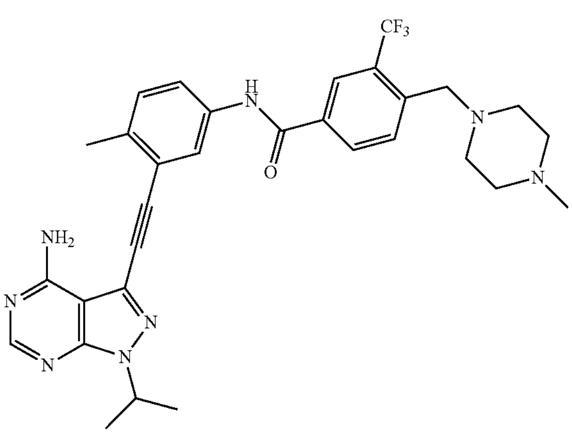 [SMILES: Cc1ccc(NC(=O)c2ccc(CN3CCN(C)CC3)c(C(F)(F)F)c2)cc1C#Cc1nn(C(C)C)c2ncnc(N)c12] | ¹H NMR (400 MHz, DMSO-d₆) δ 10.54 (s, 1H), 8.28 (d, J = 10.8 Hz, 3H), 8.08 (s, 1H), 7.94 (d, J = 8.3 Hz, 1H), 7.75 (d, J = 7.9 Hz, 1H), 7.37 (d, J = 8.3 Hz, 1H), 5.15-4.96 (m, 1H), 3.74 (s, 2H), 2.77 (br.s, 4H), 2.56 (s, 4H), 2.48 (s, 3H), 2.46 (s, 3H), 1.49 (d, J = 6.5 Hz, 6H). | 591.2807 |

| Compound | Structure | ¹H-NMR | ESI⁺ [M + H] |
|---|---|---|---|
| 17 | 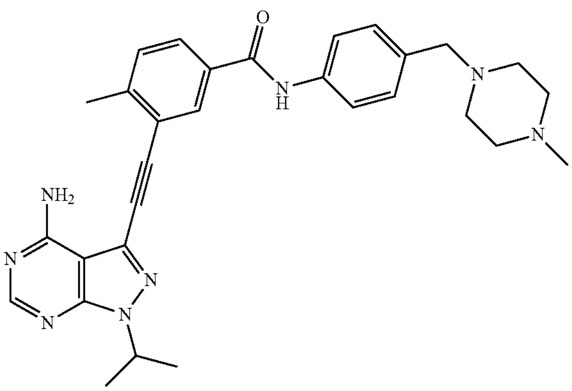 [SMILES: Cc1ccc(C(=O)Nc2ccc(CN3CCN(C)CC3)cc2)cc1C#Cc1nn(C(C)C)c2ncnc(N)c12] | ¹H NMR (400 MHz, DMSO-d₆) δ 10.54 (s, 1H), 8.28-8.25 (m, 3H), 8.09 (s, 1H), 7.94 (d, J = 7.9 Hz, 1H), 7.87 (br.s, 1H), 7.75 (d, J = 8.2 Hz, 1H), 7.36 (d, J = 8.2 Hz, 1H), 5.09-5.03 (m, 1H), 3.70 (s, 2H), 2.49 (s, 3H), 2.46 (br.s, 8H), 2.24 (s, 3H), 1.49 (d, J = 6.4 Hz, 6H). | 523.2928 |
| 18 | 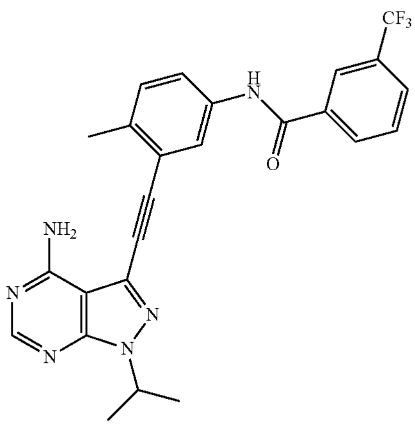 [SMILES: Cc1ccc(NC(=O)c2cccc(C(F)(F)F)c2)cc1C#Cc1nn(C(C)C)c2ncnc(N)c12] | ¹H NMR (400 MHz, DMSO-d₆) δ 10.56 (s, 1H), 8.32 (s, 1H), 8.28 (d, J = 8.0 Hz, 1H), 8.26 (s, 1H), 8.09 (s, 1H), 7.99 (d, J = 8.0 Hz, 1H), 7.81 (t, J = 8.3 Hz, 1H), 7.75 (d, J = 8.3 Hz, 1H), 7.37 (d, J = 8.3 Hz, 1H), 5.10-5.02 (m, 1H), 2.48 (s, 3H), 1.49 (d, J = 6.6 Hz, 6H). | 479.1806 |
| 19 | 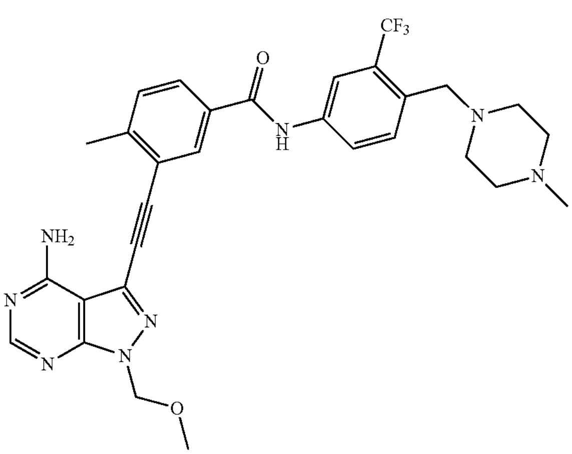 [SMILES: COCn1nc(C#Cc2cc(C(=O)Nc3ccc(CN4CCN(C)CC4)c(C(F)(F)F)c3)ccc2C)c2c(N)ncnc21] | ¹H NMR (400 MHz, DMSO-d₆) δ 10.57 (s, 1H), 8.36 (s, 1H), 8.32 (s, 1H), 8.22 (s, 1H), 8.07 (d, J = 8.3 Hz, 1H), 7.98 (d, J = 7.9 Hz, 1H), 7.72 (d, J = 8.3 Hz, 1H), 7.55 (d, J = 7.9 Hz, 1H), 5.63 (s, 2H), 3.58 (s, 2H), 3.31 (s, 3H), 2.59 (s, 3H), 2.40 (br.s, 8H), 2.19 (s, 3H). | 593.2597 |

| Compound | Structure | ¹H-NMR | ESI⁺ [M + H] |
|---|---|---|---|
| 20 | 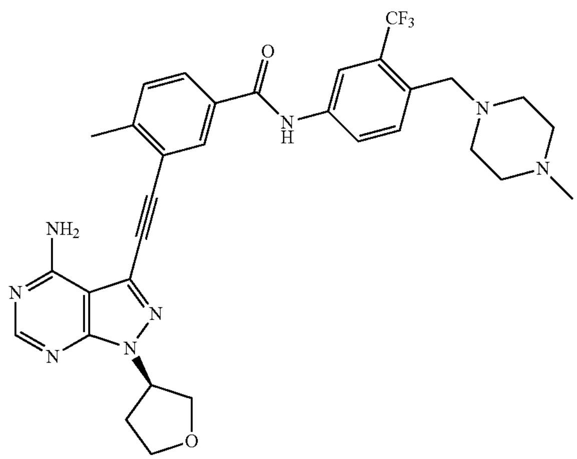 [SMILES: Cc1ccc(C(=O)Nc2ccc(CN3CCN(C)CC3)c(C(F)(F)F)c2)cc1C#Cc1nn([C@@H]2CCOC2)c2ncnc(N)c12] | ¹H NMR (400 MHz, DMSO-d₆) δ 10.59 (s, 1H), 8.36 (s, 1H), 8.28 (s, 1H), 8.23 (s, 1H), 8.10 (d, J = 8.0 Hz, 1H), 7.97 (d, J = 7.6 Hz, 1H), 7.72 (d, J = 8.0 Hz, 1H), 7.55 (d, J = 7.6 Hz, 1H), 5.58-5.41 (m, 1H), 4.18-3.98 (m, 2H), 3.91 (dd, J = 13.4, 9.1 Hz, 2H), 3.62 (s, 2H), 2.59 (s, 3H), 2.54 (s, 3H), 2.44 (br.s, 8H), 2.38-2.29 (m, 2H). | 619.2756 |
| 21 | 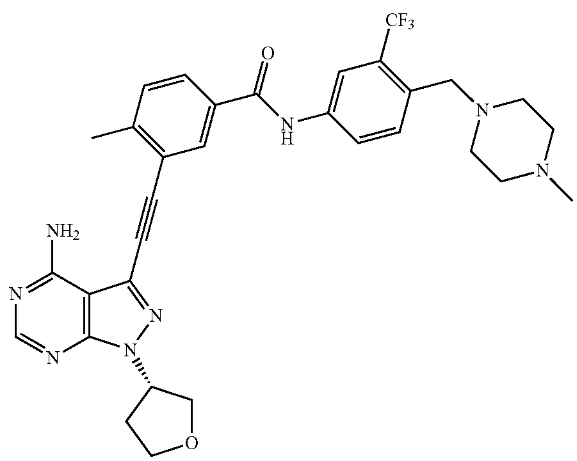 [SMILES: Cc1ccc(C(=O)Nc2ccc(CN3CCN(C)CC3)c(C(F)(F)F)c2)cc1C#Cc1nn([C@H]2CCOC2)c2ncnc(N)c12] | ¹H NMR (400 MHz, DMSO-d₆) δ 10.60 (s, 1H), 9.98 (br.s, 1H), 9.44 (br.s, 1H), 8.35 (s, 1H), 8.28 (s, 1H), 8.24 (s, 1H), 8.12 (d, J = 8.2 Hz, 1H), 7.98 (d, J = 8.0 Hz, 1H), 7.72 (d, J = 8.2 Hz, 1H), 7.55 (d, J = 8.0 Hz, 1H), 5.61-5.36 (m, 1H), 4.19-3.98 (m, 2H), 3.91 (dd, J = 12.3, 7.6 Hz, 2H), 3.67 (s, 2H), 3.08 (s, 6H), 2.91 (br.s, 2H), 2.74 (s, 3H), 2.59 (s, 3H), 2.43-2.33 (m, 2H). | 619.2761 |
| 22 | 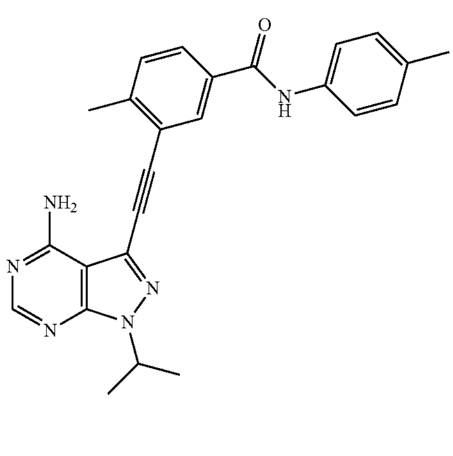 [SMILES: Cc1ccc(NC(=O)c2ccc(C)c(C#Cc3nn(C(C)C)c4ncnc(N)c34)c2)cc1] | ¹H NMR (400 MHz, DMSO-d₆) δ 10.22 (s, 1H), 8.32 (s, 1H), 8.27 (s, 1H), 7.94 (d, J = 7.8 Hz, 1H), 7.68 (d, J = 7.8 Hz, 2H), 7.52 (d, J = 7.8 Hz, 1H), 7.17 (d, J = 7.8 Hz, 2H), 5.22-4.89 (m, 1H), 2.58 (s, 3H), 2.29 (s, 3H), 1.49 (d, J = 6.4 Hz, 6H). | 425.2090 |

-continued

| Compound | Structure | ¹H-NMR | ESI⁺ [M + H] |
|---|---|---|---|
| 23 | 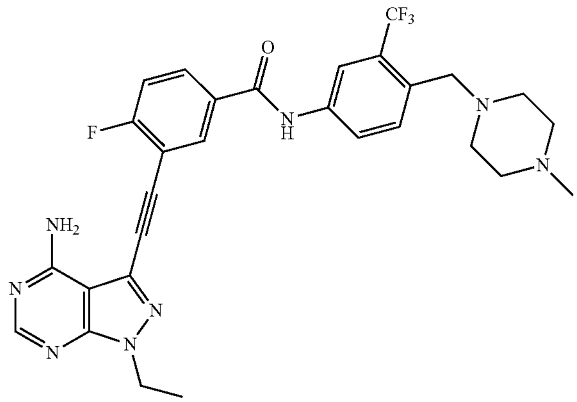 [SMILES: CCn1nc(C#Cc2cc(C(=O)Nc3ccc(CN4CCN(C)CC4)c(C(F)(F)F)c3)ccc2F)c2c(N)ncnc21] | ¹H NMR (400 MHz, DMSO-d₆) δ 10.64 (s, 1H), 8.47 (d, J = 8.1 Hz, 1H), 8.28 (s, 1H), 8.20 (s, 1H), 8.15-8.08 (m, 1H), 8.05 (d, J = 8.1 Hz, 1H), 7.73 (d, J = 8.6 Hz, 1H), 7.59 (t, J = 9.0 Hz, 1H), 4.38 (q, J = 7.2 Hz, 2H), 3.57 (s, 2H), 2.39 (br.s, 8H), 2.16 (s, 3H), 1.42 (t, J = 7.2 Hz, 3H). | 581.2405 |
| 24 | 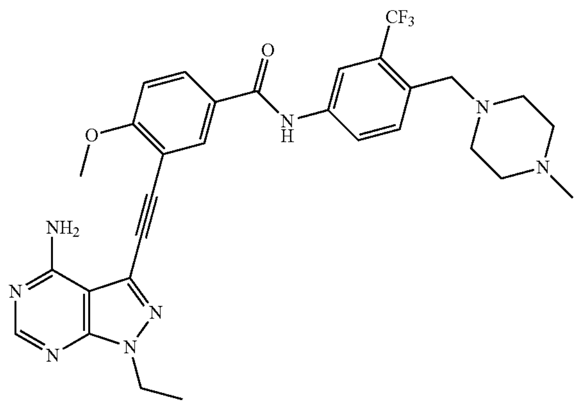 [SMILES: CCn1nc(C#Cc2cc(C(=O)Nc3ccc(CN4CCN(C)CC4)c(C(F)(F)F)c3)ccc2OC)c2c(N)ncnc21] | ¹H NMR (400 MHz, DMSO-d₆) δ 10.50 (s, 1H), 8.40 (s, 1H), 8.29 (s, 2H), 8.22 (s, 1H), 8.16-8.02 (m, 2H), 7.71 (d, J = 7.9 Hz, 1H), 7.34 (d, J = 8.8 Hz, 1H), 6.73 (br.s, 1H), 4.36 (d, J = 6.7 Hz, 2H), 4.04 (s, 3H), 3.60 (s, 2H), 2.39 (br.s, 8H), 2.34 (s, 3H), 1.42 (t, J = 6.7 Hz, 3H). | 593.2598 |
| 25 | 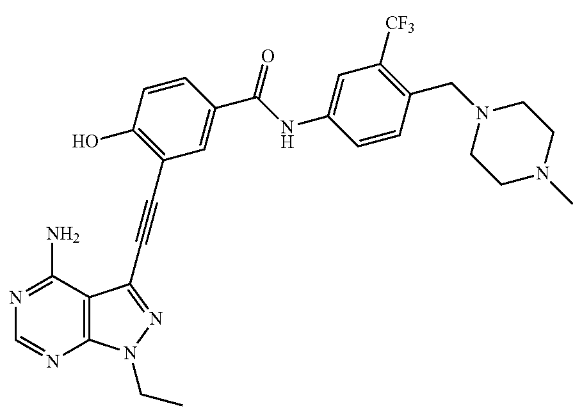 [SMILES: CCn1nc(C#Cc2cc(C(=O)Nc3ccc(CN4CCN(C)CC4)c(C(F)(F)F)c3)ccc2O)c2c(N)ncnc21] | ¹H NMR (400 MHz, DMSO-d₆) δ 10.68 (s, 1H), 8.41 (s, 1H), 8.31 (s, 1H), 8.28 (s, 1H), 8.14 (d, J = 8.6 Hz, 1H), 8.04 (d, J = 8.7 Hz, 1H), 7.98 (d, J = 8.7 Hz, 1H), 7.73 (d, J = 8.6 Hz, 1H), 7.58 (s, 1H), 4.44 (q, J = 7.2 Hz, 2H), 3.67 (s, 2H), 3.11 (br.s, 4H), 2.70 (s, 3H), 2.65 (br.s, 4H), 1.46 (t, J = 7.2 Hz, 3H). | 579.2446 |

| Compound | Structure | ¹H-NMR | ESI⁺ [M + H] |
|---|---|---|---|
| 26 | 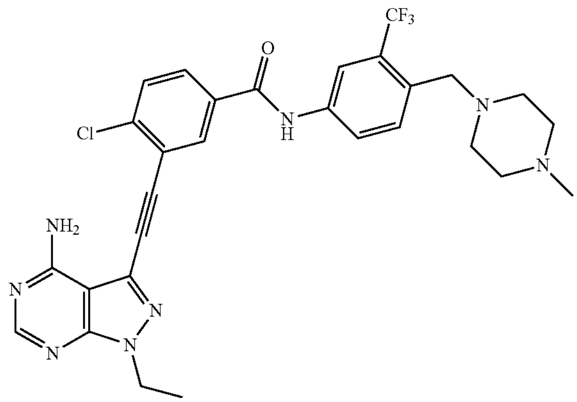 [SMILES: CCn1nc(C#Cc2cc(C(=O)Nc3ccc(CN4CCN(C)CC4)c(C(F)(F)F)c3)ccc2Cl)c2c(N)ncnc21] | ¹H NMR (400 MHz, DMSO-d₆) δ 10.67 (s, 1H), 8.48 (s, 1H), 8.29 (s, 1H), 8.20 (s, 1H), 8.05 (s, 2H), 7.83 (d, J = 8.2 Hz, 1H), 7.73 (d, J = 8.2 Hz, 1H), 4.39 (d, J = 6.9 Hz, 2H), 3.57 (s, 2H), 2.40 (br.s, 8H), 2.19 (s, 3H), 1.42 (t, J = 6.9 Hz, 3H). | 597.2107 |
| 27 | 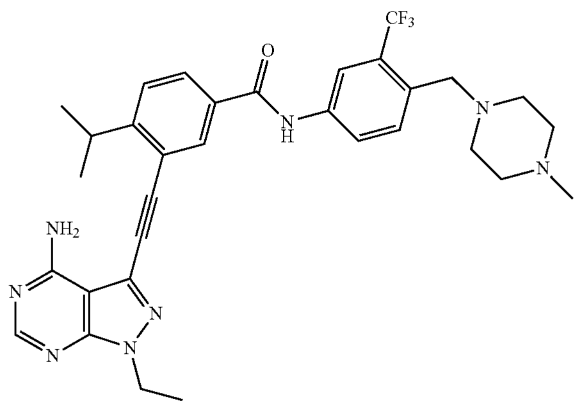 [SMILES: CCn1nc(C#Cc2cc(C(=O)Nc3ccc(CN4CCN(C)CC4)c(C(F)(F)F)c3)ccc2C(C)C)c2c(N)ncnc21] | ¹H NMR (400 MHz, DMSO-d₆) δ 10.58 (s, 1H), 8.33 (s, 1H), 8.28 (s, 1H), 8.23 (s, 1H), 8.08 (d, J = 8.1 Hz, 1H), 8.02 (d, J = 8.1 Hz, 1H), 7.72 (d, J = 8.4 Hz, 1H), 7.62 (d, J = 8.4 Hz, 1H), 4.39 (q, J = 7.2 Hz, 2H), 3.61 (s, 2H), 3.59-3.50 (m, 1H), 2.39 (br.s, 8H), 2.33 (s, 3H), 1.42 (t, J = 7.2 Hz, 3H), 1.32 (d, J = 6.9 Hz, 6H). | 605.2970 |
| 28 | 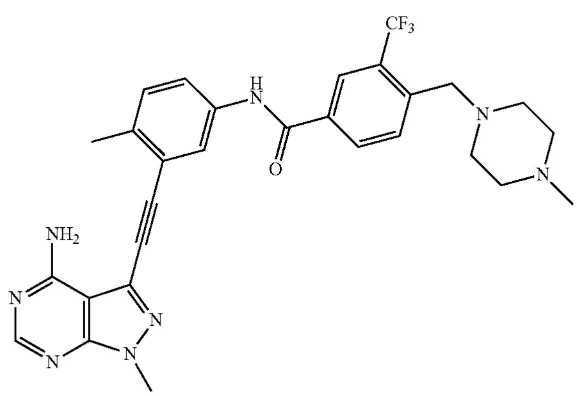 [SMILES: Cc1ccc(NC(=O)c2ccc(CN3CCN(C)CC3)c(C(F)(F)F)c2)cc1C#Cc1nn(C)c2ncnc(N)c12] | ¹H NMR (400 MHz, DMSO-d₆) δ 10.52 (s, 1H), 8.29-8.21 (m, 3H), 8.06 (s, 1H), 7.94 (d, J = 8.1 Hz, 1H), 7.74 (d, J = 8.0 Hz, 1H), 7.36 (d, J = 8.0 Hz, 1H), 3.95 (s, 3H), 3.70 (s, 2H), 2.47 (br.s, 11H), 2.24 (s, 3H). | 563.2495 |
| 29 | 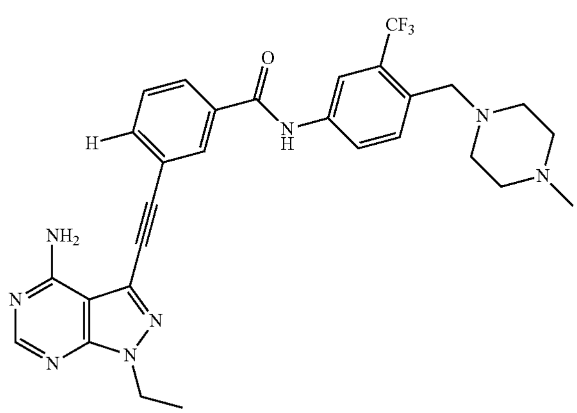 | ¹H NMR (400 MHz, DMSO-d₆) δ 10.65 (s, 1H), 8.36 (s, 1H), 8.27 (s, 1H), 8.23 (s, 1H), 8.13-8.01 (m, 2H), 7.97 (s, 1H), 7.73 (d, J = 7.6 Hz, 1H), 7.65 (s, 1H), 4.37 (q, J = 7.2 Hz, 2H), 3.58 (s, 2H), 2.43 (br.s, 8H), 2.23 (s, 3H), 1.42 (t, J = 7.2 Hz, 3H). | 563.2499 |

| Compound | Structure | ¹H-NMR | ESI⁺ [M + H] |
|---|---|---|---|
| 30 | 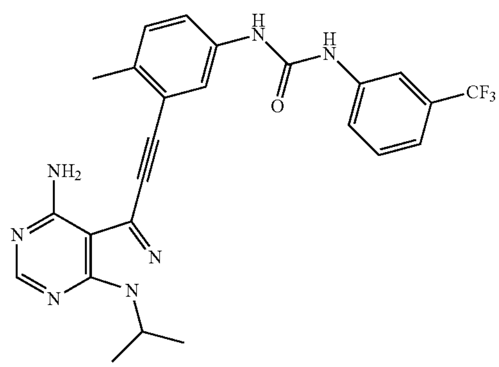 [SMILES: Cc1ccc(NC(=O)Nc2cccc(C(F)(F)F)c2)cc1C#CC(=N)c1c(N)ncnc1NC(C)C] | ¹H NMR (400 MHz, DMSO-d₆) δ 9.12 (s, 1H), 8.87 (s, 1H), 8.26 (s, 1H), 8.04 (s, 1H), 7.80 (s, 1H), 7.58 (d, J = 8.3 Hz, 1H), 7.53 (d, J = 7.8 Hz, 1H), 7.42 (d, J = 8.3 Hz, 1H), 7.32 (d, J = 7.8 Hz, 1H), 7.28 (d, J = 8.3 Hz, 1H), 5.14-4.94 (m, 1H), 2.44 (s, 3H), 1.48 (d, J = 6.6 Hz, 6H). | 494.1917 |
| 31 | 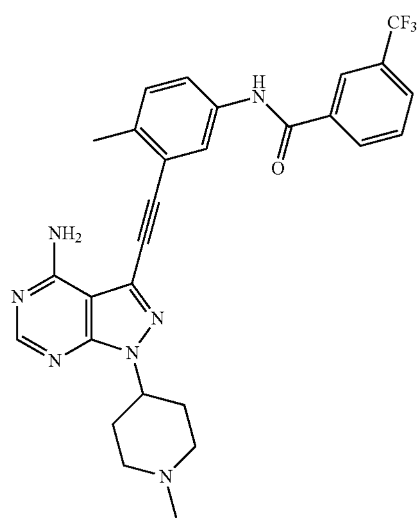 [SMILES: Cc1ccc(NC(=O)c2cccc(C(F)(F)F)c2)cc1C#Cc1nn(C2CCN(C)CC2)c2ncnc(N)c12] | ¹H NMR (400 MHz, DMSO-d₆) δ 10.56 (s, 1H), 8.32 (s, 1H), 8.29 (d, J = 7.9 Hz, 1H), 8.26 (s, 1H), 8.08 (d, J = 2.2 Hz, 1H), 7.99 (d, J = 7.9 Hz, 1H), 7.81 (t, J = 7.8 Hz, 1H), 7.76 (dd, J = 8.3, 2.2 Hz, 1H), 7.38 (d, J = 8.5 Hz, 1H), 4.68-4.61 (m, 1H), 2.94 (d, J = 8.4 Hz, 2H), 2.48 (s, 3H), 2.24 (s, 3H), 2.19 (dd, J = 24.6, 12.0 Hz, 4H), 1.91 (d, J = 9.0 Hz, 2H). | 534.2239 |
| 32 | 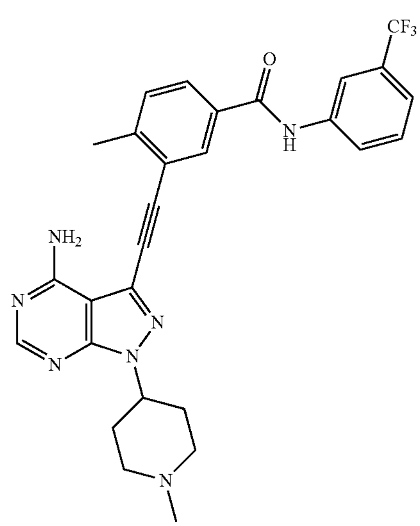 [SMILES: Cc1ccc(C(=O)Nc2cccc(C(F)(F)F)c2)cc1C#Cc1nn(C2CCN(C)CC2)c2ncnc(N)c12] | ¹H NMR (400 MHz, DMSO-d₆) δ 10.61 (s, 1H), 8.36 (d, J = 1.6 Hz, 1H), 8.26 (s, 2H), 8.09 (d, J = 8.2 Hz, 1H), 7.97 (dd, J = 8.2, 1.6 Hz, 1H), 7.62 (t, J = 8.0 Hz, 1H), 7.56 (d, J = 8.1 Hz, 1H), 7.48 (d, J = 7.5 Hz, 1H), 4.69-4.56 (m, 1H), 2.92 (d, J = 10.1 Hz, 2H), 2.59 (s, 3H), 2.23 (s, 3H), 2.20-2.02 (m, 4H), 1.90 (d, J = 13.2 Hz, 2H). | 534.2240 |

-continued

| Compound | Structure | ¹H-NMR | ESI⁺ [M + H] |
|---|---|---|---|
| 33 | 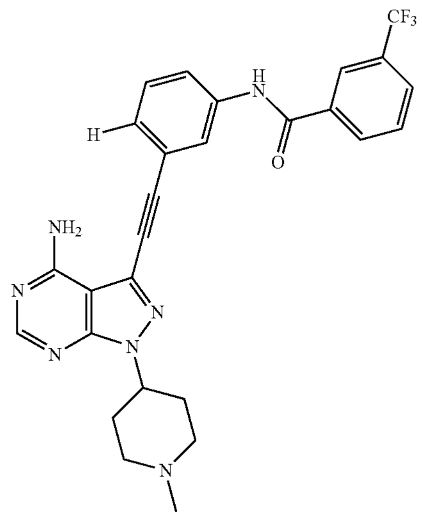 | ¹H NMR (400 MHz, DMSO-d₆) δ 10.63 (s, 1H), 8.33 (s, 1H), 8.29 (d, J = 7.9 Hz, 1H), 8.25 (s, 1H), 8.13 (s, 1H), 8.00 (d, J = 7.9 Hz, 1H), 7.86 (d, J = 7.8 Hz, 1H), 7.82 (t, J = 7.8 Hz, 1H), 7.50 (dt, J = 15.5, 7.7 Hz, 2H), 4.79-4.55 (m, 1H), 2.96 (br.s, 2H), 2.28 (s, 3H), 2.18 (t, J = 8.1 Hz, 4H), 1.92 (d, J = 4.8 Hz, 2H). | 520.2117 |
| 34 | 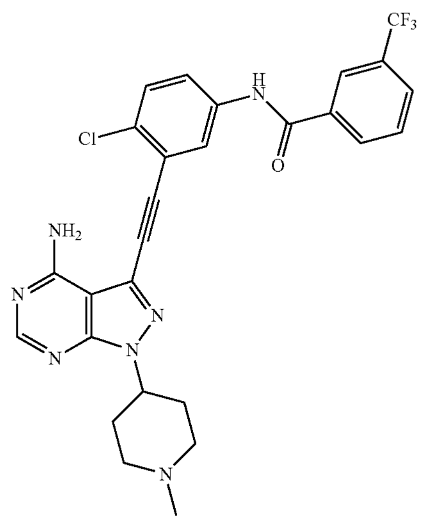 [SMILES: CN1CCC(n2nc(C#Cc3cc(NC(=O)c4cccc(C(F)(F)F)c4)ccc3Cl)c3c(N)ncnc32)CC1] | ¹H NMR (400 MHz, DMSO-d₆) δ 10.72 (s, 1H), 8.32 (s, 1H), 8.29 (d, J = 7.9 Hz, 2H), 8.26 (d, J = 2.4 Hz, 1H), 8.01 (d, J = 7.9 Hz, 1H), 7.89 (dd, J = 8.9, 2.4 Hz, 1H), 7.83 (t, J = 7.8 Hz, 1H), 7.66 (d, J = 8.9 Hz, 1H), 4.75-4.59 (m, 1H), 2.95 (d, J = 7.5 Hz, 2H), 2.26 (s, 3H), 2.23-2.08 (m, 4H), 1.92 (d, J = 9.3 Hz, 2H). | 554.1695 |
| 35 | 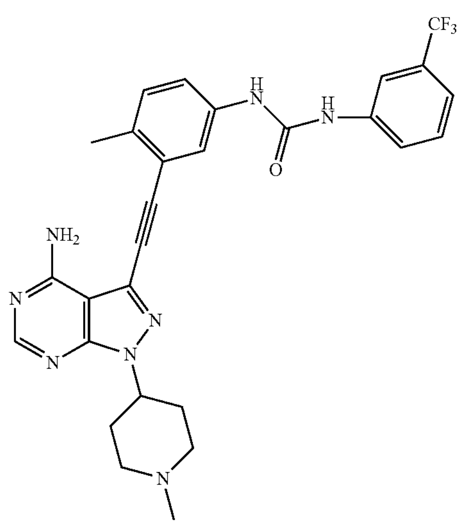 [SMILES: Cc1ccc(NC(=O)Nc2cccc(C(F)(F)F)c2)cc1C#Cc1nn(C2CCN(C)CC2)c2ncnc(N)c12] | ¹H NMR (400 MHz, DMSO-d₆) δ 9.19 (s, 1H), 8.93 (s, 1H), 8.26 (s, 1H), 8.03 (s, 1H), 7.81 (d, J = 2.2 Hz, 1H), 7.59 (d, J = 8.3 Hz, 1H), 7.52 (t, J = 7.9 Hz, 1H), 7.43 (dd, J = 8.3, 2.2 Hz, 1H), 7.32 (d, J = 7.5 Hz, 1H), 7.28 (d, J = 8.4 Hz, 1H), 4.79-4.49 (m, 1H), 2.99 (br.s, 2H), 2.44 (s, 3H), 2.31 (s, 3H), 2.20 (dd, J = 18.5, 7.4 Hz, 4H), 1.93 (d, J = 11.4 Hz, 2H). | 549.2357 |

-continued

| Compound | Structure | ¹H-NMR | ESI⁺ [M + H] |
|---|---|---|---|
| 36 | 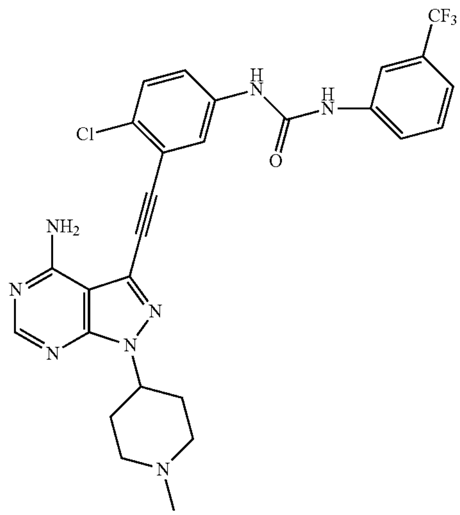 [SMILES: CN1CCC(n2nc(C#Cc3cc(NC(=O)Nc4cccc(C(F)(F)F)c4)ccc3Cl)c3c(N)ncnc32)CC1] | ¹H NMR (400 MHz, DMSO-d$_6$) δ 9.59 (s, 1H), 9.51 (s, 1H), 8.29 (s, 1H), 8.02 (s, 1H), 7.98 (t, J = 1.4 Hz, 1H), 7.60 (d, J = 8.5 Hz, 1H), 7.55 (d, J = 1.4 Hz, 2H), 7.52 (d, J = 8.1 Hz, 1H), 7.33 (d, J = 7.6 Hz, 1H), 4.83 (t, J = 11.2 Hz, 1H), 3.24 (d, J = 10.6 Hz, 2H), 2.70 (br.s, 2H), 2.52 (s, 3H), 2.31 (dd, J = 22.7, 10.7 Hz, 2H), 2.06 (d, J = 12.1 Hz, 2H). | 569.1805 |
| 37 | 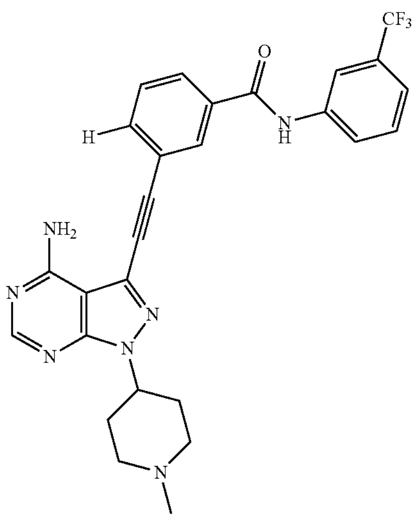 [SMILES: CN1CCC(n2nc(C#Cc3cccc(C(=O)Nc4cccc(C(F)(F)F)c4)c3)c3c(N)ncnc32)CC1] | ¹H NMR (400 MHz, DMSO-d$_6$) δ 10.74 (s, 1H), 8.41 (s, 1H), 8.28 (s, 1H), 8.26 (s, 1H), 8.10 (d, J = 8.4 Hz, 1H), 8.06 (d, J = 7.9 Hz, 1H), 7.99 (d, J = 7.9 Hz, 1H), 7.65 (d, J = 7.8 Hz, 1H), 7.62 (t, J = 8.2 Hz, 1H), 7.47 (d, J = 7.8 Hz, 1H), 4.84-4.78 (m, 1H), 3.20 (d, J = 11.6 Hz, 2H), 2.67 (br.s, 2H), 2.49 (s, 3H), 2.31 (dd, J = 22.6, 11.2 Hz, 2H), 2.02 (d, J = 11.4 Hz, 2H). | 520.2088 |
| 38 | 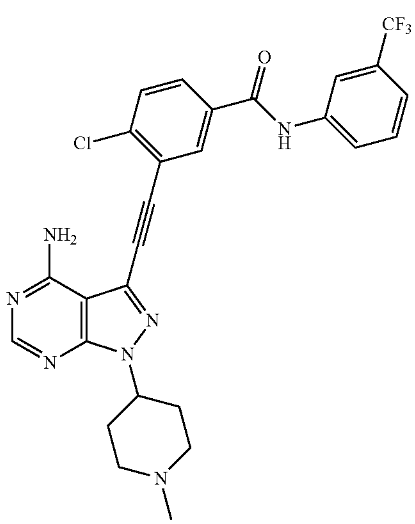 [SMILES: CN1CCC(n2nc(C#Cc3cc(C(=O)Nc4cccc(C(F)(F)F)c4)ccc3Cl)c3c(N)ncnc32)CC1] | ¹H NMR (400 MHz, DMSO-d$_6$) δ 10.79 (s, 1H), 8.57 (d, J = 1.8 Hz, 1H), 8.30 (s, 1H), 8.27 (s, 1H), 8.19 (br.s, 1H), 8.12-8.07 (m, 2H), 7.84 (d, J = 8.5 Hz, 1H), 7.63 (t, J = 8.0 Hz, 1H), 7.49 (d, J = 7.6 Hz, 1H), 6.65 (br.s, 1H), 4.93 (t, J = 10.8 Hz, 1H), 3.37 (br.s, 2H), 2.95 (br.s, 2H), 2.64 (s, 3H), 2.40 (dd, J = 22.9, 11.2 Hz, 2H), 2.11 (d, J = 12.0 Hz, 2H). | 554.1691 |

| Compound | Structure | ¹H-NMR | ESI⁺ [M + H] |
|---|---|---|---|
| 39 | 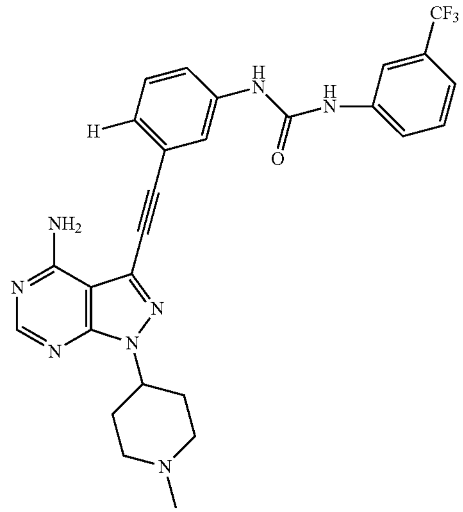 [SMILES: CN1CCC(n2nc(C#Cc3cccc(NC(=O)Nc4cccc(C(F)(F)F)c4)c3)c3c(N)ncnc32)CC1] | ¹H NMR (400 MHz, DMSO-d$_6$) δ 9.45 (s, 1H), 9.25 (s, 1H), 8.26 (s, 1H), 8.04 (s, 1H), 7.87 (s, 1H), 7.60 (d, J = 8.0 Hz, 1H), 7.58-7.47 (m, 2H), 7.38 (d, J = 7.1 Hz, 2H), 7.33 (d, J = 7.5 Hz, 1H), 4.89-4.65 (m, 1H), 3.42 (br.s, 2H), 3.12 (d, J = 7.1 Hz, 2H), 2.43 (s, 3H), 2.25 (dd, J = 22.2, 11.0 Hz, 2H), 1.99 (d, J = 10.7 Hz, 2H). | 535.2200 |
| 40 | 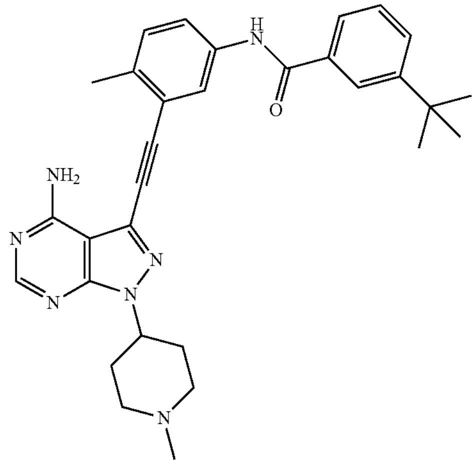 [SMILES: Cc1ccc(NC(=O)c2cccc(C(C)(C)C)c2)cc1C#Cc1nn(C2CCN(C)CC2)c2ncnc(N)c12] | ¹H NMR (400 MHz, DMSO-d$_6$) δ 10.30 (s, 1H), 8.29 (s, 1H), 8.11 (d, J = 2.0 Hz, 1H), 7.96 (s, 1H), 7.80 (d, J = 7.8 Hz, 1H), 7.75 (dd, J = 8.3, 2.0 Hz, 1H), 7.64 (d, J = 7.9 Hz, 1H), 7.47 (t, J = 7.8 Hz, 1H), 7.36 (d, J = 8.5 Hz, 1H), 5.04-4.98 (m, 1H), 3.56 (br.s, 2H), 3.28 (br.s, 2H), 2.84 (s, 3H), 2.48 (s, 3H), 2.43 (d, J = 12.9 Hz, 2H), 2.20 (d, J = 11.9 Hz, 2H), 1.35 (s, 9H). | 522.2980 |
| 41 | 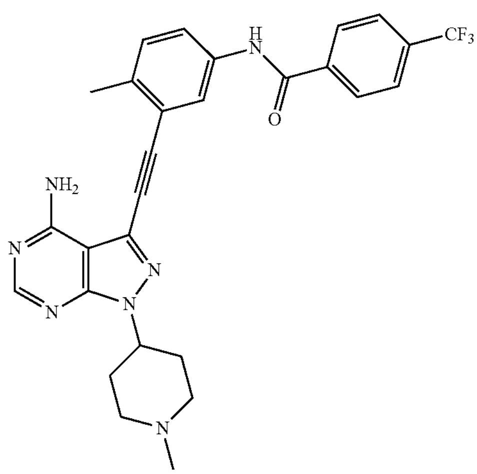 [SMILES: Cc1ccc(NC(=O)c2ccc(C(F)(F)F)cc2)cc1C#Cc1nn(C2CCN(C)CC2)c2ncnc(N)c12] | ¹H NMR (400 MHz, DMSO-d$_6$) δ 10.59 (s, 1H), 8.27 (s, 1H), 8.18 (d, J = 7.2 Hz, 2H), 8.11 (s, 1H), 7.94 (d, J = 7.2 Hz, 2H), 7.76 (d, J = 7.2 Hz, 1H), 7.37 (d, J = 7.2 Hz, 1H), 4.77-4.68 (m, 1H), 2.87 (br.s, 2H), 2.61 (s, 3H), 2.48 (s, 3H), 2.42-2.23 (m, 4H), 2.09 (d, J = 11.7 Hz, 2H). | 534.2069 |

-continued

| Compound | Structure | ¹H-NMR | ESI⁺ [M + H] |
|---|---|---|---|
| 42 | 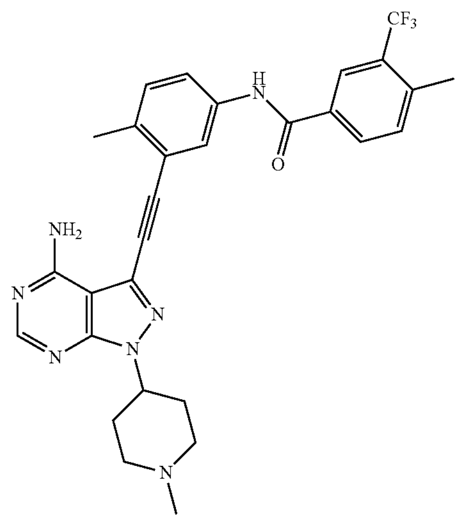 [SMILES: Cc1ccc(NC(=O)c2ccc(C)c(C(F)(F)F)c2)cc1C#Cc1nn(C2CCN(C)CC2)c2ncnc(N)c12] | ¹H NMR (400 MHz, DMSO-d₆) δ 10.52 (s, 1H), 8.28 (s, 1H), 8.27 (s, 1H), 8.19 (d, J = 7.5 Hz, 1H), 8.11 (s, 1H), 7.75 (d, J = 7.5 Hz, 1H), 7.65 (d, J = 8.3 Hz, 1H), 7.37 (d, J = 8.3 Hz, 1H), 5.06-4.80 (m, 1H), 3.38 (br.s, 2H), 3.00 (br.s, 2H), 2.68 (s, 3H), 2.54 (s, 3H), 2.48 (s, 3H), 2.39 (d, J = 12.9 Hz, 2H), 2.12 (d, J = 12.8 Hz, 2H). | 548.2392 |
| 43 | 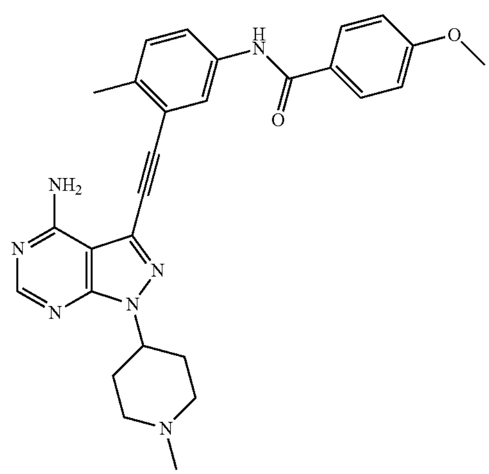 [SMILES: COc1ccc(C(=O)Nc2ccc(C)c(C#Cc3nn(C4CCN(C)CC4)c4ncnc(N)c34)c2)cc1] | ¹H NMR (400 MHz, DMSO-d₆) δ 10.18 (s, 1H), 8.29 (s, 1H), 8.12 (s, 1H), 7.98 (d, J = 8.6 Hz, 2H), 7.72 (d, J = 8.4 Hz, 1H), 7.34 (d, J = 8.4 Hz, 1H), 7.08 (d, J = 8.6 Hz, 2H), 5.08-4.80 (m, 1H), 3.85 (s, 3H), 3.58-3.44 (m, 2H), 3.21-2.92 (m, 2H), 2.72 (s, 3H), 2.47 (s, 3H), 2.43-2.29 (m, 2H), 2.20-2.08 (m, 2H). | 496.2454 |
| 44 | 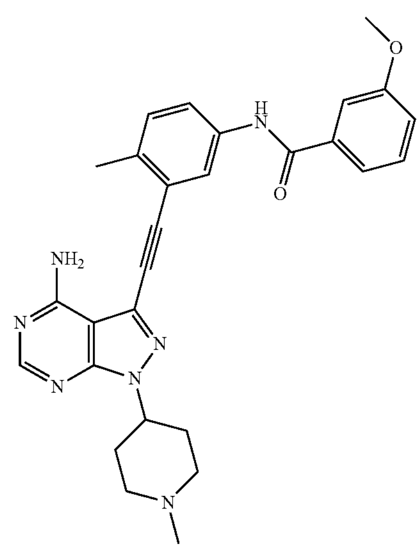 [SMILES: COc1cccc(C(=O)Nc2ccc(C)c(C#Cc3nn(C4CCN(C)CC4)c4ncnc(N)c34)c2)c1] | ¹H NMR (400 MHz, DMSO-d₆) δ 10.31 (s, 1H), 8.29 (s, 1H), 8.12 (s, 1H), 7.73 (d, J = 8.4 Hz, 1H), 7.55 (d, J = 7.4 Hz, 1H), 7.50 (s, 1H), 7.47 (t, J = 7.9 Hz, 1H), 7.36 (d, J = 8.4 Hz, 1H), 7.18 (d, J = 7.6 Hz, 1H), 5.06-4.87 (m, 1H), 3.85 (s, 3H), 3.58-3.39 (m, 2H), 3.22-2.99 (m, 2H), 2.76 (s, 3H), 2.47 (s, 3H), 2.44-2.28 (m, 2H), 2.22-2.06 (m, 2H). | 496.2453 |

| Compound | Structure | ¹H-NMR | ESI⁺ [M + H] |
|---|---|---|---|
| 45 | 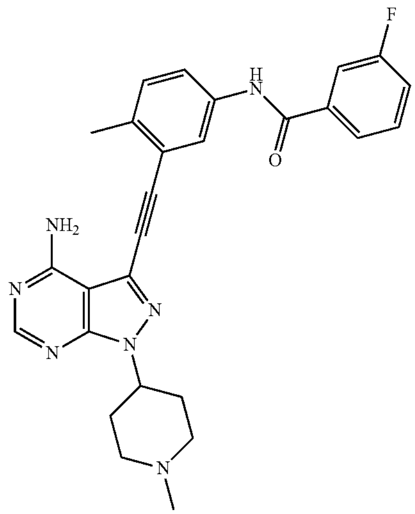 [SMILES: Cc1ccc(NC(=O)c2cccc(F)c2)cc1C#Cc1nn(C2CCN(C)CC2)c2ncnc(N)c12] | ¹H NMR (400 MHz, DMSO-d$_6$) δ 10.40 (s, 1H), 8.26 (s, 1H), 8.08 (d, J = 1.9 Hz, 1H), 7.84 (d, J = 7.8 Hz, 1H), 7.79 (d, J = 9.3 Hz, 1H), 7.75 (dd, J = 8.3, 1.9 Hz, 1H), 7.61 (dd, J = 13.9, 7.9 Hz, 1H), 7.48 (dd, J = 11.7, 5.3 Hz, 1H), 7.36 (d, J = 8.4 Hz, 1H), 4.76-4.52 (m, 1H), 2.95 (d, J = 6.7 Hz, 2H), 2.48 (s, 3H), 2.27 (s, 3H), 2.21-2.16 (m, 4H), 1.91 (d, J = 7.8 Hz, 2H). | 484.2242 |
| 46 | 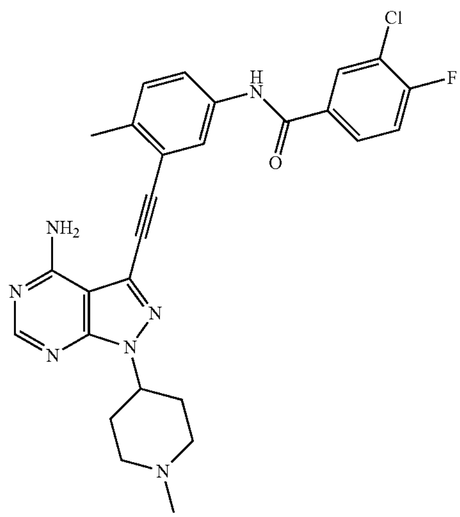 | ¹H NMR (400 MHz, DMSO-d$_6$) δ 10.44 (s, 1H), 8.27 (s, 1H), 8.23 (d, J = 5.9 Hz, 1H), 8.07 (s, 1H), 8.02 (s, 1H), 7.74 (d, J = 8.3 Hz, 1H), 7.62 (t, J = 8.9 Hz, 1H), 7.36 (d, J = 8.3 Hz, 1H), 4.75-4.66 (m, 1H), 3.03 (d, J = 8.4 Hz, 2H)., 2.48 (s, 3H), 2.34 (s, 3H), 2.32-2.10 (m, 4H), 1.95 (d, J = 10.3 Hz, 2H). | 518.1846 |
| 47 | 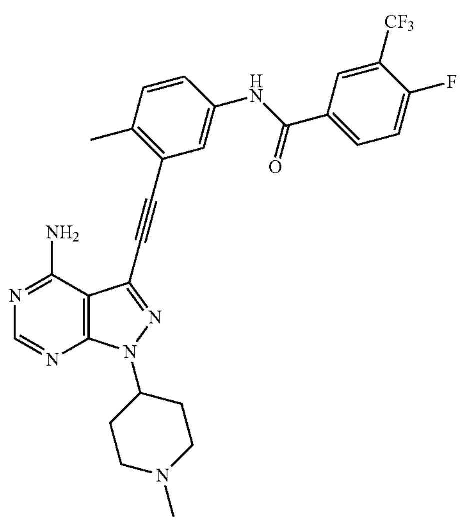 [SMILES: Cc1ccc(NC(=O)c2ccc(F)c(C(F)(F)F)c2)cc1C#Cc1nn(C2CCN(C)CC2)c2ncnc(N)c12] | ¹H NMR (400 MHz, DMSO-d$_6$) δ 10.56 (s, 1H), 8.39-8.35 (m, 2H), 8.29 (s, 1H), 8.09 (d, J = 2.0 Hz, 1H), 7.80-7.67 (m, 1H), 7.38 (d, J = 8.4 Hz, 1H), 5.00-4.84 (m, 1H), 3.39 (br.s, 2H), 3.00 (br.s, 2H), 2.69 (s, 3H), 2.48 (s, 3H), 2.35 (d, J = 12.0 Hz, 2H), 2.13 (d, J = 11.7 Hz, 2H). | 552.2145 |

-continued

| Compound | Structure | ¹H-NMR | ESI⁺ [M + H] |
|---|---|---|---|
| 48 | 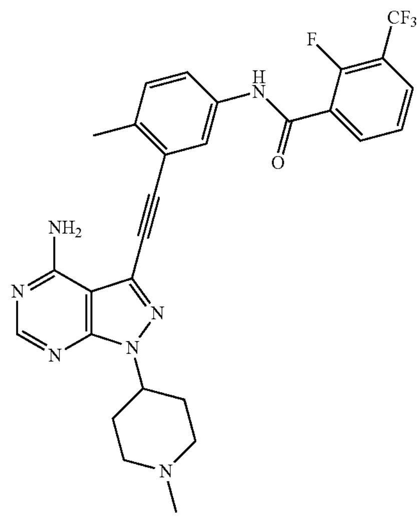 [SMILES: Cc1ccc(NC(=O)c2cccc(C(F)(F)F)c2F)cc1C#Cc1nn(C2CCN(C)CC2)c2ncnc(N)c12] | ¹H NMR (400 MHz, DMSO-d$_6$) δ 10.40 (s, 1H), 8.29 (s, 1H), 8.11 (d, J = 2.0 Hz, 1H), 8.00 (d, J = 8.5 Hz, 2H), 7.72 (dd, J = 8.4, 2.0 Hz, 1H), 7.63 (d, J = 8.5 Hz, 2H), 7.36 (d, J = 8.4 Hz, 1H), 5.04-4.88 (m, 1H), 3.47 (d, J = 11.4 Hz, 2H), 3.11 (t, J = 11.0 Hz, 2H), 2.76 (s, 3H), 2.47 (s, 3H), 2.38 (t, J = 12.0 Hz, 2H), 2.16 (d, J = 12.0 Hz, 2H). | 552.2135 |
| 49 | 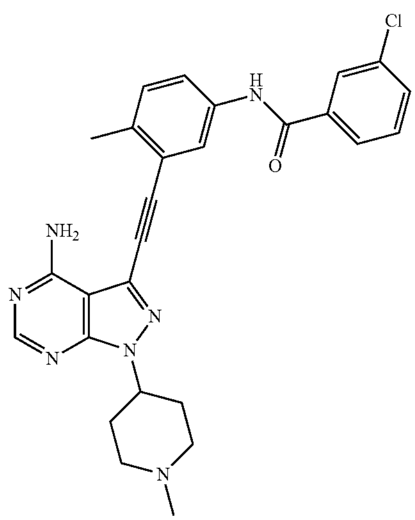 | ¹H NMR (400 MHz, DMSO-d$_6$) δ 10.43 (s, 1H), 8.26 (s, 1H), 8.08 (s, 1H), 8.03 (s, 1H), 7.94 (d, J = 7.5 Hz, 1H), 7.75 (d, J = 8.2 Hz, 1H), 7.69 (d, J = 7.6 Hz, 1H), 7.59 (t, J = 7.8 Hz, 1H), 7.36 (d, J = 8.2 Hz, 1H), 4.67-4.60 (m, 1H), 2.94 (d, J = 8.3 Hz, 2H), 2.48 (s, 3H), 2.26 (s, 3H), 2.23-2.05 (m, 4H), 1.91 (d, J = 9.9 Hz, 2H). | 500.1956 |
| 50 | 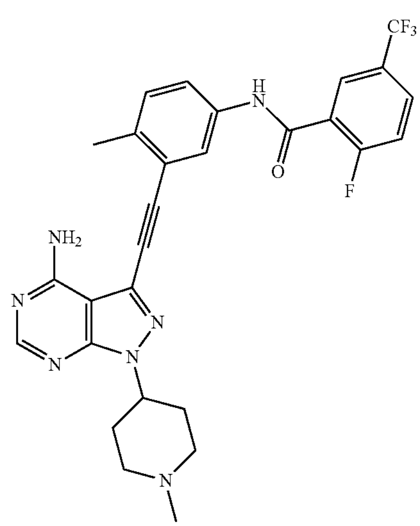 [SMILES: Cc1ccc(NC(=O)c2cc(C(F)(F)F)ccc2F)cc1C#Cc1nn(C2CCN(C)CC2)c2ncnc(N)c12] | ¹H NMR (400 MHz, DMSO-d$_6$) δ 10.69 (s, 1H), 8.26 (s, 1H), 8.09 (d, J = 4.6 Hz, 1H), 8.02 (s, 2H), 7.79-7.57 (m, 2H), 7.37 (d, J = 4.0 Hz, 1H), 4.67-4.60 (m, 1H), 2.93 (d, J = 8.3 Hz, 2H), 2.48 (s, 3H), 2.25 (s, 3H), 2.21-2.05 (m, 4H), 1.90 (d, J = 10.7 Hz, 2H). | 552.2173 |

-continued
| Compound | Structure | ¹H-NMR | ESI⁺ [M + H] |
|---|---|---|---|
| 51 | 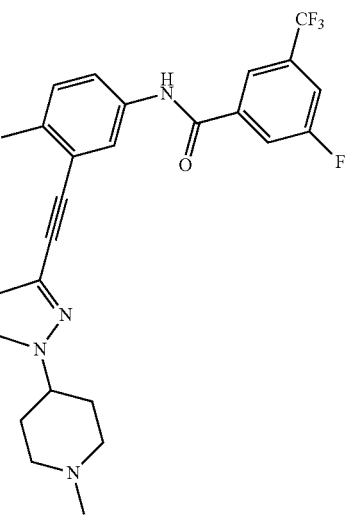 | ¹H NMR (400 MHz, DMSO-d$_6$) δ 10.73 (s, 1H), 8.29 (s, 1H), 8.06 (d, J = 2.0 Hz, 1H), 8.05-7.94 (m, 2H), 7.64 (dd, J = 8.3, 2.0 Hz, 1H), 7.57 (t, J = 7.8 Hz, 1H), 7.38 (d, J = 8.4 Hz, 1H), 5.03-4.87 (m, 1H), 3.49 (d, J = 11.6 Hz, 2H), 3.15 (t, J = 11.0 Hz, 2H), 2.78 (s, 3H), 2.48 (s, 3H), 2.38 (dd, J = 23.1, 11.3 Hz, 2H), 2.16 (d, J = 12.0 Hz, 2H). | 552.2127 |
| 52 | 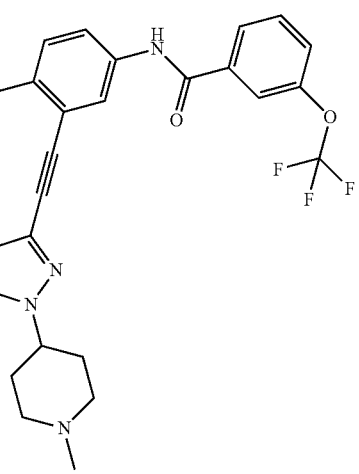 | ¹H NMR (400 MHz, DMSO-d$_6$) δ 10.47 (s, 1H), 8.29 (s, 1H), 8.11 (d, J = 1.8 Hz, 1H), 8.04 (d, J = 7.7 Hz, 1H), 7.93 (s, 1H), 7.71 (t, J = 7.9 Hz, 2H), 7.63 (d, J = 8.0 Hz, 1H), 7.37 (d, J = 8.4 Hz, 1H), 5.03-4.92 (m, 1H), 3.51 (d, J = 11.7 Hz, 2H), 3.18 (t, J = 11.0 Hz, 2H), 2.79 (s, 3H), 2.48 (s, 3H), 2.39 (dd, J = 23.1, 11.4 Hz, 2H), 2.17 (d, J = 12.2 Hz, 2H). | 550.2185 |
| 53 | 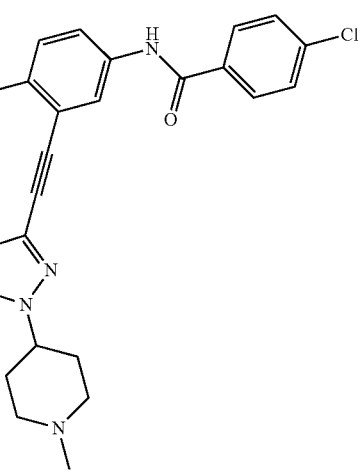 | ¹H NMR (400 MHz, DMSO-d$_6$) δ 10.59 (s, 1H), 8.30 (s, 1H), 8.19 (s, 1H), 8.13 (d, J = 9.0 Hz, 1H), 8.11 (s, 1H), 8.02 (s, 1H), 8.00 (d, J = 8.1 Hz, 1H), 7.72 (d, J = 8.1 Hz, 1H), 7.39 (d, J = 8.5 Hz, 1H), 5.18-4.88 (m, 1H), 3.54 (d, J = 10.8 Hz, 2H), 3.29-3.13 (m, 2H), 2.82 (s, 3H), 2.49 (s, 3H), 2.46-2.29 (m, 2H), 2.19 (d, J = 12.3 Hz, 2H). | 500.1968 |

-continued

| Compound | Structure | ¹H-NMR | ESI⁺ [M + H] |
|---|---|---|---|
| 54 | 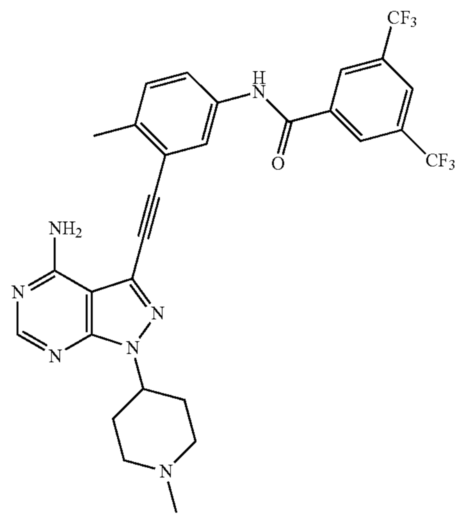 [SMILES: Cc1ccc(NC(=O)c2cc(C(F)(F)F)cc(C(F)(F)F)c2)cc1C#Cc1nn(C2CCN(C)CC2)c2ncnc(N)c12] | ¹H NMR (400 MHz, DMSO-d$_6$) δ 10.71 (s, 1H), 8.57 (s, 2H), 8.33 (s, 1H), 8.22 (s, 1H), 8.00 (d, J = 1.5 Hz, 1H), 7.70 (d, J = 8.3 Hz, 1H), 7.34 (d, J = 8.4 Hz, 1H), 4.64-4.58 (m, 1H), 2.90 (d, J = 7.9 Hz, 2H), 2.44 (s, 3H), 2.21 (s, 3H), 2.11 (q, J = 13.2 Hz, 4H), 1.87 (d, J = 9.0 Hz, 2H). | 602.2123 |
| 55 | 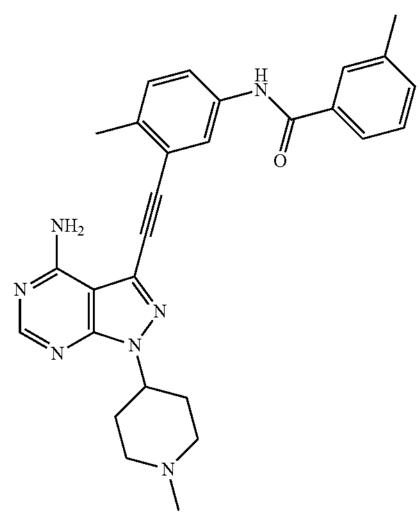 [SMILES: Cc1cccc(C(=O)Nc2ccc(C)c(C#Cc3nn(C4CCN(C)CC4)c4ncnc(N)c34)c2)c1] | ¹H NMR (400 MHz, DMSO-d$_6$) δ 10.28 (s, 1H), 8.26 (s, 1H), 8.09 (s, 1H), 7.79 (s, 1H), 7.76 (d, J = 6.9 Hz, 2H), 7.42 (s, 2H), 7.34 (d, J = 8.2 Hz, 1H), 4.73-4.54 (m, 1H), 2.92 (d, J = 9.4 Hz, 2H), 2.47 (s, 3H), 2.41 (s, 3H), 2.24 (s, 3H), 2.22-2.03 (m, 4H), 1.90 (d, J = 10.3 Hz, 2H). | 480.2500 |
| 56 | 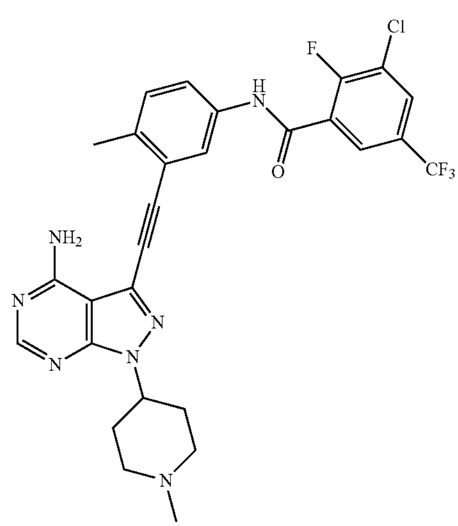 [SMILES: Cc1ccc(NC(=O)c2cc(C(F)(F)F)cc(Cl)c2F)cc1C#Cc1nn(C2CCN(C)CC2)c2ncnc(N)c12] | ¹H NMR (400 MHz, DMSO-d$_6$) δ 10.79 (s, 1H), 8.33 (d, J = 4.5 Hz, 1H), 8.30 (s, 1H), 8.09 (d, J = 3.4 Hz, 1H), 8.04 (d, J = 2.0 Hz, 1H), 7.63 (dd, J = 8.4, 2.0 Hz, 1H), 7.39 (d, J = 8.4 Hz, 1H), 4.94 (m, 1H), 3.42 (s, 2H), 3.04 (s, 2H), 2.73 (s, 3H), 2.48 (s, 3H), 2.35 (dd, J = 22.9, 11.0 Hz, 2H), 2.14 (d, J = 12.5 Hz, 2H). | 586.1752 |

| Compound | Structure | ¹H-NMR | ESI⁺ [M + H] |
|---|---|---|---|
| 57 | 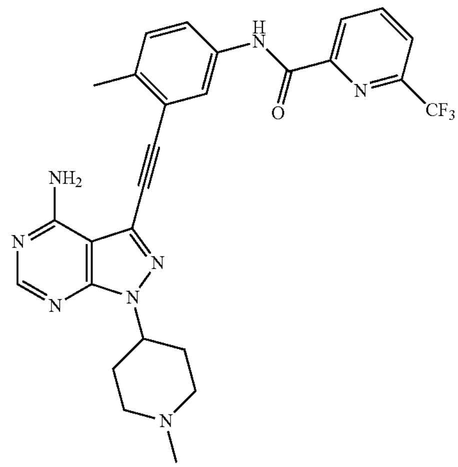 [SMILES: Cc1ccc(NC(=O)c2cccc(C(F)(F)F)n2)cc1C#Cc1nn(C2CCN(C)CC2)c2ncnc(N)c12] | ¹H NMR (400 MHz, DMSO-d₆) δ 10.50 (s, 1H), 8.44-8.33 (m, 2H), 8.29 (s, 1H), 8.23-8.16 (m, 2H), 7.87 (dd, J = 8.4, 1.8 Hz, 1H), 7.39 (d, J = 8.4 Hz, 1H), 5.06-4.78 (m, 1H), 3.44 (d, J = 11.5 Hz, 2H), 3.06 (t, J = 11.1 Hz, 2H), 2.73 (s, 3H), 2.49 (s, 3H), 2.37 (dd, J = 22.7, 11.1 Hz, 2H), 2.15 (d, J = 11.8 Hz, 2H). | 535.2178 |
| 58 | 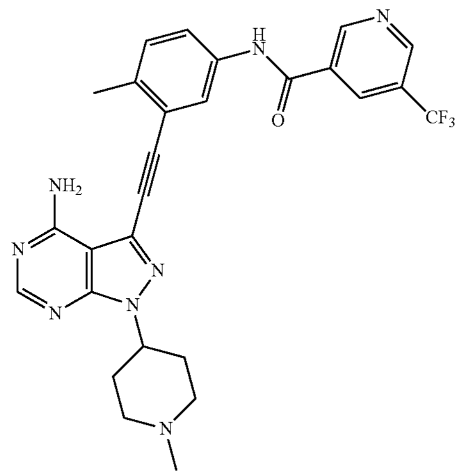 [SMILES: Cc1ccc(NC(=O)c2cncc(C(F)(F)F)c2)cc1C#Cc1nn(C2CCN(C)CC2)c2ncnc(N)c12] | ¹H NMR (400 MHz, DMSO-d₆) δ 10.71 (s, 1H), 9.40 (s, 1H), 9.21 (s, 1H), 8.71 (s, 1H), 8.27 (s, 1H), 8.08 (s, 1H), 7.75 (d, J = 8.2 Hz, 1H), 7.39 (d, J = 8.4 Hz, 1H), 4.74-4.59 (m, 1H), 2.97 (s, 2H), 2.49 (s, 3H), 2.29 (s, 3H), 2.20 (br.s, 4H), 1.92 (s, 2H). | 535.2174 |
| 59 | 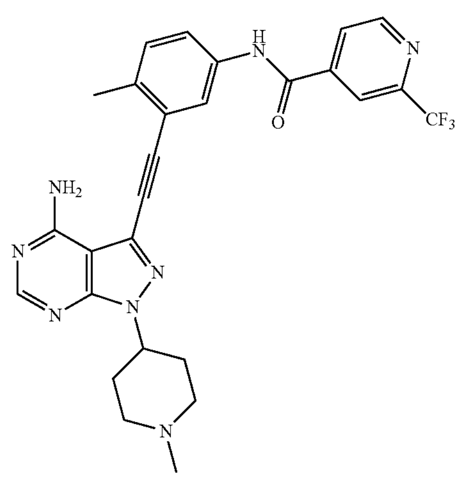 [SMILES: Cc1ccc(NC(=O)c2ccnc(C(F)(F)F)c2)cc1C#Cc1nn(C2CCN(C)CC2)c2ncnc(N)c12] | ¹H NMR (400 MHz, DMSO-d₆) δ 10.93 (s, 1H), 8.99 (d, J = 4.7 Hz, 1H), 8.41 (s, 1H), 8.26 (s, 2H), 8.11 (s, 1H), 7.79 (d, J = 8.1 Hz, 1H), 7.37 (d, J = 8.3 Hz, 1H), 4.87 (t, J = 10.8 Hz, 1H), 3.36 (d, J = 7.3 Hz, 2H), 2.90 (br.s, 2H), 2.60 (s, 3H), 2.47 (s, 3H), 2.38 (d, J = 11.5 Hz, 2H), 2.07 (d, J = 11.3 Hz, 2H). | 535.2186 |

| Compound | Structure | ¹H-NMR | ESI⁺ [M + H] |
|---|---|---|---|
| 60 | 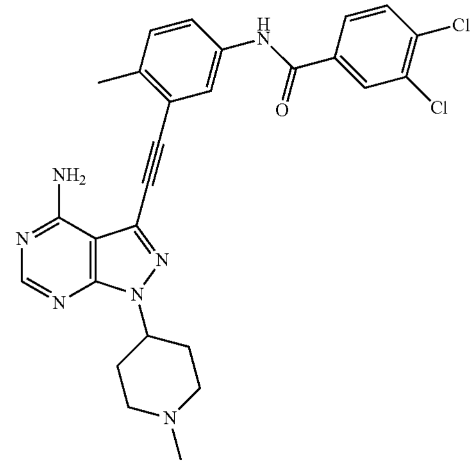 [SMILES: Cc1ccc(NC(=O)c2ccc(Cl)c(Cl)c2)cc1C#Cc1nn(C2CCN(C)CC2)c2ncnc(N)c12] | ¹H NMR (400 MHz, DMSO-d₆) δ 10.48 (s, 1H), 8.29 (s, 1H), 8.24 (s, 1H), 8.10 (s, 1H), 7.96 (d, J = 8.4 Hz, 1H), 7.85 (d, J = 8.4 Hz, 1H), 7.71 (d, J = 8.2 Hz, 1H), 7.37 (d, J = 8.4 Hz, 1H), 5.06-4.84 (m, 1H), 3.47 (d, J = 8.0 Hz, 2H), 3.12 (br.s, 2H), 2.76 (s, 3H), 2.48 (s, 3H), 2.37 (dd, J = 24.9, 12.6 Hz, 2H), 2.16 (d, J = 12.8 Hz, 2H). | 534.1577 |
| 61 | 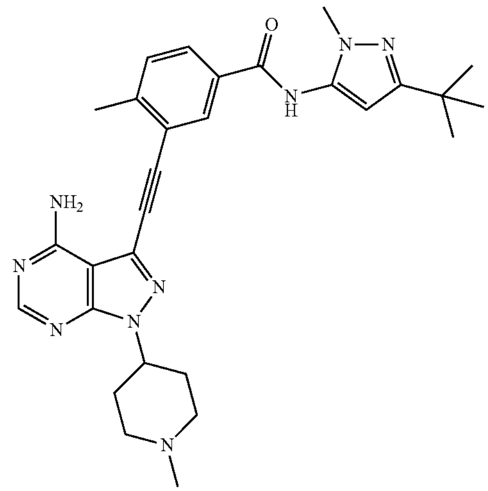 [SMILES: Cc1ccc(C(=O)Nc2cc(C(C)(C)C)nn2C)cc1C#Cc1nn(C2CCN(C)CC2)c2ncnc(N)c12] | ¹H NMR (400 MHz, DMSO-d₆) δ 10.31 (s, 1H), 8.31 (s, 1H), 8.27 (s, 1H), 7.94 (d, J = 7.8 Hz, 1H), 7.54 (d, J = 8.1 Hz, 1H), 6.12 (s, 1H), 4.74-4.68 (m, 1H), 3.64 (s, 3H), 3.04 (d, J = 9.3 Hz, 2H), 2.58 (s, 3H), 2.34 (s, 3H), 2.32-2.09 (m, 4H), 2.07-1.86 (m, 2H), 1.24 (s, 9H). | 526.3123 |
| 62 | 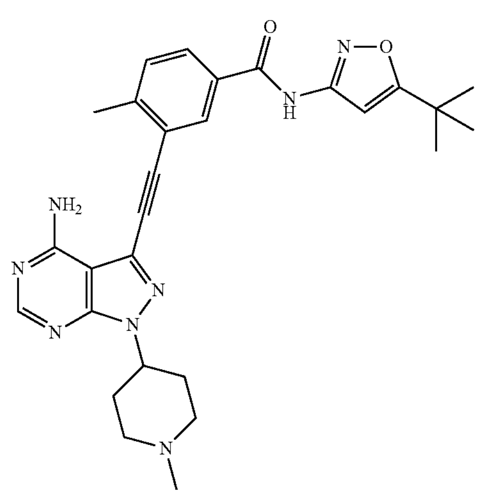 [SMILES: Cc1ccc(C(=O)Nc2cc(C(C)(C)C)on2)cc1C#Cc1nn(C2CCN(C)CC2)c2ncnc(N)c12] | ¹H NMR (400 MHz, DMSO-d₆) δ 11.40 (s, 1H), 8.37 (s, 1H), 8.27 (s, 1H), 7.98 (d, J = 7.7 Hz, 1H), 7.52 (d, J = 8.0 Hz, 1H), 6.74 (s, 1H), 4.70 (br.s, 1H), 3.03 (d, J = 8.9 Hz, 2H), 2.57 (s, 3H), 2.34 (s, 3H), 2.31-2.11 (m, 4H), 1.95 (d, J = 9.9 Hz, 2H), 1.33 (s, 9H). | 513.2719 |

| Compound | Structure | ¹H-NMR | ESI⁺ [M + H] |
|---|---|---|---|
| 63 | 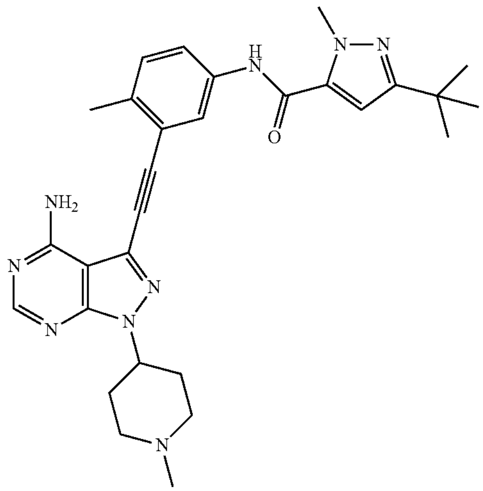 [SMILES: Cc1ccc(NC(=O)c2cc(C(C)(C)C)nn2C)cc1C#Cc1nn(C2CCN(C)CC2)c2ncnc(N)c12] | ¹H NMR (400 MHz, DMSO-d₆) δ 10.19 (s, 1H), 8.26 (s, 1H), 8.04 (d, J = 2.0 Hz, 1H), 7.70 (dd, J = 8.3, 2.0 Hz, 1H), 7.35 (d, J = 8.4 Hz, 1H), 6.97 (s, 1H), 4.74-4.54 (m, 1H), 4.04 (s, 3H), 2.93 (d, J = 9.9 Hz, 2H), 2.47 (s, 3H), 2.24 (s, 3H), 2.22-2.02 (m, 4H), 1.90 (d, J = 10.9 Hz, 2H), 1.29 (s, 9H). | 526.3041 |
| 64 | 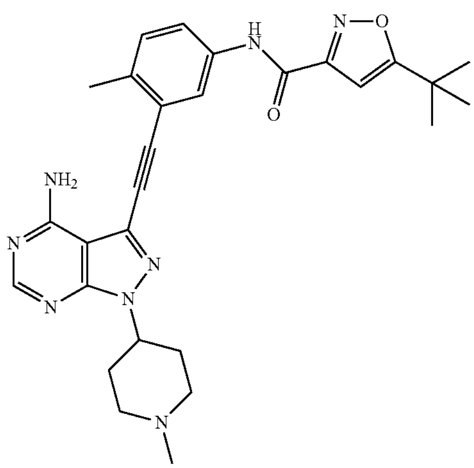 [SMILES: Cc1ccc(NC(=O)c2cc(C(C)(C)C)on2)cc1C#Cc1nn(C2CCN(C)CC2)c2ncnc(N)c12] | ¹H NMR (400 MHz, DMSO-d₆) δ 10.71 (s, 1H), 8.27 (s, 1H), 8.06 (d, J = 2.1 Hz, 1H), 7.70 (dd, J = 8.4, 2.1 Hz, 1H), 7.34 (d, J = 8.4 Hz, 1H), 6.67 (s, 1H), 4.97 (t, J = 11.5 Hz, 1H), 3.51 (br.s, 2H), 3.22 (br.s, 2H), 2.80 (s, 3H), 2.45 (s, 3H), 2.33 (dd, J = 25.3, 10.0 Hz, 2H), 2.16 (d, J = 12.2 Hz, 2H), 1.34 (s, 9H). | 513.2726 |
| 65 | 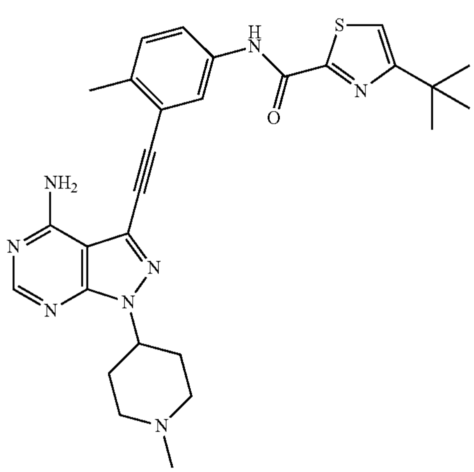 [SMILES: Cc1ccc(NC(=O)c2nc(C(C)(C)C)cs2)cc1C#Cc1nn(C2CCN(C)CC2)c2ncnc(N)c12] | ¹H NMR (400 MHz, DMSO-d₆) δ 10.00 (s, 1H), 8.30 (d, J = 7.6 Hz, 2H), 8.14 (s, 1H), 7.82 (d, J = 7.6 Hz, 1H), 7.36 (d, J = 7.9 Hz, 1H), 5.08-4.92 (m, 1H), 3.54 (d, J = 7.9 Hz, 2H), 3.30-3.15 (m, 2H), 2.82 (s, 3H), 2.47 (s, 3H), 2.43 (d, J = 11.2 Hz, 2H), 2.19 (d, J = 11.5 Hz, 2H), 1.47 (s, 9H). | 529.2495 |

-continued

| Compound | Structure | ¹H-NMR | ESI⁺ [M + H] |
|---|---|---|---|
| 66 | 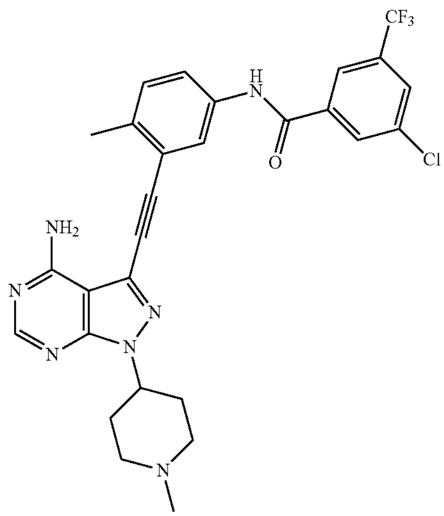 [SMILES: Cc1ccc(NC(=O)c2cc(Cl)cc(C(F)(F)F)c2)cc1C#Cc1nn(C2CCN(C)CC2)c2ncnc(N)c12] | ¹H NMR (400 MHz, DMSO-d$_6$) δ 10.62 (s, 1H), 8.34 (s, 1H), 8.31 (s, 1H), 8.27 (s, 1H), 8.15 (s, 1H), 8.10 (d, J = 1.8 Hz, 1H), 7.72 (dd, J = 8.3, 1.8 Hz, 1H), 7.39 (d, J = 8.3 Hz, 1H), 5.03-4.98 (m, 1H), 3.56 (d, J = 9.5 Hz, 2H), 3.26 (d, J = 11.0 Hz, 2H), 2.85 (s, 3H), 2.49 (s, 3H), 2.40 (dd, J = 23.4, 11.6 Hz, 2H), 2.20 (d, J = 11.9 Hz, 2H). | 568.1842 |
| 67 | 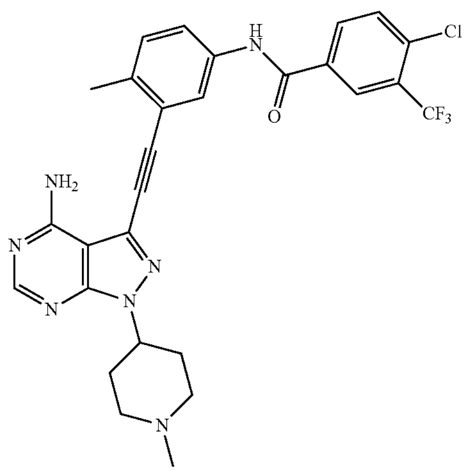 [SMILES: Cc1ccc(NC(=O)c2ccc(Cl)c(C(F)(F)F)c2)cc1C#Cc1nn(C2CCN(C)CC2)c2ncnc(N)c12] | ¹H NMR (400 MHz, DMSO-d$_6$) δ 10.61 (s, 1H), 8.41 (s, 1H), 8.28 (d, J = 10.8 Hz, 2H), 8.11 (s, 1H), 7.96 (d, J = 8.4 Hz, 1H), 7.71 (d, J = 8.2 Hz, 1H), 7.39 (d, J = 8.4 Hz, 1H), 5.03-4.97 (m, 1H), 3.55 (d, J = 10.6 Hz, 2H), 3.24 (d, J = 11.2 Hz, 2H), 2.83 (s, 3H), 2.48 (s, 3H), 2.39 (dd, J = 21.0, 9.5 Hz, 2H), 2.20 (d, J = 12.6 Hz, 2H). | 568.1836 |
| 68 | 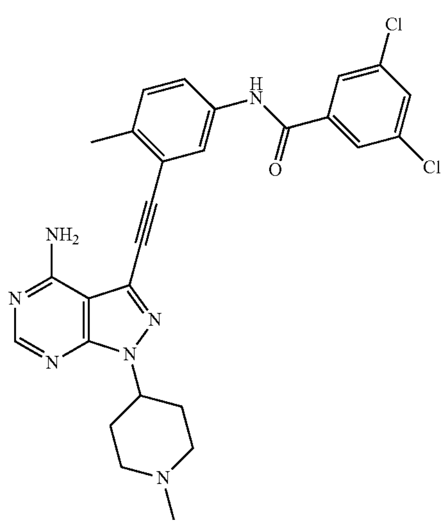 [SMILES: Cc1ccc(NC(=O)c2cc(Cl)cc(Cl)c2)cc1C#Cc1nn(C2CCN(C)CC2)c2ncnc(N)c12] | ¹H NMR (400 MHz, DMSO-d$_6$) δ 10.50 (s, 1H), 8.26 (s, 1H), 8.06 (d, J = 2.0 Hz, 1H), 8.00 (d, J = 1.8 Hz, 2H), 7.89 (t, J = 1.7 Hz, 1H), 7.73 (dd, J = 8.3, 2.0 Hz, 1H), 7.37 (d, J = 8.3 Hz, 1H), 4.82-4.53 (m, 1H), 2.95 (d, J = 6.9 Hz, 2H), 2.48 (s, 3H), 2.27 (s, 3H), 2.24-2.10 (m, 4H), 1.91 (d, J = 8.3 Hz, 2H). | 534.1575 |

| Compound | Structure | ¹H-NMR | ESI⁺ [M + H] |
|---|---|---|---|
| 69 | 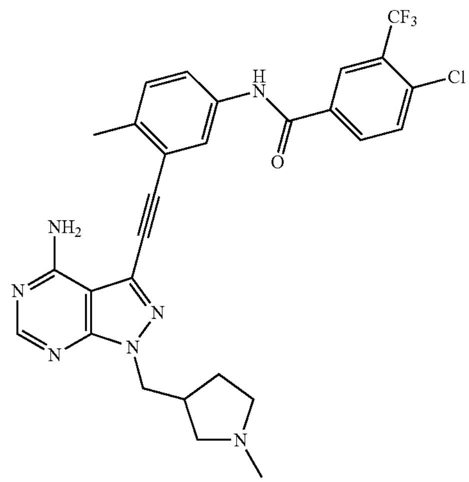 [SMILES: Cc1ccc(NC(=O)c2ccc(Cl)c(C(F)(F)F)c2)cc1C#Cc1nn(CC2CCN(C)C2)c2ncnc(N)c12] | ¹H NMR (400 MHz, DMSO-d$_6$) δ 10.60 (s, 1H), 8.42 (s, 1H), 8.29 (d, J = 7.3 Hz, 1H), 8.28 (s, 1H), 8.07 (d, J = 1.9 Hz, 1H), 7.95 (d, J = 8.4 Hz, 1H), 7.74 (dd, J = 8.3, 2.0 Hz, 1H), 7.38 (d, J = 8.5 Hz, 1H), 4.30 (d, J = 7.5 Hz, 2H), 2.76 (s, 1H), 2.55-2.52 (m, 1H), 2.48 (s, 3H), 2.42-2.32 (m, 3H), 2.22 (s, 3H), 1.90-1.76 (m, 1H), 1.53 (dt, J = 19.9, 6.6 Hz, 1H). | 568.1843 |
| 70 | 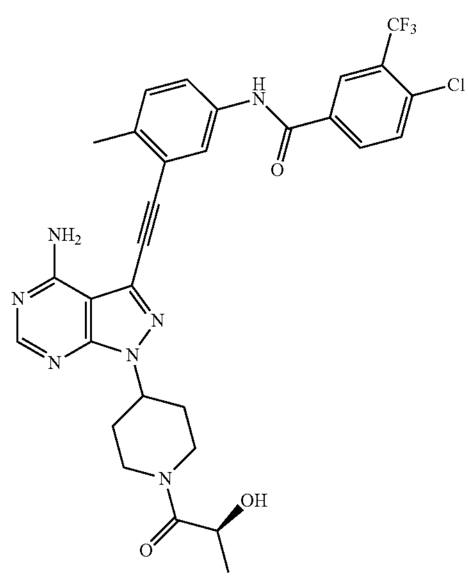 [SMILES: Cc1ccc(NC(=O)c2ccc(Cl)c(C(F)(F)F)c2)cc1C#Cc1nn(C2CCN(C(=O)[C@H](C)O)CC2)c2ncnc(N)c12] | ¹H NMR (400 MHz, DMSO-d$_6$) δ 10.58 (s, 1H), 8.40 (s, 1H), 8.28 (s, 1H), 8.27 (d, J = 8.5 Hz, 1H), 8.05 (s, 1H), 7.94 (d, J = 8.3 Hz, 1H), 7.72 (d, J = 7.9 Hz, 1H), 7.36 (d, J = 8.4 Hz, 1H), 5.09-4.87 (m, 2H), 4.50 (s, 2H), 4.17 (t, J = 13.7 Hz, 1H), 3.29-3.18 (m, 1H), 3.01-2.73 (m, 1H), 2.47 (s, 3H), 2.22-2.03 (m, 1H), 1.98 (br.s, 3H), 1.20 (d, J = 6.3 Hz, 3H). | 626.1896 |

| Compound | Structure | ¹H-NMR | ESI⁺ [M + H] |
|---|---|---|---|
| 71 | 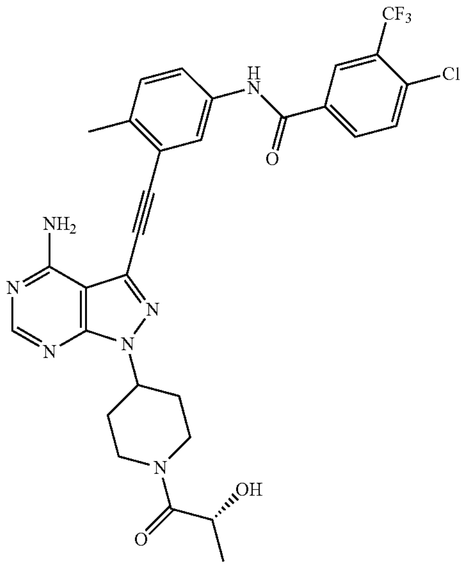 [SMILES: Cc1ccc(NC(=O)c2ccc(Cl)c(C(F)(F)F)c2)cc1C#Cc1nn(C2CCN(C(=O)[C@@H](C)O)CC2)c2ncnc(N)c12] | ¹H NMR (400 MHz, DMSO-d₆) δ 10.59 (s, 1H), 8.41 (d, J = 1.4 Hz, 1H), 8.28 (s, 1H), 8.28 (dd, J = 8.0, 2.0 Hz, 1H), 8.06 (d, J = 1.4 Hz, 1H), 7.95 (d, J = 8.4 Hz, 1H), 7.73 (dd, J = 8.0, 2.0 Hz, 1H), 7.37 (d, J = 8.4 Hz, 1H), 4.99 (ddd, J = 19.0, 11.9, 6.1 Hz, 2H), 4.61-4.40 (m, 2H), 4.18 (t, J = 14.0 Hz, 1H), 3.27 (dd, J = 14.4, 9.9 Hz, 1H), 2.97-2.76 (m, 1H), 2.48 (s, 3H), 2.21-2.05 (m, 1H), 1.99 (br.s, 3H), 1.23 (dd, J = 10.1, 6.6 Hz, 3H). | 626.1890 |
| 72 | 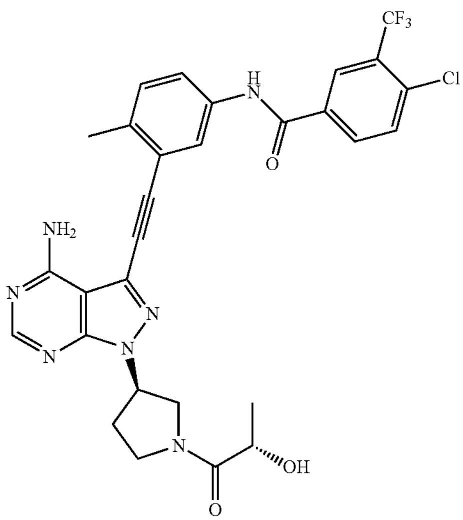 [SMILES: Cc1ccc(NC(=O)c2ccc(Cl)c(C(F)(F)F)c2)cc1C#Cc1nn([C@@H]2CCN(C(=O)[C@H](C)O)C2)c2ncnc(N)c12] | ¹H NMR (400 MHz, DMSO-d₆) δ 10.60 (s, 1H), 8.42 (s, 1H), 8.29 (s, 1H), 8.28 (d, J = 8.6 Hz, 1H), 8.06 (s, 1H), 7.95 (d, J = 8.3 Hz, 1H), 7.75 (t, J = 6.9 Hz, 1H), 7.37 (d, J = 8.3 Hz, 1H), 5.50 (dd, J = 16.1, 10.1 Hz, 1H), 4.92 (dd, J = 16.9, 6.7 Hz, 1H), 4.43-4.16 (m, 1H), 4.02 (d, J = 5.4 Hz, 1H), 3.93-3.72 (m, 2H), 3.72-3.47 (m, 1H), 2.47 (s, 3H), 2.38 (dd, J = 13.2, 6.7 Hz, 2H), 1.21 (dd, J = 16.5, 10.0 Hz, 3H). | 612.1741 |
| 73 | 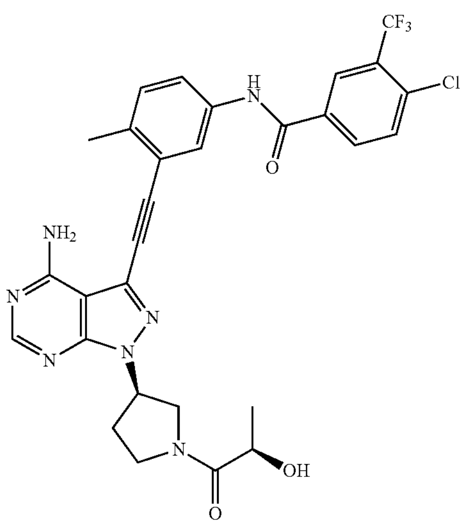 [SMILES: Cc1ccc(NC(=O)c2ccc(Cl)c(C(F)(F)F)c2)cc1C#Cc1nn([C@@H]2CCN(C(=O)[C@@H](C)O)C2)c2ncnc(N)c12] | ¹H NMR (400 MHz, DMSO-d₆) δ 10.59 (s, 1H), 8.42 (s, 1H), 8.29 (s, 1H), 8.28 (d, J = 9.6 Hz, 1H), 8.06 (s, 1H), 7.95 (d, J = 8.3 Hz, 1H), 7.75 (d, J = 8.3 Hz, 1H), 7.37 (d, J = 8.4 Hz, 1H), 5.57-5.36 (m, 1H), 4.94 (t, J = 6.7 Hz, 1H), 4.40-4.21 (m, 1H), 4.13 (dd, J = 11.0, 7.0 Hz, 1H), 3.98-3.87 (m, 1H), 3.87-3.75 (m, 1H), 3.63-3.50 (m, 1H), 2.48 (s, 3H), 2.39 (dd, J = 13.1, 6.4 Hz, 2H), 1.20 (dd, J = 19.5, 6.4 Hz, 3H). | 612.1732 |

-continued

| Compound | Structure | ¹H-NMR | ESI⁺ [M + H] |
|---|---|---|---|
| 74 | 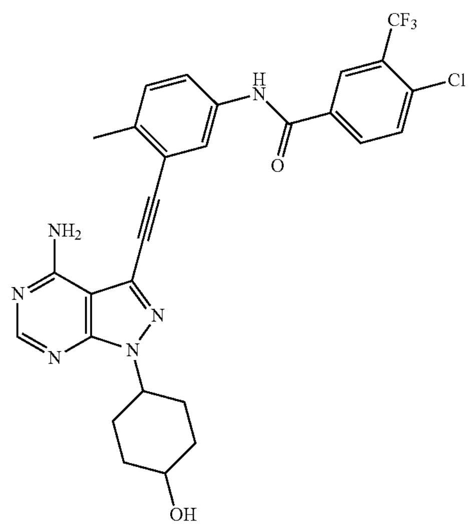 [SMILES: Cc1ccc(NC(=O)c2ccc(Cl)c(C(F)(F)F)c2)cc1C#Cc1nn(C2CCC(O)CC2)c2ncnc(N)c12] | ¹H NMR (400 MHz, DMSO-d₆) δ 10.59 (s, 1H), 8.41 (s, 1H), 8.28 (d, J = 5.9 Hz, 2H), 8.06 (s, 1H), 7.94 (d, J = 7.9 Hz, 1H), 7.73 (d, J = 7.7 Hz, 1H), 7.37 (d, J = 7.9 Hz, 1H), 4.70 (s, 1H), 4.64 (d, J = 9.9 Hz, 1H), 3.56 (s, 1H), 2.14-1.81 (m, 6H), 1.53-1.31 (m, 2H). | 569.1679 |
| 75 | 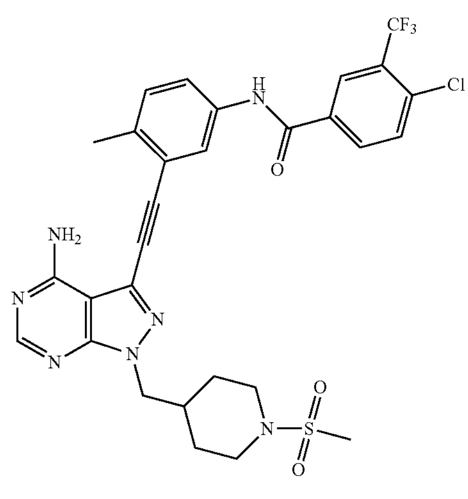 [SMILES: Cc1ccc(NC(=O)c2ccc(Cl)c(C(F)(F)F)c2)cc1C#Cc1nn(CC2CCN(S(C)(=O)=O)CC2)c2ncnc(N)c12] | ¹H NMR (400 MHz, DMSO-d₆) δ 10.59 (s, 1H), 8.41 (s, 1H), 8.28 (s, 2H), 8.07 (s, 1H), 7.95 (d, J = 8.4 Hz, 1H), 7.73 (d, J = 8.2 Hz, 1H), 7.37 (d, J = 8.4 Hz, 1H), 4.29 (d, J = 6.9 Hz, 2H), 3.54 (d, J = 11.9 Hz, 2H), 2.83 (s, 3H), 2.68 (t, J = 11.1 Hz, 2H), 2.48 (s, 3H), 2.24-1.98 (m, 1H), 1.62 (d, J = 11.9 Hz, 2H), 1.30 (ddd, J = 15.6, 13.0, 3.6 Hz, 2H). | 646.1609 |
| 76 | 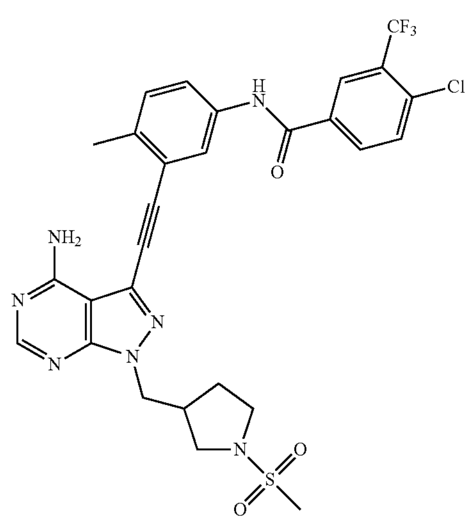 [SMILES: Cc1ccc(NC(=O)c2ccc(Cl)c(C(F)(F)F)c2)cc1C#Cc1nn(CC2CCN(S(C)(=O)=O)C2)c2ncnc(N)c12] | ¹H NMR (400 MHz, DMSO-d₆) δ 10.59 (s, 1H), 8.42 (s, 1H), 8.29 (s, 1H), 8.28 (d, J = 7.6 Hz, 1H), 8.07 (s, 1H), 7.94 (d, J = 8.1 Hz, 1H), 7.74 (d, J = 7.6 Hz, 1H), 7.37 (d, J = 8.1 Hz, 1H), 4.54-4.31 (m, 2H), 3.41-3.36 (m, 2H), 3.24 (dd, J = 16.0, 7.6 Hz, 1H), 3.16-3.04 (m, 1H), 2.92 (s, 3H), 2.84 (dt, J = 14.4, 7.4 Hz, 1H), 2.48 (s, 3H), 1.96 (dd, J = 11.6, 5.8 Hz, 1H), 1.72 (td, J = 15.7, 7.7 Hz, 1H). | 632.1462 |

| Compound | Structure | ¹H-NMR | ESI⁺ [M + H] |
|---|---|---|---|
| 77 | 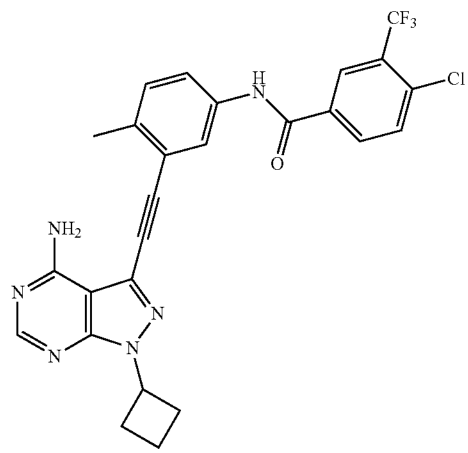 [SMILES: Cc1ccc(NC(=O)c2ccc(Cl)c(C(F)(F)F)c2)cc1C#Cc1nn(C2CCC2)c2ncnc(N)c12] | ¹H NMR (400 MHz, DMSO-d₆) δ 10.59 (s, 1H), 8.42 (s, 1H), 8.28 (d, J = 9.1 Hz, 1H), 8.26 (s, 1H), 8.08 (s, 1H), 7.95 (d, J = 8.4 Hz, 1H), 7.74 (d, J = 8.2 Hz, 1H), 7.38 (d, J = 8.4 Hz, 1H), 5.41-5.24 (m, 1H), 2.78-2.61 (m, 2H), 2.49 (s, 3H), 2.47-2.36 (m, 2H), 1.95-1.82 (m, 2H). | 525.1417 |
| 78 | 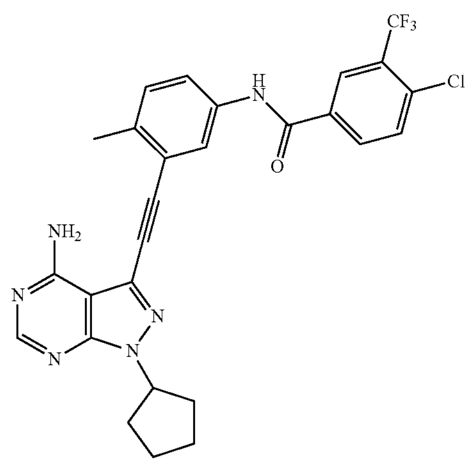 [SMILES: Cc1ccc(NC(=O)c2ccc(Cl)c(C(F)(F)F)c2)cc1C#Cc1nn(C2CCCC2)c2ncnc(N)c12] | ¹H NMR (400 MHz, DMSO-d₆) δ 10.59 (s, 1H), 8.42 (s, 1H), 8.28 (d, J = 8.2 Hz, 1H), 8.26 (s, 1H), 8.07 (s, 1H), 7.95 (d, J = 8.4 Hz, 1H), 7.74 (d, J = 8.2 Hz, 1H), 7.37 (d, J = 8.4 Hz, 1H), 5.31-5.15 (m, 1H), 2.48 (s, 3H), 2.12 (dt, J = 12.0, 6.7 Hz, 2H), 2.02 (td, J = 13.4, 7.0 Hz, 2H), 1.96-1.84 (m, 2H), 1.76-1.64 (m, 2H). | 539.1579 |
| 79 | 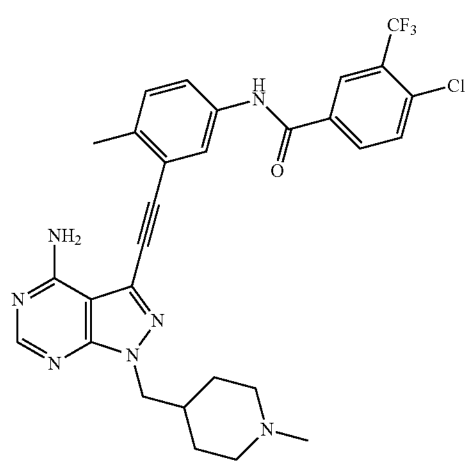 [SMILES: Cc1ccc(NC(=O)c2ccc(Cl)c(C(F)(F)F)c2)cc1C#Cc1nn(CC2CCN(C)CC2)c2ncnc(N)c12] | ¹H NMR (400 MHz, DMSO-d₆) δ 10.60 (s, 1H), 8.41 (s, 1H), 8.29 (s, 1H), 8.28 (d, J = 9.0 Hz, 1H), 8.10 (d, J = 1.7 Hz, 1H), 7.95 (d, J = 8.4 Hz, 1H), 7.71 (dd, J = 8.3, 1.8 Hz, 1H), 7.38 (d, J = 8.4 Hz, 1H), 4.32 (d, J = 6.5 Hz, 2H), 3.36 (d, J = 11.4 Hz, 2H), 2.91 (t, J = 9.9 Hz, 2H), 2.72 (s, 3H), 2.48 (s, 3H), 2.25-2.16 (m, 1H), 1.73 (d, J = 12.8 Hz, 2H), 1.48 (dd, J = 23.2, 11.4 Hz, 2H). | 582.1997 |

-continued

| Compound | Structure | ¹H-NMR | ESI+ [M + H] |
|---|---|---|---|
| 80 | 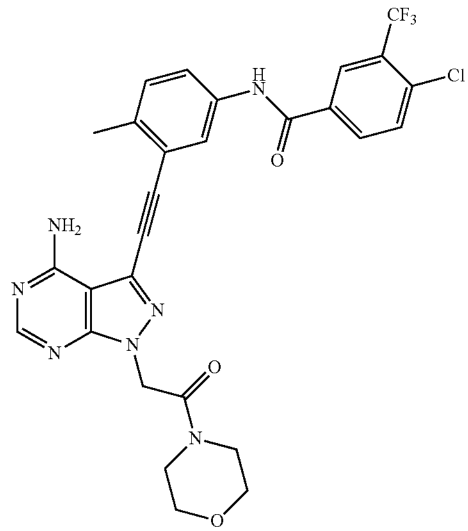 [SMILES: Cc1ccc(NC(=O)c2ccc(Cl)c(C(F)(F)F)c2)cc1C#Cc1nn(CC(=O)N2CCOCC2)c2ncnc(N)c12] | ¹H NMR (400 MHz, DMSO-d$_6$) δ 10.60 (s, 1H), 8.42 (s, 1H), 8.29 (d, J = 8.4 Hz, 2H), 8.05 (s, 1H), 7.94 (d, J = 8.3 Hz, 1H), 7.76 (d, J = 8.4 Hz, 1H), 7.37 (d, J = 8.3 Hz, 1H), 5.38 (s, 2H), 3.68 (s, 2H), 3.60 (s, 4H), 3.45 (s, 2H), 2.48 (s, 3H). | 598.1586 |
| 81 | 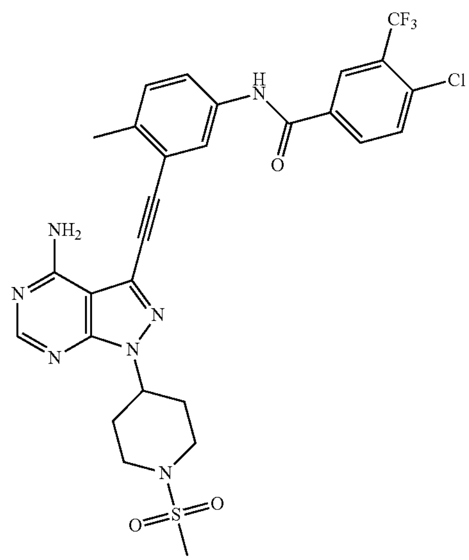 [SMILES: Cc1ccc(NC(=O)c2ccc(Cl)c(C(F)(F)F)c2)cc1C#Cc1nn(C2CCN(S(C)(=O)=O)CC2)c2ncnc(N)c12] | ¹H NMR (400 MHz, DMSO-d$_6$) δ 10.60 (s, 1H), 8.42 (s, 1H), 8.29 (s, 1H), 8.07 (s, 2H), 7.95 (d, J = 8.0 Hz, 1H), 7.74 (d, J = 7.9 Hz, 1H), 7.38 (d, J = 8.0 Hz, 1H), 4.99-4.75 (m, 1H), 3.73 (d, J = 11.0 Hz, 2H), 3.04 (t, J = 11.5 Hz, 2H), 2.96 (s, 3H), 2.49 (s, 3H), 2.19 (d, J = 10.2 Hz, 2H), 2.08 (d, J = 10.9 Hz, 2H). | 632.1462 |
| 82 | 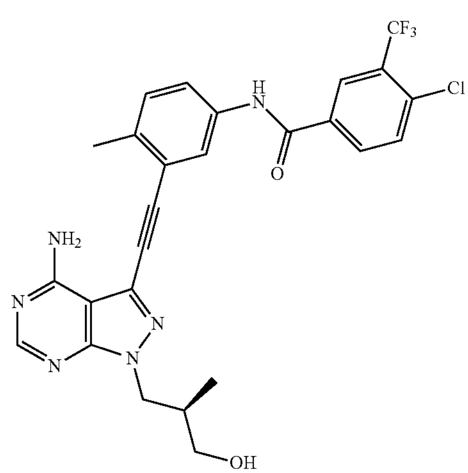 [SMILES: Cc1ccc(NC(=O)c2ccc(Cl)c(C(F)(F)F)c2)cc1C#Cc1nn(C[C@@H](C)CO)c2ncnc(N)c12] | ¹H NMR (400 MHz, DMSO-d$_6$) δ 10.59 (s, 1H), 8.41 (s, 1H), 8.31 (s, 1H), 8.28 (d, J = 8.4 Hz, 1H), 8.06 (d, J = 1.8 Hz, 1H), 7.94 (d, J = 8.4 Hz, 1H), 7.74 (dd, J = 8.4, 1.8 Hz, 1H), 7.37 (d, J = 8.4 Hz, 1H), 4.67 (t, J = 5.3 Hz, 1H), 4.36 (dd, J = 13.7, 6.0 Hz, 1H), 4.18 (dd, J = 13.6, 8.1 Hz, 1H), 3.35 (d, J = 5.6 Hz, 2H), 2.48 (s, 3H), 2.24 (dq, J = 12.9, 6.4 Hz, 1H), 0.79 (d, J = 6.8 Hz, 3H). | 543.1522 |

-continued
| Compound | Structure | ¹H-NMR | ESI⁺ [M + H] |
|---|---|---|---|
| 83 | 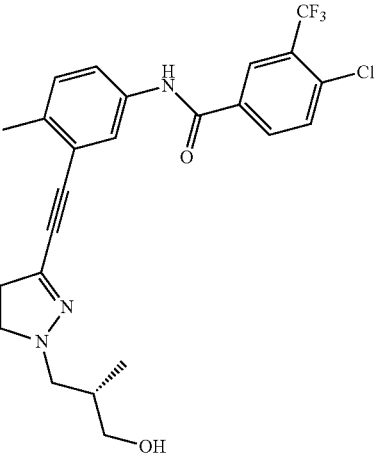 | ¹H NMR (400 MHz, DMSO-d₆) δ 10.59 (s, 1H), 8.41 (d, J = 1.5 Hz, 1H), 8.28 (d, J = 8.4 Hz, 2H), 8.06 (d, J = 2.0 Hz, 1H), 7.94 (d, J = 8.4 Hz, 1H), 7.74 (dd, J = 8.4, 2.0 Hz, 1H), 7.37 (d, J = 8.4 Hz, 1H), 4.67 (t, J = 5.3 Hz, 1H), 4.36 (dd, J = 13.7, 6.1 Hz, 1H), 4.18 (dd, J = 13.7, 8.1 Hz, 1H), 3.35 (d, J = 5.8 Hz, 2H), 2.48 (s, 3H), 2.24 (dq, J = 13.1, 6.4 Hz, 1H), 0.79 (d, J = 6.8 Hz, 3H). | 543.1524 |
| 84 | 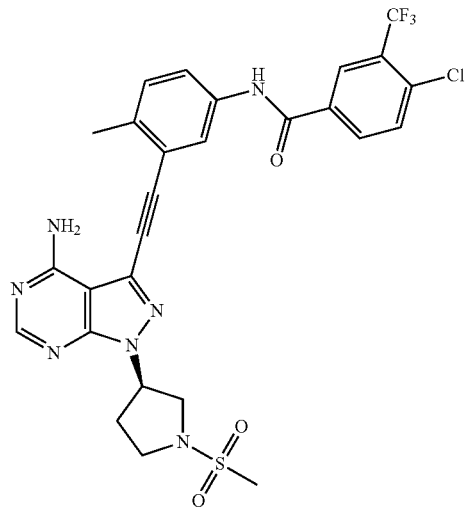 [SMILES: Cc1ccc(NC(=O)c2ccc(Cl)c(C(F)(F)F)c2)cc1C#Cc1nn([C@@H]2CCN(S(C)(=O)=O)C2)c2ncnc(N)c12] | ¹H NMR (400 MHz, DMSO-d₆) δ 10.59 (s, 1H), 8.42 (d, J = 1.4 Hz, 1H), 8.31 (s, 1H), 8.28 (d, J = 8.4 Hz, 1H), 8.07 (d, J = 2.0 Hz, 1H), 7.95 (d, J = 8.4 Hz, 1H), 7.75 (dd, J = 8.4, 2.0 Hz, 1H), 7.37 (d, J = 8.4 Hz, 1H), 5.56-5.46 (m, 1H), 3.84 (dd, J = 10.8, 7.1 Hz, 1H), 3.68-3.62 (m, 1H), 3.59 (dd, J = 12.2, 4.7 Hz, 1H), 3.54-3.46 (m, 1H), 3.00 (s, 3H), 2.48 (s, 3H), 2.44 (dd, J = 11.0, 5.6 Hz, 2H). | 618.1307 |
| 85 | 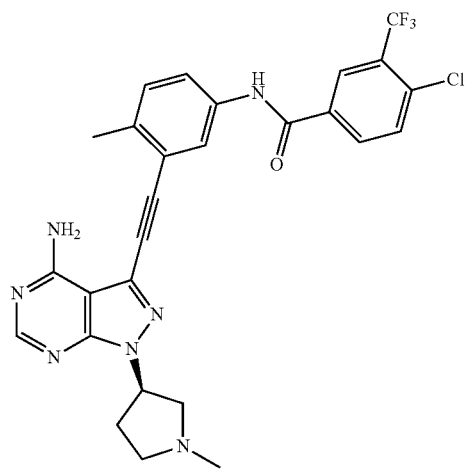 [SMILES: Cc1ccc(NC(=O)c2ccc(Cl)c(C(F)(F)F)c2)cc1C#Cc1nn([C@@H]2CCN(C)C2)c2ncnc(N)c12] | ¹H NMR (400 MHz, DMSO-d₆) δ 10.61 (s, 1H), 8.41 (d, J = 1.6 Hz, 1H), 8.30 (s, 1H), 8.28 (dd, J = 8.4, 1.6 Hz, 1H), 8.11 (d, J = 2.0 Hz, 1H), 7.95 (d, J = 8.4 Hz, 1H), 7.70 (dd, J = 8.4, 2.0 Hz, 1H), 7.38 (d, J = 8.4 Hz, 1H), 5.65-5.51 (m, 1H), 3.53 (d, J = 7.8 Hz, 1H), 3.45-3.39 (m, 2H), 3.23-3.19 (m, 1H), 2.75 (s, 3H), 2.61-2.49 (m, 1H), 2.49 (s, 3H), 2.43-2.31 (m, 1H). | 554.1689 |

-continued

| Compound | Structure | ¹H-NMR | ESI⁺ [M + H] |
|---|---|---|---|
| 86 | 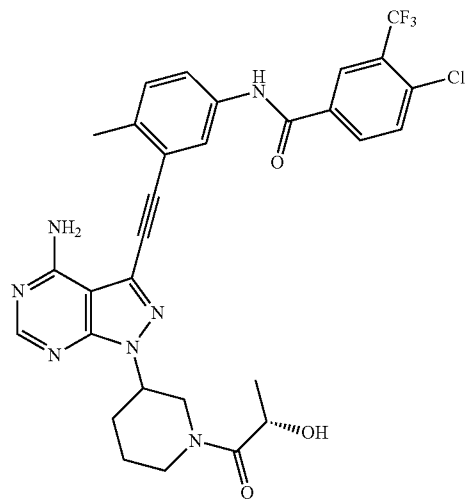 [SMILES: Cc1ccc(NC(=O)c2ccc(Cl)c(C(F)(F)F)c2)cc1C#Cc1nn(C2CCCN(C(=O)[C@H](C)O)C2)c2ncnc(N)c12] | ¹H NMR (400 MHz, DMSO-d₆) δ 10.59 (s, 1H), 8.42 (s, 1H), 8.29 (s, 1H), 8.28 (d, J = 8.1 Hz, 1H), 8.08 (s, 1H), 7.94 (d, J = 8.4 Hz, 1H), 7.73 (dd, J = 8.1, 1.6 Hz, 1H), 7.37 (d, J = 8.4 Hz, 1H), 5.08-4.86 (m, 1H), 4.84-4.59 (m, 1H), 4.44 (ddd, J = 61.3, 32.2, 13.8 Hz, 2H), 4.29-3.94 (m, 1H), 3.67-3.15 (m, 1H), 2.94 (ddd, J = 36.5, 19.9, 7.5 Hz, 1H), 2.48 (s, 3H), 2.25 (dd, J = 30.2, 18.8 Hz, 1H), 2.11 (d, J = 16.6 Hz, 1H), 1.98-1.81 (m, 1H), 1.76-1.44 (m, 1H), 1.21 (d, J = 6.4 Hz, 3H). | 626.1896 |
| 87 | 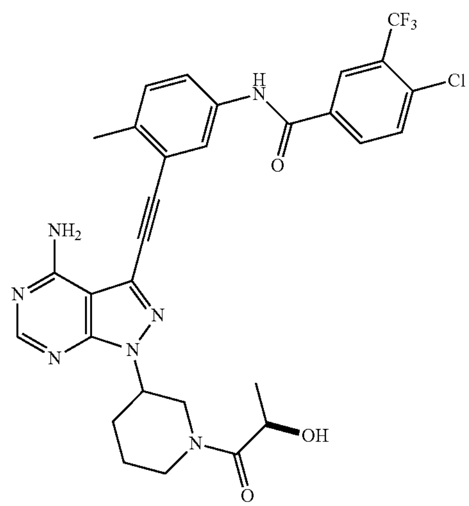 [SMILES: Cc1ccc(NC(=O)c2ccc(Cl)c(C(F)(F)F)c2)cc1C#Cc1nn(C2CCCN(C(=O)[C@@H](C)O)C2)c2ncnc(N)c12] | ¹H NMR (400 MHz, DMSO-d₆) δ 10.60 (s, 1H), 8.42 (s, 1H), 8.29 (s, 1H), 8.28 (d, J = 7.3 Hz, 1H), 8.08 (s, 1H), 7.94 (d, J = 8.4 Hz, 1H), 7.74 (d, J = 8.2 Hz, 1H), 7.37 (d, J = 8.4 Hz, 1H), 5.10-4.86 (m, 1H), 4.85-4.59 (m, 1H), 4.44 (ddd, J = 61.6, 32.2, 12.7 Hz, 2H), 4.29-3.94 (m, 1H), 3.68-3.15 (m, 1H), 3.15-2.69 (m, 1H), 2.48 (s, 3H), 2.26 (dd, J = 29.1, 18.2 Hz, 1H), 2.11 (d, J = 17.1 Hz, 1H), 2.00-1.79 (m, 1H), 1.58 (ddd, J = 34.2, 24.2, 10.4 Hz, 1H), 1.21 (d, J = 6.4 Hz, 3H). | 626.1888 |
| 88 | 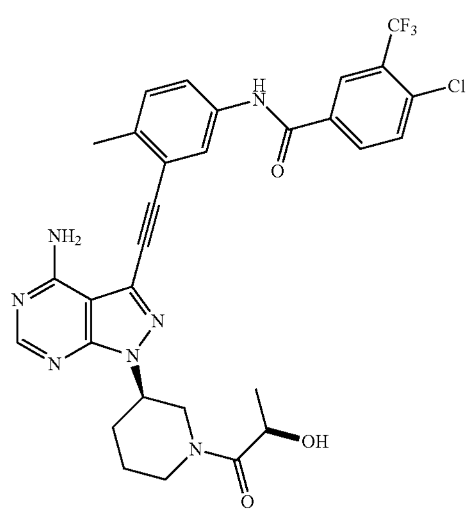 [SMILES: Cc1ccc(NC(=O)c2ccc(Cl)c(C(F)(F)F)c2)cc1C#Cc1nn([C@@H]2CCCN(C(=O)[C@@H](C)O)C2)c2ncnc(N)c12] | ¹H NMR (400 MHz, DMSO-d₆) δ 10.60 (s, 1H), 8.42 (s, 1H), 8.29 (s, 1H), 8.28 (d, J = 8.3 Hz, 1H), 8.08 (d, J = 1.8 Hz, 1H), 7.95 (d, J = 8.4 Hz, 1H), 7.74 (dd, J = 8.3, 1.8 Hz, 1H), 7.38 (d, J = 8.4 Hz, 1H), 5.00 (d, J = 31.3 Hz, 1H), 4.82-4.61 (m, 1H), 4.58-4.29 (m, 2H), 4.16 (dd, J = 71.0, 13.3 Hz, 1H), 3.68-3.11 (m, 1H), 3.13-2.73 (m, 1H), 2.30-2.16 (m, 1H), 2.11 (d, J = 11.5 Hz, 1H), 1.89 (t, J = 13.6 Hz, 1H), 1.74-1.44 (m, 1H), 1.21 (d, J = 6.5 Hz, 3H). | 626.1896 |

-continued

| Compound | Structure | ¹H-NMR | ESI⁺ [M + H] |
|---|---|---|---|
| 89 | 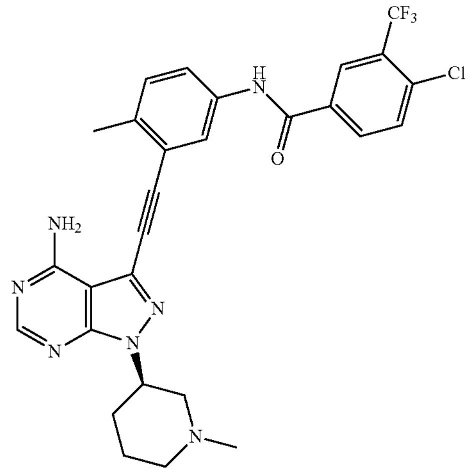 [SMILES: Cc1ccc(NC(=O)c2ccc(Cl)c(C(F)(F)F)c2)cc1C#Cc1nn([C@@H]2CCCN(C)C2)c2ncnc(N)c12] | ¹H NMR (400 MHz, DMSO-d₆) δ 10.60 (s, 1H), 8.41 (s, 2H), 8.28 (d, J = 7.5 Hz, 1H), 8.07 (s, 1H), 7.95 (d, J = 8.0 Hz, 1H), 7.73 (d, J = 7.5 Hz, 1H), 7.37 (d, J = 8.0 Hz, 1H), 4.85 (s, 1H), 3.02 (s, 1H), 2.84 (s, 1H), 2.56 (s, 1H), 2.48 (s, 3H), 2.32 (s, 3H), 2.14 (s, 1H), 1.98 (s, 2H), 1.84 (s, 1H), 1.70 (s, 1H). | 568.1834 |
| 90 | 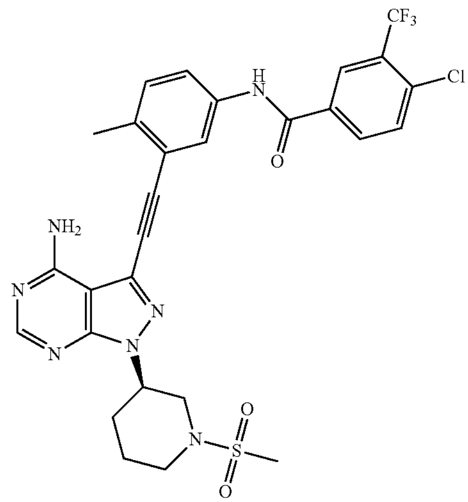 [SMILES: Cc1ccc(NC(=O)c2ccc(Cl)c(C(F)(F)F)c2)cc1C#Cc1nn([C@@H]2CCCN(S(C)(=O)=O)C2)c2ncnc(N)c12] | ¹H NMR (400 MHz, DMSO-d₆) δ 10.60 (s, 1H), 8.41 (s, 1H), 8.30 (s, 1H), 8.28 (d, J = 11.5 Hz, 1H), 8.08 (s, 1H), 7.95 (d, J = 7.9 Hz, 1H), 7.73 (d, J = 7.3 Hz, 1H), 7.37 (d, J = 7.6 Hz, 1H), 4.88-4.79 (m, 1H), 3.76 (d, J = 8.1 Hz, 1H), 3.61 (d, J = 10.1 Hz, 1H), 3.17 (t, J = 10.5 Hz, 1H), 2.93 (s, 3H), 2.90-2.76 (m, 1H), 2.48 (s, 3H), 2.26-2.05 (m, 2H), 1.99 (d, J = 13.0 Hz, 1H), 1.74 (d, J = 10.6 Hz, 1H). | 632.1461 |
| 91 | 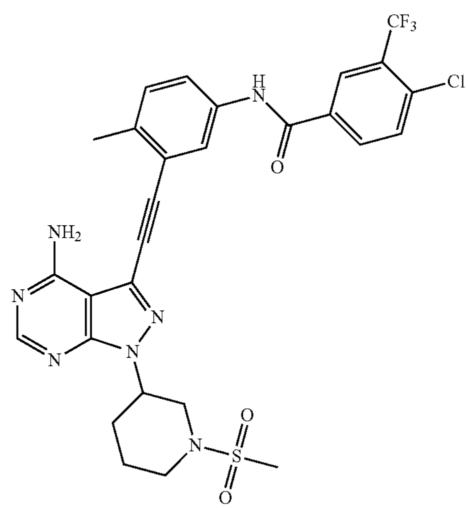 [SMILES: Cc1ccc(NC(=O)c2ccc(Cl)c(C(F)(F)F)c2)cc1C#Cc1nn(C2CCCN(S(C)(=O)=O)C2)c2ncnc(N)c12] | ¹H NMR (400 MHz, DMSO-d₆) δ 10.59 (s, 1H), 8.41 (s, 1H), 8.29 (s, 2H), 8.07 (s, 1H), 7.95 (d, J = 7.3 Hz, 1H), 7.72 (d, J = 5.4 Hz, 1H), 7.38 (d, J = 7.3 Hz, 1H), 4.87-4.78 (m, 1H), 3.76 (d, J = 10.8 Hz, 1H), 3.61 (d, J = 9.5 Hz, 1H), 3.24-3.10 (m, 1H), 2.93 (s, 3H), 2.89-2.76 (m, 1H), 2.47 (s, 3H), 2.24-2.06 (m, 2H), 1.98 (d, J = 12.8 Hz, 1H), 1.78-1.69 (m, 1H). | 632.1465 |

-continued

| Compound | Structure | ¹H-NMR | ESI⁺ [M + H] |
|---|---|---|---|
| 92 | 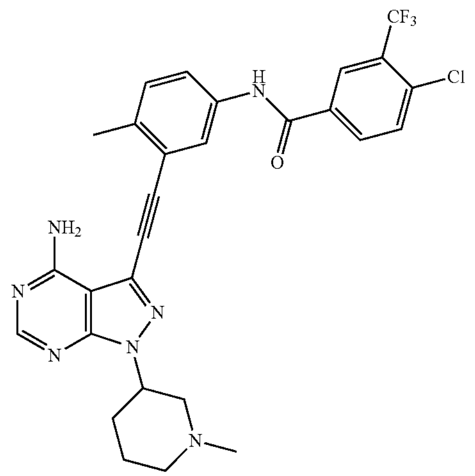 [SMILES: Cc1ccc(NC(=O)c2ccc(Cl)c(C(F)(F)F)c2)cc1C#Cc1nn(C2CCCN(C)C2)c2ncnc(N)c12] | ¹H NMR (400 MHz, DMSO-d₆) δ 10.60 (s, 1H), 8.41 (s, 1H), 8.28 (d, J = 8.0 Hz, 1H), 8.27 (s, 1H), 8.07 (s, 1H), 7.95 (d, J = 8.3 Hz, 1H), 7.73 (d, J = 8.0 Hz, 1H), 7.37 (d, J = 8.3 Hz, 1H), 4.87-4.69 (m, 1H), 2.96 (d, J = 8.9 Hz, 1H), 2.81 (d, J = 10.1 Hz, 1H), 2.48 (s, 3H), 2.43-2.29 (m, 1H), 2.24 (s, 3H), 1.95 (br.s, 3H), 1.82 (d, J = 13.1 Hz, 1H), 1.75-1.58 (m, 1H). | 568.1840 |
| 93 | 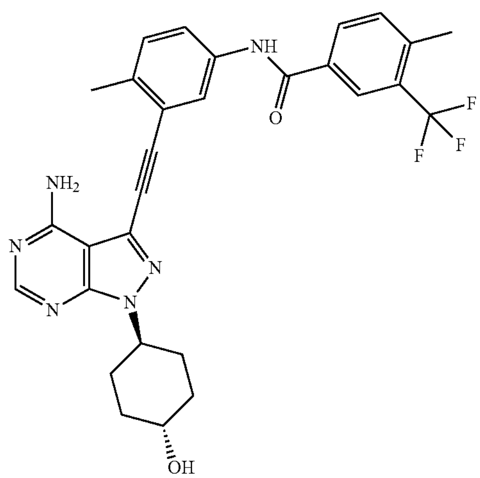 [SMILES: Cc1ccc(NC(=O)c2ccc(C)c(C(F)(F)F)c2)cc1C#Cc1nn([C@H]2CC[C@H](O)CC2)c2ncnc(N)c12] | ¹H NMR (400 MHz, DMSO-d₆) δ 10.48 (s, 1H), 8.27 (s, 1H), 8.26 (s, 1H), 8.18 (d, J = 8.0 Hz, 1H), 8.07 (d, J = 2.2 Hz, 1H), 7.74 (dd, J = 8.3, 2.2 Hz, 1H), 7.64 (d, J = 8.0 Hz, 1H), 7.36 (d, J = 8.5 Hz, 1H), 4.71 (s, 1H), 4.69-4.56 (m, 1H), 3.63-3.47 (m, 1H), 2.54 (s, 3H), 2.47 (s, 3H), 2.10-1.83 (m, 6H), 1.46-1.36 (m, 2H). | 549.2 |
| 94 | 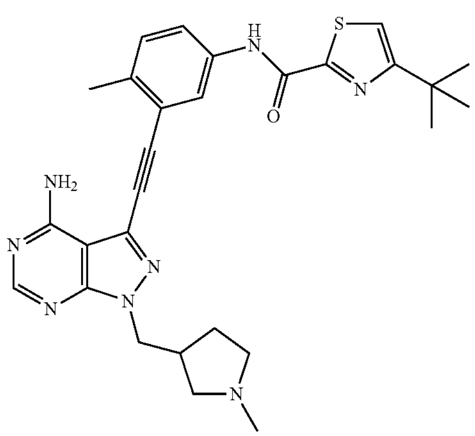 [SMILES: Cc1ccc(NC(=O)c2nc(C(C)(C)C)cs2)cc1C#Cc1nn(CC2CCN(C)C2)c2ncnc(N)c12] | ¹H NMR (400 MHz, DMSO-d₆) δ 10.02 (s, 1H), 8.32 (s, 1H), 8.28 (s, 1H), 8.13 (s, 1H), 7.84 (d, J = 8.3 Hz, 1H), 7.36 (d, J = 8.4 Hz, 1H), 4.35 (d, J = 7.4 Hz, 2H), 2.91-2.54 (m, 5H), 2.48 (s, 3H), 2.38 (s, 3H), 1.95-1.87 (m, 1H), 1.66-1.58 (m, 1H), 1.47 (s, 9H). | 529.2 |

| Compound | Structure | ¹H-NMR | ESI⁺ [M + H] |
|---|---|---|---|
| 95 | 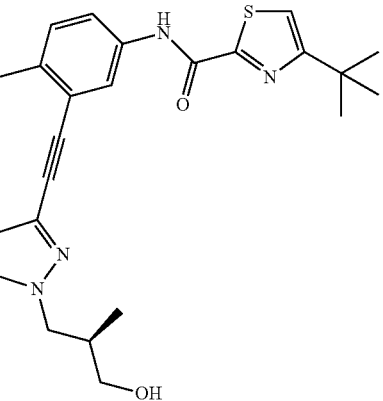 | ¹H NMR (400 MHz, DMSO-d₆) δ 10.01 (s, 1H), 8.32 (s, 1H), 8.27 (s, 1H), 8.12 (d, J = 1.5 Hz, 1H), 7.84 (d, J = 8.3 Hz, 1H), 7.36 (d, J = 8.4 Hz, 1H), 4.69 (s, 1H), 4.36 (dd, J = 13.6, 5.9 Hz, 1H), 4.18 (dd, J = 13.6, 8.2 Hz, 1H), 3.49-3.39 (m, 2H), 2.48 (s, 3H), 2.28-2.20 (m, 1H), 1.47 (s, 9H), 0.79 (d, J = 6.8 Hz, 3H). | 504.2 |
| 96 | 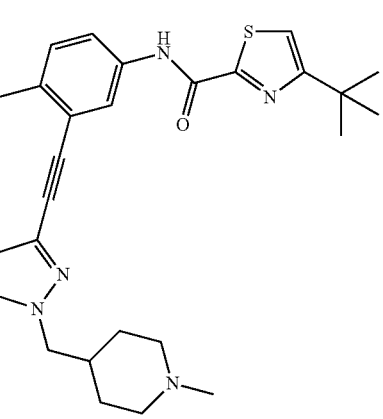 | ¹H NMR (400 MHz, DMSO-d₆) δ 10.02 (s, IH), 8.32 (s, 1H), 8.28 (s, 1H), 8.14 (s, 1H), 7.82 (d, J = 8.2 Hz, 1H), 7.36 (d, J = 8.4 Hz, 1H), 4.29 (d, J = 6.2 Hz, 2H), 3.22-3.08 (m, 2H), 2.54 (s, 3H), 2.48 (s, 3H), 2.19-2.06 (m, 1H), 2.06-1.93 (m, 2H), 1.71-1.60 (m, 2H), 1.47 (s, 9H), 1.45-1.35 (m, 2H). | 543.3 |
| 97 | 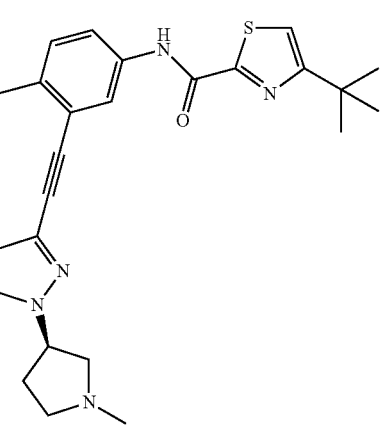 | ¹H NMR (400 MHz, DMSO-d₆) δ 10.02 (s, 1H), 8.32 (s, 1H), 8.27 (s, 1H), 8.14 (d, J = 2.1 Hz, 1H), 7.83 (dd, J = 8.3, 2.1 Hz, 1H), 7.36 (d, J = 8.4 Hz, 1H), 5.51-5.38 (m, 1H), 3.22-3.10 (m, 1H), 2.97-2.83 (m, 3H), 2.48 (s, 3H), 2.44 (s, 3H), 2.42-2.36 (m, 1H), 2.33-2.25 (m, 2H), 1.47 (s, 9H). | 515.2 |

| Compound | Structure | ¹H-NMR | ESI⁺ [M + H] |
|---|---|---|---|
| 98 | 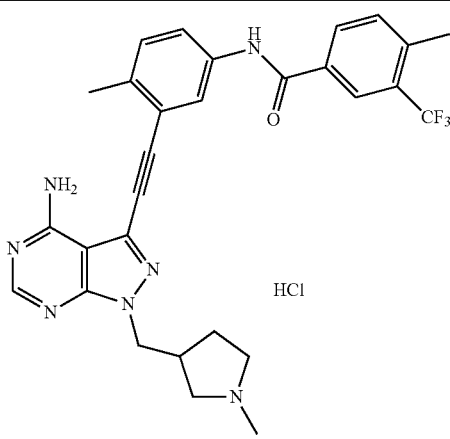 HCl | ¹H NMR (400 MHz, DMSO-d$_6$) δ 10.95 (s, 1H), 10.58 (s, 1H), 8.29 (s, 1H), 8.28 (s, 1H), 8.21 (d, J = 9.0 Hz, 1H), 8.12 (d, J = 2.2 Hz, 1H), 7.76 (dd, J = 8.3, 2.2 Hz, 1H), 7.64 (d, J = 8.0 Hz, 1H), 7.36 (d, J = 8.5 Hz, 1H), 4.54-4.41 (m, 2H), 3.29-3.12 (m, 2H), 3.07-2.88 (m, 2H), 2.77 (s, 3H), 2.54 (s, 3H), 2.48 (s, 3H), 2.16-1.99 (m, 1H), 1.89-1.80 (m, 1H). | 547.2 |
| 99 | 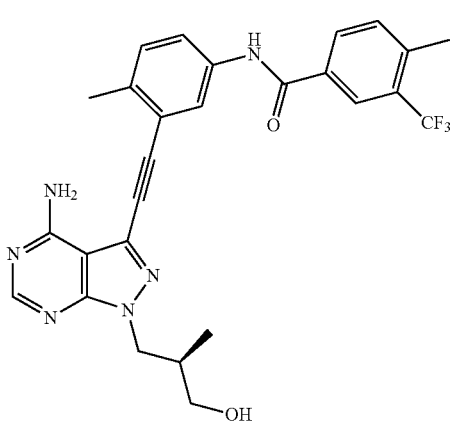 [SMILES: Cc1ccc(NC(=O)c2ccc(C)c(C(F)(F)F)c2)cc1C#Cc1nn(C[C@@H](C)CO)c2ncnc(N)c12] | ¹H NMR (400 MHz, DMSO-d$_6$) δ 10.48 (s, 1H), 8.27 (s, 2H), 8.18 (d, J = 7.9 Hz, 1H), 8.08 (d, J = 2.2 Hz, 1H), 7.75 (dd, J = 8.3, 2.2 Hz, 1H), 7.64 (d, J = 8.0 Hz, 1H), 7.36 (d, J = 8.5 Hz, 1H), 4.68 (s, 1H), 4.36 (dd, J = 13.7, 6.1 Hz, 1H), 4.18 (dd, J = 13.7, 8.1 Hz, 1H), 3.34 (s, 2H), 2.54 (s, 3H), 2.48 (s, 3H), 2.28-2.20 (m, 1H), 0.79 (d, J = 6.8 Hz, 3H). | 523.2 |
| 100 | 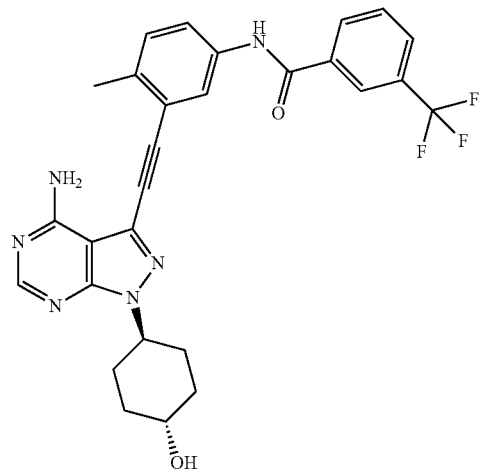 [SMILES: Cc1ccc(NC(=O)c2cccc(C(F)(F)F)c2)cc1C#Cc1nn([C@H]2CC[C@H](O)CC2)c2ncnc(N)c12] | ¹H NMR (400 MHz, DMSO-d$_6$) δ 10.55 (s, 1H), 8.32-8.26 (M, 3H), 8.08 (s, 1H), 7.99 (d, J = 7.6 Hz, 1H), 7.80 (t, J = 7.8 Hz, 1H), 7.75 (d, J = 8.2 Hz, 1H), 7.36 (d, J = 8.4 Hz, 1H), 4.73 (d, J = 4.0 Hz, 1H), 4.64 (t, J = 11.1 Hz, 1H), 3.61-3.47 (m, 1H), 2.47 (s, 3H), 2.09-1.83 (m, 6H), 1.49-1.31 (m, 2H). | 535.2 |

| Compound | Structure | ¹H-NMR | ESI⁺ [M + H] |
|---|---|---|---|
| 101 | 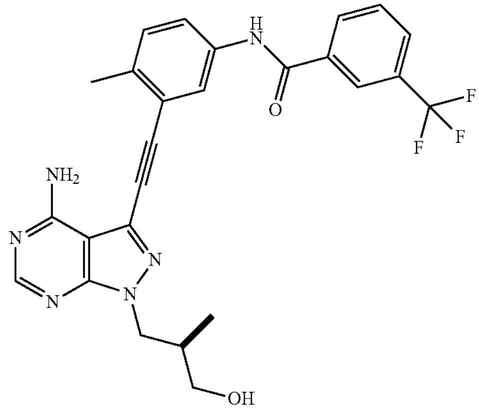 [SMILES: Cc1ccc(NC(=O)c2cccc(C(F)(F)F)c2)cc1C#Cc1nn(C[C@@H](C)CO)c2ncnc(N)c12] | ¹H NMR (400 MHz, DMSO-d₆) δ 10.55 (s, 1H), 8.32 (s, 1H), 8.29 (s, 1H), 8.27 (s, 1H), 8.08 (d, J = 2.2 Hz, 1H), 7.99 (d, J = 7.8 Hz, 1H), 7.81 (t, J = 7.8 Hz, 1H), 7.76 (dd, J = 8.3, 2.2 Hz, 1H), 7.37 (d, J = 8.5 Hz, 1H), 4.67 (s, 1H), 4.36 (dd, J = 13.7, 6.1 Hz, 1H), 4.18 (dd, J = 13.7, 8.1 Hz, 1H), 3.34 (s, 2H), 2.48 (s, 3H), 2.28-2.20 (m, 1H), 0.79 (d, J = 6.8 Hz, 3H). | 509.2 |
| 102 | 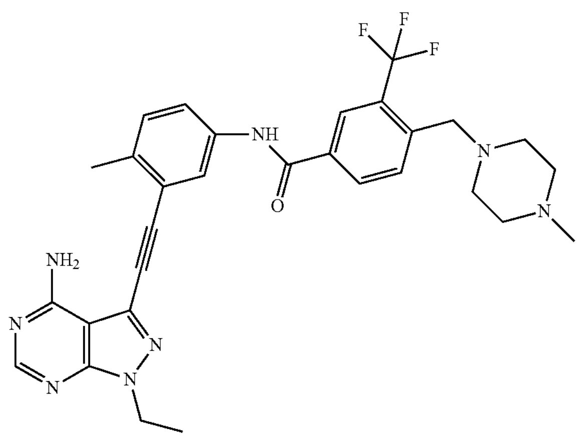 [SMILES: CCn1nc(C#Cc2cc(NC(=O)c3ccc(CN4CCN(C)CC4)c(C(F)(F)F)c3)ccc2C)c2c(N)ncnc21] | ¹H NMR (400 MHz, DMSO-d₆) δ 10.52 (s, 1H), 8.27 (s, 2H), 8.24 (d, J = 8.1 Hz, 1H), 8.06 (d, J = 2.1 Hz, 1H), 7.94 (d, J = 8.1 Hz, 1H), 7.74 (dd, J = 8.3, 2.1 Hz, 1H), 7.36 (d, J = 8.4 Hz, 1H), 4.37 (q, J = 7.2 Hz, 2H), 3.69 (s, 2H), 2.47 (s, 3H), 2.46-2.25 (m, 8H), 2.17 (s, 3H), 1.41 (t, J = 7.2 Hz, 3H). | 577.3 |
| 103 | 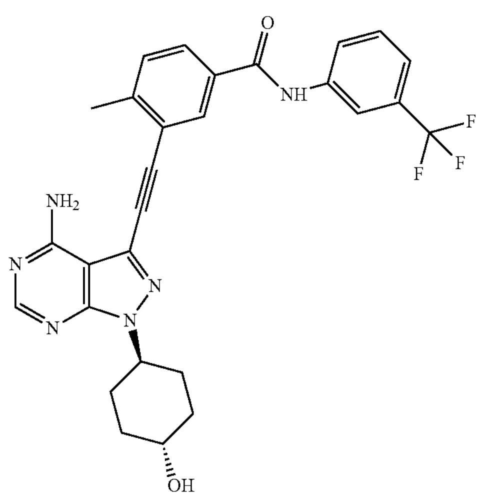 [SMILES: Cc1ccc(C(=O)Nc2cccc(C(F)(F)F)c2)cc1C#Cc1nn([C@H]2CC[C@H](O)CC2)c2ncnc(N)c12] | ¹H NMR (400 MHz, DMSO-d₆) δ 10.59 (s, 1H), 8.34 (d, J = 1.8 Hz, 1H), 8.26 (s, 2H), 8.09 (d, J = 8.4 Hz, 1H), 7.97 (dd, J = 8.0, 1.8 Hz, 1H), 7.62 (t, J = 8.0 Hz, 1H), 7.55 (d, J = 8.1 Hz, 1H), 7.47 (d, J = 7.8 Hz, 1H), 4.78-4.58 (m, 2H), 3.62-3.49 (m, 1H), 2.58 (s, 3H), 2.08-1.85 (m, 6H), 1.50-1.31 (m, 2H). | 535.2 |

-continued

| Compound | Structure | ¹H-NMR | ESI⁺ [M + H] |
|---|---|---|---|
| 104 | 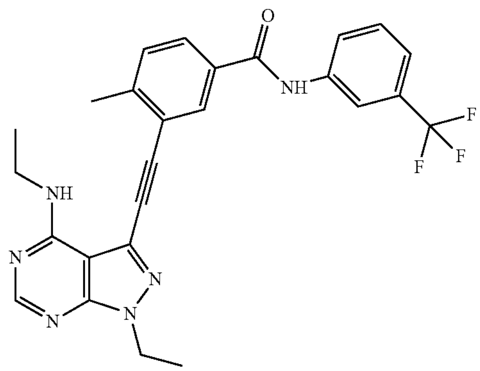 [SMILES: CCNc1ncnc2c1c(C#Cc1cc(C(=O)Nc3cccc(C(F)(F)F)c3)ccc1C)nn2CC] | ¹H NMR (400 MHz, DMSO-d₆) δ 10.60 (s, 1H), 8.34 (s, 1H), 8.32 (d, J = 1.7 Hz, 1H), 8.27 (s, 1H), 8.09 (d, J = 8.4 Hz, 1H), 7.99 (dd, J = 8.0, 1.9 Hz, 1H), 7.62 (t, J = 8.0 Hz, 1H), 7.57 (d, J = 8.1 Hz, 1H), 7.47 (d, J = 7.8 Hz, 1H), 6.99 (s, 1H), 4.38 (q, J = 7.2 Hz, 2H), 3.69-3.56 (m, 2H), 2.61 (s, 3H), 1.42 (t, J = 7.2 Hz, 3H), 1.24 (t, J = 7.1 Hz, 3H). | 493.2 |
| 105 | 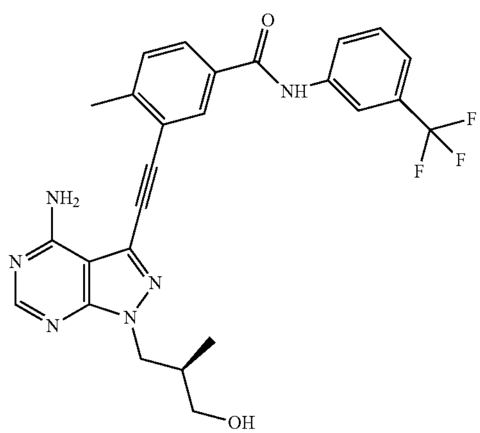 [SMILES: Cc1ccc(C(=O)Nc2cccc(C(F)(F)F)c2)cc1C#Cc1nn(C[C@@H](C)CO)c2ncnc(N)c12] | ¹H NMR (400 MHz, DMSO-d₆) δ 10.60 (s, 1H), 8.35 (d, J = 1.8 Hz, 1H), 8.27 (s, 1H), 8.26 (s, 1H), 8.09 (d, J = 8.5 Hz, 1H), 7.97 (dd, J = 8.0, 1.8 Hz, 1H), 7.62 (t, J = 8.0 Hz, 1H), 7.55 (d, J = 8.1 Hz, 1H), 7.47 (d, J = 7.8 Hz, 1H), 4.68 (s, 1H), 4.37 (dd, J = 13.7, 6.1 Hz, 1H), 4.19 (dd, J = 13.7, 8.2 Hz, 1H), 3.42-3.34 (m, 2H), 2.59 (s, 3H), 2.28-2.20 (m, 1H), 0.79 (d, J = 6.8 Hz, 3H). | 509.2 |
| 106 | 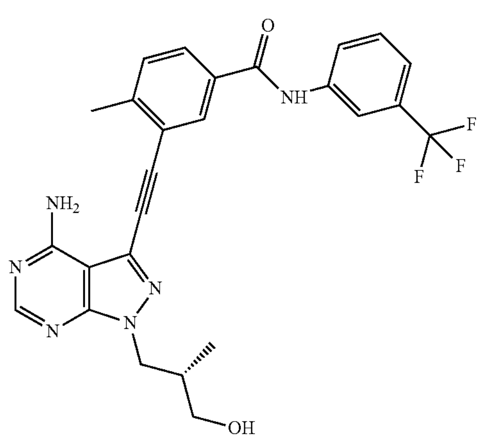 [SMILES: Cc1ccc(C(=O)Nc2cccc(C(F)(F)F)c2)cc1C#Cc1nn(C[C@H](C)CO)c2ncnc(N)c12] | ¹H NMR (400 MHz, DMSO-d₆) δ 10.60 (s, 1H), 8.35 (d, J = 1.8 Hz, 1H), 8.27 (s, 1H), 8.26 (s, 1H), 8.09 (d, J = 8.2 Hz, 1H), 7.97 (dd, J = 8.0, 1.8 Hz, 1H), 7.62 (t, J = 8.0 Hz, 1H), 7.55 (d, J = 8.1 Hz, 1H), 7.47 (d, J = 7.8 Hz, 1H), 4.68 (s, 1H), 4.37 (dd, J = 13.7, 6.0 Hz, 1H), 4.19 (dd, J = 13.7, 8.1 Hz, 1H), 3.34 (s, 2H), 2.59 (s, 3H), 2.28-2.20 (m, 1H), 0.79 (d, J = 6.8 Hz, 3H). | 509.2 |

| Compound | Structure | ¹H-NMR | ESI⁺ [M + H] |
|---|---|---|---|
| 107 | 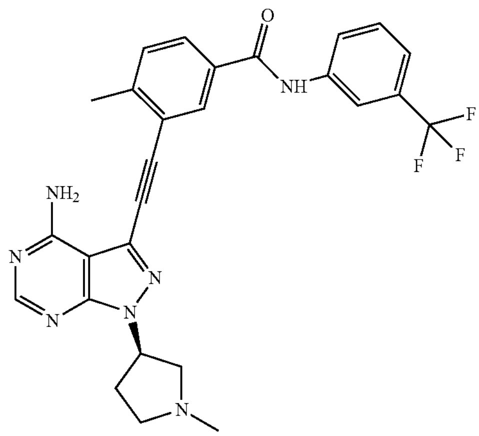 [SMILES: Cc1ccc(C(=O)Nc2cccc(C(F)(F)F)c2)cc1C#Cc1nn([C@@H]2CCN(C)C2)c2ncnc(N)c12] | ¹H NMR (400 MHz, DMSO-d₆) δ 10.60 (s, 1H), 8.35 (d, J = 1.9 Hz, 1H), 8.27 (s, 2H), 8.09 (d, J = 8.2 Hz, 1H), 7.97 (dd, J = 8.0, 1.9 Hz, 1H), 7.62 (t, J = 8.0 Hz, 1H), 7.55 (d, J = 8.1 Hz, 1H), 7.47 (d, J = 7.8 Hz, 1H), 5.43-5.36 (m, 1H), 3.05-2.97 (m, 1H), 2.78-2.63 (m, 3H), 2.59 (s, 3H), 2.41-2.36 (m, 1H), 2.32 (s, 3H), 2.29-2.21 (m, 1H). | 520.2 |
| 108 | 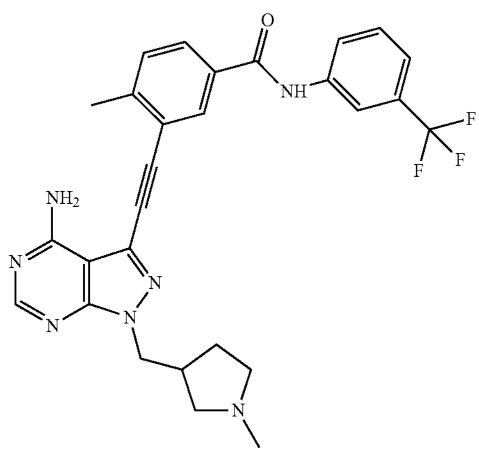 [SMILES: Cc1ccc(C(=O)Nc2cccc(C(F)(F)F)c2)cc1C#Cc1nn(CC2CCN(C)C2)c2ncnc(N)c12] | ¹H NMR (400 MHz, DMSO-d₆) δ 10.61 (s, 1H), 8.35 (d, J = 1.7 Hz, 1H), 8.28 (s, 1H), 8.26 (s, 1H), 8.09 (d, J = 8.1 Hz, 1H), 7.97 (dd, J = 8.0, 1.7 Hz, 1H), 7.62 (t, J = 8.0 Hz, 1H), 7.55 (d, J = 8.1 Hz, 1H), 7.47 (d, J = 7.1 Hz, 1H), 4.30 (d, J = 7.6 Hz, 2H), 2.82-2.68 (m, 1H), 2.59 (s, 3H), 2.55-2.52 (m, 1H), 2.42-2.31 (m, 3H), 2.21 (s, 3H), 1.91-1.75 (m, 1H), 1.57-1.49 (m, 1H). | 534.2 |
| 109 | 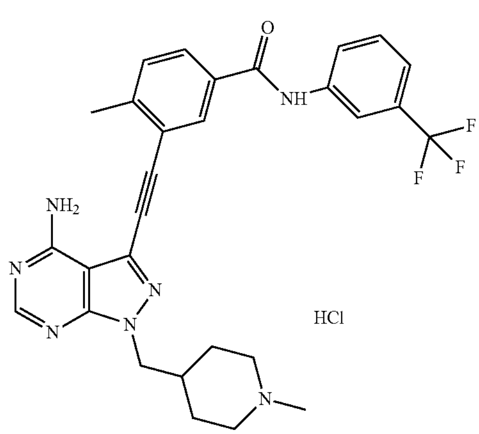 [SMILES: Cc1ccc(C(=O)Nc2cccc(C(F)(F)F)c2)cc1C#Cc1nn(CC2CCN(C)CC2)c2ncnc(N)c12 ; Cl] | ¹H NMR (400 MHz, DMSO-d₆) δ 10.68 (s, 1H), 10.21 (s, 1H), 8.38 (d, J = 1.8 Hz, 1H), 8.28 (s, 2H), 8.12 (d, J = 8.2 Hz, 1H), 8.00 (dd, J = 8.0, 1.8 Hz, 1H), 7.62 (t, J = 8.0 Hz, 1H), 7.55 (d, J = 8.1 Hz, 1H), 7.47 (d, J = 7.8 Hz, 1H), 4.30 (d, J = 6.1 Hz, 2H), 3.29 (s, 2H), 2.85 (s, 2H), 2.66 (s, 3H), 2.58 (s, 3H), 2.20 (s, 1H), 1.69 (d, J = 13.0 Hz, 2H), 1.60-1.52 (m, 2H). | 548.2 |

| Compound | Structure | ¹H-NMR | ESI⁺ [M + H] |
|---|---|---|---|
| 110 | 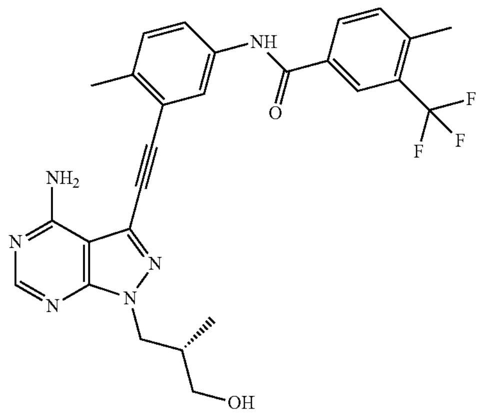 [SMILES: Cc1ccc(NC(=O)c2ccc(C)c(C(F)(F)F)c2)cc1C#Cc1nn(C[C@H](C)CO)c2ncnc(N)c12] | ¹H NMR (400 MHz, DMSO-d₆) δ 10.48 (s, 1H), 8.27 (s, 2H), 8.18 (d, J = 7.9 Hz, 1H), 8.07 (d, J = 2.2 Hz, 1H), 7.75 (dd, J = 8.3, 2.2 Hz, 1H), 7.64 (d, J = 8.0 Hz, 1H), 7.36 (d, J = 8.5 Hz, 1H), 4.67 (t, J = 5.3 Hz, 1H), 4.36 (dd, J = 13.7, 6.0 Hz, 1H), 4.18 (dd, J = 13.7, 8.1 Hz, 1H), 3.35 (d, J = 5.6 Hz, 2H), 2.54 (s, 3H), 2.48 (s, 3H), 2.28-2.20 (m, 1H), 0.79 (d, J = 6.8 Hz, 3H). | 523.2 |
| 111 | 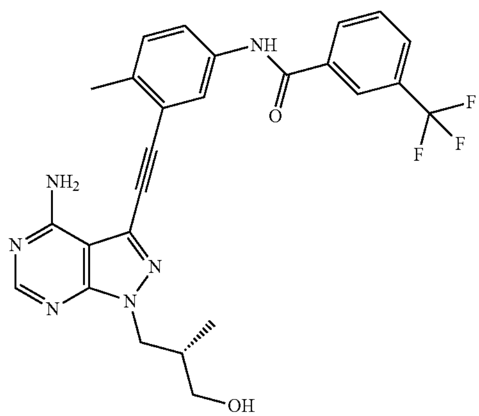 [SMILES: Cc1ccc(NC(=O)c2cccc(C(F)(F)F)c2)cc1C#Cc1nn(C[C@H](C)CO)c2ncnc(N)c12] | ¹H NMR (400 MHz, DMSO-d₆) δ 10.55 (s, 1H), 8.32 (s, 1H), 8.29 (s, 1H), 8.27 (s, 1H), 8.08 (d, J = 2.2 Hz, 1H), 7.99 (d, J = 7.8 Hz, 1H), 7.81 (t, J = 7.8 Hz, 1H), 7.76 (dd, J = 8.3, 2.2 Hz, 1H), 7.37 (d, J = 8.5 Hz, 1H), 4.67 (t, J = 5.3 Hz, 1H), 4.36 (dd, J = 13.7, 6.1 Hz, 1H), 4.18 (dd, J = 13.7, 8.1 Hz, 1H), 3.35 (d, J = 5.6 Hz, 2H), 2.48 (s, 3H), 2.28-2.20 (m, 1H), 0.79 (d, J = 6.8 Hz, 3H). | 509.2 |
| 112 | 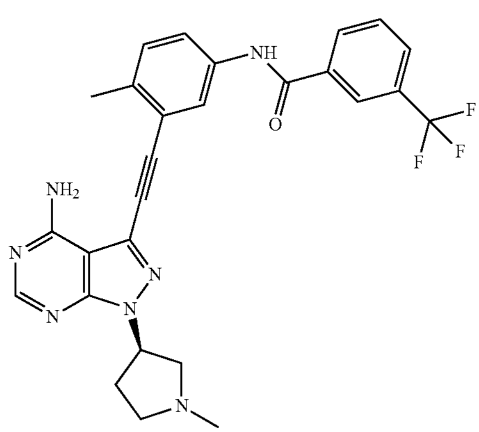 [SMILES: Cc1ccc(NC(=O)c2cccc(C(F)(F)F)c2)cc1C#Cc1nn([C@@H]2CCN(C)C2)c2ncnc(N)c12] | ¹H NMR (400 MHz, DMSO-d₆) δ 10.55 (s, 1H), 8.32 (s, 1H), 8.29 (s, 1H), 8.27 (s, 1H), 8.10 (d, J = 2.2 Hz, 1H), 7.99 (d, J = 7.8 Hz, 1H), 7.81 (t, J = 7.8 Hz, 1H), 7.75 (dd, J = 8.3, 2.2 Hz, 1H), 7.37 (d, J = 8.5 Hz, 1H), 5.47-5.34 (m, 1H), 3.08 (t, J = 8.6 Hz, 1H), 2.85-2.69 (m, 3H), 2.49 (s, 3H), 2.36 (s, 3H), 2.34-2.22 (m, 2H). | 520.2 |

-continued

| Compound | Structure | ¹H-NMR | ESI⁺ [M + H] |
|---|---|---|---|
| 113 | 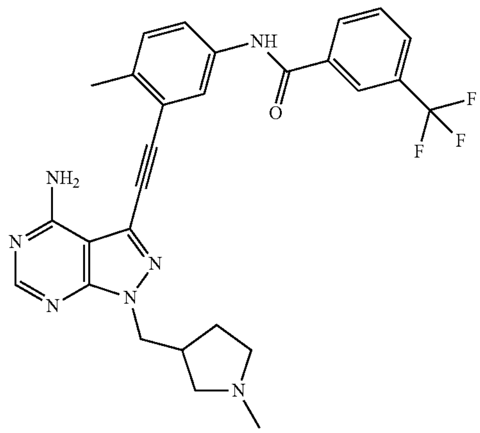 [SMILES: Cc1ccc(NC(=O)c2cccc(C(F)(F)F)c2)cc1C#Cc1nn(CC2CCN(C)C2)c2ncnc(N)c12] | ¹H NMR (400 MHz, DMSO-d₆) δ 10.59 (s, 1H), 8.33 (s, 1H), 8.31 (s, 1H), 8.28 (s, 1H), 8.11 (d, J = 2.2 Hz, 1H), 7.99 (d, J = 7.8 Hz, 1H), 7.81 (t, J = 7.8 Hz, 1H), 7.76 (dd, J = 8.3, 2.2 Hz, 1H), 7.37 (d, J = 8.5 Hz, 1H), 4.44-4.30 (m, 2H), 2.92-2.71 (m, 3H), 2.71-2.58 (m, 2H), 2.48 (s, 3H), 2.42 (s, 3H), 2.00-1.85 (m, 1H), 1.70-1.56 (m, 1H). | 534.2 |
| 114 | 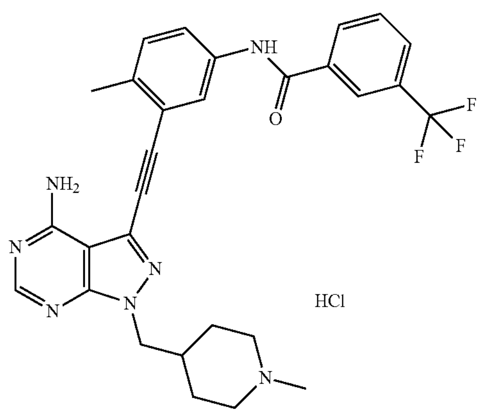 [SMILES: Cc1ccc(NC(=O)c2cccc(C(F)(F)F)c2)cc1C#Cc1nn(CC2CCN(C)CC2)c2ncnc(N)c12 ; Cl] | ¹H NMR (400 MHz, DMSO-d₆) δ 10.63 (s, 1H), 10.13 (s, 1H), 8.33 (s, 1H), 8.31 (d, J = 8.2 Hz, 1H), 8.28 (s, 1H), 8.13 (d, J = 2.2 Hz, 1H), 7.99 (d, J = 7.8 Hz, 1H), 7.81 (t, J = 7.8 Hz, 1H), 7.75 (dd, J = 8.3, 2.2 Hz, 1H), 7.37 (d, J = 8.5 Hz, 1H), 4.30 (s, 2H), 3.32-3.25 (m, 2H), 2.87 (s, 2H), 2.67 (s, 3H), 2.48 (s, 3H), 2.20 (s, 1H), 1.70 (d, J = 12.9 Hz, 2H), 1.60-1.52 (m, 2H). | 548.2 |
| 115 | 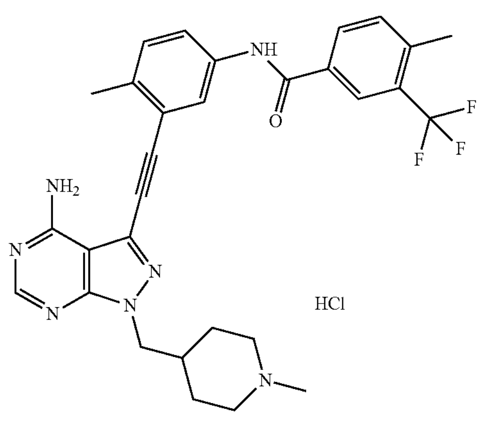 [SMILES: Cc1ccc(NC(=O)c2ccc(C)c(C(F)(F)F)c2)cc1C#Cc1nn(CC2CCN(C)CC2)c2ncnc(N)c12 ; Cl] | ¹H NMR (400 MHz, DMSO-d₆) δ 10.58 (s, 1H), 10.32 (s, 1H), 8.28 (s, 2H), 8.21 (d, J = 8.0 Hz, 1H), 8.12 (d, J = 2.2 Hz, 1H), 7.76 (dd, J = 8.3, 2.2 Hz, 1H), 7.64 (d, J = 8.1 Hz, 1H), 7.36 (d, J = 8.5 Hz, 1H), 4.28 (d, J = 6.1 Hz, 2H), 3.26-3.15 (m, 1H), 2.88 (t, J = 12.2 Hz, 2H), 2.67 (s, 3H), 2.54 (s, 3H), 2.48 (s, 3H), 2.44-2.29 (m, 1H), 2.20 (s, 1H), 1.71-1.53 (m, 4H). | 562.3 |

| Compound | Structure | ¹H-NMR | ESI⁺ [M + H] |
|---|---|---|---|
| 116 | 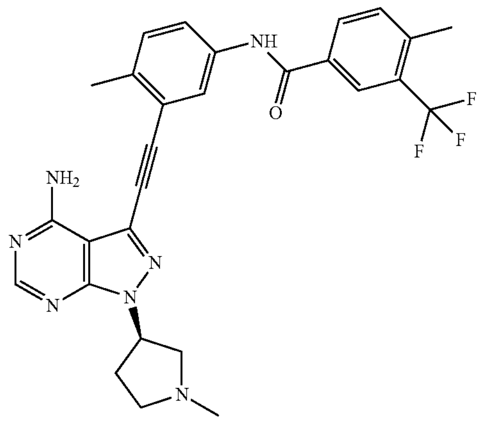 [SMILES: Cc1ccc(NC(=O)c2ccc(C)c(C(F)(F)F)c2)cc1C#Cc1nn([C@@H]2CCN(C)C2)c2ncnc(N)c12] | ¹H NMR (400 MHz, DMSO-d$_6$) δ 10.52 (s, 1H), 8.27 (s, 1H), 8.26 (s, 1H), 8.19 (d, J = 7.9 Hz, 1H), 8.11 (d, J = 2.2 Hz, 1H), 7.74 (dd, J = 8.3, 2.2 Hz, 1H), 7.63 (d, J = 8.0 Hz, 1H), 7.36 (d, J = 8.5 Hz, 1H), 5.50-5.46 (m, 1H), 3.32-3.27 (m, 1H), 3.13-2.90 (m, 3H), 2.53 (s, 6H), 2.48 (s, 3H), 2.46-2.38 (m, 1H), 2.36-2.28 (m, 1H). | 534.2 |
| 117 | 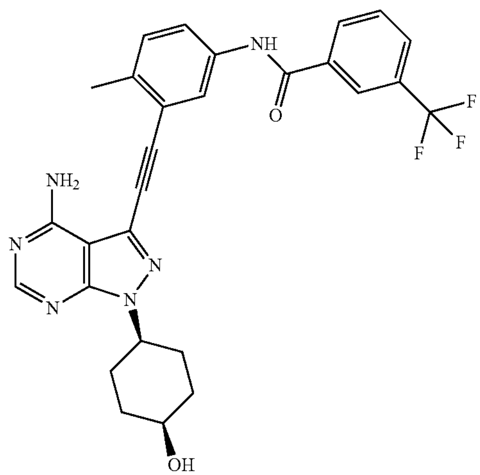 [SMILES: Cc1ccc(NC(=O)c2cccc(C(F)(F)F)c2)cc1C#Cc1nn([C@H]2CC[C@@H](O)CC2)c2ncnc(N)c12] | ¹H NMR (400 MHz, DMSO-d$_6$) δ 10.55 (s, 1H), 8.36-8.22 (m, 3H), 8.08 (d, J = 1.9 Hz, 1H), 7.99 (d, J = 7.7 Hz, 1H), 7.81 (t, J = 7.8 Hz, 1H), 7.76 (dd, J = 8.3, 1.9 Hz, 1H), 7.37 (d, J = 8.4 Hz, 1H), 4.75-4.61 (m, 1H), 4.51 (d, J = 2.5 Hz, 1H), 3.90 (s, 1H), 2.42-2.26 (m, 2H), 1.82 (d, J = 11.7 Hz, 2H), 1.64 (t, J = 12.8 Hz, 4H). | 535.2 |
| 118 | 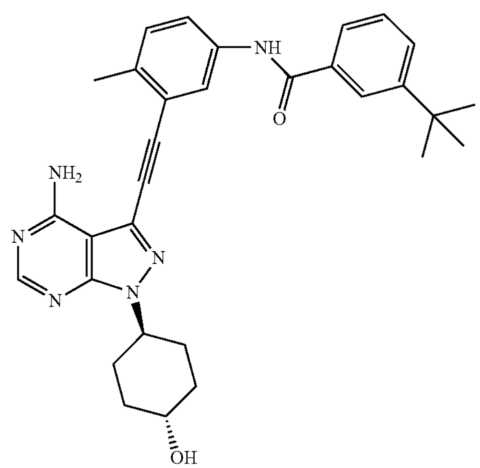 [SMILES: Cc1ccc(NC(=O)c2cccc(C(C)(C)C)c2)cc1C#Cc1nn([C@H]2CC[C@H](O)CC2)c2ncnc(N)c12] | ¹H NMR (400 MHz, DMSO-d$_6$) δ 10.28 (s, 1H), 8.26 (s, 1H), 8.07 (d, J = 2.1 Hz, 1H), 7.95 (s, 1H), 7.79 (d, J = 7.7 Hz, 1H), 7.75 (dd, J = 8.4, 2.1 Hz, 1H), 7.64 (d, J = 7.9 Hz, 1H), 7.47 (t, J = 7.7 Hz, 1H), 7.34 (d, J = 8.5 Hz, 1H), 4.80-4.56 (m, 2H), 3.55 (t, J = 10.4 Hz, 1H), 2.47 (s, 3H), 2.11-1.83 (m, 6H), 1.51-1.37 (m, 2H), 1.35 (s, 9H). | 523.3 |

| Compound | Structure | ¹H-NMR | ESI⁺ [M + H] |
|---|---|---|---|
| 119 | 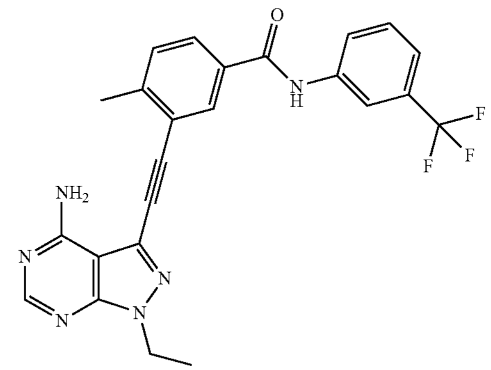 [SMILES: CCn1nc(C#Cc2cc(C(=O)Nc3cccc(C(F)(F)F)c3)ccc2C)c2c(N)ncnc21] | ¹H NMR (400 MHz, DMSO-d₆) δ 10.60 (s, 1H), 8.35 (d, J = 1.7 Hz, 1H), 8.27 (s, 1H), 8.26 (s, 1H), 8.09 (d, J = 8.2 Hz, 1H), 7.97 (dd, J = 8.0, 1.8 Hz, 1H), 7.62 (t, J = 8.0 Hz, 1H), 7.55 (d, J = 8.1 Hz, 1H), 7.47 (d, J = 7.7 Hz, 1H), 4.38 (q, J = 7.2 Hz, 2H), 2.59 (s, 3H), 1.42 (t, J = 7.2 Hz, 3H). | 465.2 |

Example 30

Preparation of 3-(4-amino-1-(piperidin-4-yl)-1H-pyrazolo [3, 4-d] pyrimidin-3-yl) ethynyl)-4-methyl-((4-methylpiperazin-1-yl) methyl)-3-(trifluoromethyl) phenyl) benzamide (Compound 120)

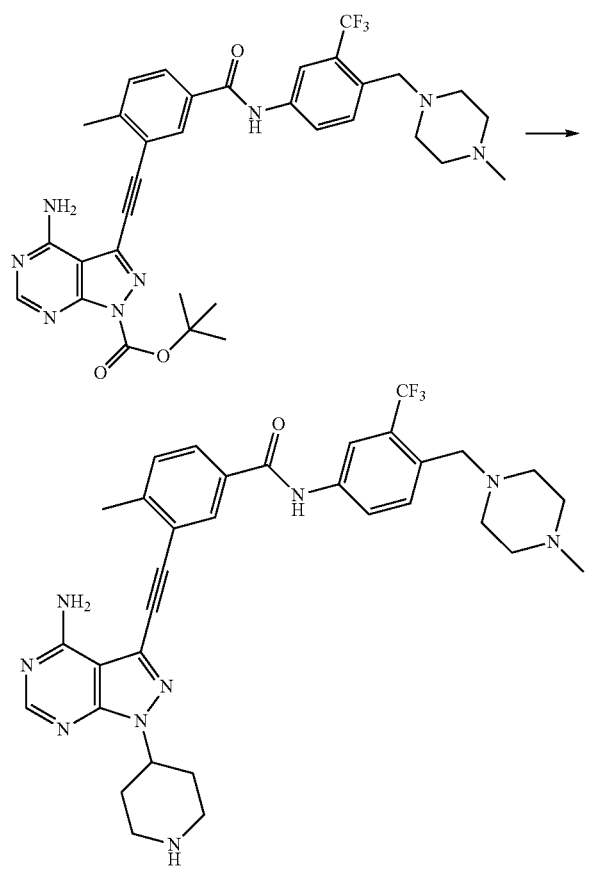

To a solution of N-Tert-butyl-4-(4-amino-3-((2-methyl-5-((4-((4-methylpiperazin-1-yl)methyl)-3-yl) phenyl) carbamoyl) phenyl) ethynyl)-1H-pyrazolo[3,4-d] pyrimidin-1-yl) piperidine-1-carboxylate (1.46 g, 2 mmol) in 20 mL DCM cooled to 0° C., 10 mL trifluoroacetic acid was added. The solution was allowed to warm to room temperature. The reaction was completed after 0.5 h, and the solution was evaporated in vacue. The residue was dissolved in water and the pH was adjusted to 8. Then a large amount of solid was precipitated and the mixture was filtered in vacuum. The cake afforded was washed with water, dried in vacuo to give compound 120 as a light yellow powder (1.2 g, 94.9% yield). ¹H NMR (400 MHz, DMSO-d₆) δ 10.56 (s, 1H), 8.35 (s, 1H), 8.28 (s, 1H), 8.22 (s, 1H), 8.08 (d, J=7.9 Hz, 1H), 7.98 (d, J=7.9 Hz, 1H), 7.72 (d, J=8.2 Hz, 1H), 7.55 (d, J=8.2 Hz, 1H), 5.09-4.98 (m, 1H), 4.36-4.32 (m, 1H), 3.58 (s, 2H), 3.21-3.08 (m, 2H), 2.99 (d, J=7.0 Hz, 2H), 2.58 (s, 3H), 2.42 (br.s, 8H), 2.31 (d, J=11.7 Hz, 2H), 2.22 (s, 3H), 2.12 (d, J=11.6 Hz, 2H). MS m/z (ESI): 632.3071 [M+H].

Example 31

Preparation of 3-((1-(1-acryloyloxy-4-yl)-4-amino-1H-pyrazolo [3,4-d] pyrimidin-3-yl) ethynyl)-4-methyl-N-(4-((4-methylpiperazin-1-yl)methyl)-3-(trifluoromethyl) phenyl) benzamide (Compound 121)

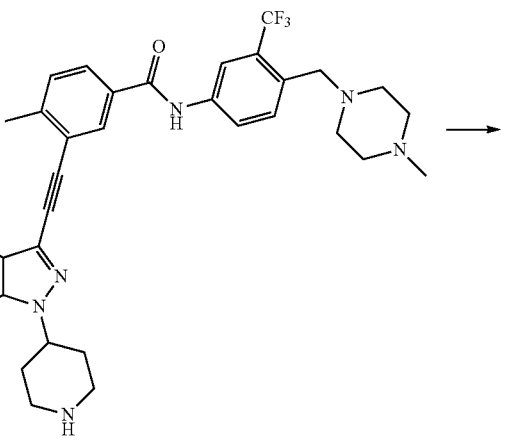

-continued

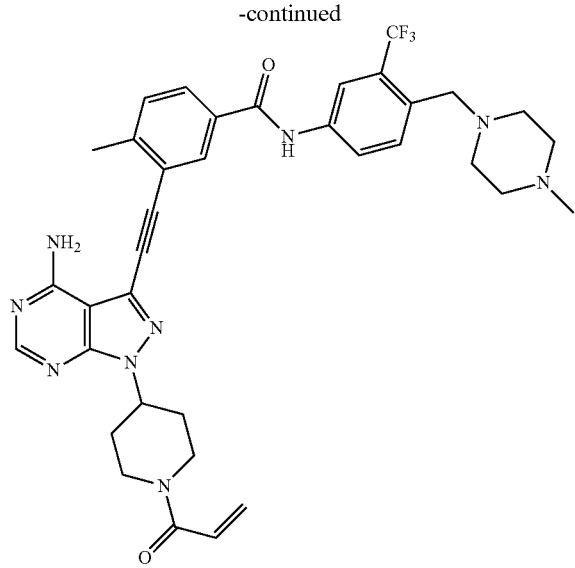

To a solution of (4-amino-1-(piperidin-4-yl)-1H-pyrazolo [3,4-d]pyrimidin-3-yl) ethynyl)-4-methyl-N-(4-((4-methyl-piperazin-1-yl)-3-(trifluoromethyl) phenyl) benzamide (510 mg, 0.807 mmol, 1.0 eq) in 10 mL DCM, triethylamine (72 mg, 0.888 mmol, 1.1 eq) in dichloromethane (4 mL) was slowly dropwise added, and the mixture was cooled to 0° C. To the solution allyl chloride (72 μL, 0.888 mmol, 1.1 eq) in DCM (4 mL) was added slowly. When the reaction was completed. The mixture was washed successively with saturated ammonium chloride aqueous solution, saturated sodium bicarbonate aqueous solution and saturated sodium chloride aqueous solution. The remaining organic layer was dried over anhydrous magnesium sulfate, filtered and evaporated under reduced pressure to afford the residue recrystallized from acetone:ether (1:1) to give compound 121 as a light yellow powder (440.1 mg, yield 72.3%). $^1$H NMR (400 MHz, DMSO-$d_6$) δ 10.54 (s, 1H), 8.33 (s, 1H), 8.27 (s, 1H), 8.21 (s, 1H), 8.06 (d, J=7.7 Hz, 1H), 7.96 (d, J=7.7 Hz, 1H), 7.71 (d, J=7.8 Hz, 1H), 7.54 (d, J=7.8 Hz, 1H), 6.88 (dd, J=17.7, 10.2 Hz, 1H), 6.14 (d, J=17.7 Hz, 1H), 5.71 (d, J=10.2 Hz, 1H), 5.08-4.94 (m, 1H), 4.56 (d, J=10.5 Hz, 1H), 4.21 (d, J=10.9 Hz, 1H), 3.57 (s, 2H), 2.97-2.84 (m, 1H), 2.73-2.62 (m, 1H), 2.57 (s, 3H), 2.39 (br.s, 8H), 2.19 (s, 3H), 2.01 (br.s, 4H). MS m/z (ESI): 686.3181 [M+H].

Example 32 Kinase Inhibition Assays

The aim of this experiment is to detect the inhibitory activity of the compounds of the present invention against in vitro protein kinases using isotope labeling (labeled gamma phosphate groups on ATP). Kinase inhibition profiles were determined using KinaseProfiler services provided by Euro fins, and ATP concentrations used are the Km of corresponding kinases. In this study, we examined Abl (T315I) (h), ALK (h), ARK5 (h), Axl (h), Blk (h), Bmx (h), BTK (h), B-Raf (H), ckit (h), cSRC (h), CDK7, CHK1 (h), c-RAF (h), DDR2 (h), EGFR (h), EphA1 (h), EphA2 (h), EphA8 (h (H), FGF (h), Ft (h), Ft (h), F (h), F (h), Ft (h), Hb (h), ErbB2 (h), FAK (h) (H), JK3β (h), IKKα (h), IKKβ (h), Itk (h), JAK3 (h), JNK1α1 (h), KDR (h), Lyn (h), MAPK1 (h), MEK1 (h (H), PKA (h), PKB [alpha](h), PKB [beta] (h), PKC [alpha] (h), Ret (H), RIPK2 (h), Src (1-530) (h), TAK1 (h), TBK1 (h), Tec (h) activated, Tie2 (h), TrkA (h), ULK3 (h) Yes (h), PI3 Kinase a (h) and other kinase in vitro inhibitory activity.

The kinase inhibitory activity of the test compound is expressed as $IC_{50}$ (half inhibitory concentration) or the inhibitory rate of the test compound at a concentration of 10 μM for kinase activity. $IC_{50}$ values can be obtained by calculating the inhibition rate of the kinase activity by the test compound at a series of different concentrations. The assay was as follows: In a reaction tube, the buffer (8 mM MOPS, pH 7.0, 0.2 mM EDTA, 10 mM MnCl2), the kinase to be tested (5-10 mU), the substrate to be tested kinase, 10 mM acetic acid Magnesium and gamma 33P-ATP solutions, as well as different concentrations of the test compound. MgATP was then added to the reaction to initiate the enzymatic reaction and incubated at room temperature for 40 minutes. The reaction was finally quenched with 5 μl of 3% phosphate buffer and 10 μL of the reaction solution was titrated onto a filtermat A membrane, washed three times with 75 mM phosphate solution for 5 minutes each, and washed again with methanol. Finally, the filtermat A film is dried and scintigraphized, and the size of the scintillation count reflects the degree to which the substrate is phosphorylated, thereby demonstrating that the kinase activity is inhibited. Among them, the percentage of the remaining active protein=the active protein of the experimental group÷the active protein of the control group×100%.

Table 1 shows the $IC_{50}$ values for some of the test compounds for partial kinase inhibitory activity. ("--" in the following tables indicates that no tests have been made.)

TABLE 1

Inhibitory activity of compounds 3, 31, 93, 120 and 121 for various kinases

| Kinase | Compound 3 | Compound 31 | Compound 93 | Compound 120 | Compound 121 |
|---|---|---|---|---|---|
| Abl | <1 | — | 2 | — | — |
| Abl(T315I) | — | — | 3 | — | 133 |
| c-Src(1-530) | <1 | 2 | 3 | — | — |
| c-Src(T341M) | 30 | 3733 | — | — | — |
| B-Raf(V600E) | 15 | 5 | 87 | — | — |
| B-Raf | 92 | 22 | 110 | — | — |
| c-RAF | 27 | 19 | 52 | — | — |
| Yes | <1 | <1 | 1 | <1 | 2 |
| Fyn | 5 | 3 | 6 | — | — |
| Blk | 19 | 12 | 16 | — | — |
| Bcr-Abl | <1 | — | — | — | — |
| KDR | 17 | 12 | 32 | — | — |
| FGFR1 | 3 | — | 7 | — | — |
| FGFR2 | — | — | 40 | — | — |
| EphA2 | 16 | 18 | — | 13 | — |
| EphB2 | 26 | 10 | 33 | — | — |
| EphB4 | 23 | 11 | — | 28 | — |
| ErbB2 | — | 251 | 165 | — | — |
| DDR1 | 9 | 4 | 15 | — | — |
| DDR2 | 128 | 74 | 65 | — | — |
| TAK1 | 61 | 203 | 50 | — | — |
| TrkA | 27 | — | — | 91 | 52 |
| Btk | 67 | 127 | — | — | — |
| Bmx | 6 | 18 | 21 | 11 | 22 |
| IKKα | 353 | — | — | — | — |
| IKKβ | 164 | — | — | — | — |
| Axl | 578 | — | — | — | — |
| PDGFRα | 890 | 396 | — | — | — |
| JAK2 | 2911 | — | — | — | — |
| EGFR | 3518 | — | 651 | — | — |
| Arg | — | — | 4 | — | — |
| BRK | — | — | 121 | — | — |
| CSK | — | — | 9 | — | — |
| EGFR(T790M) | — | — | 19 | — | — |
| EGFR(T790M, L858R) | — | — | 8 | — | — |
| Flt1 | — | — | 15 | — | — |
| Flt4 | — | — | 16 | — | — |

TABLE 1-continued

Inhibitory activity of compounds 3, 31, 93, 120 and 121 for various kinases

| Kinase | Compound 3 | Compound 31 | Compound 93 | Compound 120 | Compound 121 |
|---|---|---|---|---|---|
| Hck | — | — | 3 | — | — |
| Lck | — | — | 14 | — | — |
| LIMK1 | — | — | 255 | — | — |
| Lyn | — | — | 4 | — | — |
| Mer | — | — | 52 | — | — |
| PTK5 | — | — | 19 | — | — |
| Pyk2 | — | — | 116 | — | — |
| Ret | — | — | 4 | — | — |
| SAPK2b | — | — | 84 | — | — |
| Tie2 | — | — | 10 | — | — |
| Txk | — | — | 8 | — | — |

($IC_{50}$: nM)

The results of Table 1 showed that some of the test compounds have a good inhibitory activity against kinases such as Abl, Abl (T315I), C-Src (1-530), c-Src (T341M), B-Raf (V600E), B-Raf, c-RAF, Yes, Fyn, Blk, Bcr-Abl, KDR, FGFR1, FGFR2, EphA2, EphB2 (T790M, L858R), Flt1, Flt4, Hck, Lck, LIMK1, Lyn, Mer, PTK5, EphB4, ErbB2, DDR2, TAK1, TrkA, Btk, Bmx, Arg, BRK, CSK, EGFR (T790M), Pyk2, Ret, SAPK2b, Tie2, and Txk; and have moderate inhibitory activity against partial kinases such as IKKα, IKKβ, Axl, and PDGFRα.

Table 2 shows the $IC_{50}$ values of the partially tested compounds for c-Src (1-530) kinase inhibitory activity.

TABLE 2

Inhibitory activity of partially tested compounds against c-Src kinase

| Compound No. | $IC_{50}$ (nM) |
|---|---|
| 1 | 4 |
| 5 | 2 |
| 6 | 9 |
| 7 | 19 |
| 8 | 7 |
| 9 | 15 |
| 10 | 83 |
| 11 | 10 |
| 12 | 139 |
| 13 | 11 |
| 14 | 3 |
| 16 | 7 |
| 17 | 4 |
| 18 | 4 |
| 19 | 8 |
| 20 | 7 |
| 21 | 7 |
| 24 | 59 |
| 25 | 3191 |
| 26 | 11 |
| 29 | 5 |
| 30 | 20 |
| 120 | 12 |
| 121 | 15 |

($IC_{50}$: nM)

The results in Table 2 show that some of the test compounds have a good inhibitory activity against Src kinase.

Table 3 shows the inhibitory effects of compounds 3, 31, 120 and 121 on Abl (T315I) (h), ALK (h), ARK5 (h), Axl (h), Blk (h), Bmx (h), BTK (h), B-Raf (h), cKit (h), cSRC (h), CDK7, CHK1 (h), c-RAF (h), DDR2 (h), EGFR (h), EphA1 (h), EphA2 (h), EphA8 (h), EphB2 (h), EphB4 (h), ErbB2 (h) (h), FK (h), FK (h), FK (h), FGFR1 (h), Flt3 (h), Fms (h), Fyn (h), Hck (h), GSK3β (h), IKKα(h) (h), MEK1 (h), Met (h), mTOR (h), PAK1 (h), JK1 (h), JNK1α1 (h), KDR (h), Lyn (h) (h), PKK (h), PKA (h), PKBα (h), PKBβ (h), PKCα (h), Ret (h), RIPK2 (h), Src (1-530) (h), TK1 (h), TBK1 (h), Tec (h) activated, Tie2 (h), TrkA (h), ULK3 (h), Yes (h), and PI3KA (h) kinase activity at concentrations of 10 μM (values represent the percentage of residual active protein).

TABLE 3

Compounds 3, 31, 120 and 121 inhibit the partial kinase at a concentration of 10 μM.

The percentage of the remaining active protein (%)

| Kinase | Compound 31 | Compound 3 | Compound 121 | Compound 120 |
|---|---|---|---|---|
| Abl(T315I)(h) | — | — | — | −1 |
| ALK(h) | 33 | 27 | — | — |
| ARK5(h) | 115 | 105 | — | — |
| Axl(h) | 15 | −4 | — | — |
| Blk(h) | −1 | −1 | — | — |
| Bmx(h) | 0 | 0 | — | −1 |
| BTK(h) | −3 | −3 | — | — |
| B-Raf(h) | 1 | 5 | — | — |
| cKit(h) | — | — | 59 | 18 |
| cSRC(h) | — | — | 0 | 0 |
| CDK7 | 70 | 70 | — | — |
| CHK1(h) | 100 | 91 | — | — |
| c-RAF(h) | 2 | 5 | — | — |
| DDR2(h) | — | — | 4 | 3 |
| EGFR(h) | 15 | 30 | — | — |
| EphA1(h) | 1 | 1 | — | — |
| EphA2(h) | — | — | −3 | −4 |
| EphA8(h) | −4 | −5 | — | — |
| EphB2(h) | −1 | 0 | — | — |
| EphB4(h) | — | — | 0 | −1 |
| ErbB2(h) | 2 | 3 | — | — |
| FAK(h) | 26 | 43 | — | — |
| Fer(h) | 92 | 23 | — | — |
| FGFR1(h) | 0 | 1 | −1 | −1 |
| Flt3(h) | — | — | — | 0 |
| Fms(h) | 1 | 0 | — | — |
| Fyn(h) | −1 | 0 | −1 | 1 |
| Hck(h) | — | — | 1 | −2 |
| GSK3β(h) | 99 | 130 | — | — |
| IKKα(h) | 14 | 2 | — | — |
| IKKβ(h) | 42 | 1 | — | — |
| Itk(h) | 92 | 5 | — | — |
| JAK3(h) | 29 | −1 | — | — |
| JNK1α1(h) | 36 | 66 | — | — |
| KDR(h) | 3 | 2 | — | — |
| Lyn(h) | 0 | 0 | 2 | −2 |
| MAPK1(h) | 66 | 99 | — | — |
| MEK1(h) | 52 | 73 | — | — |
| Met(h) | 102 | 24 | — | 81 |
| mTOR(h) | 81 | 96 | — | 96 |
| PAK1(h) | 36 | 57 | — | — |
| PDGFRα(h) | 3 | 5 | — | — |
| Pim-1(h) | 34 | 46 | — | — |
| PKA(h) | 58 | 17 | — | — |
| PKBα(h) | 56 | 73 | — | — |
| PKBβ(h) | 14 | 52 | — | — |
| PKCα(h) | 92 | 101 | — | — |
| Ret(h) | — | — | −2 | −16 |
| RIPK2(h) | 15 | 3 | — | — |
| Src(1-530)(h) | 0 | −1 | — | — |
| TAK1(h) | 2 | 1 | — | — |
| TBK1(h) | 83 | 75 | — | — |
| Tec(h) activated | 13 | 4 | — | — |
| Tie2 (h) | 3 | 3 | — | — |
| TrkA(h) | 14 | −2 | — | 0 |
| ULK3(h) | — | — | — | 1 |
| Yes(h) | 0 | 0 | — | 0 |
| PI3 Kinase a(h) | 98 | 93 | — | — |

("—" in the following tables indicates that no tests have been made.)

The results in Table 3 show that some of the test compounds have a good inhibitory activity against Abl (T315I), Axl, Blk, Bmx, BTK, B-Raf, cSRC, c-RAF, DDR2, EphA1, EphA2, EphA8, EphB2, ErbB4, FGFR1, Flt3, Fms, Fyn, Hck, IKKα, IKKβ, Itk, JAK3, KDR, Lyn, PDGFRα, Ret, RIPK2, Src (1-530), TAK1, Tec, Tie2, TrkA, ULK3, and Yes. Some of the test compounds have moderate inhibitory activity against ALK, cKit, EGFR, FAK, Fer, JNK1α1, PKA, and PKBβ.

Table 4 shows the inhibitory rate of compound 93 and compound 100 at the concentration of 10 μM for the kinase activity of Abl, ACK1, ALK, respectively (values represent the percentage of residual active protein).

TABLE 4

The inhibitory rate of Compound 93 and Compound 100 on partial kinases at 10 μM concentration.

| Kinase | Compound 93 | Compound 100 | Kinase | Compound 93 | Compound 100 |
|---|---|---|---|---|---|
| Abl(h) | −3 | — | MEK1(h) | 34 | 72 |
| Abl(m) | −2 | — | MARK1(h) | 94 | — |
| Abl (H396P)(h) | 1 | — | MELK(h) | 23 | 30 |
| Abl (M351T)(h) | 0 | — | Mer(h) | 0 | — |
| Abl (Q252H)(h) | 2 | — | Met(h) | 133 | — |
| Abl(T315I)(h) | 1 | — | Met(D1246H)(h) | 124 | — |
| Abl(Y253F)(h) | 0 | — | Met(D1246N)(h) | 103 | — |
| ACK1(h) | 4 | 8 | Met(M1268T)(h) | 136 | — |
| ALK(h) | 92 | — | Met(Y1248C)(h) | 139 | — |
| ALK1(h) | 71 | — | Met(Y1248D)(h) | 105 | — |
| ALK2(h) | 77 | — | Met(Y1248H)(h) | 123 | — |
| ALK4(h) | 79 | — | MINK(h) | 25 | — |
| ALK6(h) | 18 | — | MKK4(m) | 49 | — |
| Arg(h) | 0 | — | MKK6(h) | 43 | — |
| AMPKα1(h) | 109 | 112 | MKK7β(h) | 70 | — |
| AMPKα2(h) | 90 | — | MLCK(h) | 62 | 100 |
| A-Raf(h) | 7 | — | MLK1(h) | 7 | 10 |
| Arg(m) | −1 | — | Mnk2(h) | 96 | 84 |
| ARK5(h) | 108 | 115 | MRCKα(h) | 101 | 101 |
| ASK1(h) | 127 | 105 | MRCKβ(h) | 87 | — |
| Aurora-A(h) | 64 | — | MSK1(h) | 95 | 99 |
| Aurora-B(h) | 475 | — | MSK2(h) | 70 | — |
| Aurora-C(h) | 101 | — | MSSK1(h) | 56 | 68 |
| Axl(h) | 56 | — | MST1(h) | 109 | 95 |
| Blk(h) | 0 | — | MST2(h) | 63 | — |
| Blk(m) | 1 | — | MST3(h) | 114 | — |
| Bmx(h) | −1 | — | MST4(h) | 73 | — |
| BRK(h) | −1 | 46 | mTOR(h) | 101 | — |
| BrSK1(h) | 116 | 105 | mTOR/FKBP12(h) | 119 | — |
| BrSK2(h) | 93 | — | MuSK(h) | 70 | 65 |
| BTK(h) | 10 | — | NEK2(h) | 117 | — |
| BTK(R28H)(h) | 71 | — | NEK3(h) | 102 | — |
| B-Raf(h) | 7 | — | NEK6(h) | 98 | — |
| B-Raf(V599E)(h) | 14 | — | NEK7(h) | 98 | — |
| CaMKI(h) | 62 | 91 | NEK9(h) | 59 | — |
| CaMKIIβ(h) | 85 | — | NIM1(h) | 131 | — |
| CaMKIIγ(h) | 90 | — | NEK11(h) | 50 | 76 |
| CaMKIδ(h) | 92 | — | NLK(h) | 82 | 63 |
| CaMKIIδ(h) | 89 | — | p70S6K(h) | 33 | 30 |
| CaMKIV(h) | 93 | — | PAK1(h) | 87 | 89 |
| CaMKK2(h) | 55 | 90 | PAK2(h) | 68 | — |
| CDK1/cyclinB(h) | 104 | — | PAK4(h) | 88 | — |
| CDK2/cyclinA(h) | 100 | — | PAK5(h) | 89 | — |
| CDK2/cyclinE(h) | 102 | — | PAK6(h) | 92 | — |
| CDK3/cyclinE(h) | 93 | — | PAR-1Bα(h) | 98 | 103 |
| CDK4/cyclinD3(h) | 86 | — | PASK(h) | 113 | 109 |
| CDK5/p25(h) | 87 | — | PEK(h) | 39 | 46 |
| CDK5/p35(h) | 127 | — | PDGFRα(h) | 60 | — |
| CDK6/cyclinD3(h) | 120 | — | PDGFRα(D842V)(h) | 0 | — |
| CDK7/cyclinH/MAT1(h) | 103 | — | PDGFRα(V561D)(h) | 0 | — |
| CDK9/cyclin T1(h) | 113 | — | PDGFRβ(h) | 87 | — |
| CHK1(h) | 114 | 112 | PDK1(h) | 113 | 111 |
| CHK2(h) | 111 | — | PhKγ2(h) | 113 | 117 |
| CHK2(I157T)(h) | 103 | — | Pim-1(h) | 99 | 94 |
| CHK2(R145W)(h) | 102 | — | Pim-2(h) | 112 | — |
| CK1γ1(h) | 83 | — | Pim-3(h) | 99 | — |
| CK1γ2(h) | 114 | — | PKA(h) | 60 | 49 |
| CK1γ3(h) | 103 | — | PKBα(h) | 101 | — |
| CK1δ(h) | 88 | — | PKBβ(h) | 127 | — |
| CK1(y) | 86 | — | PKBγ(h) | 94 | — |
| CK2(h) | 105 | — | PKCα(h) | 110 | 98 |
| CK2α2(h) | 92 | — | PKCβI(h) | 100 | 94 |
| CLK1(h) | 64 | 67 | PKCβII(h) | 99 | — |

TABLE 4-continued

The inhibitory rate of Compound 93 and Compound 100 on partial kinases at 10 μM concentration.

The percentage of the remaining active protein (%)

| Kinase | Compound 93 | Compound 100 | Kinase | Compound 93 | Compound 100 |
|---|---|---|---|---|---|
| CLK2(h) | 47 | — | PKCγ(h) | 90 | — |
| CLK3(h) | 83 | — | PKCδ(h) | 96 | — |
| CLK4(h) | 58 | — | PKCε(h) | 117 | — |
| cKit(h) | 89 | — | PKCη(h) | 72 | — |
| cKit(D816V)(h) | 9 | — | PKCι(h) | 91 | — |
| cKit(D816H)(h) | 1 | — | PKCμ(h) | 91 | — |
| cKit(V560G)(h) | 0 | — | PKCθ(h) | 103 | — |
| cKit(V654A)(h) | 7 | — | PKCζ(h) | 99 | — |
| CSK(h) | −1 | −4 | PKD2(h) | 108 | 115 |
| c-RAF(h) | 24 | — | PKG1α(h) | 118 | 112 |
| cSRC(h) | 0 | — | PKG1β(h) | 115 | — |
| DAPK1(h) | 97 | 101 | PKR(h) | 75 | — |
| DAPK2(h) | 95 | — | Plk1(h) | 92 | 99 |
| DCAMKL2(h) | 102 | 120 | Plk3(h) | 93 | 95 |
| DCAMKL3(h) | 101 | — | PRAK(h) | 77 | 101 |
| DDR1(h) | −2 | 2 | PRK2(h) | 97 | 134 |
| DDR2(h) | 16 | — | PrKX(h) | 105 | 109 |
| DMPK(h) | 91 | 62 | PTK5(h) | 1 | — |
| DRAK1(h) | 140 | — | Pyk(h) | 5 | — |
| DYRK1A(h) | 95 | — | Ret(h) | 2 | — |
| DYRK1B(h) | 92 | — | Ret (V804L)(h) | 1 | — |
| DYRK2(h) | 107 | — | Ret(V804M)(h) | −2 | — |
| eEF-2K(h) | 121 | 106 | RIPK2(h) | 21 | — |
| EGFR(h) | 11 | — | ROCK-I(h) | 126 | 87 |
| EGFR(L858R)(h) | 21 | — | ROCK-II(h) | 56 | — |
| EGFR(L861Q)(h) | 0 | — | ROCK-II(r) | 85 | — |
| EGFR(T790M)(h) | 4 | — | Ron(h) | 121 | — |
| EGFR(T790M, L858R)(h) | 0 | — | Ros(h) | 82 | — |
| EphA1(h) | 1 | 0 | Rse(h) | 2 | — |
| EphA2(h) | −3 | — | Rsk1(h) | 11 | 60 |
| EphA3(h) | 3 | — | Rsk1(r) | 20 | — |
| EphA4(h) | −2 | — | Rsk2(h) | 44 | — |
| EphA5(h) | −1 | — | Rsk3(h) | 38 | — |
| EphA7(h) | 0 | — | Rsk4(h) | 44 | — |
| EphA8(h) | 2 | — | SAPK2a(h) | 3 | — |
| EphB2(h) | −1 | — | SAPK2a(T106M)(h) | 88 | — |
| EphB1(h) | −1 | −3 | SAPK2b(h) | −2 | — |
| EphB3(h) | 5 | — | SAPK3(h) | 68 | — |
| EphB4(h) | 1 | — | SAPK4(h) | 80 | — |
| ErbB2(h) | 4 | — | SGK(h) | 90 | 111 |
| ErbB4(h) | −3 | — | SGK2(h) | 97 | — |
| FAK(h) | 45 | — | SGK3(h) | 98 | — |
| Fer(h) | 67 | — | SIK(h) | 7 | 17 |
| Fes(h) | 34 | — | Snk(h) | 109 | 100 |
| FGFR1(h) | 1 | — | SNRK(h) | 92 | 97 |
| FGFR1(V561M)(h) | 40 | — | Src(1-530)(h) | 0 | — |
| FGFR2(h) | 0 | — | Src(T341M)(h) | 20 | — |
| FGFR2(N549H)(h) | −1 | — | SRPK1(h) | 106 | 103 |
| FGFR3(h) | 3 | — | SRPK2(h) | 107 | — |
| FGFR4(h) | 33 | — | STK25(h) | 66 | 91 |
| Fgr(h) | 2 | 0 | STK33(h) | 109 | 91 |
| Flt1(h) | 3 | — | Syk(h) | 95 | 112 |
| Flt3(D835Y)(h) | 118 | — | TAK1(h) | 1 | 6 |
| Flt3(h) | 73 | — | TAO1(h) | 18 | 15 |
| Flt4(h) | 1 | — | TAO2(h) | 5 | — |
| Fms(h) | 4 | 0 | TAO3(h) | 2 | — |
| Fms(Y969C)(h) | 13 | — | TBK1(h) | 104 | 106 |
| Fyn(h) | 0 | — | Tec(h) activated | 24 | — |
| GCK(h) | 49 | 29 | TGFBR1(h) | 105 | — |
| GCN2(h) | 50 | — | Tie2 (h) | 1 | — |
| GRK1(h) | 94 | 88 | Tie2(R849W)(h) | 0 | — |
| GRK5(h) | 99 | — | Tie2(Y897S)(h) | 0 | — |
| GRK6(h) | 100 | — | TLK1(h) | 95 | 105 |
| GRK7(h) | 101 | — | TLK2(h) | 93 | — |
| GSK3α(h) | 79 | — | TrkA(h) | 72 | 66 |
| GSK3β(h) | 26 | — | TrkB(h) | 4 | — |
| Haspin(h) | 93 | 106 | TrkC(h) | 17 | — |
| Hck(h) | 0 | −1 | TSSK1(h) | 100 | 97 |
| Hck(h) activated | −1 | — | TSSK2(h) | 96 | — |
| HIPK1(h) | 107 | 114 | Txk(h) | 1 | −1 |
| HIPK2(h) | 99 | — | TYK2(h) | 36 | — |
| HIPK3(h) | 81 | — | ULK2(h) | 100 | 105 |
| IGF-1R(h) | 66 | — | ULK3(h) | 14 | — |

TABLE 4-continued

The inhibitory rate of Compound 93 and Compound 100 on partial kinases at 10 μM concentration.

The percentage of the remaining active protein (%)

| Kinase | Compound 93 | Compound 100 | Kinase | Compound 93 | Compound 100 |
|---|---|---|---|---|---|
| IGF-1R(h), activated | 91 | — | Wee1(h) | 95 | 108 |
| IKKα(h) | 7 | 13 | WNK2(h) | 105 | 99 |
| IKKβ(h) | 33 | — | WNK3(h) | 39 | — |
| IKKε(h) | 94 | — | VRK2(h) | 85 | — |
| IR(h) | 97 | 71 | Yes(h) | 0 | — |
| IR(h), activated | 89 | — | ZAP-70(h) | 121 | — |
| IRE1(h) | 94 | 87 | ZIPK(h) | 110 | 105 |
| IRR(h) | 107 | 85 | ATM(h) | 102 | 87 |
| IRAK1(h) | 30 | 84 | ATR/ATRIP(h) | 94 | — |
| IRAK4(h) | 101 | — | DNA-PK(h) | 94 | 114 |
| Itk(h) | 102 | — | PI3 Kinase (p110b/p85a)(h) | 78 | — |
| JAK1(h) | 3 | 0 | PI3 Kinase (p120g)(h) | 87 | — |
| JAK2(h) | 64 | 7 | PI3 Kinase (p110d/p85a)(h) | 74 | — |
| JAK3(h) | 7 | 7 | PI3 Kinase (p110a/p85a)(m) | 90 | — |
| JNK1α1(h) | 35 | 79 | PI3 Kinase (p110a/p65a)(m) | 94 | — |
| JNK2α2(h) | 13 | 12 | PI3 Kinase (p110a(E545K)/p85a)(m) | 87 | — |
| JNK3(h) | 40 | 26 | PI3 Kinase (p110a(H1047R)/p85a)(m) | 94 | — |
| KDR(h) | 2 | 5 | PI3 Kinase (p110b/p85b)(m) | 93 | — |
| Lck(h) | 0 | 0 | PI3 Kinase (p110b/p85a)(m) | 84 | — |
| Lck(h) activated | 0 | — | PI3 Kinase (p110d/p85a)(m) | 78 | — |
| LIMK1(h) | 5 | 20 | PI3 Kinase (p110a(E542K)/p85a)(m) | 92 | — |
| LKB1(h) | 94 | 106 | PI3 Kinase (p110a/p85a)(h) | 79 | — |
| LOK(h) | 16 | 5 | PI3 Kinase (p110a(E542K)/p85a)(h) | 85 | 93 |
| Lyn(h) | 0 | 1 | PI3 Kinase (p110a(H1047R)/p85a)(h) | 89 | — |
| Lyn(m) | −1 | — | PI3 Kinase (p110a(E545K)/p85a)(h) | 92 | — |
| LRRK2(h) | 15 | 49 | PI3 Kinase (p110a/p65a)(h) | 92 | — |
| LTK(h) | 73 | — | PI3KC2a(h) | 92 | — |
| MAPK1(h) | 87 | 93 | PI3KC2g(h) | 98 | — |
| MAPK2(h) | 108 | — | PIP4K2a(h) | 100 | 101 |
| MAPK2(m) | 101 | — | PIP5K1a(h) | 102 | 99 |
| MAPKAP-K2(h) | 104 | 107 | PIP5K1g(h) | 98 | 91 |
| MAPKAP-K3(h) | 96 | — | | | |

("—" in the following tables indicates that no tests have been made.)

Table 4 shows that some of the test compounds have a good inhibitory activity against Abl, Abl (T315I), Arg, Blk, Bmx, BRK, cKit (D816H), cKit (V560G), CSK, cSRC, DDR1, EGFR (T790M), EGFR (T790M, L858R), EphA1, EphA2, EphA3, EphA4, EphA5 EphA7, EphA2, EphB1, EphB3, EphB4, ErbB2, ErbB4, FGFR1, FGFR2, FGFR3, Fgr, Flt1, Flt4, Fms, Fyn, Hck, JAK1, KDR, Lck, LIMK1, Lyn, Mer, PDGFRα (D842V), PDGFRα (V561D), PTK5, Pyk2, Ret, Rse, SAPK2a, SAPK2b, Src, TAK1, TAO2, TAO3, Tie2, TrkB, Txk, and Yes.

Example 33 Cell Proliferation Inhibition Assay

The purpose of this experiment is to detect the inhibitory activity of the compounds of the present invention on the proliferation of human tumor cells in vitro, using MTT (tetramethylazo salt) colorimetric method.

1) Materials:

Reagents: RPMI-1640, fetal bovine serum, trypsin were purchased from Gibco BRL Company (Invitrogen Corporation, USA), DMEM were purchased from ATCC (American Type Culture Collection). Tetramethylthiazole salt (MTT), dimethyl sulfoxide (DMSO) is a product of Sigma (USA). Compound 3, Compound 31, Compound 93, Compound 100 were synthesized by inventor, each compound in vitro experiments used was formulated with 100% DMSO in 10 mM stock solution and stored at −20° C. in the dark to keep it in place and diluted with the complete culture medium to the desired concentration.

Cell lines and culture: The human breast cancer cell lines MDA-MB-231, MCF-7, SKBR-3, BT474, MDA-MB-468, MDA-MB-453, MDA-MB-435, large B-cell lymphoma cell lines OCI-LY10, HBL-1, human pancreatic cancer cell lines Panc-1, Miapaca-2, human lung cancer cell lines A549, H358, H1975, human leukemia cell line THP-1, human hepatoma cell line HepG2, human melanoma cell line A2058 and so on are purchased in the United States ATCC (American type culture collection), saved by our laboratory. Above all human lymphoma cell lines, large B cell lymphoma cell lines, T cell lymphoma cell lines were cultured in RPMI-1640 complete medium containing 10% fetal bovine serum, 100 U/mL penicillin, 100 μg/mL streptomycin at 37° C. in a humidified 5% $CO_2$ incubator. The remaining cell lines were cultured in DMEM complete medium containing 10% fetal bovine serum (MV4-11 cells 20%), 100 U/ml penicillin, 100 μg/mL streptomycin at 5% $CO_2$, and 37° C.

2) Method:

The cells were seeded in 96-well plates with 200 μL of cell suspension per well and incubated overnight in a cell culture medium with a cell concentration of $1\sim2\times10^4$ cells/mL. The next day, the supernatant was discarded (the suspension cell was centrifuged before it) and the cells were treated with gradient concentrations of the test compound, respectively. At the same time, the drug-free negative control group and the equal volume of solvent control group, DMSO concentration of 0.1%, each dose group set up three wells, 37° C., 5% $CO_2$ conditions. After 72 hours, add 20 μL of MTT reagent at a concentration of 5 mg/mL per well. After incubation for 2-4 h, the supernatant was discarded and 150 μL of DMSO was added to each well. The mixture was shaken for 15 min. Determine the absorbance (A) value ($\lambda$=570 nm, A value is proportional to the number of living cells), whichever is the average. Relative cell proliferation inhibition rate=$(A570_{Control} - A570_{treatment}) \times 100\% / A570_{Control}$. The experiment was repeated at least 3 times. Experimental data were expressed as mean, data statistics using t test, P<0.05 for the difference was statistically significant. The inhibitory effects of the following compounds on cell proliferation were expressed as $IC_{50}$ or inhibition rates.

3) Result:

The proliferation inhibitory activity of human breast cancer cell lines MDA-MB-231, MCF-7, SKBR-3, BT474, MDA-MB-468, MDA-MB-453, MDA-MB-435, large B-cell lymphoma cell lines OCI-LY-10, HBL-1, human pancreatic cancer cell lines Panc-1, Miapaca-2, human lung cancer cell line A549, H358, human leukemia cell line THP-1, human hepatoma cell line HepG2, and human melanoma cell line A2058 were tested by the above method. The results are shown in Table 5.

TABLE 5

Proliferation inhibitory activities of compound 3 and compound 31 against various cell lines.

| Cell lines | Compound 3 | Compound 31 |
|---|---|---|
| HBL-1 | ~10 | — |
| OCI-LY10 | 2.168 | — |
| RAMOS | ~10 | — |
| MV4-11 | 0.020 | — |
| THP-1 | 5.11 | 7.378 |
| PANC-1 | 6.556 | — |
| Miapaca-2 | 0.01277 | 0.04036 |
| CFPAC | 0.607 | 0.4721 |
| H4 | — | 1.807 |
| U87 | 0.742 | 5.420 |
| A2058 | 1.908 | — |
| H358 | 1.665 | — |
| A549 | 0.1988 | 1.423 |
| HepG2 | 8.672 | 6.167 |
| plc/prf/5 | — | 3.974 |
| Hela | 5.41 | 7.23 |
| PC-3 | — | 3.974 |
| MDA-MB-231 | 0.0113 | 0.01533 |
| MDA-MB-435 | 0.008654 | 0.0147 |
| MDA-MB-453 | 3.369 | — |
| MDA-MB-468 | 4.478 | 3.216 |
| BT474 | >10 | >10 |
| MCF-7 | — | 1.987 |
| SKBR-3 | 4.523 | 1.265 |
| MM.1S | 0.872 | 2.383 |
| HCT116 | 0.178 | 0.2303 |
| HT29 | 0.1663 | 0.3496 |
| SW1990 | 0.3559 | 0.2061 |
| A375 | 0.02088 | 0.02657 |

($IC_{50}$: μM).
("—" in the following tables indicates that no tests have been made.)

Table 5 shows that compound 3 and compound 31 have a good inhibitory activity against MV4-11, Miapaca-2, MDA-MB-231, MDA-MB-435 and A375 cell lines; compound 3 and compound 31 have moderate inhibitory activity against other tumor cell lines like CFPAC, U87, MM.1S, HCT116, HT29 and A549.

TABLE 6

Proliferation inhibitory activities of compound 93 and compound 100 against various cell lines.

| Cell lines | Compound 93 | Compound 100 |
|---|---|---|
| RAMOS | ~10 | — |
| MV4-11 | 0.1379 | 0.079 |
| PANC-1 | 1.7-5 | |
| Hela | 6.3 | 4.51 |
| H4 | 0.67 | — |
| U251 | 0.1 | — |
| Miapaca-2 | <0.6 | <0.6 |
| SMMC7721 | >10 | |
| ZR-75-1 | ~10 | ~10 |
| A549 | >10 | >10 |
| HepG2 | ~10 | 7.36 |
| MDA-MB-415 | ~10 | ~10 |
| PC-9 | 0.1-0.3 | — |
| MDA-MB-231 | 0.03 | 0.01 |
| MDA-MB-435 | 0.008 | 0.004 |
| BT474 | >10 | >10 |
| plc/prf/5 | ~10 | ~10 |
| HCT116 | 3.89 | 2.3 |
| HT29 | 0.23 | 0.03 |
| DU145 | >10 | 0.02917 |
| A375 | ~0.03 | ~0.03 |
| H1437 | 2.34 | 1.1 |

($IC_{50}$: μM).
("—" in the following tables indicates that no tests have been made.)

The result in table 6 shows that compound 93 and compound 100 have a good inhibitory activity against MV4-11, Miapaca-2, MDA-MB-231, MDA-MB-435 and A375 cell lines; compound 93 and compound 100 have moderate inhibitory activity against other tumor cell lines like U251, H4, HCT116 and Hela.

The inhibitory activity of some of the tested compounds on MDA-MB-231 and MDA-MB-435 cells was shown in Table 7. The $IC_{50}$<100 nM is represented by the symbol ++++, 100 nM<$IC_{50}$<500 nM is represented by the symbol +++, 500 nM<$IC_{50}$<1000 nM is represented by the symbol ++, $IC_{50}$>1000 nM is represented by the symbol +.

TABLE 7

Proliferative inhibitory activities of test compounds against MDA-MB-231 and MDA-MB-435 cell lines.

| Compounds No. | MDA-MB-231 | MDA-MB-435 |
|---|---|---|
| 1 | +++ | +++ |
| 2 | ++++ | ++++ |
| 3 | ++++ | ++++ |
| 4 | +++ | +++ |
| 5 | ++++ | ++++ |
| 6 | ++++ | ++++ |
| 7 | ++++ | ++++ |
| 8 | ++++ | ++++ |
| 9 | +++ | ++++ |
| 10 | +++ | + |
| 11 | ++ | ++++ |
| 12 | + | + |
| 13 | ++++ | +++ |
| 14 | +++ | + |
| 15 | +++ | +++ |
| 16 | ++++ | ++++ |
| 17 | +++ | + |
| 18 | ++++ | +++ |
| 19 | ++++ | ++++ |
| 20 | ++++ | ++++ |

TABLE 7-continued

Proliferative inhibitory activities of test compounds against MDA-MB-231 and MDA-MB-435 cell lines.

| Compounds No. | MDA-MB-231 | MDA-MB-435 |
|---|---|---|
| 21 | ++++ | ++++ |
| 22 | +++ | + |
| 23 | + | +++ |
| 24 | +++ | + |
| 25 | + | + |
| 26 | ++++ | ++++ |
| 27 | + | + |
| 28 | ++++ | ++++ |
| 29 | ++++ | ++++ |
| 30 | +++ | + |
| 31 | ++++ | ++++ |
| 32 | ++++ | +++ |
| 33 | ++ | +++ |
| 34 | ++ | +++ |
| 35 | ++ | ++++ |
| 36 | ++ | +++ |
| 37 | + | +++ |
| 38 | ++ | +++ |
| 39 | + | ++ |
| 40 | ++++ | ++++ |
| 41 | ++ | + |
| 42 | ++++ | ++++ |
| 43 | + | + |
| 44 | +++ | +++ |
| 45 | ++ | + |
| 46 | ++ | + |
| 47 | ++ | ++ |
| 48 | +++ | +++ |
| 49 | ++++ | ++ |
| 50 | +++ | +++ |
| 51 | ++ | + |
| 52 | ++++ | ++++ |
| 53 | ++++ | +++ |
| 54 | ++++ | ++++ |
| 55 | +++ | +++ |
| 56 | + | + |
| 57 | ++ | + |
| 58 | +++ | ++++ |
| 59 | +++ | +++ |
| 60 | +++ | ++ |
| 61 | +++ | +++ |
| 62 | ++++ | ++++ |
| 63 | +++ | ++++ |
| 64 | +++ | ++++ |
| 65 | ++++ | ++++ |
| 66 | ++++ | ++++ |
| 67 | ++++ | ++++ |
| 68 | +++ | +++ |
| 69 | ++++ | + |
| 70 | ++++ | ++ |
| 71 | ++++ | ++++ |
| 72 | ++++ | + |
| 73 | ++++ | + |
| 74 | ++++ | ++++ |
| 75 | +++ | + |
| 76 | ++++ | +++ |
| 77 | ++ | + |
| 78 | ++++ | ++ |
| 79 | ++++ | ++ |
| 80 | ++++ | + |
| 81 | ++++ | +++ |
| 82 | ++++ | +++ |
| 83 | ++++ | +++ |
| 84 | ++++ | +++ |
| 85 | ++++ | + |
| 86 | ++++ | + |
| 87 | ++++ | + |
| 88 | ++++ | +++ |
| 89 | ++++ | +++ |
| 90 | ++++ | ++ |
| 91 | ++++ | +++ |
| 92 | ++++ | +++ |
| 93 | ++++ | ++++ |
| 94 | +++ | +++ |
| 95 | +++ | ++++ |
| 96 | +++ | +++ |
| 97 | +++ | +++ |
| 98 | ++++ | ++++ |
| 99 | ++++ | +++ |
| 100 | ++++ | ++++ |
| 101 | ++++ | ++++ |
| 102 | ++++ | ++++ |
| 103 | ++++ | ++++ |
| 104 | +++ | +++ |
| 105 | ++++ | +++ |
| 106 | ++++ | ++++ |
| 107 | ++++ | ++++ |
| 108 | ++++ | +++ |
| 109 | ++++ | ++++ |
| 110 | ++++ | ++++ |
| 111 | ++++ | ++++ |
| 112 | ++++ | ++++ |
| 113 | ++++ | ++++ |
| 114 | ++++ | ++++ |
| 115 | ++++ | +++ |
| 116 | +++ | +++ |
| 117 | ++++ | ++++ |
| 118 | ++++ | ++++ |
| 119 | +++ | +++ |
| 120 | ++++ | +++ |
| 121 | ++++ | ++++ |

The result in table 7 shows that some of the test compounds have a good inhibitory activity against MDA-MB-231 and MDA-MB-435 cell lines

Example 34 the In Vivo Pharmacodynamics Experiment of Compound 3, Compound 31, Compound 93 and Compound 100

The aim of this experiment is to detect the in vivo antitumor effect of the compounds in the present invention. The in vivo antitumor activity of the inventive compound 3, the compound 31, the compound 93 and the compound 100 was tested using the nude mouse subcutaneous tumor model. The cell line used was a breast cancer cell line MDA-MB-231. The clinically commonly used anti-breast cancer drug paclitaxel and dasatinib used in breast cancer clinical trials were positive controls.

1) Materials:
Fetal calf serum, trypsin were purchased from Gibco BRL Company (Invitrogen Corporation, USA), DMEM were purchased from ATCC (American Type Culture Collection), human breast cancer cell line MDA-MB-231 was purchased from ATCC, USA Corporation, nude mice were purchased from Beijing Huafukang Biological Technology Co., Ltd. Paclitaxe was purchased from China Shanghai Han Hong Biotechnology Co., Ltd. Dasatinib was purchased from Nanjing Kang Man Lin Chemical Industry Co., Ltd.

2) Methods:
MDA-MB-231 cells were injected into nude mice (6-8 weeks) subcutaneously with a concentration of $5 \times 10^7$ cells/0.1 mL per mouse. When the tumors grew to volumes of 200 mm$^3$, all the mice were randomized into groups (6 mice for each group) and dosed with indicated compounds. Each group of drugs was dissolved in 5% DMSO+25% PEG-400+70% water.

Group 1:
Drug solvent control group, daily oral administration of blank solvent 200 uL;

Compound 3 was administered orally at a dose of 30 mg/kg per day;

Compound 3 was administered orally at a dose of 15 mg/kg per day;

Compound 3 was administered orally at a dose of 7.5 mg/kg per day;

Positive control paclitaxel at a dose 10 mg/kg per week tail vein injection;

The positive control of dasatinib was administered orally at a dose of 40 mg/kg daily.

Group 2:

Compound 31 was administered orally at a dose of 40 mg/kg per day;

Compound 31 was administered orally at a dose of 20 mg/kg per day;

Compound 31 was administered orally at a dose of 10 mg/kg per day;

Positive control paclitaxel at a dose 10 mg/kg per week tail vein injection;

The positive control of dasatinib was administered orally at a dose of 40 mg/kg daily.

Group 3:

Compound 93 was administered orally at a dose of 40 mg/kg per day;

Compound 93 was administered orally at a dose of 20 mg/kg per day;

Compound 93 was administered orally at a dose of 10 mg/kg per day;

Positive control paclitaxel at a dose 10 mg/kg per week tail vein injection;

The positive control of dasatinib was administered orally at a dose of 40 mg/kg daily.

Group 4:

Compound 100 was administered orally at a dose of 40 mg/kg per day;

Compound 100 was administered orally at a dose of 20 mg/kg per day;

Compound 100 was administered orally at a dose of 10 mg/kg per day;

Positive control paclitaxel at a dose 10 mg/kg per week tail vein injection;

The positive control of dasatinib was administered orally at a dose of 40 mg/kg daily.

Observation indexes: mouse body weight and the tumor size were measured once every three days, the tumor volume is calculated (length×width$^2$×0.5). Daily observation of each group of mice with diarrhea, convulsions, rash, weight decreased significantly and other reactions.

Figure 2:
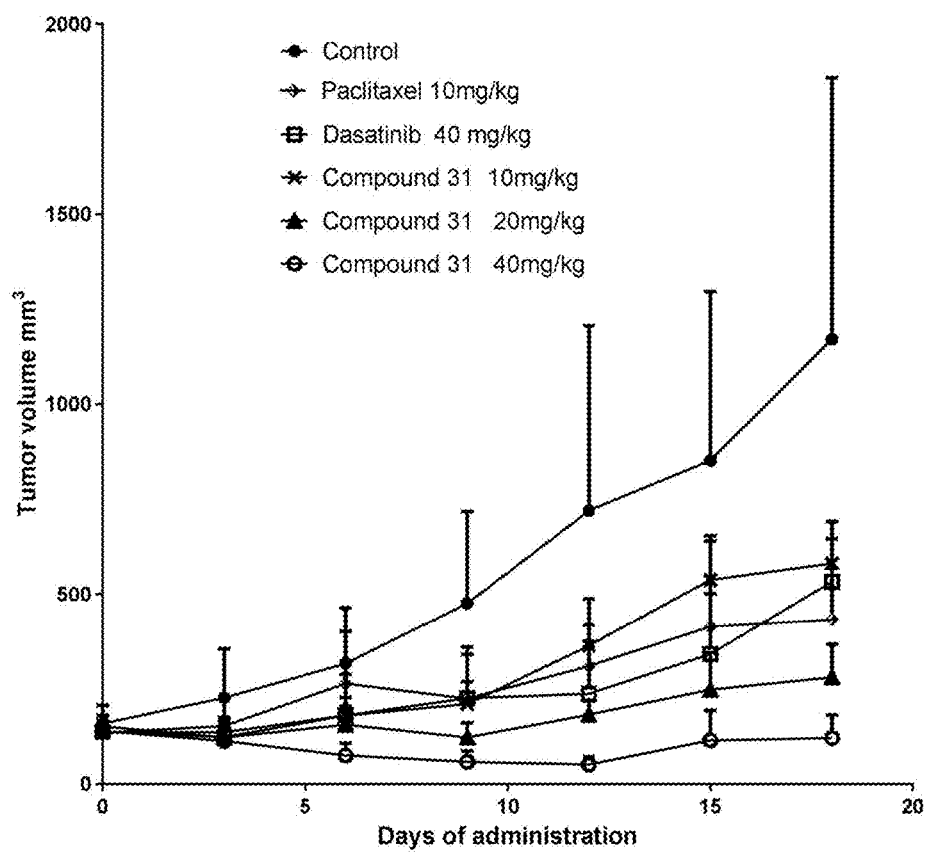
FIG. 2: Compound 31 for in vivo pharmacodynamics experiments in nude mice.
Figure 3:
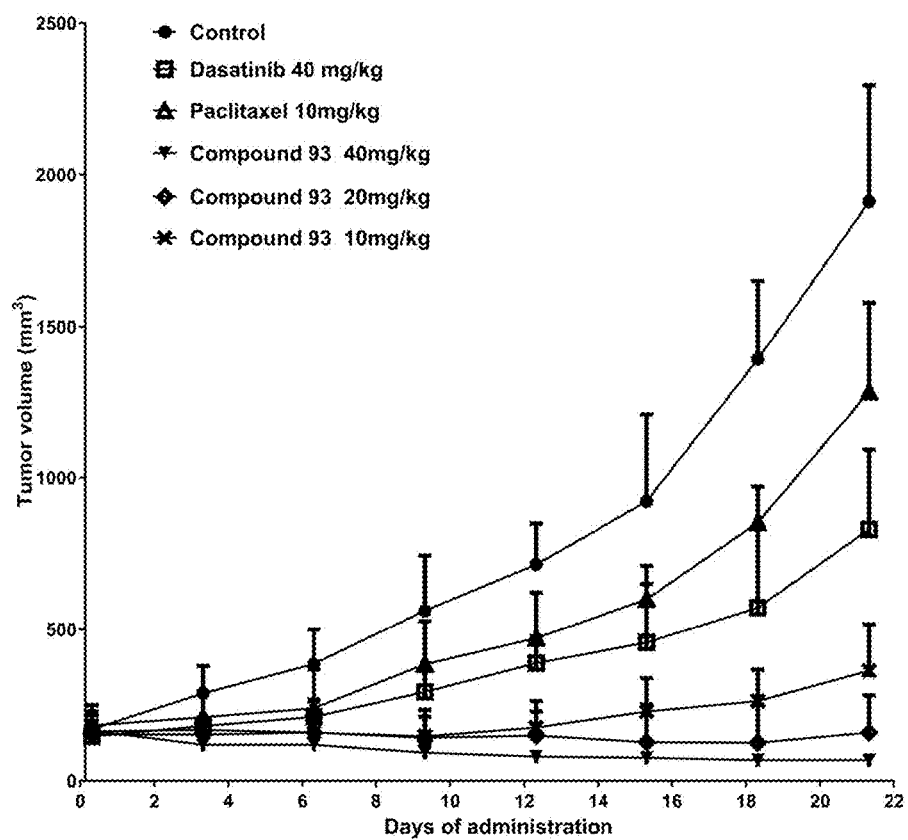
FIG. 3: Pharmacodynamics experiments of compound 93 against nude mice.
Figure 4:
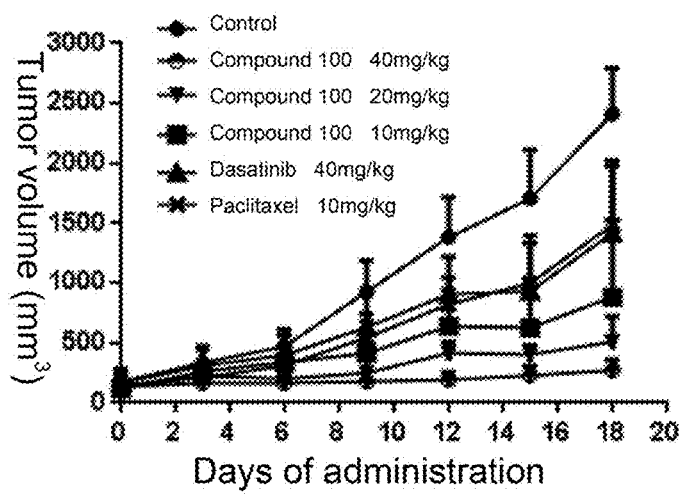
FIG. 4: Experimental efficacy of Compound 100 against nude mice in vivo.

3) Results:

The tumor growth curve of group 1 is shown in FIG. 1; the tumor growth curve of group 2 is shown in FIG. 2; the tumor growth curve of group 3 is shown in FIG. 3; and the tumor growth curve of group 4 is shown in FIG. 4.

The results showed that the compound 3 had significant inhibitory effect on the growth of the breast cancer cell line MDA-MB-231, and the tumor growth was significantly inhibited at 30 mg/kg daily, and showed better than the positive control (paclitaxel). Compound 31 has a significant inhibitory effect on the growth of breast cancer cell line MDA-MB-231 and can significantly inhibit tumor growth at a dose of 20 mg/kg per day and exhibited a superior inhibitory effect compared to positive control (paclitaxel and dasatinib). Compound 93 has a significant inhibitory effect on breast cancer cell line MDA-MB-231, which can significantly inhibit tumor growth at a dose of 20 mg/kg per day and exhibit a superior inhibitory effect compared to the positive control (paclitaxel). Compound 100 has a significant inhibitory effect on MDA-MB-231 breast cancer cell line in vivo, at a dose of 40 mg/kg per day, it can significantly inhibit tumor growth and better than the positive control (paclitaxel and dasatinib). No side effects such as weight loss, rash and diarrhea were observed during the administration of these test compounds, indicating that the test compound 3, compound 31, compound 93, and compound 100 have a low toxicity in the test dose range.

Example 35 the Test of Anti-Angiogenesis Activity of Compound 31 in Transgenic Zebrafish The purpose of this experiment is to detect the inhibitory activity of the compounds of the invention on the in vivo neovascularization, and the transgenic FLK1-GFP fluorescent zebrafish is used to investigate the inhibitory effect of the compounds of the present invention on the interlobular vessels of zebrafish at multiple concentrations. Angiogenesis inhibitory activity of the test compound is represented by the extent of inhibition vascular section between zebrafish with concentrations of 10 μg/mL, 5 μg/mL and 2.5 μg/mL. The positive control is Dasatinib, a drug in breast cancer clinical trials.

1) Materials:

Transgenic FLK1-GFP fluorescent zebrafish: they are cultured in our laboratory.

Experimental reagent: dimethyl sulfoxide (DMSO); test compound; dasatinib.

The main experimental equipment: fluorescence microscope; stereomicroscope; CCD camera.

2) Methods:

Zebrafish Embryo Access: The zebrafish used in this experiment is a vascular fluorescence transgenic zebrafish (FLK1: GFP). The breeding and breeding of zebrafish is based on Westerfield's method. In the day before egg collection, the male and female zebrafish were paired by the ratio 1:1 a. The next day, they natural mating and spawning at a temperature of about 28° C. and sufficient light. Sufficient zebrafish embryos were collected, washed and placed in embryonic culture medium and placed in a 28° C. incubator. The use of morphological and development criteria to identify survival at any time, dead embryos were white, should be promptly removed to prevent water quality deterioration.

Drug treatment: Healthy embryos were randomly collected in 24 plates at 10 hpf (Hour post fertilization), 10 zebrafish embryos per well, and then add different concentrations of compound solution. Compound 31 concentrations were set at 10 μg/mL, 5 μg/mL and 2.5 μg/mL, respectively. The concentration of dasatinib was set at 10 ug/mL. At the same time set a blank control, do not add any compound.

Results observed: After zebrafish embryos fertilized 31 h, stripped shell eggs. The embryos were then placed on slides and fixed with 1.5% methylcellulose containing 1‰ of triacaine, followed by observing the count of Inter segmental vessels (ISVs) under fluorescence microscopy.

Figure 5:
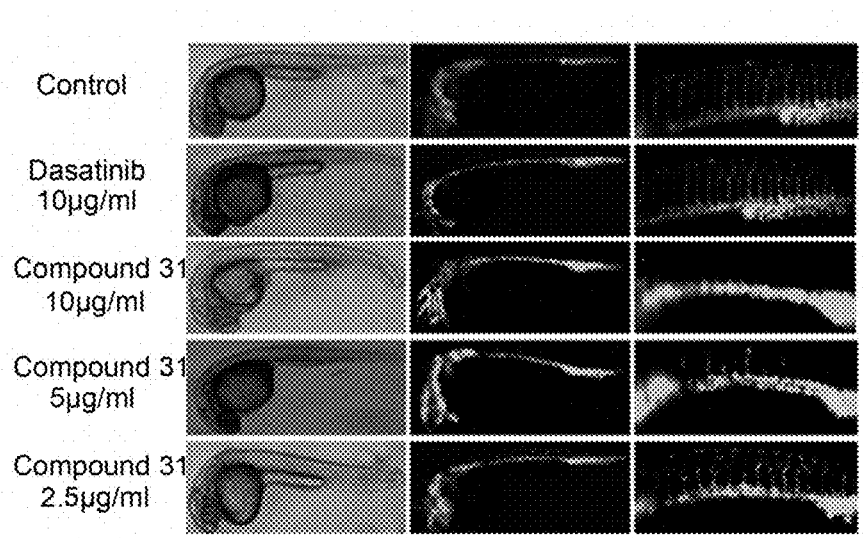
FIG. 5: The vascular inhibition of Compound 31 on FLK1 transgenic zebrafish at different concentrations.

3) Results:

FIG. 5 reflects the vascular inhibition of compound 31 at different concentrations for FLK1 transgenic zebrafish. The results showed that compound 31 could inhibit the angiogenesis of zebrafish significantly compared with the control group. The results of this experiment show that compound 31 in the examples of the present invention have a good anti-angiogenesis activity in FLK1 transgenic zebrafish, and this result reflects that compound 31 has a good inhibitory activity against VEGFR2.

What is claimed is:

1. A 3-ethynylpyrazolopyrimidine derivative of formula I, or a pharmaceutically acceptable salt or hydrate thereof:

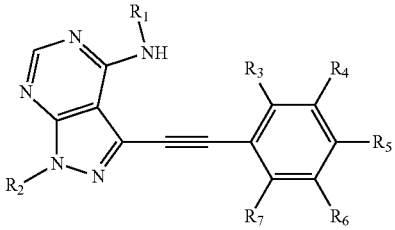

I wherein, $R_1$ is —H, $C_1$-$C_4$ alkyl,

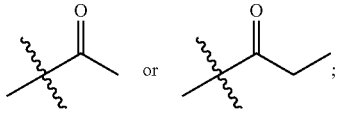

$R_2$ is —H, $C_1$-$C_8$ alkyl,

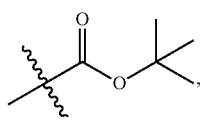 [SMILES: *C(=O)OC(C)(C)C]

$R_8$ substituted $C_3$-$C_8$ cycloalkyl,

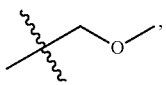 [SMILES: *COC]

$C_3$-$C_8$ epoxyalkyl,

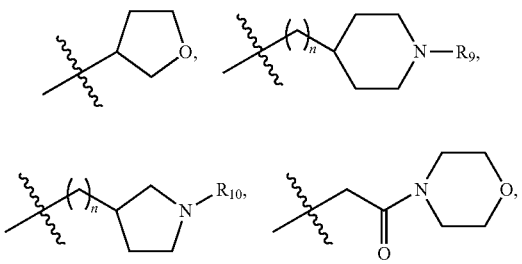

$R_3$-$R_5$ and $R_7$ are independently selected from —H, $C_1$-$C_8$ alkyl, —OH, $C_1$-$C_8$ alkoxyl, or halogen;

$R_6$ is selected from

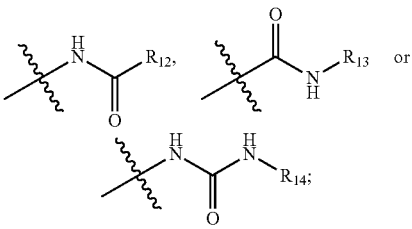

$R_8$-$R_{11}$ are independently selected from —H, $C_1$-$C_8$ alkyl, halogen, —OH,

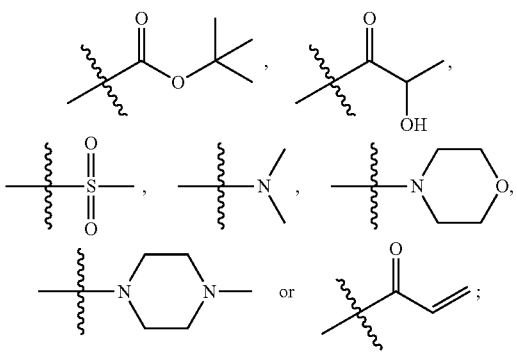

$R_{12}$-$R_{14}$ are independently selected from

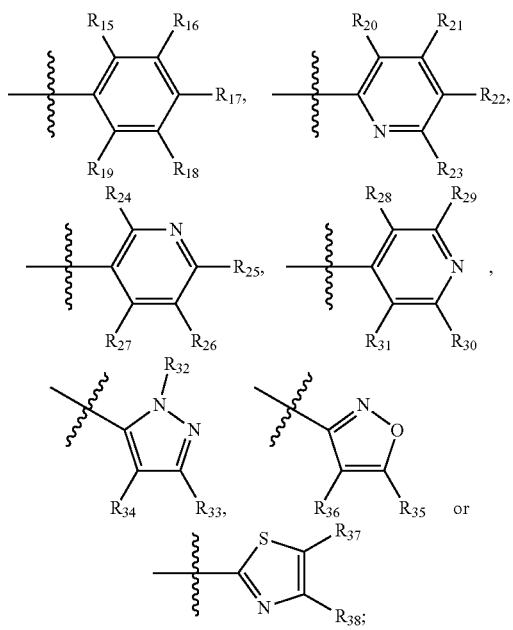

$R_{15}$-$R_{19}$ are selected from —H, $C_1$-$C_8$ alkyl, —OH, $C_1$-$C_8$ alkoxyl, halogen, —$CF_3$, —$OCF_3$,

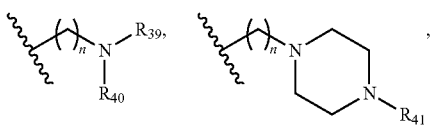

-continued

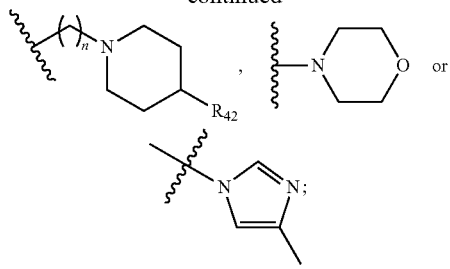

$R_{20}$-$R_{38}$ are independently selected from —H, halogen, $C_1$-$C_8$ alkyl, $C_3$-$C_8$ cycloalkyl, —$OCF_3$ or —$CF_3$;
$R_{39}$-$R_{42}$ are $C_1$-$C_8$ alkyl, $C_3$-$C_8$ cycloalkyl or $C_1$-$C_8$ hydroxyalkyl; and
n=0-6.

2. The 3-ethynylpyrazolopyrimidine derivative of formula I according to claim 1, or a pharmaceutically acceptable salt or hydrate thereof, wherein:
$R_1$ is —H or

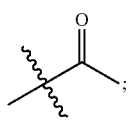 [SMILES: *C(C)=O]

$R_2$ is —H, $C_1$-$C_4$ alkyl,

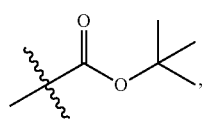 [SMILES: *C(=O)OC(C)(C)C]

$R_8$ substituted $C_3$-$C_8$ cycloalkyl,

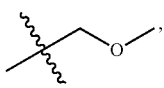 [SMILES: *COC]

$C_3$-$C_8$ epoxyalkyl,

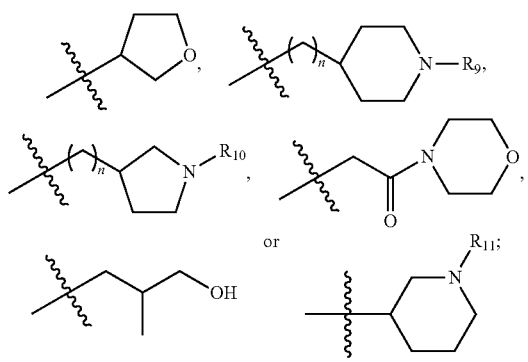

$R_3$-$R_5$ and $R_7$ are independently selected from —H, $C_1$-$C_4$ alkyl, —OH, $C_1$-$C_4$ alkoxyl, or halogen;

$R_6$ is selected from

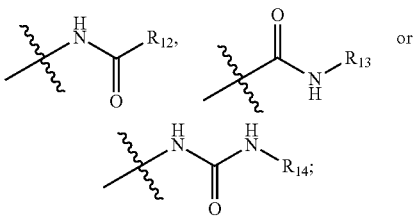

$R_8$-$R_{11}$ independently represent —H, $C_1$-$C_4$ alkyl, —OH,

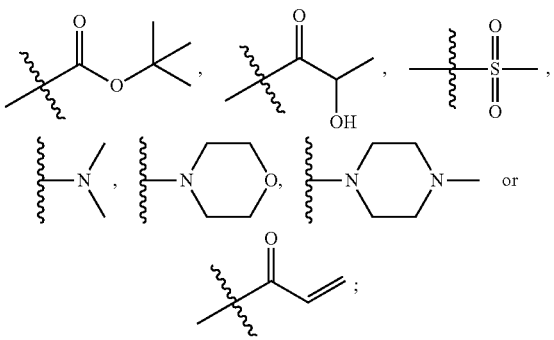

$R_{12}$-$R_{14}$ are independently selected from

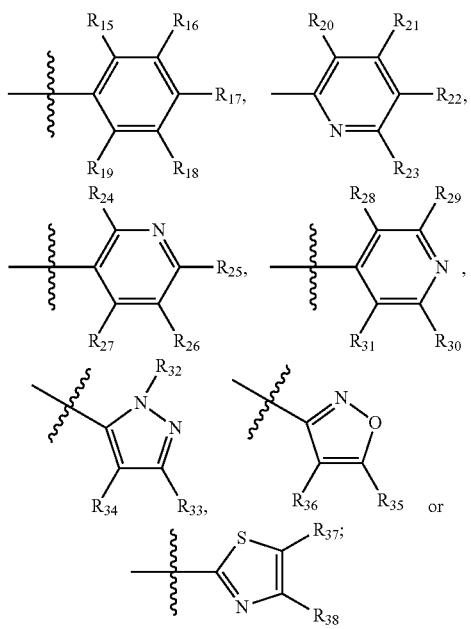

$R_{15}$-$R_{19}$ are —H, $C_1$-$C_4$ alkyl, —OH, $C_1$-$C_4$ alkoxyl, halogen, —$CF_3$, —$OCF_3$,

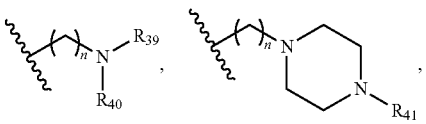

-continued

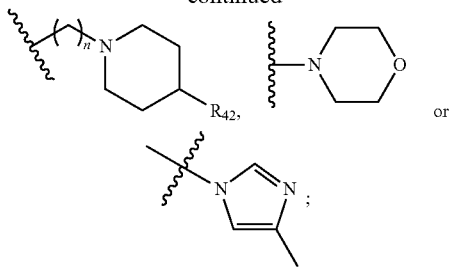

$R_{20}$-$R_{38}$ independently selected from —H, halogen, $C_1$-$C_4$ alkyl, $C_3$-$C_4$ cycloalkyl, —$OCF_3$ or —$CF_3$;
$R_{39}$-$R_{42}$ are independently selected from $C_1$-$C_4$ alkyl, $C_3$-$C_8$ cycloalkyl or $C_1$-$C_4$ hydroxyalkyl; and
n=0-4.

3. The 3-ethynylpyrazolopyrimidine derivative of formula I according to claim 2, or a pharmaceutically acceptable salt or hydrate thereof, wherein:

$R_1$ is —H or;

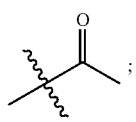

$R_2$ is —H, $C_1$-$C_4$ alkyl,

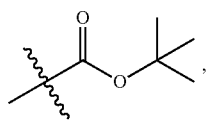 [SMILES: *C(=O)OC(C)(C)C]

$R_8$ substituted $C_3$-$C_8$ cycloalkyl,

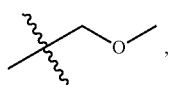

$C_3$-$C_8$ epoxyalkyl,

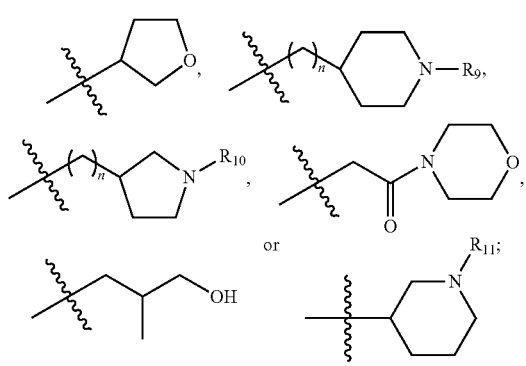

$R_3$-$R_5$ and $R_7$ are —H, $C_1$-$C_4$ alkyl, —OH, $C_1$-$C_4$ alkoxyl, or halogen;

$R_6$ is selected from

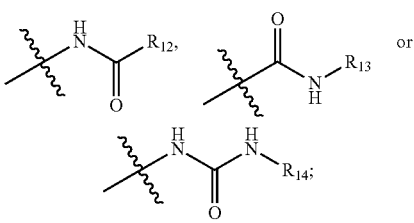

$R_8$-$R_{11}$ are independently selected from —H, $C_1$-$C_4$ alkyl, —OH,

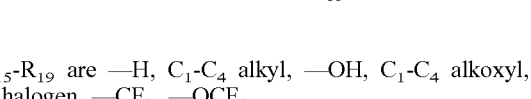

$R_{12}$-$R_{14}$ represent

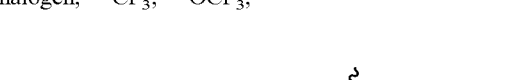

$R_{15}$-$R_{19}$ are —H, $C_1$-$C_4$ alkyl, —OH, $C_1$-$C_4$ alkoxyl, halogen, —$CF_3$, —$OCF_3$,

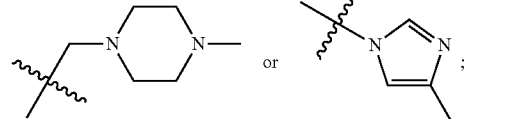

$R_{20}$-$R_{38}$ independently represent —H, halogen, $C_1$-$C_4$ alkyl, $C_3$-$C_4$ cycloalkyl, —$OCF_3$ or —$CF_3$; and
n=0-2.

4. The 3-ethynylpyrazolopyrimidine derivative of formula I according to claim 3, or a pharmaceutically acceptable salt or hydrate thereof, wherein:

$R_1$ is —H or

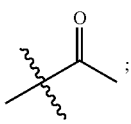 [SMILES: *C(C)=O]

;

$R_2$ is —H, $C_1$-$C_4$ alkyl,

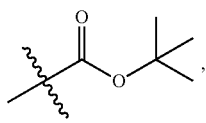 [SMILES: *C(=O)OC(C)(C)C]

, $R_8$ substituted $C_3$-$C_8$ cycloalkyl,

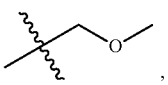 [SMILES: *COC]

, $C_3$-$C_8$ epoxyalkyl,

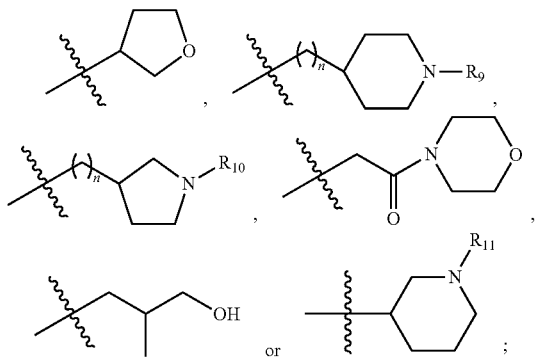

;

$R_3$-$R_5$ and $R_7$ are —H, $C_1$-$C_4$ alkyl, —OH, $C_1$-$C_4$ alkoxyl, —F, or —Cl;

$R_6$ is selected from

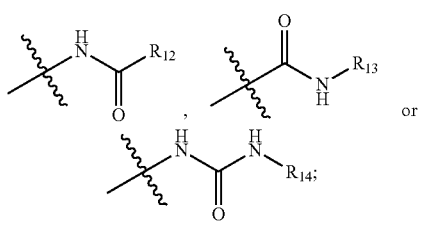

$R_8$-$R_{11}$ are independently selected from —H, $C_1$-$C_4$ alkyl, —OH,

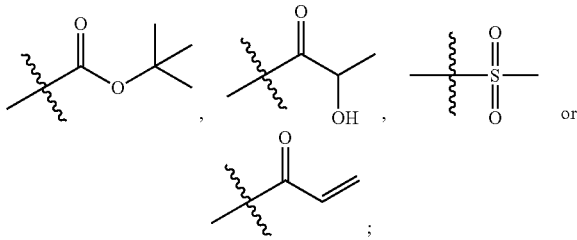

;

$R_{12}$-$R_{14}$ represent

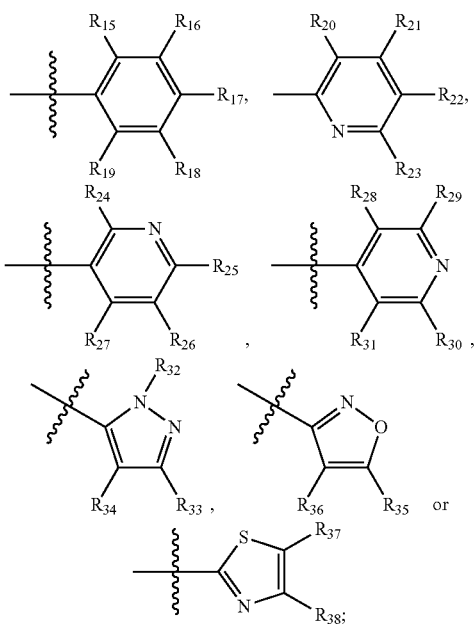

$R_{15}$-$R_{19}$ are independently selected from —H, $C_1$-$C_4$ alkyl, —OH, $C_1$-$C_4$ alkoxyl, —F, —Cl, —$CF_3$, —$OCF_3$,

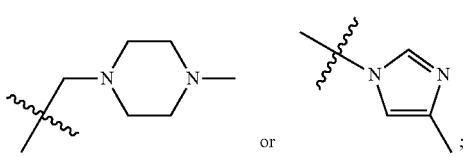

;

$R_{20}$-$R_{38}$ independently represent —H, $C_1$-$C_4$ alkyl or —$CF_3$; and
n=0 or 1.

5. The 3-ethynylpyrazolopyrimidine derivative of formula I according to claim 2, or a pharmaceutically acceptable salt or hydrate thereof, wherein:

when $R_6$ is

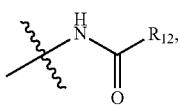

the structure is shown in formula II:

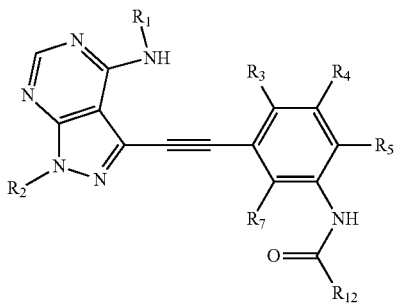

wherein $R_1$ is —H or

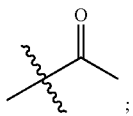

;

$R_2$ is —H, $C_1$-$C_4$ alkyl,

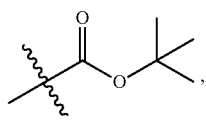 [SMILES: *C(=O)OC(C)(C)C]

, $R_8$ substituted $C_3$-$C_8$ cycloalkyl,

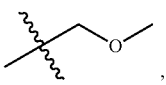 [SMILES: *COC]

, $C_3$-$C_8$ epoxyalkyl,

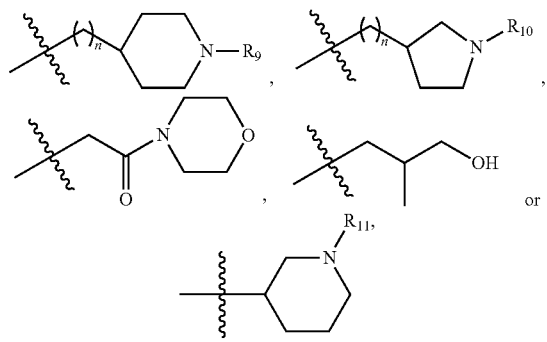

or n=0-4;

$R_3$-$R_5$, and $R_7$ are —H, $C_1$-$C_4$ alkyl, —OH, $C_1$-$C_4$ alkoxyl or halogen;

$R_8$-$R_{11}$ are independently selected from —H, $C_1$-$C_4$ alkyl, —OH,

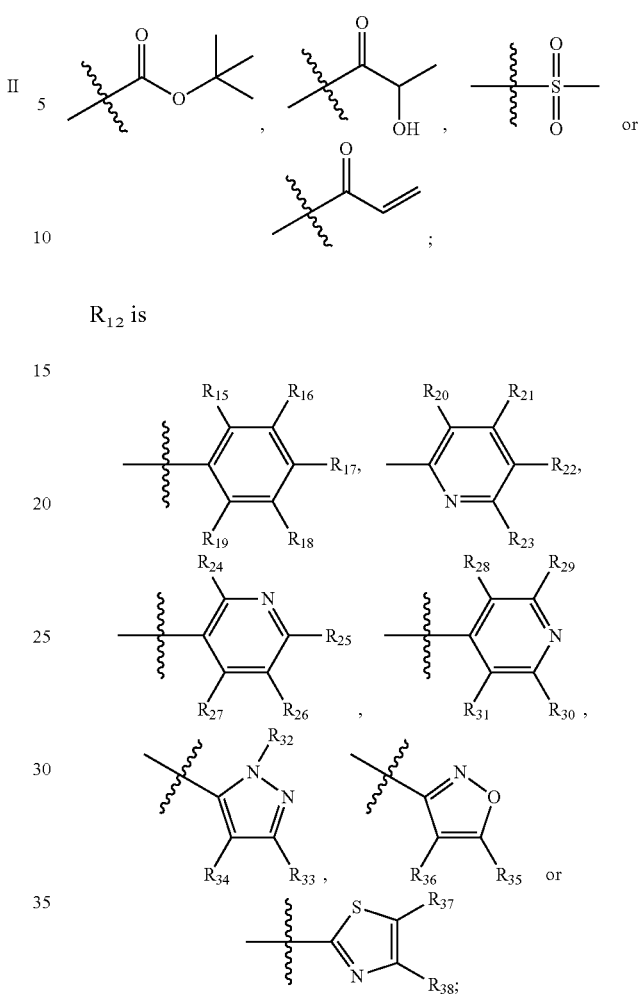

;

$R_{12}$ is

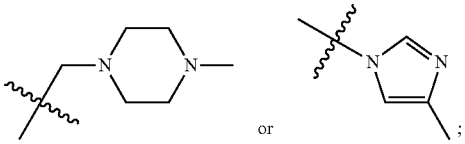

$R_{15}$-$R_{19}$ represent —H, $C_1$-$C_4$ alkyl, —OH, $C_1$-$C_4$ alkoxyl, halogen, —$CF_3$, —$OCF_3$, $R_{20}$-$R_{38}$ are independently selected from —H, $C_1$-$C_4$ alkyl or —$CF_3$.

6. The 3-ethynylpyrazolopyrimidine derivative of formula II according to claim 5, or a pharmaceutically acceptable salt or hydrate thereof, wherein:

$R_1$ is —H or

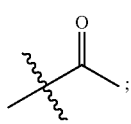 [SMILES: *C(C)=O]

;

$R_2$ is $C_1$-$C_4$ alkyl, $R_8$ substituted $C_3$-$C_8$ cycloalkyl,

265

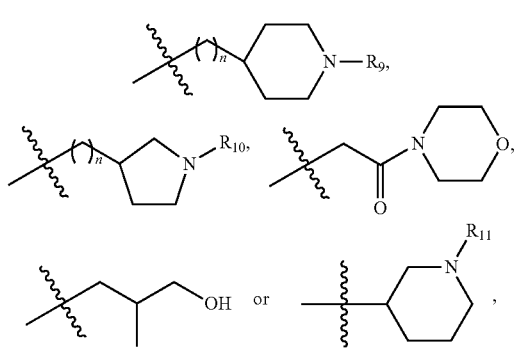

n=0 or 1;
R$_3$-R$_5$, and R$_7$ independently represent —H, methyl or —Cl;
R$_8$-R$_{11}$ are independently selected from —H, C$_1$-C$_4$ alkyl, —OH,

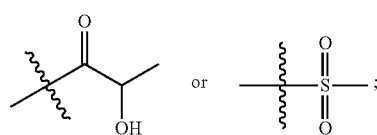

R$_{12}$ is

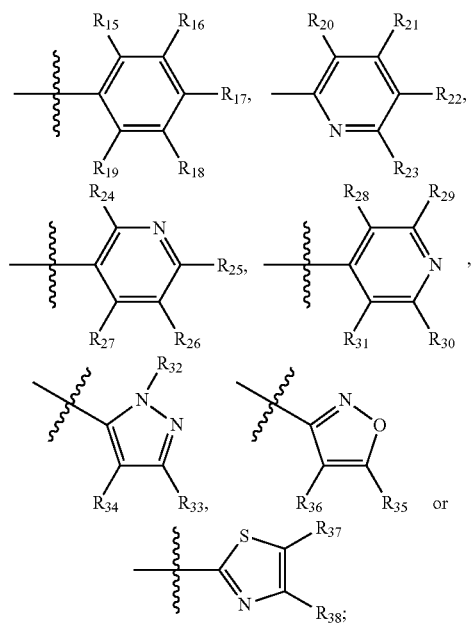

R$_{15}$-R$_{19}$ are —H, C$_1$-C$_4$ alkyl, methoxyl, —F, —Cl, —CF$_3$, —OCF$_3$ or

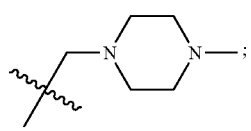 [SMILES: *CN1CCN(C)CC1]

and

266

R$_{20}$-R$_{38}$ are independently selected from —H, C$_1$-C$_4$ alkyl or —CF$_3$.

7. The 3-ethynylpyrazolopyrimidine derivative of formula I according to claim 2, or a pharmaceutically acceptable salt or hydrate thereof, wherein:

when R$_6$ is

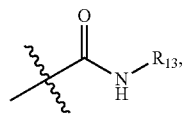

the structure is shown in formula III:

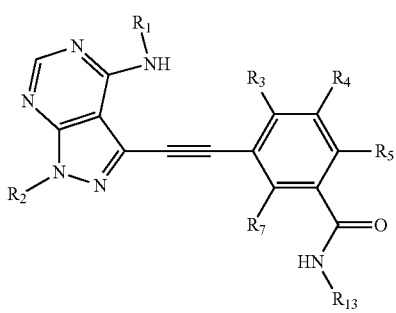

III wherein, R$_t$ is —H or

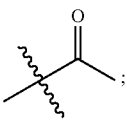 [SMILES: *C(C)=O]

R$_2$ is —H, C$_1$-C$_4$ alkyl,

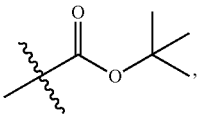

R$_8$ substituted C$_3$-C$_8$ cycloalkyl,

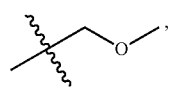

C$_3$-C$_8$ epoxyalkyl,

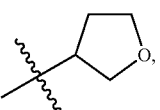 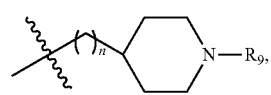

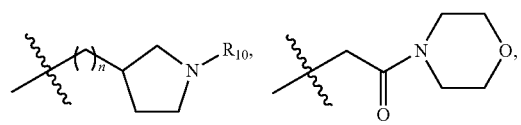

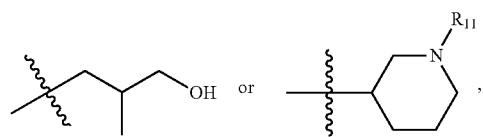

n=0-4;

R$_3$-R$_5$, and R$_7$ independently represent —H, C$_1$-C$_4$ alkyl, —OH, C$_1$-C$_4$ alkoxyl or halogen;

R$_8$-R$_{11}$ are independently selected from —H, C$_1$-C$_4$ alkyl, —OH,

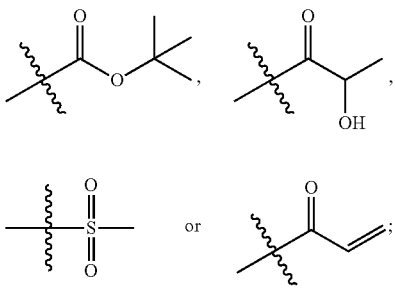

R$_{13}$ is

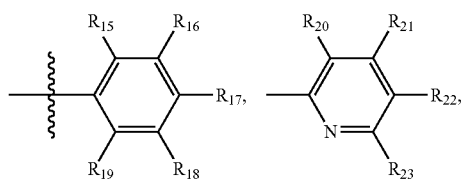

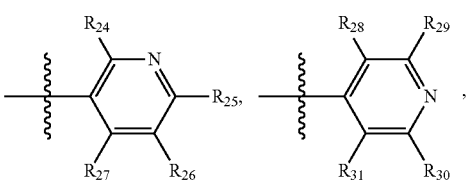

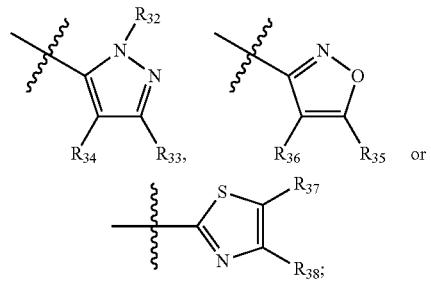

R$_{15}$-R$_{19}$ are —H, C$_1$-C$_4$ alkyl, —OH, C$_1$-C$_4$ alkoxyl, halogen, —CF$_3$, —OCF$_3$,

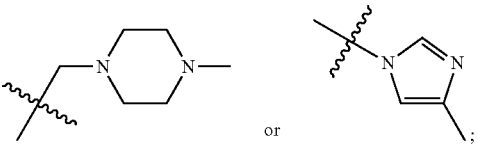

and

R$_{20}$-R$_{38}$ are independently selected from —H, C$_1$-C$_4$ alkyl or —CF$_3$.

8. The 3-ethynylpyrazolopyrimidine derivative of formula III according to claim 7, or a pharmaceutically acceptable salt or hydrate thereof, wherein:

R$_1$ is —H

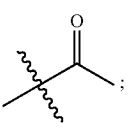 [SMILES: *C(C)=O]

R$_2$ is C$_1$-C$_4$ alkyl, R$_8$ substituted C$_3$-C$_8$ cycloalkyl,

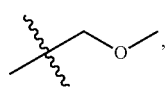 [SMILES: *COC]

C$_3$-C$_8$ epoxyalkyl,

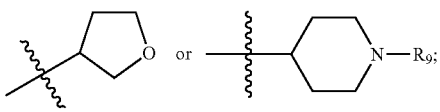

R$_3$-R$_5$, and R$_7$ represent —H, C$_1$-C$_4$ alkyl, —OH or —Cl; R$_8$ and R$_9$ are independently selected from —H, C$_1$-C$_4$ alkyl,

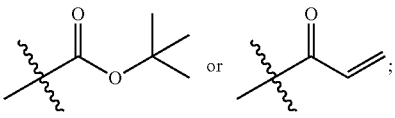

R$_{13}$ is

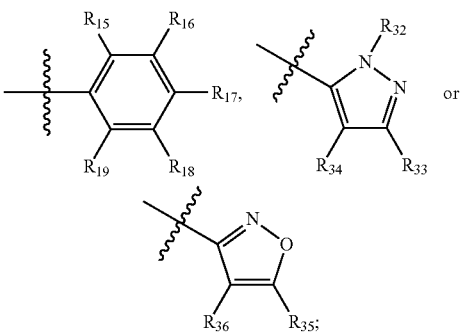

269

$R_{15}$-$R_{19}$ are —H, $C_1$-$C_4$ alkyl, —$CF_3$ or

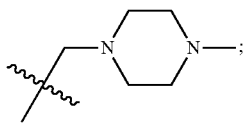 [SMILES: *CN1CCN(C)CC1]

and $R_{20}$-$R_{38}$ are independently selected from —H or $C_1$-$C_4$ alkyl.

9. The 3-ethynylpyrazolopyrimidine derivative of formula III according to claim 7, or a pharmaceutically acceptable salt or hydrate thereof, wherein:

when $R_{13}$ is

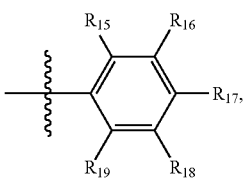

the structure is shown in formula IV:

IV

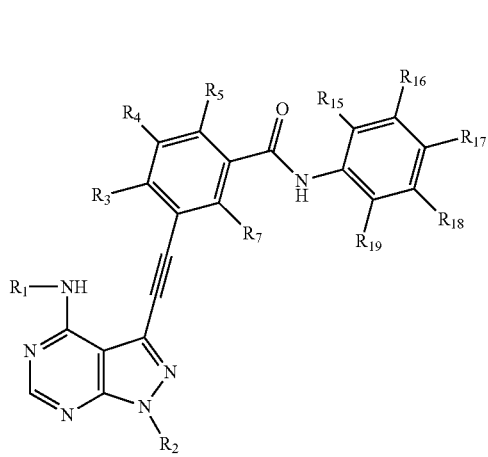

wherein, $R_1$ is —H or

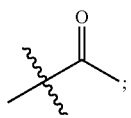 [SMILES: *C(C)=O]

$R_2$ is —H, $C_1$-$C_4$ alkyl,

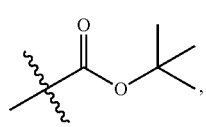

$R_8$ substituted $C_3$-$C_8$ cycloalkyl,

270

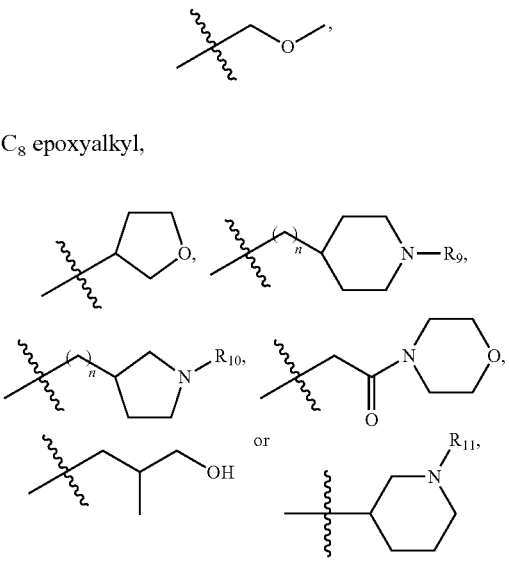

$C_3$-$C_8$ epoxyalkyl,

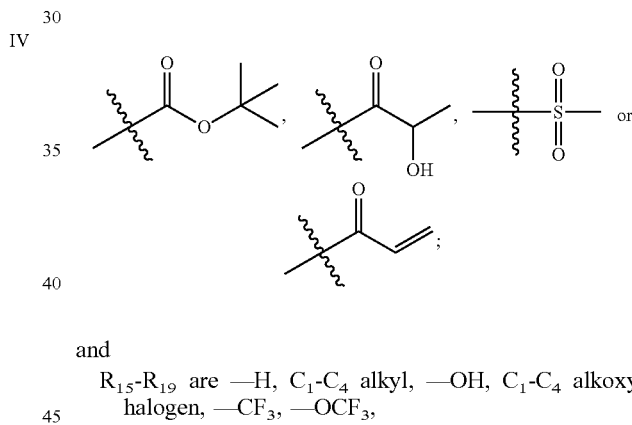

n=0-4;

$R_3$-$R_5$, and $R_7$ independently represent —H, $C_1$-$C_4$ alkyl, —OH, $C_1$-$C_4$ alkoxyl or halogen;

$R_8$-$R_{11}$ are independently selected from H, $C_1$-$C_4$ alkyl, —OH, —OH,

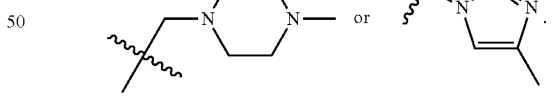

and $R_{15}$-$R_{19}$ are —H, $C_1$-$C_4$ alkyl, —OH, $C_1$-$C_4$ alkoxyl, halogen, —$CF_3$, —$OCF_3$,

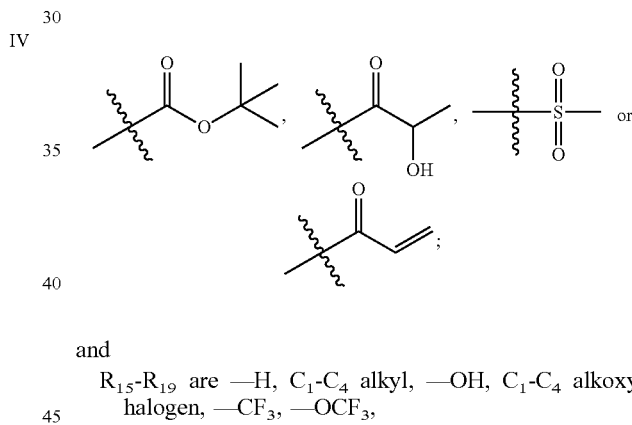

(see above)

10. The 3-ethynylpyrazolopyrimidine derivative of formula IV according to claim 9, or a pharmaceutically acceptable salt or hydrate thereof, wherein:

$R_1$ is —H or

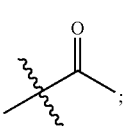 [SMILES: *C(C)=O]

$R_2$ is $C_1$-$C_4$ alkyl, $R_8$ substituted $C_3$-$C_8$ cycloalkyl,

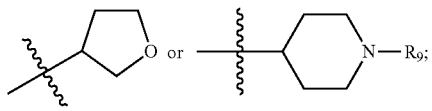

$C_3$-$C_8$ epoxyalkyl,

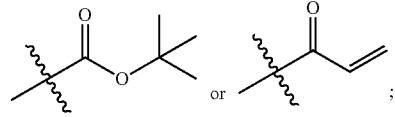

$R_3$-$R_5$, and $R_7$ are independently selected from —H, $C_1$-$C_4$ alkyl, —OH or —Cl;

$R_8$ and $R_9$ independently represent H, $C_1$-$C_4$ alkyl,

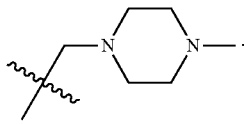

and $R_{15}$-$R_{19}$ are independently selected from —H, $C_1$-$C_4$ alkyl, —$CF_3$ or

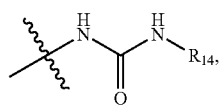

11. The 3-ethynylpyrazolopyrimidine derivative of formula I according to claim 2, or a pharmaceutically acceptable salt or hydrate thereof, wherein:

when $R_6$ is

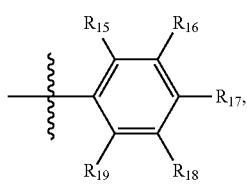

$R_{14}$ is

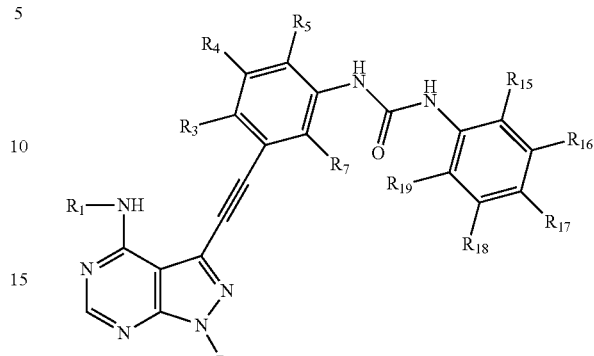

the structure is shown in formula V:

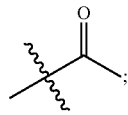

wherein, $R_1$ is —H or

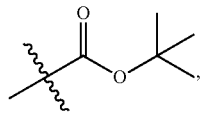 [SMILES: *C(=O)OC(C)(C)C]

$R_2$ is —H, $C_1$-$C_4$ alkyl,

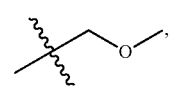 [SMILES: *COC]

$R_8$ substituted $C_3$-$C_8$ cycloalkyl,

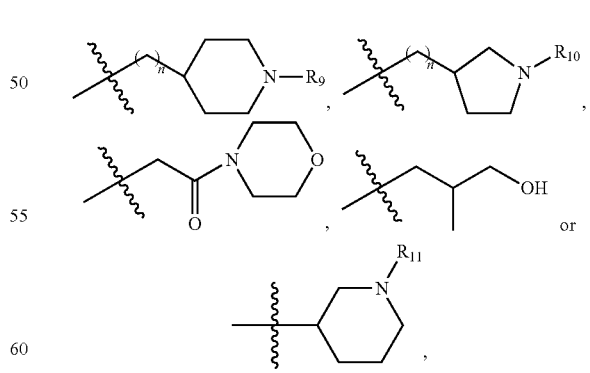

$C_3$-$C_8$ epoxyalkyl,

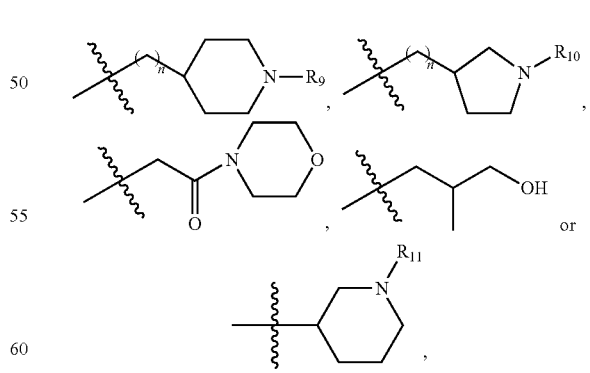

n=0-4;
$R_3$-$R_5$, and $R_7$ are —H, $C_1$-$C_4$ alkyl, —OH, $C_1$-$C_4$ alkoxyl or halogen;
$R_8$-$R_{11}$ are independently selected from —H, $C_1$-$C_4$ alkyl, —OH

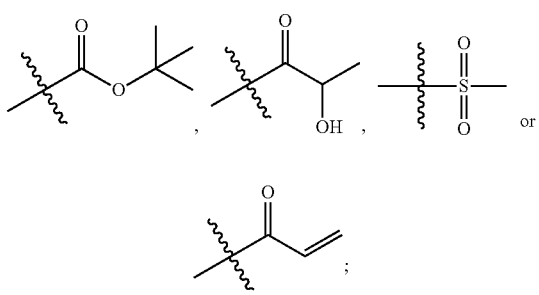

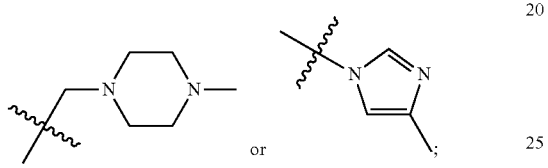

$R_{15}$-$R_{19}$ represent —H, $C_1$-$C_4$ alkyl, —OH, $C_1$-$C_4$ alkoxyl, halogen, —$CF_3$, —$OCF_3$,

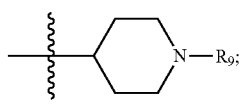

and $R_{20}$-$R_{38}$ are independently selected from —H, $C_1$-$C_4$ alkyl or —$CF_3$.

12. The 3-ethynylpyrazolopyrimidine derivative of formula V according to claim 11, or a pharmaceutically acceptable salt or hydrate thereof, wherein:

R is —H;

$R_2$ is $C_1$-$C_4$ alkyl or

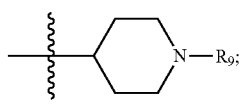

$R_3$-$R_5$, and $R_7$ represent —H, $C_1$-$C_4$ alkyl or —Cl;

$R_9$ is $C_1$-$C_4$ alkyl; and $R_{15}$-$R_{19}$ are independently selected from —H or —$CF_3$.

13. The 3-ethynylpyrazolopyrimidine derivative selected from the group consisting of:

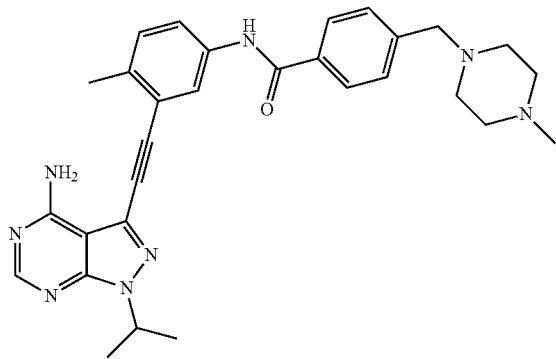

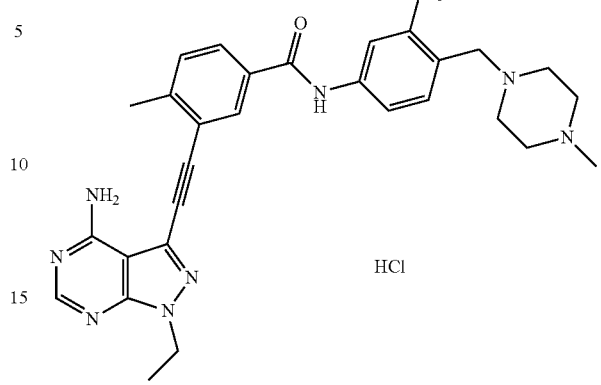

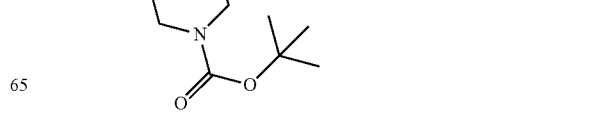

275
-continued
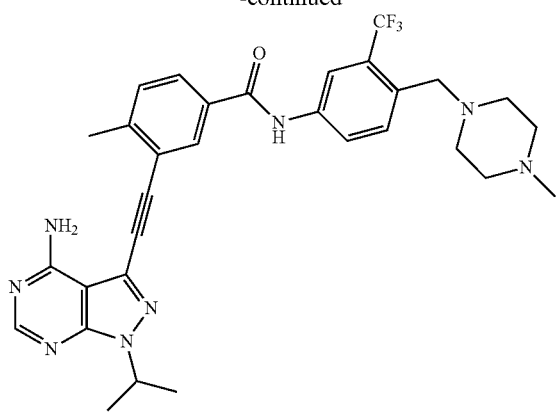
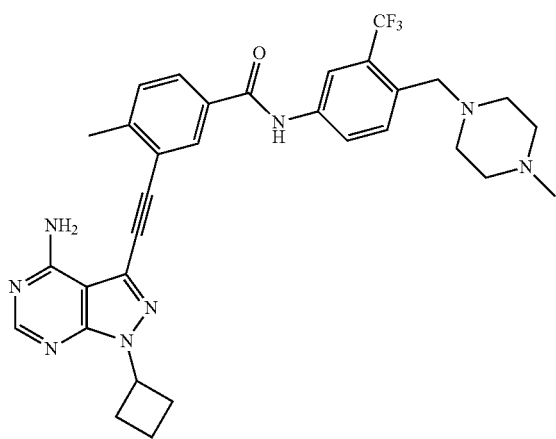
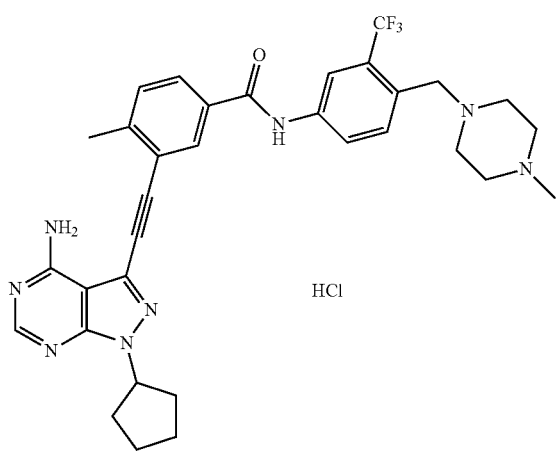
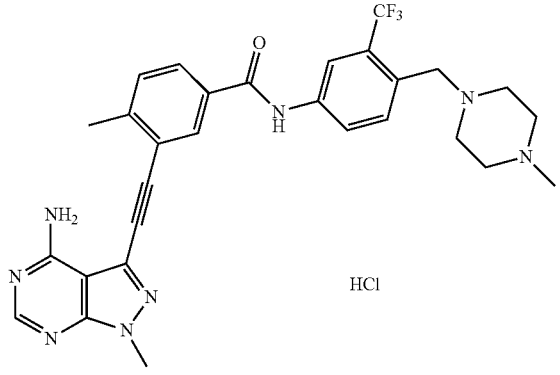
276
-continued
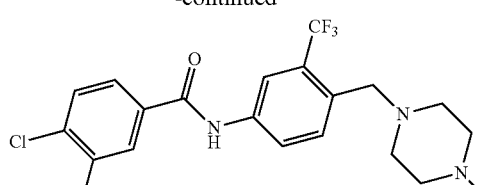

277
-continued
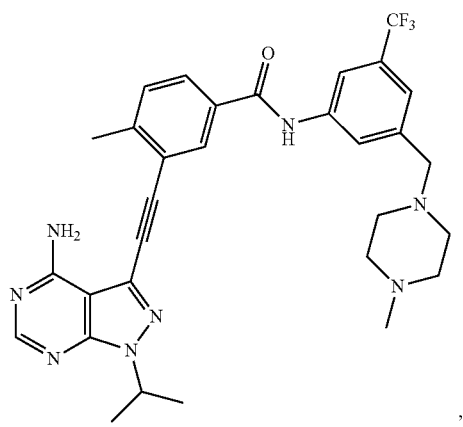
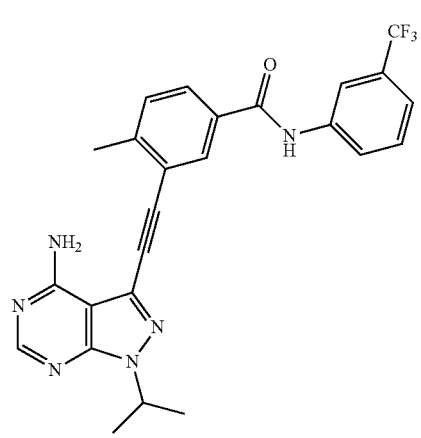
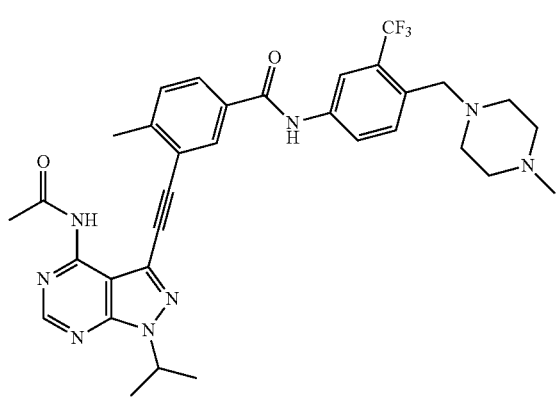
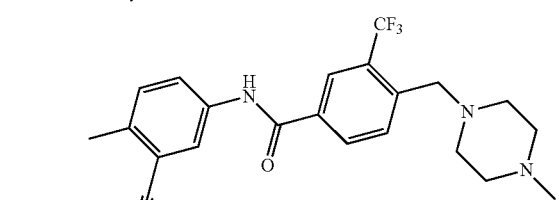
278
-continued
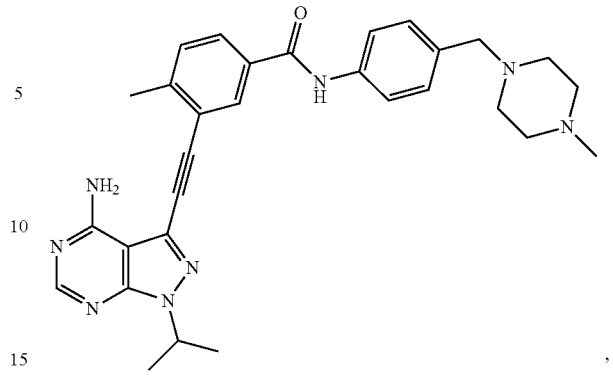
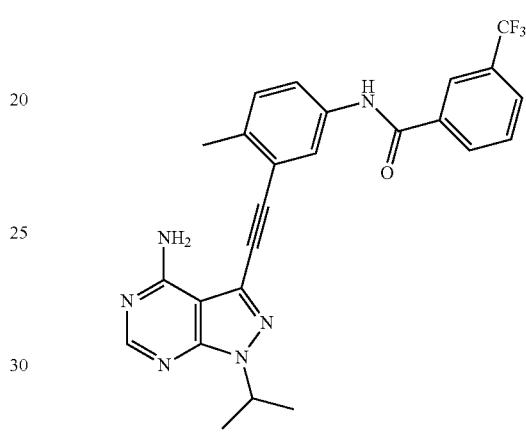
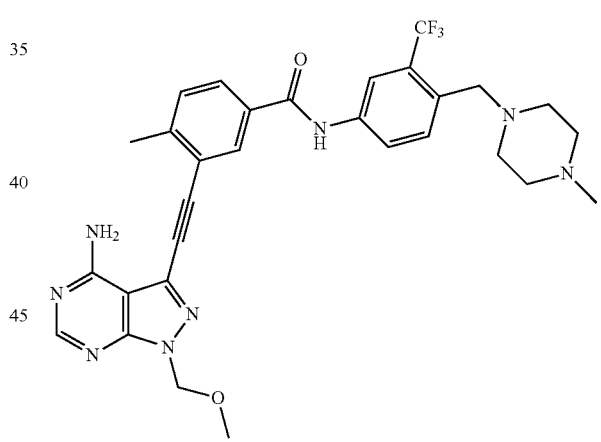
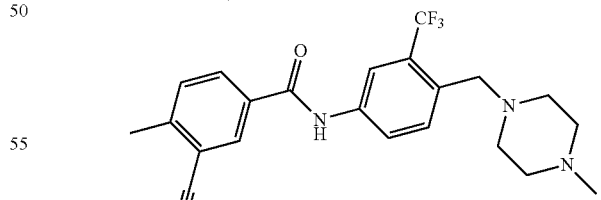
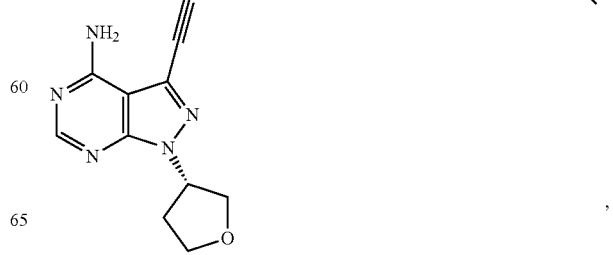

279
-continued
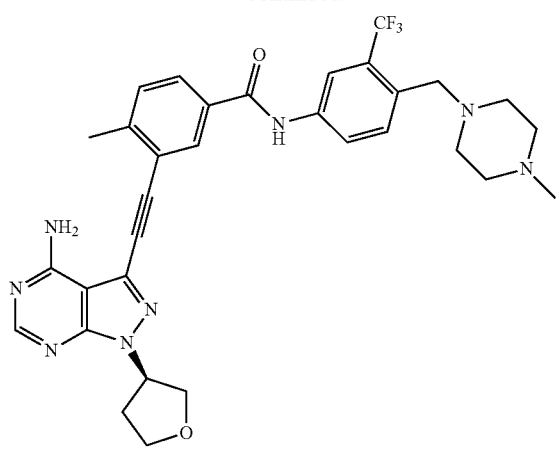
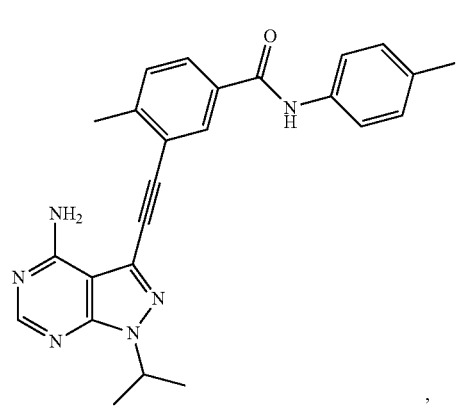
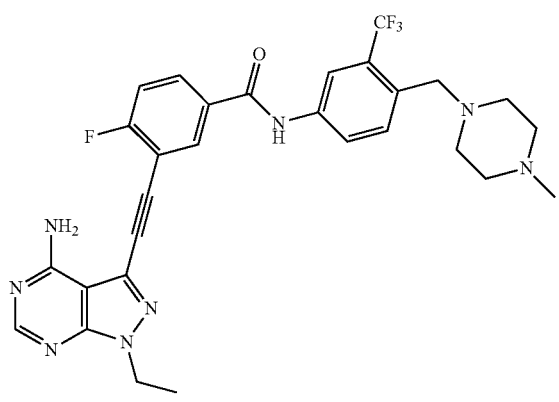
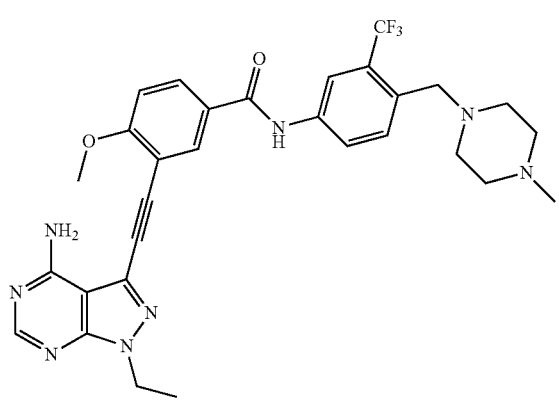
,
280
-continued
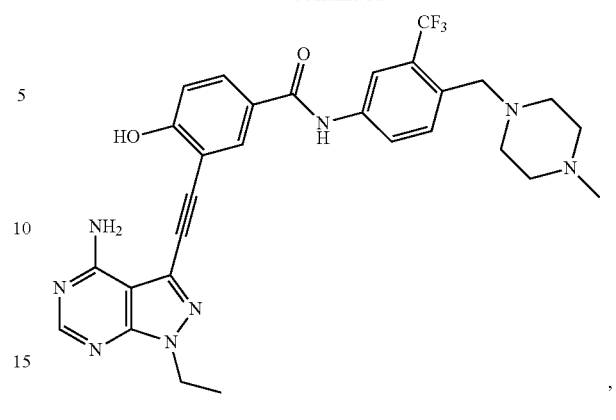
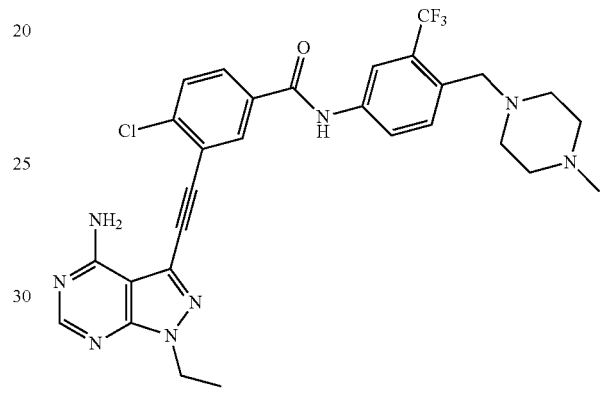
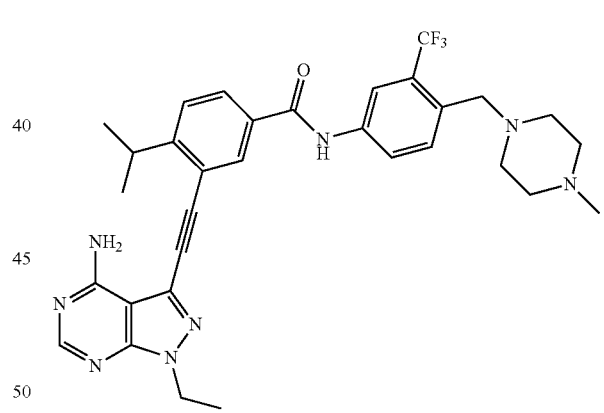
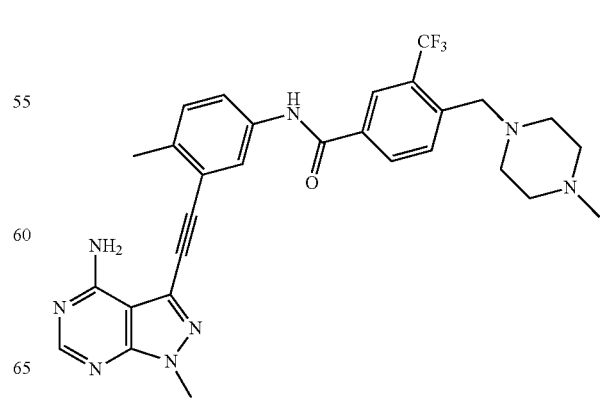
, 281
-continued
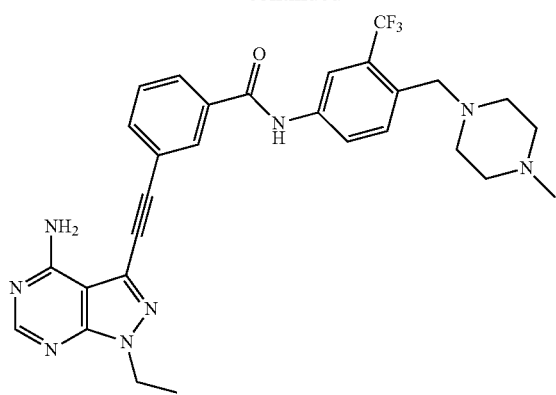
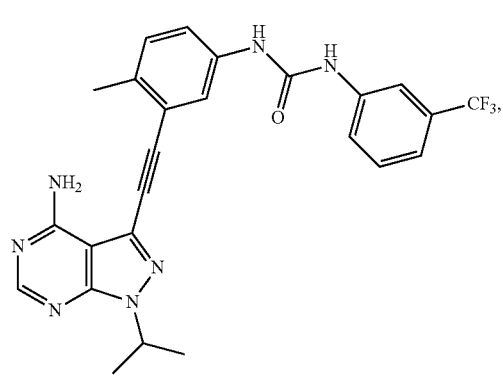
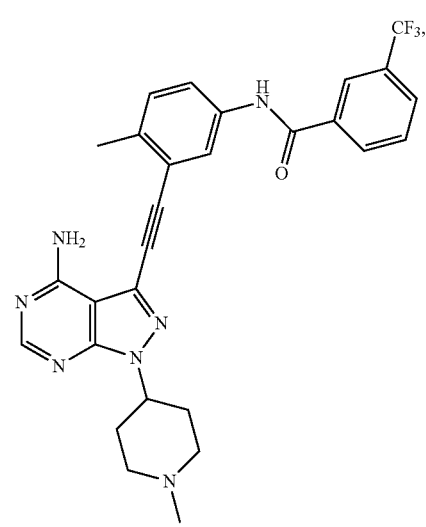
282
-continued
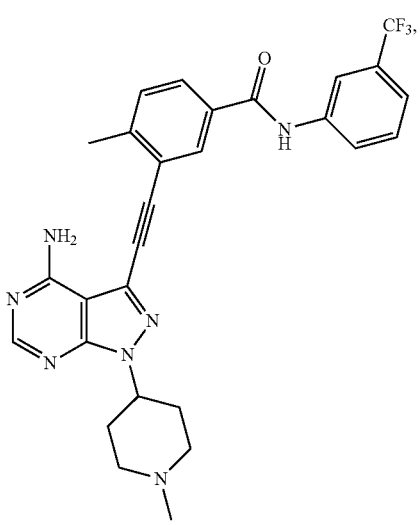
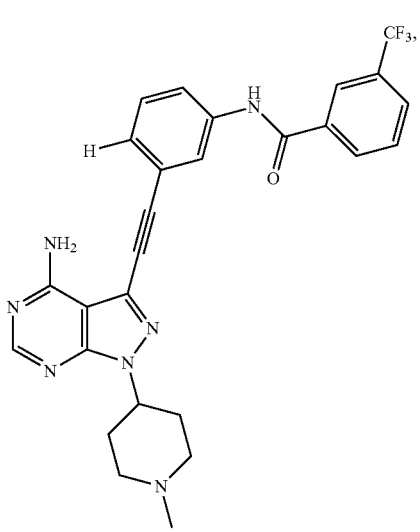
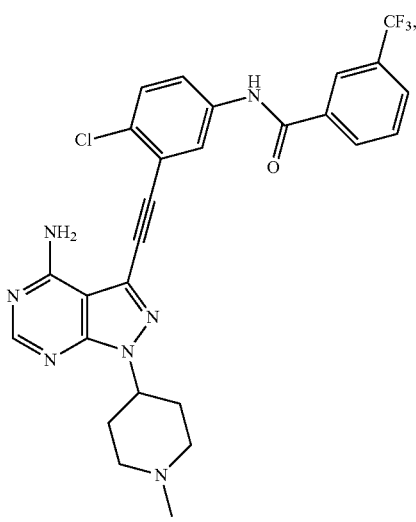

283
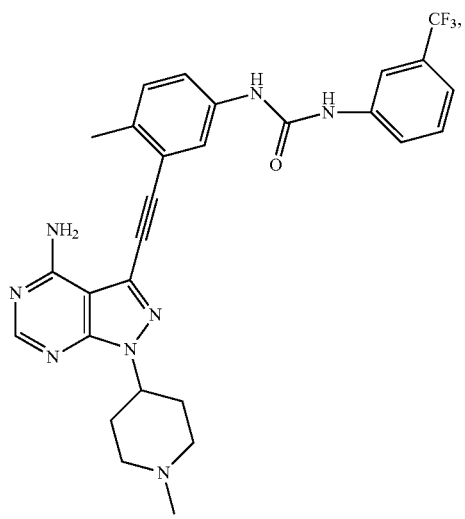
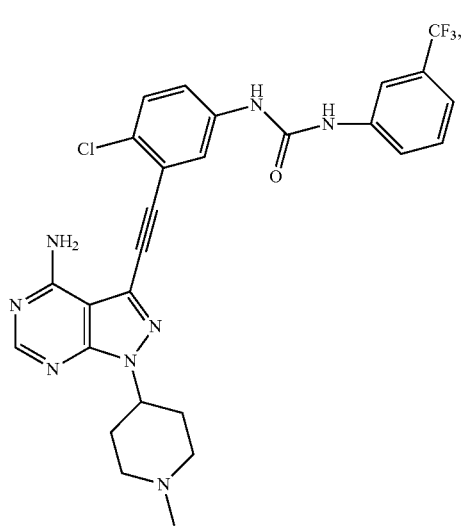
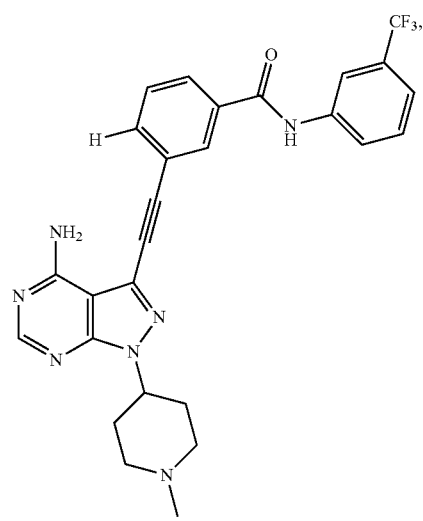
284
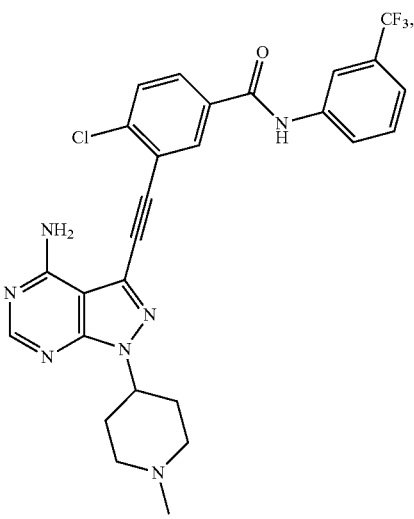
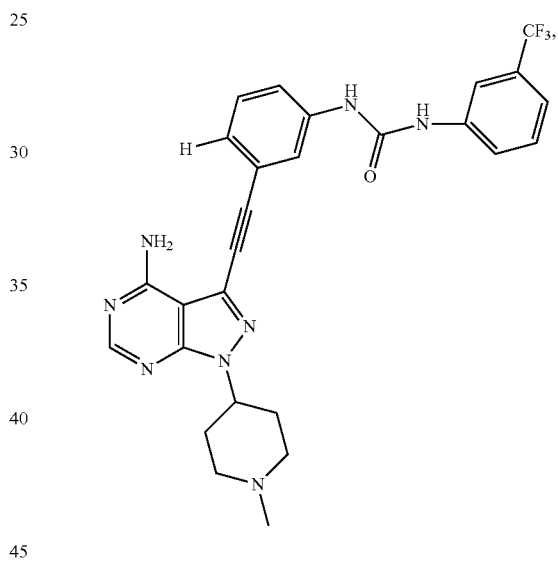
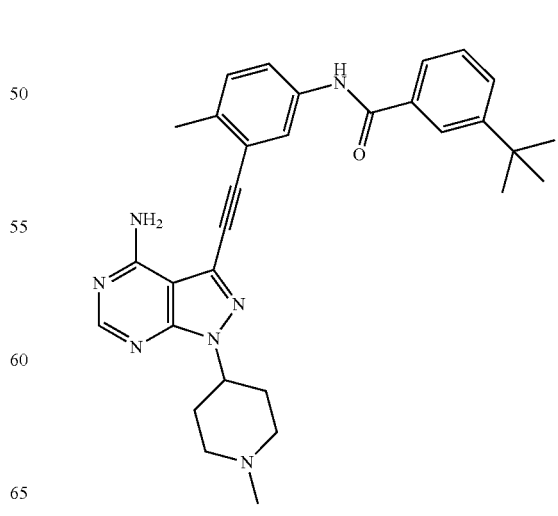

285
-continued
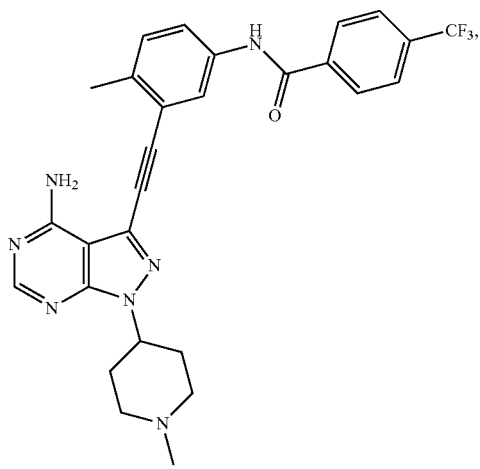
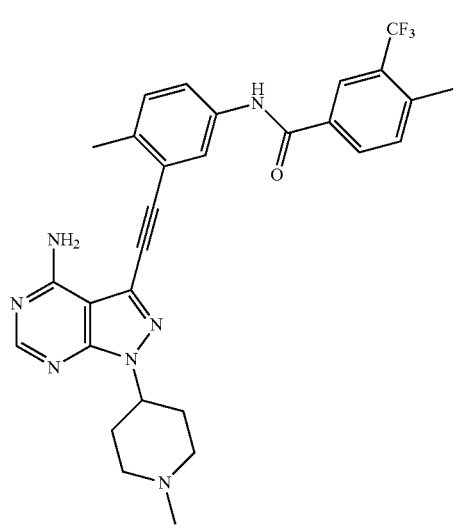
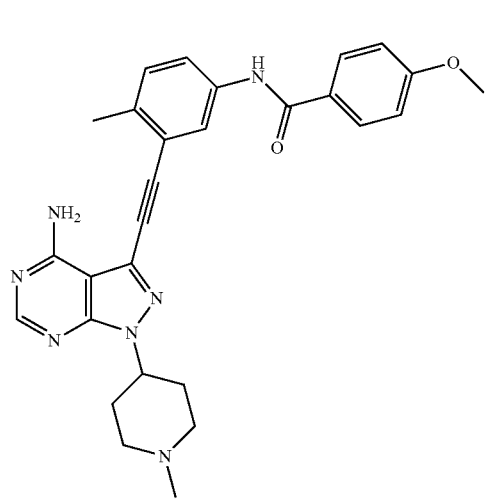
286
-continued
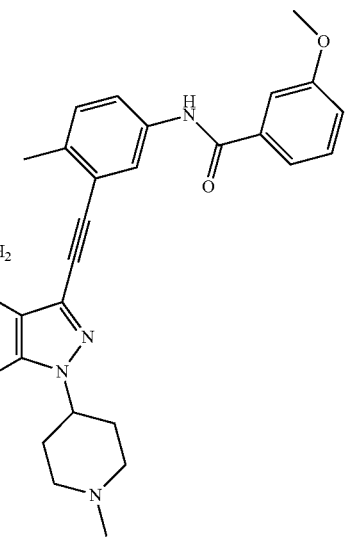
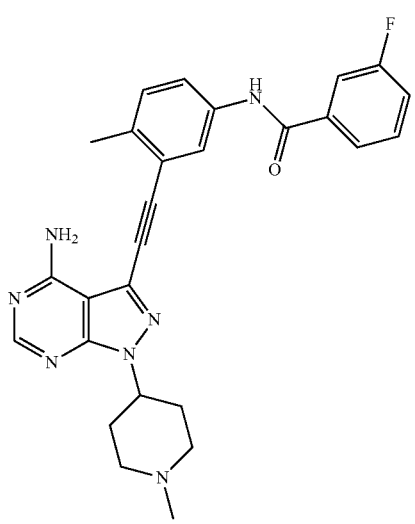
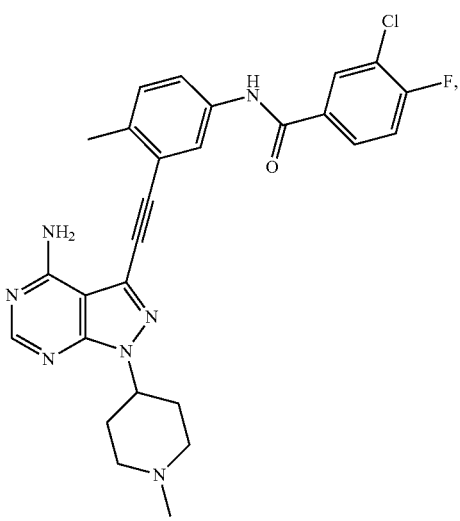

287
-continued
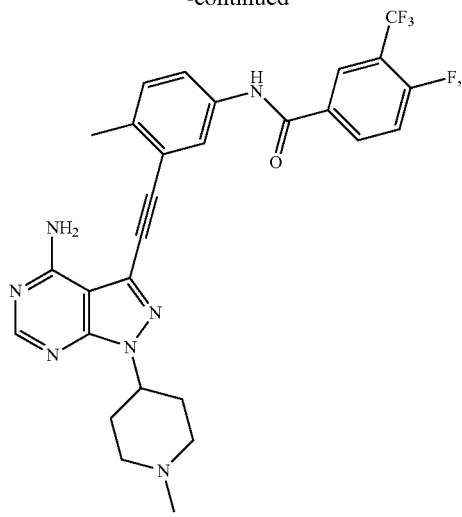
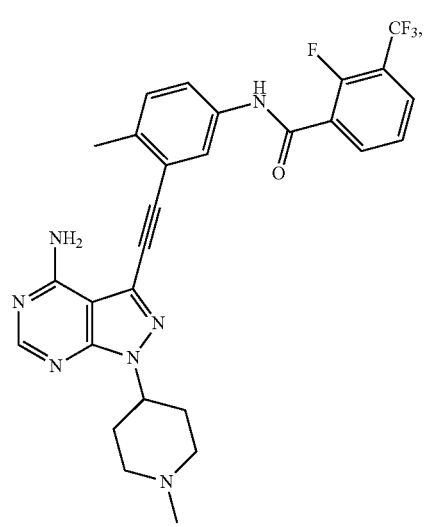
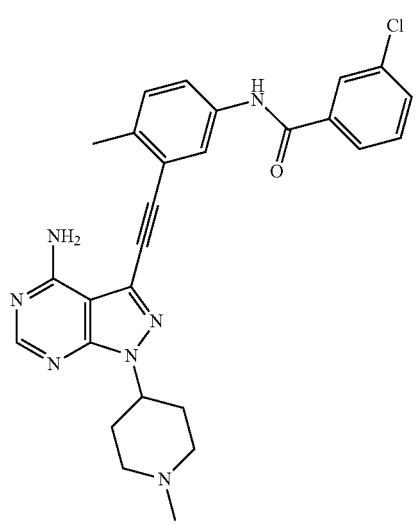
288
-continued
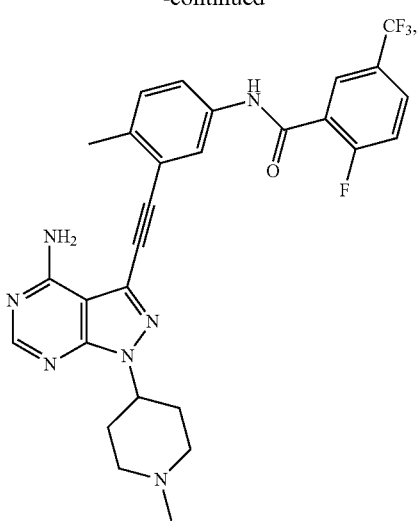
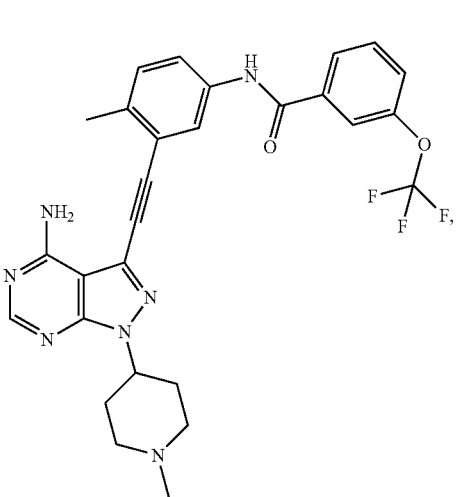

289
-continued
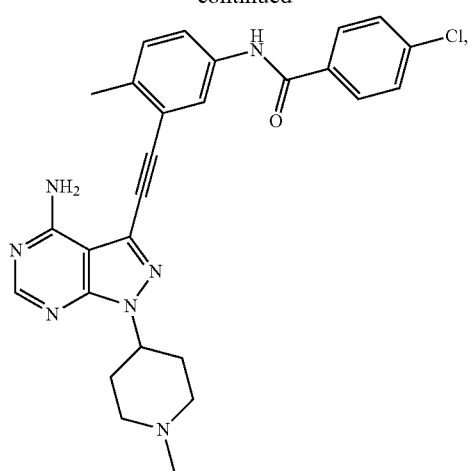
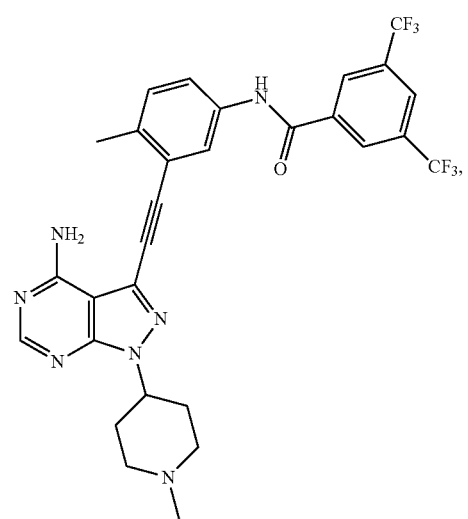
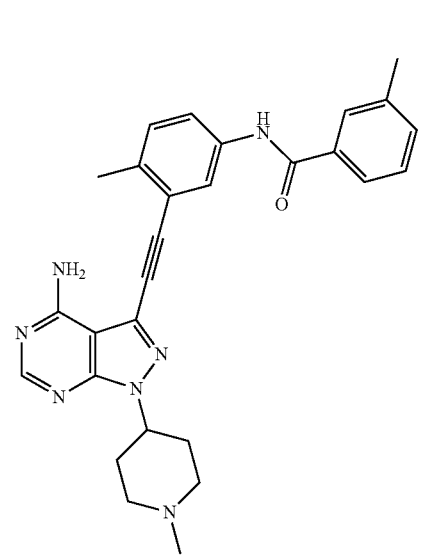
290
-continued
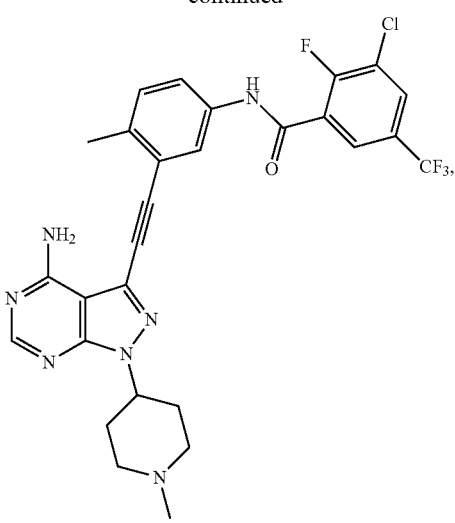
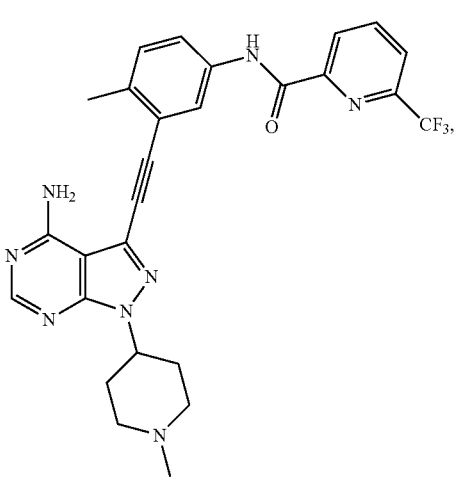
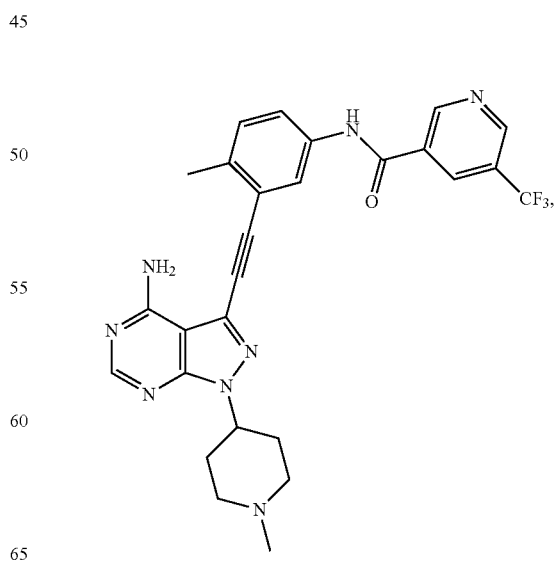

291
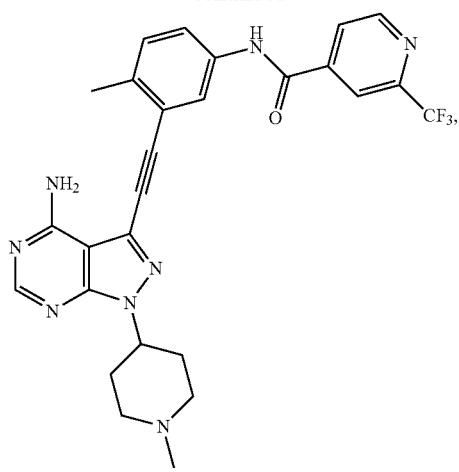
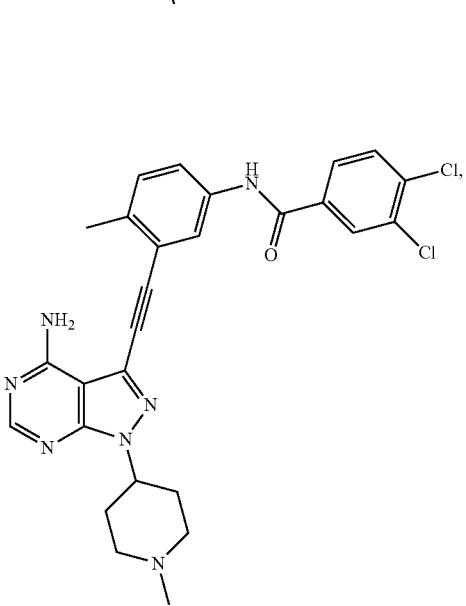
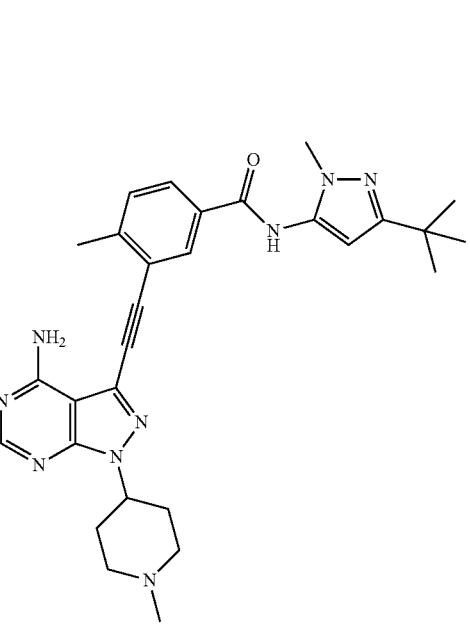
292
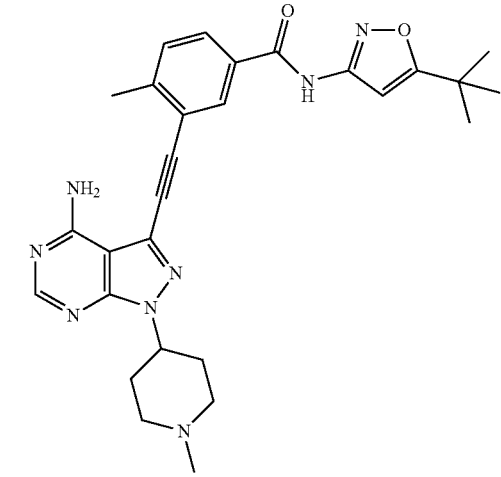
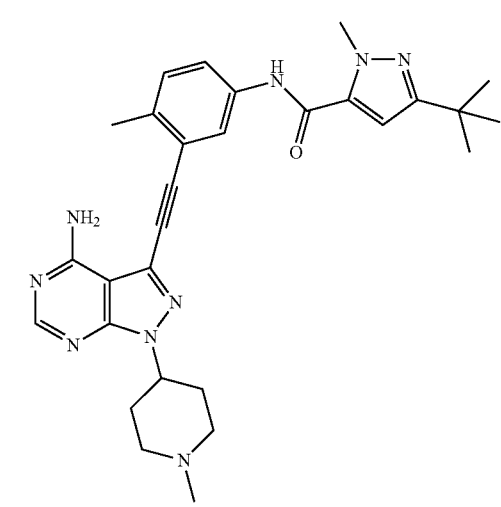
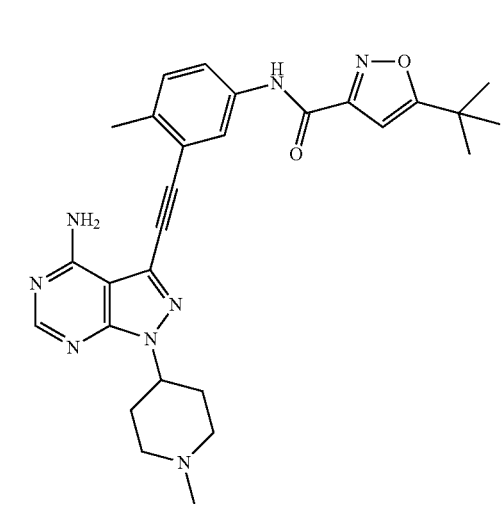

293
-continued
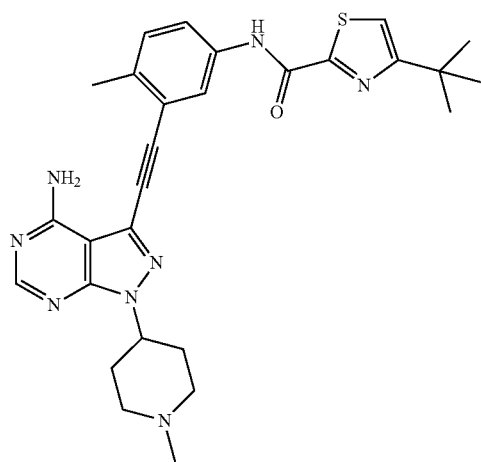
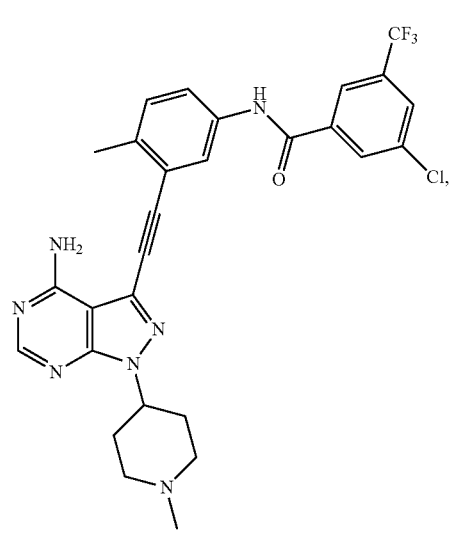
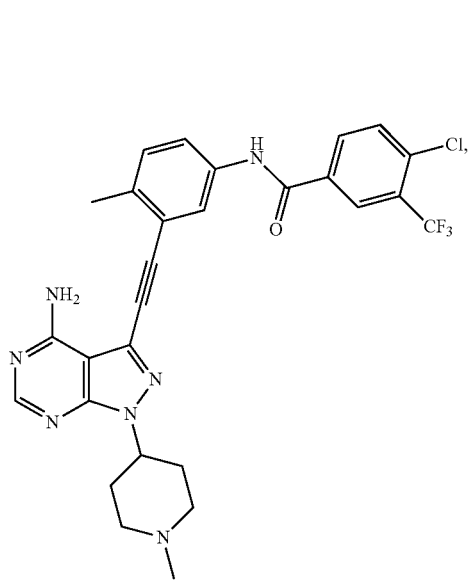
294
-continued
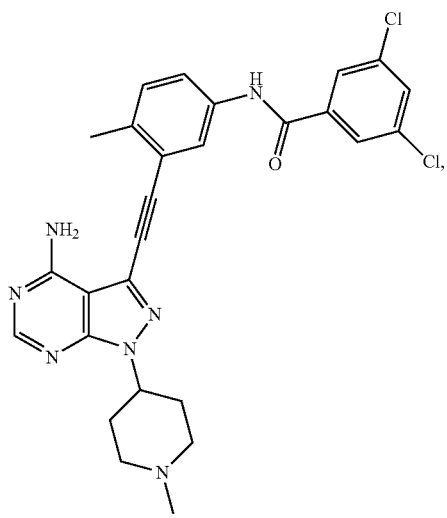
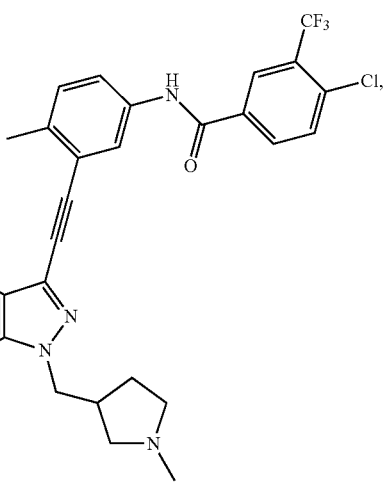
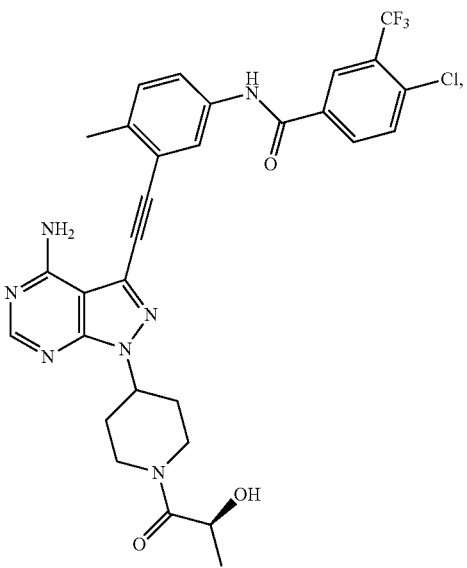

295
-continued
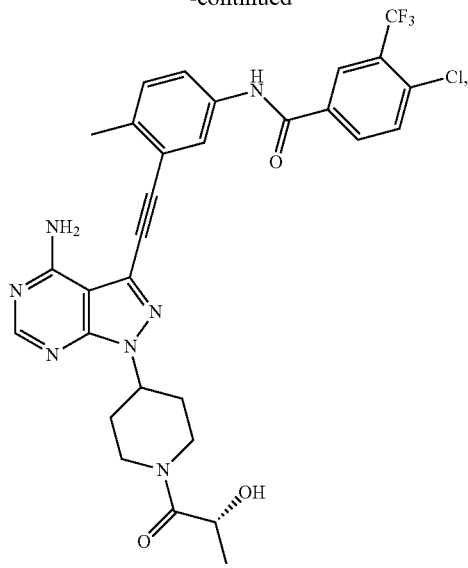
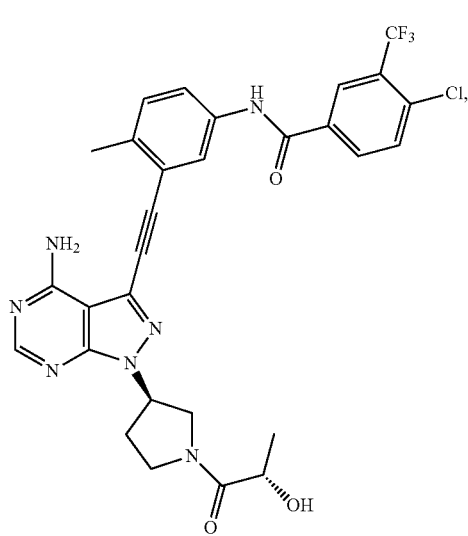
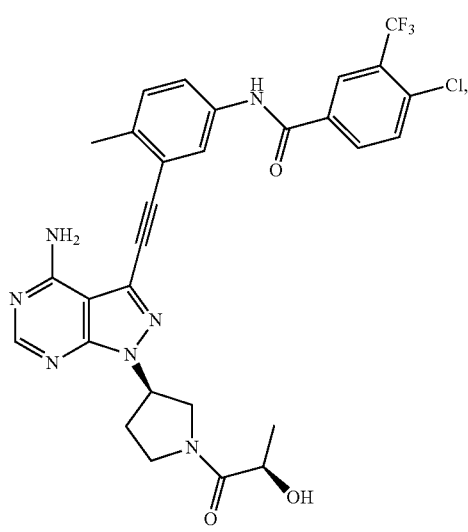
296
-continued
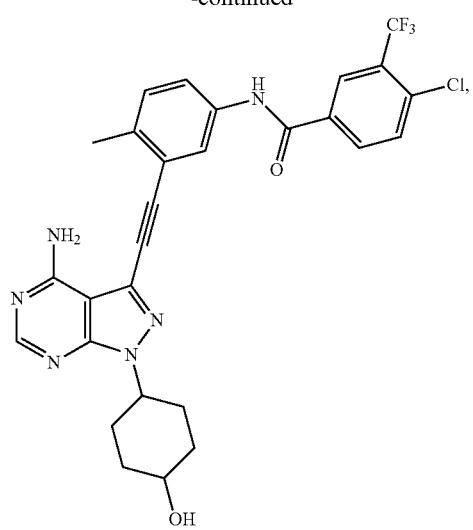
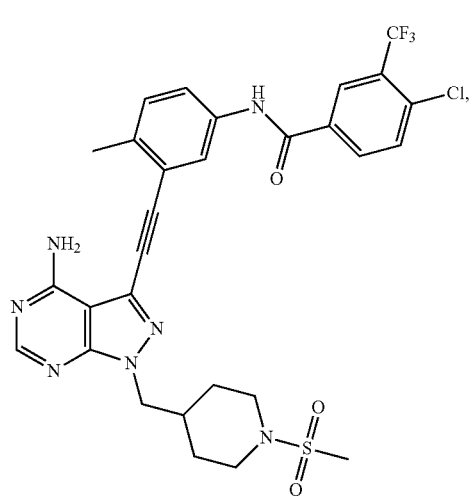
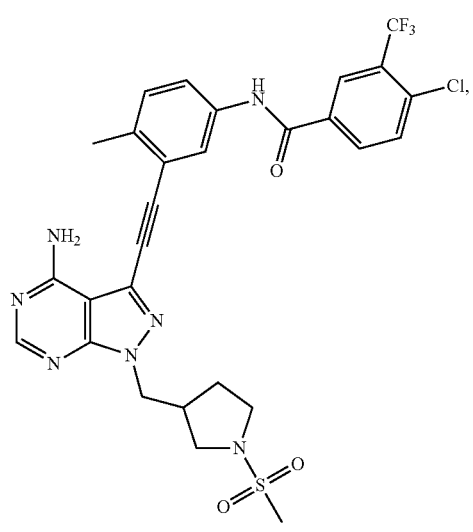

297
-continued
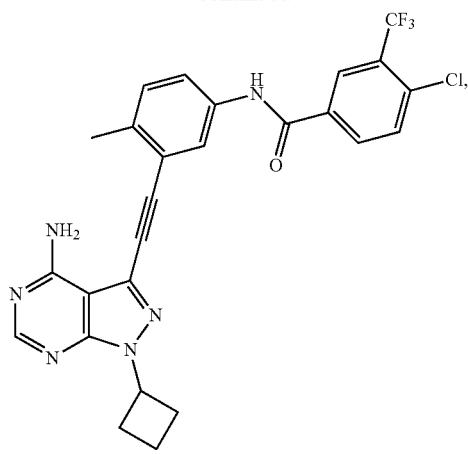
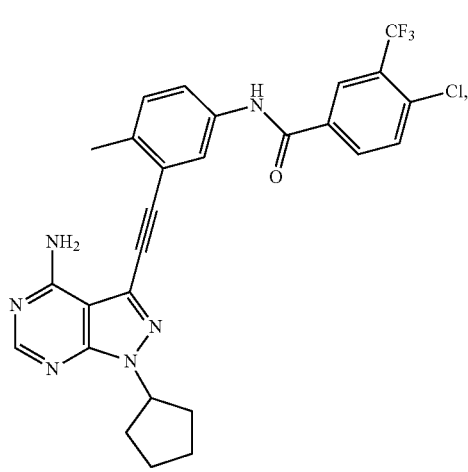
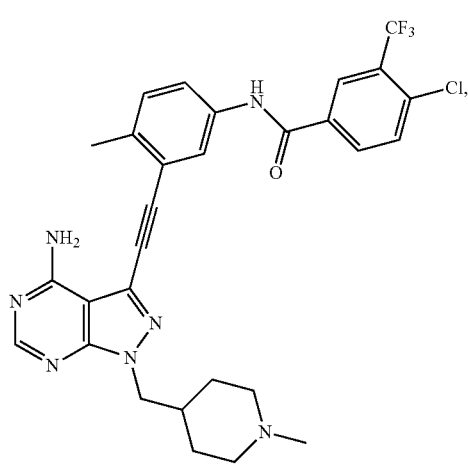
298
-continued
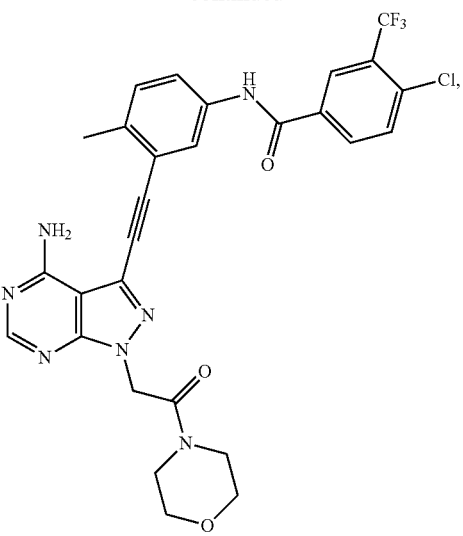
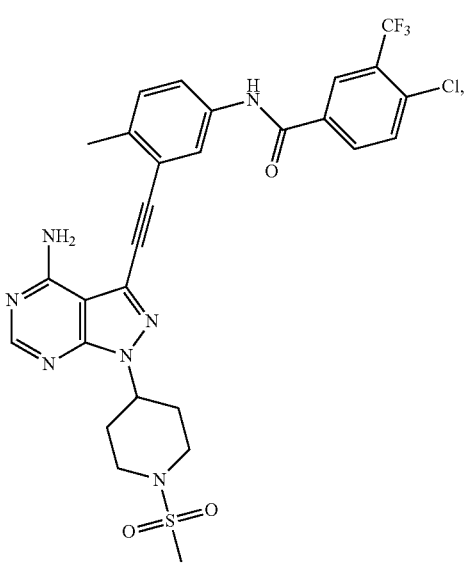
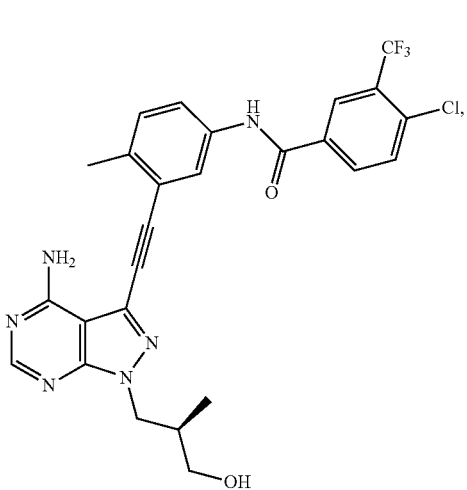

299
-continued
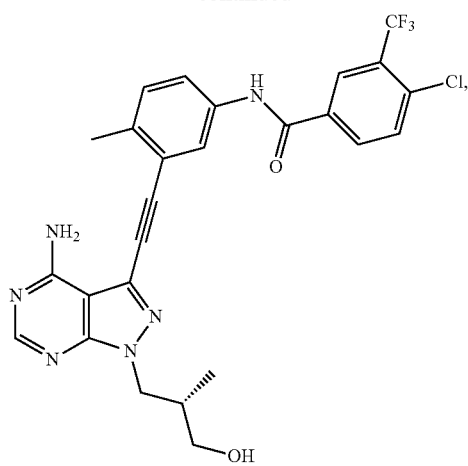
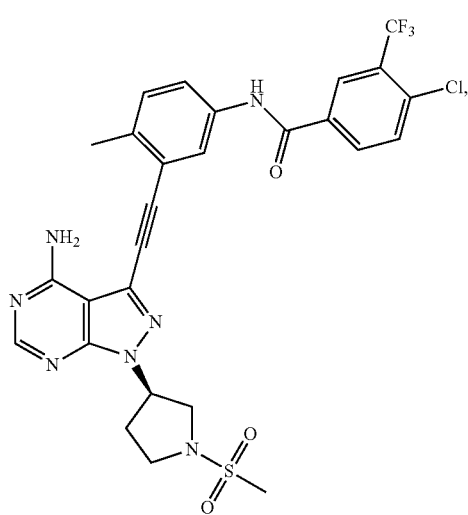
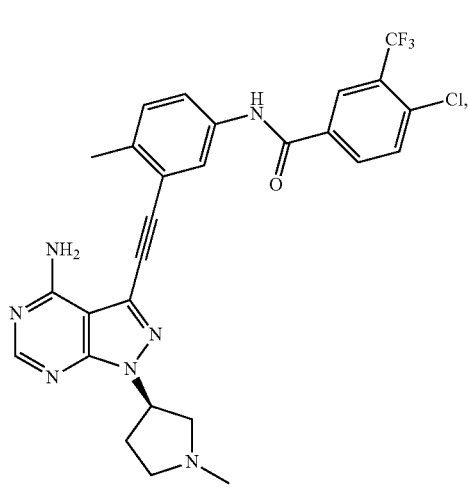
300
-continued
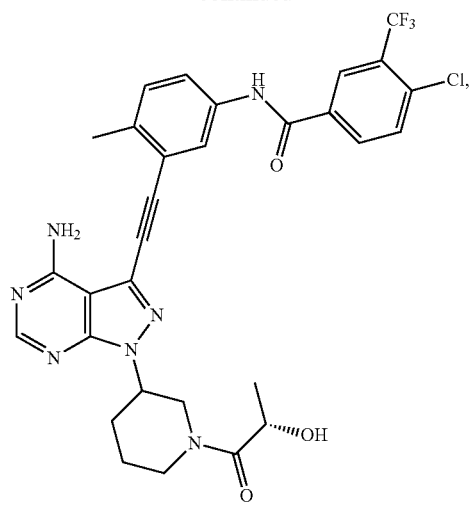
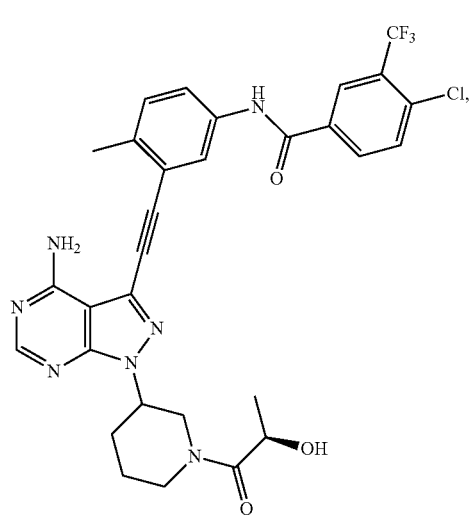
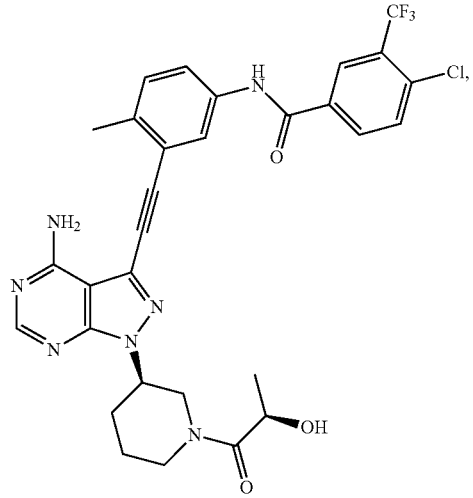

301
-continued
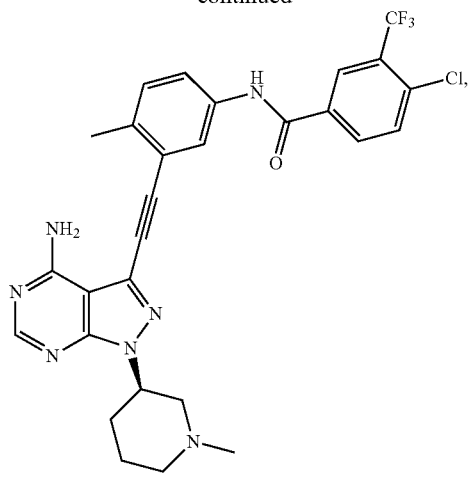
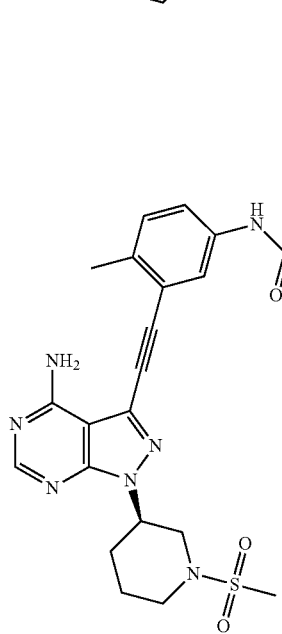
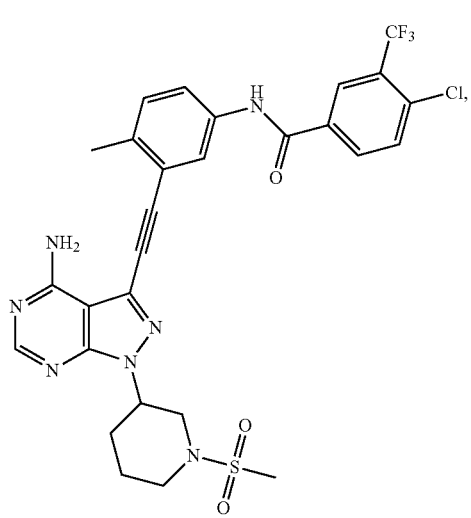
302
-continued
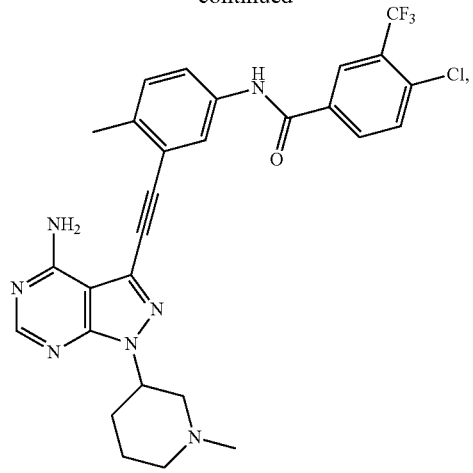
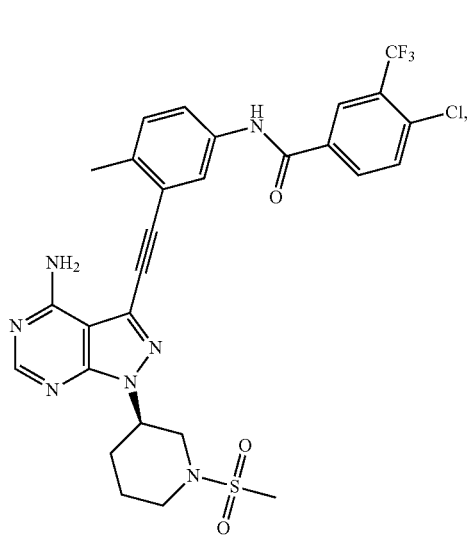
and
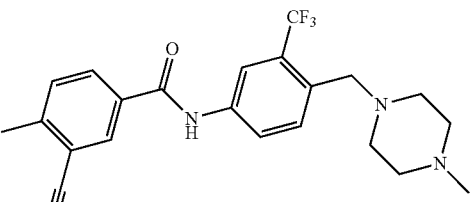

or a pharmaceutically acceptable salt or hydrate thereof.

14. A pharmaceutical composition comprising a 3-ethynylpyrazolopyrimidine derivative, or a pharmaceutically acceptable salt or hydrate thereof, according to claim 1.

15. A method for inhibiting a kinase, the method comprising:
administering a 3-ethynylpyrazolopyrimidine derivative of formula I of claim 1, or a pharmaceutically acceptable salt or hydrate thereof, or a pharmaceutically acceptable preparation thereof, to an in vitro cell line that comprises kinase activity, or to a subject in need thereof; wherein
the kinase is selected from the group consisting of Abl, Abl (T315I), cSrc, cSrc (I 530), cSrc (T341M), CDK7, BRaf (V600E), BRaf, c-RAF, cKit, CHK1, Yes, Fyn, Blk, Bcr-Abl, KDR, FGFR1, FGFR2, EphA1, EphA2, EphA8, EphB2, EphB4, ErbB2, DDR1, DDR2, TAK1, TrkA, Btk, Bmx, IKKα, IKKβ, Axl, PDGFRα, JAK2, Arg, BRK, CSK, EGFR, EGFR (T790M), EGFR (T790M, L858R), Flt 1, Flt3, Flt4, Hck, Lck, LIMK1, Lyn, Mer, PTK5, Pvk2, Ret, Ret (V804L), Ret (V804M), SAPK2b, Tie2 and Txk.

16. A method for treating cancer, the method comprising:
administering a 3-ethynylpyrazolopyrimidine derivative of formula I of claim 1, or a pharmaceutically acceptable salt or hydrate thereof, or a pharmaceutically acceptable preparation thereof, to a patient in need thereof, wherein
the cancer is selected from the group consisting of breast cancer, lung cancer, pancreatic cancer, malignant melanoma, leukemia, colorectal cancer, hepatocarcinoma, stomach cancer, thyroid cancer, lymphoma, renal cancer and malignant glioma.

17. The 3-ethynylpyrazolopyrimidine derivative of formula I according to claim 1, or a pharmaceutically acceptable salt or hydrate thereof, represented by the following formula:

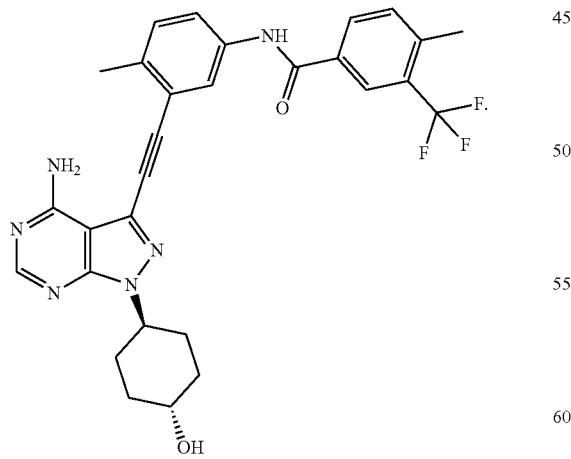

18. The 3-ethynylpyrazolopyrimidine derivative of formula I according to claim 1, or a pharmaceutically acceptable salt or hydrate thereof, selected from the group consisting of:

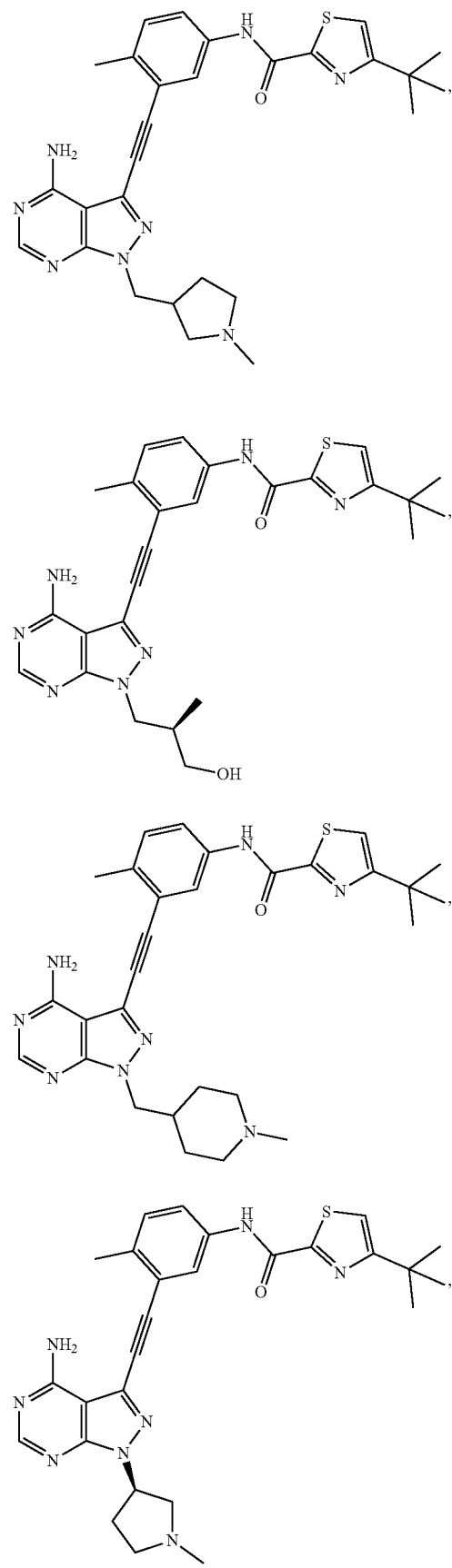

305
-continued
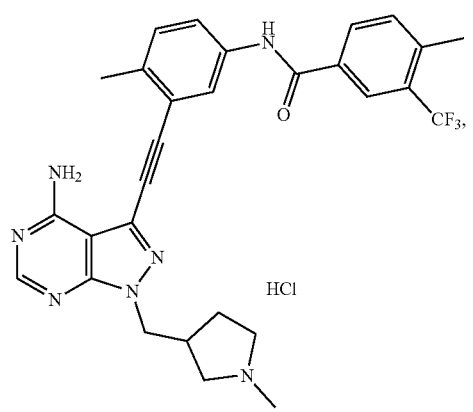
HCl
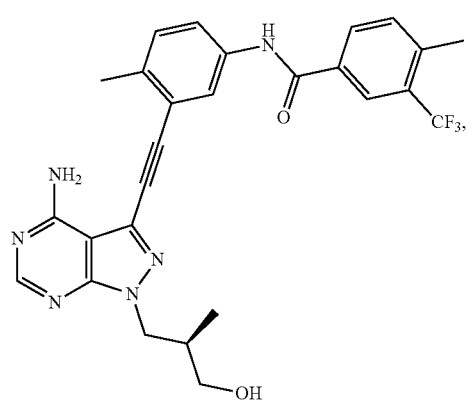
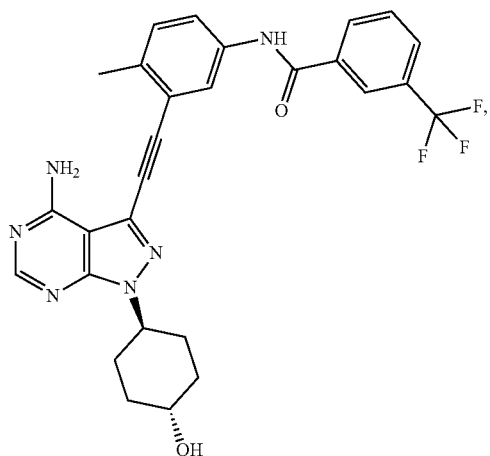 [SMILES: Cc1ccc(NC(=O)c2ccc(C)c(C(F)(F)F)c2)cc1C#Cc1nn([C@H]2CC[C@H](O)CC2)c2ncnc(N)c12]
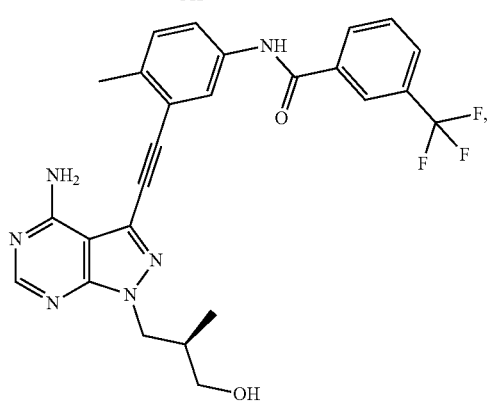
306
-continued
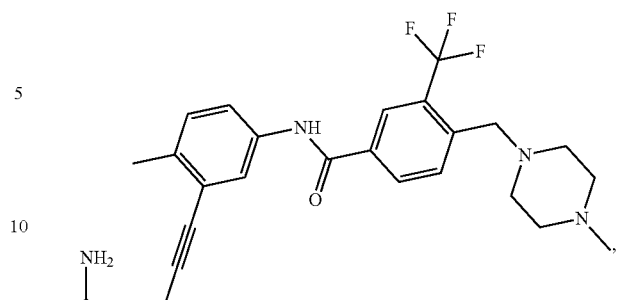
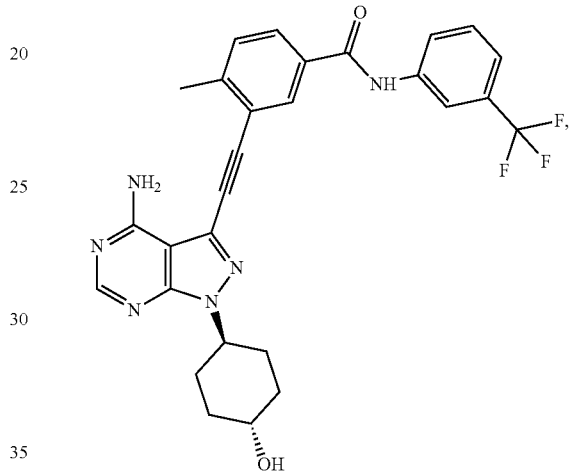
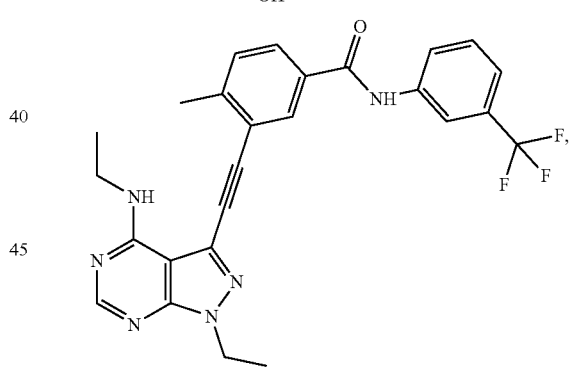
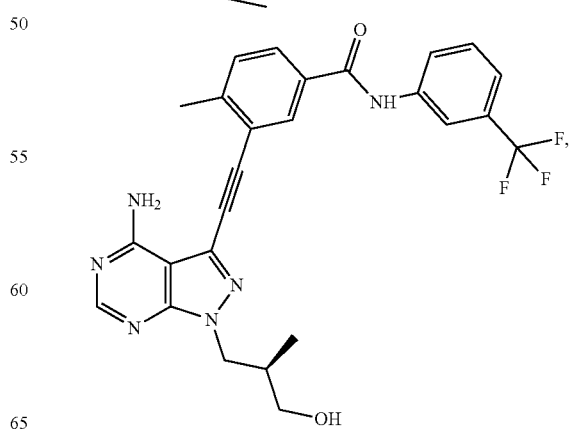

307
-continued
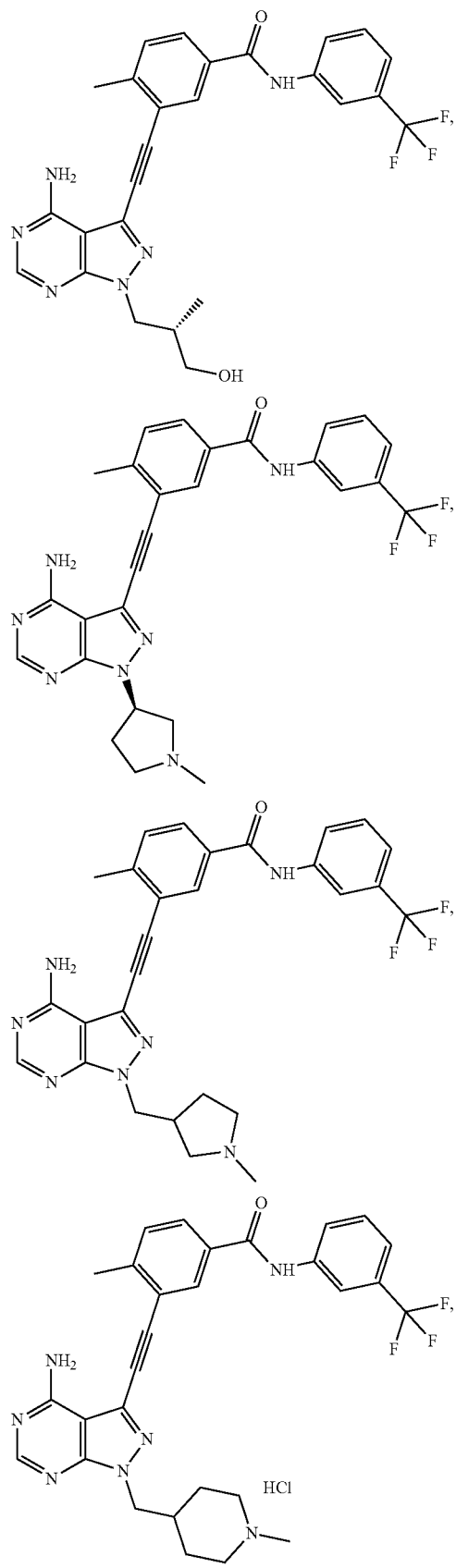
308
-continued
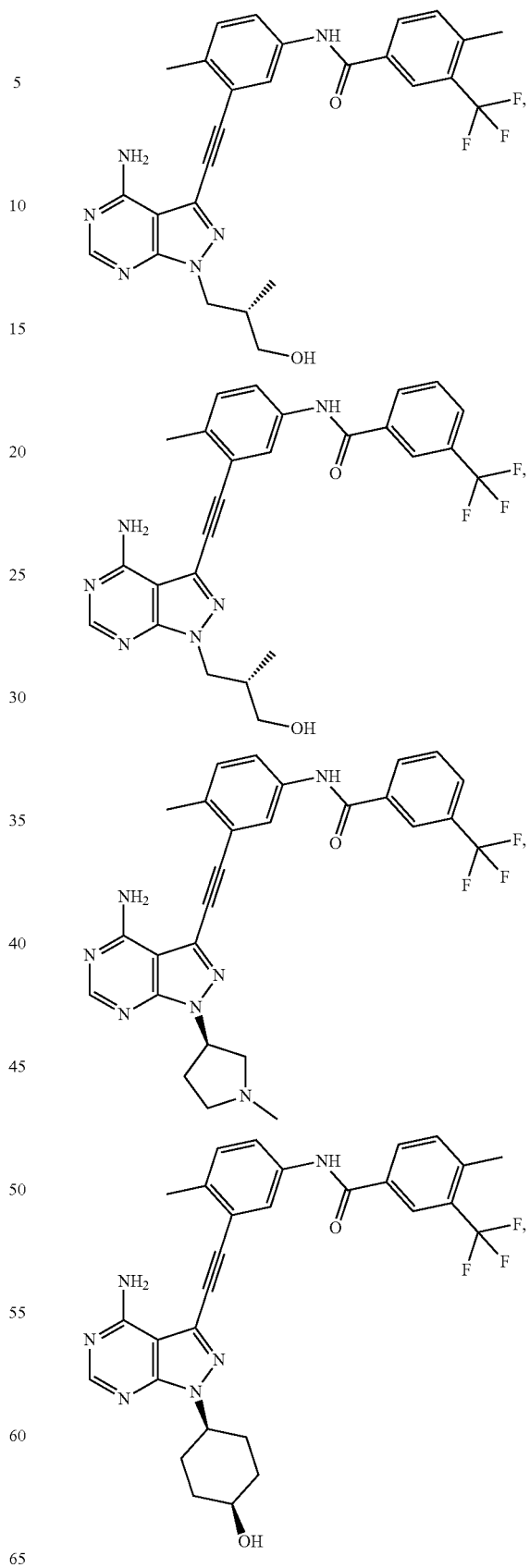

309
-continued
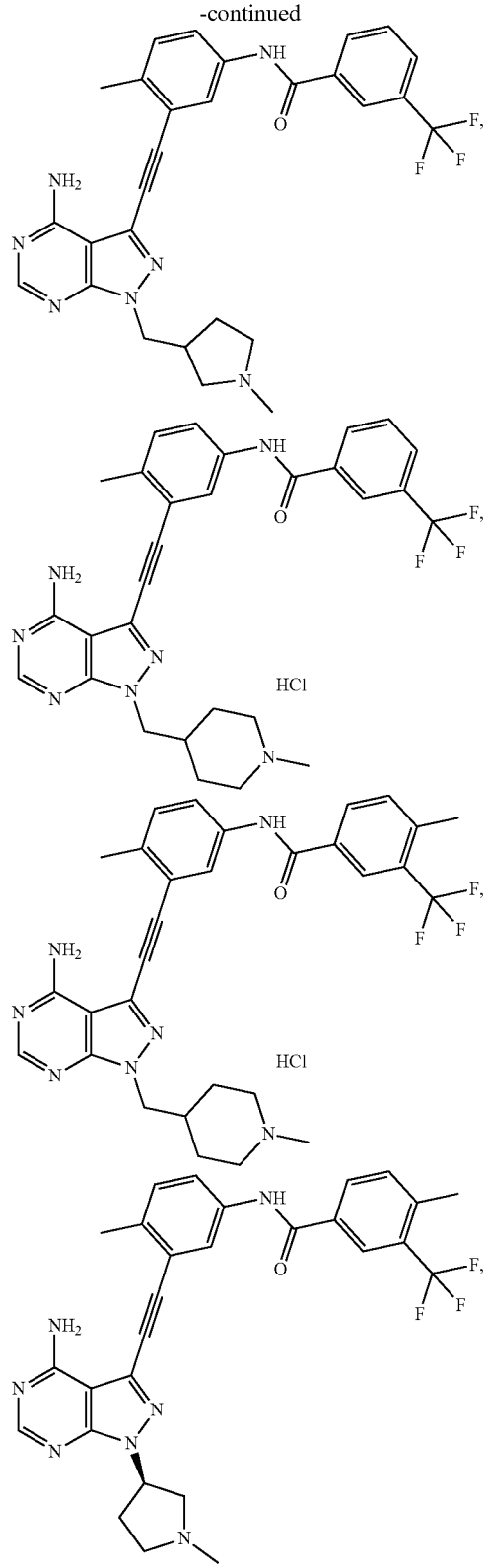
310
-continued
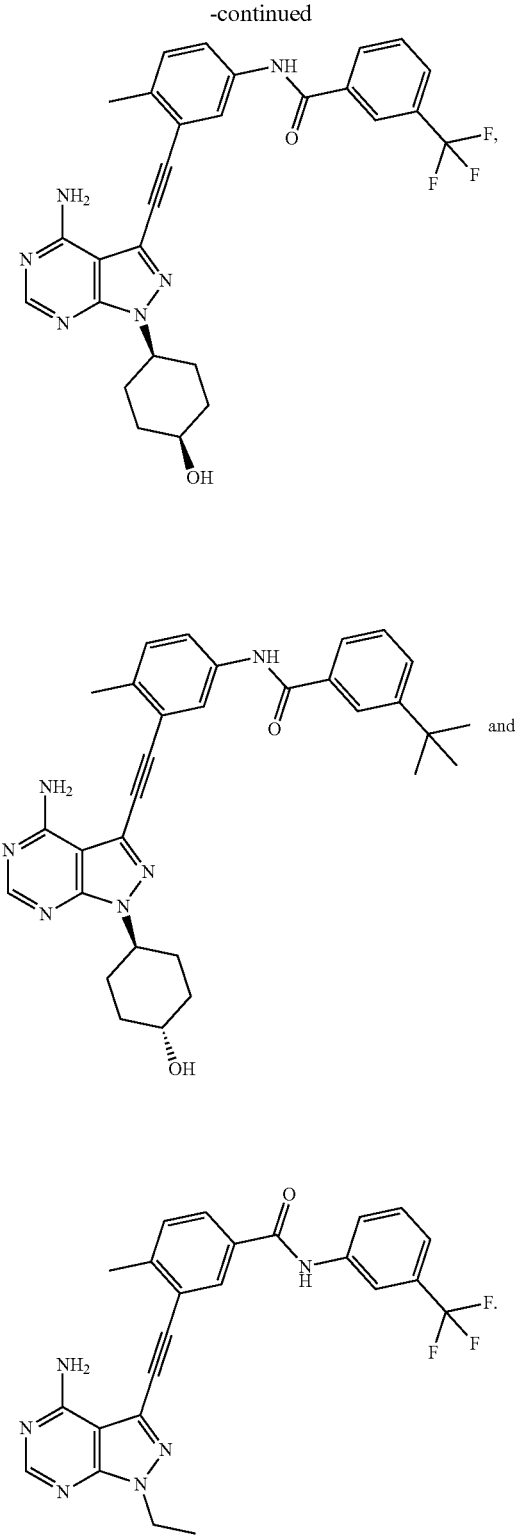
* * * * *